US012773100B2

(12) United States Patent
Giles

(10) Patent No.: US 12,773,100 B2
(45) Date of Patent: Oct. 27, 2026

(54) MEDICAL DEVICES WITH DISTAL CONTROL

(71) Applicant: MicroNovus, LLC, Dallas, TX (US)

(72) Inventor: Brian Giles, Dallas, TX (US)

(73) Assignee: MicroNovus, LLC, Dallas, TX (US)

( * ) Notice: Subject to any disclaimer, the term of this patent is extended or adjusted under 35 U.S.C. 154(b) by 1004 days.

(21) Appl. No.: 17/370,986

(22) Filed: Jul. 8, 2021

(65) Prior Publication Data

US 2021/0330310 A1 Oct. 28, 2021

Related U.S. Application Data

(63) Continuation-in-part of application No. 16/192,755, filed on Nov. 15, 2018, now Pat. No. 11,141,141,
(Continued)

(51) Int. Cl.
*A61B 17/00* (2006.01)
*A61B 1/00* (2006.01)
(Continued)

(52) U.S. Cl.
CPC ........ *A61B 1/0055* (2013.01); *A61B 1/00148* (2022.02); *A61B 1/0057* (2013.01);
(Continued)

(58) Field of Classification Search
CPC ........... A61B 2017/00985; A61B 2017/00309; A61B 2017/00323; A61M 25/0074;
(Continued)

(56) References Cited

U.S. PATENT DOCUMENTS 3,674,014 A 7/1972 Tillander
4,321,931 A 3/1982 Hon
(Continued)

FOREIGN PATENT DOCUMENTS

JP 2000-126301 5/2000
JP 2008-539887 A 11/2008
(Continued)

OTHER PUBLICATIONS

Product Brochure in 2 pages for SPIROL® Spring-Reinforced Epidural Catheter (retrieved on or about Feb. 25, 2016 from http://www.bd.com/anesthesia/products/epidural_twist.asp)—see footnote below.
(Continued)

*Primary Examiner* — Devin B Henson
(74) *Attorney, Agent, or Firm* — Knobbe, Martens, Olson & Bear, LLP

(57) ABSTRACT

According to some embodiments, the device comprises a tubular member with a longitudinal axis having a proximal end and a distal end, at least one partial cut located at, along or near the distal end of the tubular member, wherein the distal end of the tubular member is configured to at least partially rotate when the force imparting element is advanced relative to the tubular member so at to facilitate placement of the distal end in a particular location of a subject's intraluminal network. The device further includes a transition section intermediate to the at least one partial cut and the non-cut portion of the tubular member.

20 Claims, 70 Drawing Sheets

Related U.S. Application Data which is a continuation of application No. 15/924,027, filed on Mar. 16, 2018, now Pat. No. 10,786,230, which is a continuation of application No. 15/660,811, filed on Jul. 26, 2017, now Pat. No. 9,918,705, which is a continuation of application No. PCT/US2017/041224, filed on Jul. 7, 2017, and a continuation-in-part of application No. 15/204,800, filed on Jul. 7, 2016, now Pat. No. 10,391,274, said application No. PCT/US2017/041224 is a continuation-in-part of application No. 15/204,800, filed on Jul. 7, 2016, now Pat. No. 10,391,274.

(60) Provisional application No. 63/050,078, filed on Jul. 9, 2020, provisional application No. 62/467,229, filed on Mar. 5, 2017, provisional application No. 62/359,588, filed on Jul. 7, 2016.

(51) Int. Cl.

| | |
|---|---|
| ***A61B 1/005*** | (2006.01) |
| ***A61M 25/00*** | (2006.01) |
| ***A61M 25/01*** | (2006.01) |

(52) U.S. Cl.

CPC ... *A61B 17/00234* (2013.01); *A61M 25/0074* (2013.01); *A61M 25/0097* (2013.01); *A61M 25/0102* (2013.01); *A61M 25/0136* (2013.01); *A61M 25/0138* (2013.01); *A61M 25/0147* (2013.01); *A61M 25/0158* (2013.01); *A61B 1/0008* (2013.01); *A61B 2017/00309* (2013.01); *A61B 2017/00323* (2013.01); *A61B 2017/00871* (2013.01); *A61M 25/0041* (2013.01); *A61M 25/0068* (2013.01); *A61M 2025/0079* (2013.01); *A61M 25/0105* (2013.01); *A61M 25/0133* (2013.01); *A61M 2205/0266* (2013.01)

(58) Field of Classification Search

CPC .......... A61M 25/0102; A61M 25/0133; A61M 25/0136; A61M 25/0138; A61M 25/0141; A61M 25/0147; A61M 25/0013; A61M 25/0053; A61M 2025/0004

See application file for complete search history.

(56) References Cited

U.S. PATENT DOCUMENTS

| | | | |
|---|---|---|---|
| 4,545,390 | A | 10/1985 | Leary |
| 4,548,206 | A | 10/1985 | Osborne |
| 4,619,274 | A | 10/1986 | Morrison |
| 4,721,117 | A | 1/1988 | Mar et al. |
| 4,757,827 | A | 7/1988 | Buchbinder et al. |
| 4,790,831 | A | 12/1988 | Skribiski |
| 4,867,173 | A | 9/1989 | Leoni |
| 4,867,174 | A | 9/1989 | Skribiski |
| 4,925,445 | A | 5/1990 | Sakamoto et al. |
| 4,960,410 | A | 10/1990 | Pinchuk |
| 5,040,543 | A | 8/1991 | Badera et al. |
| 5,052,404 | A | 10/1991 | Hodgson |
| 5,095,915 | A | 3/1992 | Engelson |
| 5,122,136 | A | 6/1992 | Guglielmi et al. |
| 5,171,383 | A | 12/1992 | Sagae et al. |
| 5,228,453 | A | 7/1993 | Sepetka |
| 5,269,757 | A | 12/1993 | Fagan et al. |
| 5,329,923 | A | 7/1994 | Lundquist |
| RE34,695 | E | 8/1994 | Mar et al. |
| 5,365,943 | A | 11/1994 | Jansen |
| 5,507,751 | A | 4/1996 | Goode et al. |
| 5,570,701 | A | 11/1996 | Ellis et al. |
| 5,573,520 | A | 11/1996 | Schwartz et al. |
| 5,599,492 | A | 2/1997 | Engelson |
| 5,605,543 | A | 2/1997 | Swanson |
| 5,741,429 | A | 4/1998 | Donadio, III et al. |
| 5,743,876 | A | 4/1998 | Swanson |
| 5,762,615 | A | 6/1998 | Weier |
| 5,766,151 | A | 6/1998 | Valley et al. |
| 5,772,609 | A | 6/1998 | Nguyen et al. |
| 5,843,153 | A | 12/1998 | Johnston et al. |
| 5,897,529 | A | 4/1999 | Ponzi |
| 5,961,510 | A | 10/1999 | Fugoso et al. |
| 5,984,877 | A | 11/1999 | Fleischhacker, Jr. |
| 6,001,068 | A | 12/1999 | Uchino et al. |
| 6,019,736 | A | 2/2000 | Avellanet et al. |
| 6,022,343 | A | 2/2000 | Johnson et al. |
| 6,048,338 | A | 4/2000 | Larson et al. |
| 6,053,922 | A | 4/2000 | Krause et al. |
| 6,132,388 | A | 10/2000 | Fleming et al. |
| 6,213,974 | B1 | 4/2001 | Smith et al. |
| 6,306,105 | B1 | 10/2001 | Rooney et al. |
| 6,385,472 | B1 | 5/2002 | Hall et al. |
| 6,475,167 | B1 | 11/2002 | Fleming et al. |
| 6,475,209 | B1 | 11/2002 | Larson et al. |
| 6,482,217 | B1 | 11/2002 | Pintor et al. |
| 6,575,920 | B2 | 6/2003 | Zhou |
| 6,579,246 | B2 | 6/2003 | Jacobsen et al. |
| 6,594,517 | B1 | 7/2003 | Nevo |
| 6,602,262 | B2 | 8/2003 | Griego et al. |
| 6,605,086 | B2 | 8/2003 | Hayzelden et al. |
| 6,682,493 | B2 | 1/2004 | Mirigian |
| 6,716,183 | B2 | 4/2004 | Clayman et al. |
| 6,834,201 | B2 | 12/2004 | Gillies et al. |
| 6,881,194 | B2 | 4/2005 | Miyata et al. |
| 6,890,329 | B2 | 5/2005 | Carroll et al. |
| 7,044,921 | B2 | 5/2006 | Asmus et al. |
| 7,077,811 | B2 | 7/2006 | Vrba et al. |
| 7,117,703 | B2 | 10/2006 | Kato et al. |
| 7,182,735 | B2 | 2/2007 | Shireman et al. |
| 7,211,082 | B2 | 5/2007 | Hall et al. |
| 7,235,088 | B2 | 6/2007 | Pintor et al. |
| 7,276,062 | B2 | 10/2007 | McDaniel et al. |
| 7,316,656 | B2 | 1/2008 | Shireman et al. |
| 7,344,546 | B2 | 3/2008 | Wulfman et al. |
| 7,381,198 | B2 | 6/2008 | Noriega et al. |
| 7,470,239 | B1 | 12/2008 | Rooney et al. |
| 7,485,127 | B2 | 2/2009 | Nistal |
| 7,488,338 | B2 | 2/2009 | Eidenschink |
| 7,615,032 | B2 | 11/2009 | Whittaker et al. |
| 7,618,379 | B2 | 11/2009 | Reynolds et al. |
| 7,641,621 | B2 | 1/2010 | Crank |
| 7,674,272 | B2 | 3/2010 | Torrance et al. |
| 7,691,103 | B2 | 4/2010 | Fernandez et al. |
| 7,708,704 | B2 | 5/2010 | Mitelberg et al. |
| 7,713,231 | B2 | 5/2010 | Wulfman et al. |
| 7,747,314 | B2 | 6/2010 | Parins et al. |
| 7,758,591 | B2 | 7/2010 | Griego et al. |
| 7,763,012 | B2 | 7/2010 | Petrick et al. |
| 7,771,388 | B2 | 8/2010 | Olsen et al. |
| 7,776,062 | B2 | 8/2010 | Besselink et al. |
| 7,780,611 | B2 | 8/2010 | Griego et al. |
| 7,811,294 | B2 | 10/2010 | Strommer et al. |
| 7,842,055 | B2 | 11/2010 | Pintor et al. |
| 7,867,176 | B2 | 1/2011 | Wu et al. |
| 7,878,984 | B2 | 2/2011 | Jacobsen et al. |
| 7,887,529 | B2 | 2/2011 | Eder |
| 7,892,186 | B2 | 2/2011 | Soukup et al. |
| 7,892,233 | B2 | 2/2011 | Hall et al. |
| 7,946,999 | B2 | 5/2011 | Rooney et al. |
| 7,955,272 | B2 | 6/2011 | Rooney et al. |
| 7,993,286 | B2 | 8/2011 | Reynolds et al. |
| 7,998,088 | B2 | 8/2011 | Vrba et al. |
| 7,998,090 | B2 | 8/2011 | Simpson et al. |
| 7,998,132 | B2 | 8/2011 | Gregorich et al. |
| 8,055,327 | B2 | 11/2011 | Strommer et al. |
| 8,137,336 | B2 | 3/2012 | Ostrovsky et al. |
| 8,167,821 | B2 | 5/2012 | Sharrow |
| 8,222,566 | B2 | 7/2012 | Shireman et al. |
| 8,231,647 | B2 | 7/2012 | Eidenschink |
| 8,267,873 | B2 | 9/2012 | Yanuma |
| 8,292,827 | B2 | 10/2012 | Musbach et al. |
| 8,292,829 | B2 | 10/2012 | Griego et al. |

(56) References Cited

U.S. PATENT DOCUMENTS

| | | | |
|---|---|---|---|
| 8,303,570 | B2 | 11/2012 | Gregorich et al. |
| 8,313,493 | B2 | 11/2012 | Fischer |
| 8,323,240 | B2 | 12/2012 | Wulfman et al. |
| 8,323,241 | B2 | 12/2012 | Salahieh et al. |
| 8,353,850 | B2 | 1/2013 | Ressemann et al. |
| 8,366,699 | B2 | 2/2013 | Jimenez et al. |
| 8,372,056 | B2 | 2/2013 | Eder |
| 8,376,963 | B2 | 2/2013 | Wright et al. |
| 8,382,786 | B2 | 2/2013 | Besselink et al. |
| 8,388,572 | B2 | 3/2013 | Olsen et al. |
| 8,388,629 | B2 | 3/2013 | Griego et al. |
| 8,394,091 | B2 | 3/2013 | Rioux et al. |
| 8,414,477 | B2 | 4/2013 | Tallarida et al. |
| 8,414,506 | B2 | 4/2013 | Reynolds et al. |
| 8,425,532 | B2 | 4/2013 | Flom et al. |
| 8,449,526 | B2 | 5/2013 | Snyder et al. |
| 8,454,537 | B2 | 6/2013 | Simpson et al. |
| 8,460,214 | B2 | 6/2013 | Kuban et al. |
| 8,480,668 | B2 | 7/2013 | Fernandez et al. |
| 8,556,914 | B2 | 10/2013 | Vrba et al. |
| 8,579,926 | B2 | 11/2013 | Pintor et al. |
| 8,608,726 | B2 | 12/2013 | Whittaker et al. |
| 8,672,837 | B2 | 3/2014 | Roelle et al. |
| 8,684,953 | B2 | 4/2014 | Cabiri |
| 8,708,953 | B2 | 4/2014 | Salahieh et al. |
| 8,721,564 | B2 | 5/2014 | Simpson et al. |
| 8,764,743 | B2 | 7/2014 | McDaniel et al. |
| 8,771,288 | B2 | 7/2014 | Griego et al. |
| 8,814,848 | B2 | 8/2014 | Gregorich et al. |
| 8,845,552 | B2 | 9/2014 | Griego et al. |
| 8,894,610 | B2 | 11/2014 | Macnamara et al. |
| 8,920,369 | B2 | 12/2014 | Salahieh et al. |
| 8,951,224 | B2 | 2/2015 | Wulfman et al. |
| 8,968,383 | B1 | 3/2015 | Johnson et al. |
| 9,138,566 | B2 | 9/2015 | Cabiri |
| 9,192,285 | B2 | 11/2015 | Ostrovsky et al. |
| 9,339,271 | B2 | 5/2016 | Ranucci et al. |
| 9,421,343 | B2 | 8/2016 | Berthiaume et al. |
| 9,474,639 | B2 | 10/2016 | Haggstrom et al. |
| 9,492,103 | B2 | 11/2016 | Strommer et al. |
| 9,498,363 | B2 | 11/2016 | Watson et al. |
| 9,586,025 | B2 | 3/2017 | Salahieh et al. |
| 9,636,482 | B2 | 5/2017 | McDaniel et al. |
| 9,649,473 | B2 | 5/2017 | Gregorich et al. |
| 9,808,867 | B2 | 11/2017 | Krause et al. |
| 9,918,705 | B2 * | 3/2018 | Giles .................... A61B 1/0055 |
| 10,391,274 | B2 | 8/2019 | Giles |
| 10,441,746 | B2 | 10/2019 | Besselink |
| 10,786,230 | B2 | 9/2020 | Giles |
| 11,141,141 | B2 | 10/2021 | Giles |
| 11,717,641 | B2 | 8/2023 | Giles |
| 2002/0072662 | A1 | 6/2002 | Hall et al. |
| 2002/0103430 | A1 | 8/2002 | Hastings et al. |
| 2003/0009208 | A1 | 1/2003 | Snyder et al. |
| 2003/0055450 | A1 | 3/2003 | Cheng et al. |
| 2004/0059257 | A1 | 3/2004 | Gaber |
| 2004/0236312 | A1 | 11/2004 | Nistal et al. |
| 2005/0143664 | A1 | 6/2005 | Chen et al. |
| 2005/0277808 | A1 | 12/2005 | Sonnenschein et al. |
| 2005/0283179 | A1 | 12/2005 | Lentz |
| 2006/0014418 | A1 | 1/2006 | Kato et al. |
| 2006/0089563 | A1 | 4/2006 | McAlister et al. |
| 2006/0089569 | A1 | 4/2006 | Soukup et al. |
| 2006/0100687 | A1 | 5/2006 | Fahey et al. |
| 2006/0184105 | A1 | 8/2006 | Townsend et al. |
| 2007/0123805 | A1 | 5/2007 | Shireman et al. |
| 2007/0135733 | A1 * | 6/2007 | Soukup ............ A61M 25/0136 604/95.04 |
| 2007/0185415 | A1 | 8/2007 | Ressemann et al. |
| 2007/0225739 | A1 | 9/2007 | Pintor et al. |
| 2008/0228208 | A1 | 9/2008 | Wulfman et al. |
| 2009/0156897 | A1 | 6/2009 | Omot et al. |
| 2009/0157048 | A1 | 6/2009 | Sutermeister et al. |
| 2009/0177119 | A1 * | 7/2009 | Heidner ................ A61M 25/09 600/585 |
| 2009/0306587 | A1 | 12/2009 | Milijasevic et al. |
| 2010/0069882 | A1 | 3/2010 | Jennings et al. |
| 2010/0114151 | A1 | 5/2010 | Mujwid et al. |
| 2010/0324576 | A1 | 12/2010 | Pintor et al. |
| 2010/0331776 | A1 | 12/2010 | Salahieh et al. |
| 2012/0179097 | A1 | 7/2012 | Cully et al. |
| 2013/0053766 | A1 * | 2/2013 | Hollett ............ A61M 25/09041 604/95.01 |
| 2013/0072904 | A1 | 3/2013 | Musbach et al. |
| 2013/0116705 | A1 | 5/2013 | Salahieh et al. |
| 2013/0158516 | A1 | 6/2013 | Wright et al. |
| 2013/0226026 | A1 | 8/2013 | Dillard et al. |
| 2013/0245732 | A1 | 9/2013 | Jarl et al. |
| 2014/0031843 | A1 | 1/2014 | Rottenberg et al. |
| 2014/0148673 | A1 | 5/2014 | Bogusky |
| 2014/0148759 | A1 | 5/2014 | Macnamara et al. |
| 2014/0246407 | A1 | 9/2014 | Simpson et al. |
| 2014/0276642 | A1 | 9/2014 | Cully et al. |
| 2014/0276966 | A1 | 9/2014 | Ranucci et al. |
| 2014/0350462 | A1 | 11/2014 | Ataollahi et al. |
| 2014/0378868 | A1 | 12/2014 | Griego et al. |
| 2015/0066128 | A1 | 3/2015 | Losordo et al. |
| 2015/0066129 | A1 | 3/2015 | Nageswaran et al. |
| 2015/0066131 | A1 | 3/2015 | Luong et al. |
| 2015/0099997 | A1 | 4/2015 | Cabiri |
| 2015/0119754 | A1 | 4/2015 | Ostrovski et al. |
| 2015/0164542 | A1 | 6/2015 | Wulfman et al. |
| 2015/0238336 | A1 | 8/2015 | Johnson et al. |
| 2015/0250981 | A1 | 9/2015 | Beasley et al. |
| 2016/0206860 | A1 | 7/2016 | Gupta |
| 2016/0310702 | A1 | 10/2016 | Cabiri |
| 2017/0035592 | A1 | 2/2017 | Haggstrom et al. |
| 2017/0173303 | A1 | 6/2017 | Salahieh et al. |
| 2017/0189645 | A9 | 7/2017 | Cully et al. |
| 2017/0224199 | A1 | 8/2017 | Demers et al. |
| 2017/0281909 | A1 * | 10/2017 | Northrop .......... A61M 25/0013 |
| 2018/0008251 | A1 * | 1/2018 | Giles ................ A61B 17/00234 |
| 2018/0078739 | A1 | 3/2018 | Law |
| 2019/0060612 | A1 * | 2/2019 | Besselink ......... A61M 25/0051 |
| 2019/0357751 | A1 | 11/2019 | Friedlander et al. |
| 2019/0374745 | A1 | 12/2019 | Giles |
| 2020/0078096 | A1 | 3/2020 | Barbagli et al. |
| 2022/0023593 | A1 | 1/2022 | Giles |
| 2022/0061634 | A1 | 3/2022 | Thissen et al. |
| 2023/0381450 | A1 | 11/2023 | Giles |
| 2025/0186742 | A1 | 6/2025 | Giles |

FOREIGN PATENT DOCUMENTS

| | | | |
|---|---|---|---|
| JP | 2012-531270 | | 12/2012 |
| JP | 5113386 | B2 | 1/2013 |
| JP | 2015-192845 | | 11/2015 |
| WO | WO 1999/051140 | | 10/1999 |
| WO | WO 2000/033984 | | 6/2000 |
| WO | WO 2005/105191 | | 11/2005 |
| WO | WO 2010/151698 | A2 | 12/2010 |
| WO | WO 2017/037538 | | 3/2017 |
| WO | WO 2018/009883 | A1 | 1/2018 |
| WO | WO 2023/081419 | A1 | 5/2023 |
| WO | WO 2025/064938 | | 3/2025 |

OTHER PUBLICATIONS

Dong et al., Dual-Chirality Helical Nanobelts: Linear-to-Rotary Motion Converters for Three-Dimensional Microscopy, Journal of Microelectromechanical Systems, vol. 18, No. 5, Oct. 2009.

International Search Report for related PCT App. No. PCT/US2017/41224, dated Nov. 16, 2017.

Extended European Search Report dated Feb. 4, 2020 for European Patent Office Appl. No. 17825038.7, which is in the same patent family as the present application.

U.S. Appl. No. 15/204,800 (U.S. Pat. No. 10,391,274), filed Jul. 7, 2016, Medical Device With Distal Torque Control.

U.S. Appl. No. 16/551,454, filed Aug. 26, 2019, Medical Device With Distal Torque Control.

U.S. Appl. No. 15/660,811 (U.S. Pat. No. 9,918,811), filed Jul. 26, 2017, Medical Device With Distal Control.

(56) References Cited

OTHER PUBLICATIONS

U.S. Appl. No. 17/370,986 (present application), filed Jul. 8, 2021, Medical Devices With Distal Control.
U.S. Appl. No. 15/924,027 (U.S. Pat. No. 10,786,230), filed Mar. 16, 2018, Medical Devices With Distal Control.
U.S. Appl. No. 16/192,755 (U.S. Pat. No. 11,141,141), filed Nov. 15, 2018, Medical Devices With Distal Control.
U.S. Appl. No. 17/498,701, filed Oct. 11, 2021, Medical Devices With Distal Control.
U.S. Appl. No. 15/204,800 (U.S. Pat. No. 10,391,274), filed Jul. 7, 2016, Medical Devices with Distal Torque Control.
U.S. Appl. No. 16/551,454 (U.S. Pat. No. 11,717,641), filed Aug. 26, 2019, Medical Device with Distal Torque Control.
U.S. Appl. No. 18/231,184, filed Aug. 7, 2023, Medical Device with Distal Torque Control.
U.S. Appl. No. 15/660,811 (U.S. Pat. No. 9,918,705), filed Jul. 26, 2017, Medical Devices with Distal Control.
International Search Report and Written Opinion for PCT Application No. PCT/US2022/049048, dated Mar. 27, 2023.
International Search Report and Written Opinion for PCT Application No. PCT/US2024/047842, dated Dec. 23, 2024.

* cited by examiner 15017
15012
15018
15015
D
D'
15013
15010
15011
E
E'
F
F'
15016
15012
15015
15018
15017

15015
15011
15012
15017

15015
15011
15012
15017

MEDICAL DEVICES WITH DISTAL CONTROL

CROSS-REFERENCE TO RELATED APPLICATIONS

This application claims priority to U.S. Provisional Application No. 63/050,078, filed Jul. 9, 2020. Further, this application is a continuation-in-part of Ser. No. 16/192,755 filed Nov. 15, 2018, which is a continuation of U.S. patent application Ser. No. 15/924,027 filed Mar. 16, 2018 and issued as U.S. Pat. No. 10,786,230 on Sep. 29, 2020, which is a continuation of U.S. patent application Ser. No. 15/660,811 filed Jul. 26, 2017 and issued as U.S. Pat. No. 9,918,705 on Mar. 20, 2018, which is a continuation of PCT Application PCT/US2017/041224 filed Jul. 7, 2017, which claims priority to U.S. patent application Ser. No. 15/204,800 filed Jul. 7, 2016, to U.S. Provisional Patent Application No. 62/359,588 filed Jul. 7, 2016, and to U.S. Provisional Patent Application No. 62/467,229 filed Mar. 5, 2017. U.S. patent application Ser. No. 15/660,811 claims priority to U.S. Provisional Patent Application No. 62/467,229 filed Mar. 5, 2017. U.S. patent application Ser. No. 15/660,811 is a continuation-in-part of U.S. patent application Ser. No. 15/204,800 filed Jul. 7, 2016. The contents of each of the foregoing applications are incorporated herein by reference in their entireties.

BACKGROUND

Field

The disclosure is in the general field of surgical instruments and relates specifically to catheters, guidewires, endoscopes and endoscopic devices that are used in minimally invasive procedures, such as cardiovascular and endovascular procedures to facilitate the placement of devices within endoluminal structures within the body, such as, but not limited to, blood vessels, the gastrointestinal tract and the genitourinary tract.

Description

Catheters, guidewires, endoscopes and associated endoscopic instruments have been used to diagnose and treat conditions by accessing luminal structures of the body. Luminal structures of the body may include, but are not limited to, blood vessels, the heart, the gastrointestinal (GI) tract, genitourinary (GU) tract, peritoneal cavity, thoracic cavity, the mediastinum, bronchial passages, subarachnoidal spaces, and the intracranial ventricular system. Catheters, guidewires, and endoscopes may be used in laparoscopic surgeries and other procedures where invasiveness is to be minimized. These devices are manipulated by transmitting forces from the proximal end (i.e. the end of the device external to the body) to the distal end (i.e. the end of the device within the body) along and through the longitudinal structure of the device. Precise control of the distal portion of the device is required for medical procedures, so as to precisely cannulate the desired luminal structure, such as a blood vessel. In order to achieve this, in some embodiments, multiple design criteria considered during the design process of endoluminal devices, such as a guidewires and catheters. Major design criteria include push-ability, torque-ability, and flexibility.

Push-ability refers to the ability to move the device along the longitudinal axis of the device, resulting in translational motion. Push-ability is directly dependent on the stiffness of the device, which is largely dependent on the modulus of elasticity of the material employed within the device. Devices with a high modulus of elasticity are able to transmit force along the length of the device effectively, while devices with a low modulus of elasticity do not transmit force along the device as effectively, resulting in deformation or buckling of the device.

Torque-ability refers to the ability of rotational motion to be transmitted along the length of the device and is directly dependent on the modulus of rigidity (or shear modulus) of the material employed within the device. Devices having a high modulus of rigidity are able to transmit torque along the length of the device effectively, while devices having a low modulus of rigidity do not transmit force along the device as effectively.

Flexibility refers to the ability of a device to bend and flex along its lateral axis. Flexibility is necessary to enable the device to follow the bends and turns that are present in the human vasculature. Flexibility may be affected by the type of material and/or structural factors, such as the spacing and size of slits in the device that allow bending. However, flexibility is inversely dependent to the modulus of elasticity and modulus of rigidity and thus comes at the expense of push-ability and torque-ability. In addition, in some embodiments, it is desirable for the device to have a variable stiffness along its length, which can aid the device navigating along a pathway. Various embodiments related to a variable stiffness and/or other physical characteristics that may facilitating with navigation of the device are presented herein.

Ideally a device, such as a catheter, guidewire, endoscope or endoscopic instrument, will demonstrate one-to-one rotation of the distal end with respect to the proximal end. For example, if the proximal end of a device is rotated 90 degrees clockwise, the distal end of the device will also rotate 90 degrees clockwise. Unfortunately, in practice this does not typically occur, especially when the device has one or more bends or loops along its length secondary to the tortuous path of the bodily luminal structures. The inherent tortuosity of bodily structures (blood vessels, GI and GU tracts) means that portions of the device are subjected to frictional forces as the device is maneuvered within the body.

These frictional forces can impede the transmission of forces from the proximal end to the distal end of a device. One particularly problematic area is torque transmission along a device. As a result, potential energy is oftentimes stored along the length of the device as the proximal end is rotated. As this stored up potential energy within the device overcomes the frictional forces that are being exerted along the device, a sudden rotation of the device when the potential energy is released, also known as "device whip," can occur. This can make cannulating a desired vessel difficult and may cause injury to the patient. Thus, current devices, such as catheters, guidewires endoscopes and endoscopic instruments, strive for a balance between stiffness and flexibility in a variety of ways. A need exists for improved apparatuses, systems and methods for imparting precise, reliable rotational motion to the distal aspect of a medical device.

SUMMARY

According to some embodiments, the device comprises a tubular member with a longitudinal axis having a proximal end and a distal end, at least one partial cut located at, along or near the distal end of the tubular member, the at least one partial cut comprising an orientation that is angled relative to both the longitudinal axis and an axis transverse to the longitudinal axis, a force imparting element positioned colinear to the tubular member and configured to selectively advance the distal end of the tubular member longitudinally, wherein the distal end of the tubular member is configured to at least partially rotate when the force imparting element is advanced relative to the tubular member so at to facilitate placement of the distal end in a particular location of a subject's intraluminal network, a transition section intermediate to the at least one partial cut and the non-cut portion of the tubular member wherein the transition section has at least one partial slot cut to provide a stiffness that is greater than the stiffness of the at least one partial cut located at, along or near the distal end of the tubular member and is less than the stiffness of the non-cut portion of the tubular member, and at least one tip deflection member to facilitate steering of the device within an anatomy of a subject, wherein displacement of the tip deflection member results in deflection of the distal end of the device and wherein the tip deflection occurs independent of rotation of the device, wherein the distal end of the tubular member is configured to longitudinally elongate along or near an area of the at least one partial cut.

According to some embodiments, device comprises a tubular member with a longitudinal axis having a proximal end and a distal end, at least one partial cut located at, along or near the distal end of the tubular member, the at least one partial cut comprising an orientation that is angled relative to both the longitudinal axis and an axis transverse to the longitudinal axis, a force imparting element positioned colinear to the tubular member and configured to selectively advance the distal end of the tubular member longitudinally, wherein the distal end of the tubular member is configured to at least partially rotate when the force imparting element is advanced relative to the tubular member so at to facilitate placement of the distal end in a particular location of a subject's intraluminal network, and a transition section intermediate to the at least one partial cut and the non-cut portion of the tubular member wherein the transition section has at least one partial slot cut to provide a stiffness that is greater than the stiffness of the at least one partial cut located at, along or near the distal end of the tubular member and is less than the stiffness of the non-cut portion of the tubular member, wherein the distal end of the tubular member is configured to longitudinally elongate along or near an area of the at least one partial cut.

According to some embodiments, the at least one partial cut extends throughout an entire thickness of a wall of the tubular member. In some embodiments, the at least one partial cut does not extend throughout an entire thickness of a wall of the tubular member.

According to some embodiments, the at least one partial cut comprises a spiral or helical shape. In some embodiments, an angle of the at least one partial cut relative to the longitudinal axis is between 10 and 80 degrees.

According to some embodiments, the force imparting element is secured to the tubular member along the distal end of the tubular member. In some embodiments, the force imparting element is secured to the tubular member using at least one of an adhesive and a mechanical connection. In some arrangements, the force imparting element is not secured to the tubular member.

According to some embodiments, the tubular member comprises a lumen through which the force imparting element is selectively moved. In some arrangements, the device further comprises at least one outer member or coating positioned along an exterior of the tubular member. In some embodiments, the device further comprises at least one tip deflection member to facilitate steering of the device within an anatomy of a subject, wherein displacement of the tip deflection member results in deflection of the distal end of the device and wherein the tip deflection occurs independent of rotation of the device.

According to some embodiments, the device further includes a handle assembly, wherein a first portion of the handle assembly is secured to the tubular member and a second portion of the handle assembly is secured to the force imparting element, wherein movement of the first portion relative to the second portion of the handle assembly facilitate movement of the tubular member relative to the force imparting element.

According to some embodiments, the at least one partial cut comprises a single helix oriented in a single pitch direction. In some configurations, the at least one partial cut comprises a dual chirality helix.

According to some embodiments, the device further comprises at least one pull wire to facilitate steering of the device within an anatomy of a subject, wherein movement of the pull wire helps with bending of the device and movement of the force imparting element helps with rotation of the device.

According to some embodiments, the device comprises a guidewire. In some embodiments, the device comprises a catheter (e.g., a micro-catheter) and/or any other intraluminal device.

According to some embodiments, a device comprises a tubular member with a longitudinal axis having a proximal end and a distal end, at least one partial cut located at, along or near the distal end of the tubular member, the at least one partial cut comprising an orientation that is angled relative to both the longitudinal axis and an axis transverse to the longitudinal axis, and a force imparting element positioned colinear to the tubular member and configured to selectively advance the distal end of the tubular member longitudinally, and a transition section intermediate to the at least one partial cut and the non-cut portion of the tubular member wherein the transition section has at least one partial slot cut to provide a stiffness that is greater than the stiffness of the at least one partial cut located at, along or near the distal end of the tubular member and is less than the stiffness of the non-cut portion of the tubular member, wherein movement of the force imparting element relative to the tubular member converts longitudinal displacement into rotational movement, causing the distal end of the tubular member to at least partially rotate when the force imparting element is advanced relative to the tubular member so at to facilitate placement of the distal end in a particular location of a subject's intraluminal network, and wherein the distal end of the tubular member is configured to longitudinally elongate along or near an area of the at least one partial cut.

According to some embodiments, a method of rotating a distal end of an intraluminal device includes providing an intraluminal device comprising a tubular member and a force imparting element configured to be selectively moved relative to the tubular member, wherein the tubular member comprises at least one cut along a distal end of the tubular member, wherein movement of the force imparting element relative to the tubular member, such that the force imparting element moves the distal end of the tubular member distally, causes the distal end of the tubular member to selectively rotate, and moving the force imparting element relative to the tubular member to selectively rotate the distal end of the device.

According to some embodiments, the at least one cut extends throughout an entire thickness of a wall of the tubular member. In some arrangements, the at least one cut does not extend throughout an entire thickness of a wall of the tubular member. In some embodiments, the at least one partial cut comprises a single helix oriented in a single pitch direction. In some configurations, the at least one partial cut comprises a dual chirality helix.

According to some embodiments, a device comprises a tubular member with a longitudinal axis having a proximal end and a distal end, at least one partial cut located at, along or near the distal end of the tubular member, the at least one partial cut comprising an orientation that is angled relative to both the longitudinal axis and an axis transverse to the longitudinal axis, and a force imparting element positioned collinear to the tubular member and configured to selectively impart a force onto cut portion of the tubular member, wherein said force results in longitudinal displacement of the cut portion of the tubular member, causing the distal end of the tubular member to at least partially rotate wherein the degree of rotation is relative to the amount of longitudinal displacement, so at to facilitate placement of the distal end in a particular location of a subject's intraluminal network.

According to some embodiments, tubular member can have two or more at least partial cuts wherein the at least partial cuts have the same helical angle but are out of phase with one another by a prescribed angle (e.g., as in a double helix configuration). For example, in one embodiment with two at least partial cuts, the at least two partial cuts can be out of phase by 180 degrees. The presence of two or more at least partial cuts provides increased flexibility of the cut portion of the tubular member. In addition, the presence of two or more at least partial cuts that have the same helical angle but are out of phase with one another by a prescribed angle results in less unfurling, unrolling, unwinding, etc. as compared to a single cut.

According to some embodiments, a device comprises a tubular member with a longitudinal axis having a proximal end and a distal end, at least one partial cut located at, along or near the distal end of the tubular member, the at least one partial cut comprising an orientation that is angled relative to both the longitudinal axis and an axis transverse to the longitudinal axis, and a force imparting element positioned within an interior of the tubular member and configured to selectively advance the distal end of the tubular member longitudinally, wherein movement of the force imparting element (e.g., pusher or inner member) relative to the tubular member converts longitudinal displacement into rotational movement, causing the distal end of the tubular member to at least partially rotate when the force imparting element is advanced relative to the tubular member so at to facilitate placement of the distal end in a particular location of a subject's intraluminal network, wherein the distal end of the tubular member is configured to longitudinally elongate along or near an area of the at least one partial cut. The tubular member has varying stiffness along its longitudinal axis. The varying stiffness of the tubular member can result from one or more of the following 1) one or more cuts or partial cuts in the tubular member, 2) differences in modulus of elasticity in the tubular member or the force imparting element, 3) differences in thickness of the tubular member or the force imparting element. In addition, one or more portions of the tubular member proximal to the said at least one partial cut has one or more apertures so as to reduce potential friction between the force imparting element and the tubular member.

According to some embodiments, a device comprises a tubular member with a longitudinal axis having a proximal end and a distal end, at least one partial cut located at, along or near the distal end of the tubular member, the at least one partial cut comprising an orientation that is angled relative to both the longitudinal axis and an axis transverse to the longitudinal axis, a force imparting element (e.g., pusher member) positioned within collinear with respect to the tubular member and configured to selectively advance the distal end of the tubular member longitudinally, wherein the distal end of the tubular member is configured to at least partially rotate when the force imparting element (e.g., pusher member) is advanced relative to the tubular member so at to facilitate placement of the distal end in a particular branch of a subject's intraluminal network, wherein the distal end of the tubular member is configured to longitudinally elongate along or near an area of the at least one partial cut.

According to some embodiments, a device comprises a tubular member with a longitudinal axis having a proximal end and a distal end, at least one partial cut located at, along or near the distal end of the tubular member, the at least one partial cut comprising an orientation that is angled relative to both the longitudinal axis and an axis transverse to the longitudinal axis, and a force imparting element or member (e.g., pusher member) positioned within an interior of the tubular member and configured to selectively advance the distal end of the tubular member longitudinally, wherein movement of the force imparting element (e.g., pusher member) relative to the tubular member converts longitudinal displacement into rotational movement, causing the distal end of the tubular member to at least partially rotate when the or other force imparting element is advanced relative to the tubular member so at to facilitate placement of the distal end in a particular branch of a subject's intraluminal network, wherein the distal end of the tubular member is configured to longitudinally elongate along or near an area of the at least one partial cut.

According to some embodiments, a method of selectively rotating a distal end of an intraluminal device comprises providing an intraluminal device comprising a tubular member and a force imparting element (e.g., pusher member) configured to be selectively moved relative to the tubular member, wherein the tubular member comprises at least one cut along a distal end of the tubular member, wherein movement of the force imparting element (e.g., pusher member) relative to the tubular member, such that the force imparting element moves the distal end of the tubular member distally, causes the distal end of the tubular member to selectively rotate. The method further comprises moving the force imparting element relative to the tubular member to selectively rotate the distal end of the device.

According to some embodiments, the at least one partial cut extends throughout an entire thickness of a wall of the tubular member. In some embodiments, the at least one partial cut does not extend throughout an entire thickness of a wall of the tubular member. In some embodiments, the at least one partial cut comprises a spiral or helical shape. In some embodiments, an angle of the at least one partial cut relative to the longitudinal axis is between 10 and 80 degrees (e.g., 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the device.

According to some embodiments, the force imparting element (e.g., pusher member) is secured to the tubular member along the distal end of the tubular member. In certain arrangements, the force imparting element is secure to the tubular member using at least one of an adhesive and a mechanical connection. In other embodiments, the force imparting element is not secured to the tubular member (e.g., is configured to freely move and be removed relative to the tubular member). In one embodiment, the pusher or other force imparting element is configured to abut against at least one surface along an interior of the tubular member to advance the tubular member distally when the force imparting element is moved sufficiently in a distal direction.

According to some embodiments, the tubular member comprises a lumen through which the force imparting element (e.g., pusher member) is selectively moved. In some embodiments, the pusher member or other force imparting element comprises a lumen.

According to some embodiments, the device further comprises at least one outer member or coating positioned along an exterior of the tubular member. In some embodiments, the device further comprises at least one pull member to facilitate steering of the device within an anatomy of a subject. In one embodiment, the pull member comprises a pull wire. In one embodiment, the pull member comprises a shape memory material.

According to some embodiments, the force imparting element (e.g., pusher member) comprises a coiled member configured to maintain its structural integrity during use. In some embodiments, the device additionally includes a handle assembly, wherein a first portion of the handle assembly is secured to the tubular member and a second portion of the handle assembly is secured to the force imparting element (e.g., pusher member), wherein movement of the first portion relative to the second portion of the handle assembly facilitate movement of the tubular member relative to the pusher member or other force imparting element.

According to some embodiments, the at least one partial cut comprises a single helix oriented in a single pitch direction. In other embodiments, the at least one partial cut comprises a dual chirality helix.

According to some embodiments, an intraluminal device comprises an outer member having at least one cut or feature that facilitates conversion of linear movement of an inner member relative to the outer member into rotation of a distal portion of the device. Such rotational movement can facilitate in maneuvering the distal end of the device through a vasculature or other intraluminal structure of a subject (e.g., to reach or approach a desired anatomical location), as desired or required. In some embodiments, as discussed in greater detail herein, the intraluminal device is configured to be directed to an intraluminal location (e.g., intravascular, other intraluminal, anatomical location (e.g., through the subject's airways, gastroenterological system, etc.), etc.).

As discussed in greater detail herein, the various embodiments disclosed herein can provide advantageous devices, systems and/or methods to manipulate the distal end of a medical device (e.g., catheter, microcatheter, sheath, other intraluminal device, etc.). In some embodiments, the device includes a tube or outer member comprising one or more cuts (e.g., partial or complete cuts through the wall of the tube or outer member). In some embodiments, the cuts or similar features extend throughout the entire thickness of the tube or outer member. However, in other embodiments, the cuts extend only partially through the tube or outer member, as desired or required.

In some embodiments, the distal portion of the tube or outer member comprises one or more cuts or other features. In some embodiments, such cuts are helical or spiral in shape. In some embodiments, such helical cuts have a constant or consistent orientation. However, in other arrangements, the cuts have two or more orientations (e.g., angles, pitches, etc.) relative to the longitudinal axis, opening sizes, spacing and/or other properties, as desired or required. For example, in some arrangements, the cut(s) comprises/comprise a dual helix or dual chirality helix design. However, in other embodiments, the cut comprises/comprise a single helix design (e.g., a cut having the same pitch, general direction of orientation, other properties and/or the like).

According to some embodiments, a device comprises a tube or outer member, a force imparting element (e.g., pusher, inner member, etc.) and one or more cuts or other features along the distal end of the tube. In some embodiments, linear movement of the force imparting element or member relative to the tube or outer member causes rotational movement (e.g., rotation, twisting, turning, etc.) of a distal portion of the tube. Such movement can help maneuver and/or otherwise manipulate the device through the vasculature or other intraluminal system of a subject. In some embodiments, the tube or other member is secured to the force imparting element or member along one or more locations (e.g., the distal end of the device), using one or more securement (e.g., direct or indirect) methods, features, devices, technologies, etc.

In some embodiments, the cuts (e.g., partial or complete) through the tube or outer member comprise a helical or spiral shape. For example, in some embodiments, the cuts are angled relative to the longitudinal axis of the device (or a perpendicular axis of the longitudinal axis). For example, the helical angles can range from 10 to 80 degrees (e.g., 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the device. In some embodiments, the helical angle ranges from 15 to 75 degrees.

In some embodiments, the cuts are present only along or near the distal end of the tube or distal member. For example, the cut(s) is/are located along the distal 0 to 20 percent (e.g., 0-1, 1-2, 2-3, 3-4, 4-5, 5-6, 6-7, 7-8, 8-9, 9-10, 10-15, 15-20% of the tube and/or the device, percentages between the foregoing ranges and values, etc.).

According to some embodiments, the inner member, and thus the entire intraluminal device, is cannulated or otherwise comprises a lumen. In some embodiments, such a device can allow for the passage of one or more other devices, instruments and/or other members through its interior, as desired or required. In some embodiments, the devices disclosed herein comprise one or more external members, layers, coatings and/or other members.

The present disclosure is directed to a method and apparatus with rotation of the distal end of a medical device, such as a catheter, guidewire, chronic total occlusion crossing device, endoscope or endoscopic instrument, specifically, a medical device with a dual chirality helix converting linear movement into rotational movement at the distal end.

One embodiment according to the present disclosure includes a medical device comprising: a tubular member with a longitudinal axis having a distal end and a proximal end comprising: a distal aspect terminating at the distal end with a distal helix formed by distal helical cut terminating at the proximal side of the distal aspect; a proximal aspect terminating at the proximal end with a proximal helix formed by proximal helical cut terminating at the distal side of the proximal aspect, wherein the proximal helical cut is one of right or left handed and the distal helical cut is the other of right and left handed; and a junction where the distal aspect and the proximal aspect are joined; a longitudinal displacer disposed within the tubular member and slidable relative to the tubular member; and a distal segment disposed around part of the tubular member and coupled to the tubular member at the junction. The distal helical cut has a distal helical cut width and the proximal helical cut has a proximal helical cut width and the distal helical cut width may be equal to or different from the proximal helical cut width and each of the helical cuts may range between about 0.1 micrometers to about 30 millimeters. The helical cuts each have helical cut angles which may be same or different in magnitude and may range from about 10 to about 80 degrees. The tubular member may be made of one or more of: polyimide, polyurethane, polyether block amide, nylon, nickel titanium, stainless steel braiding, and hollow helical stranded tubing or other suitable material that would be understood by a person of ordinary skill in the art. The coupling means may include: 1) adhesive, 2) welding, 3) brazing, 4) soldering, 5) mechanical linking, or other suitable means understood by a person of ordinary skill in the art. The longitudinal displacer may include a longitudinal member with an outer diameter. The tubular member has inner diameter such that the inner diameter of the tubular member is greater than the outer diameter of the longitudinal member except for a portion between the distal end of the distal aspect and the junction where the inner diameter of the tubular member is reduced to less than the outer diameter of the longitudinal member such that longitudinal movement of the longitudinal member toward the distal end of the tubular member imparts longitudinal force on the distal aspect. The medical device may include a cap disposed on the distal end of the tubular member obstructing forward movement of the longitudinal displacer. The longitudinal displacer comprises a membrane configured to elongate when fluid is injected and longitudinally displace the distal end of the dual chirality helix. The medical device may include a first magnetic element disposed on the distal aspect of the tubular member; a second magnetic element disposed on the proximal aspect of the tubular member; and a power source configured to energize at least one of the first and second magnetic elements. The distal and proximal helices are comprised of at least one of: a shape memory alloy and a shape memory polymer. The first magnetic element may be one of: a magnet, an electret, a wire, and a coil configured to carry current and generate a magnetic field, and the second magnetic element may be one of: a magnet, a ferromagnetic material, an electret, a wire, and a coil configured to carry current and generate a magnetic field.

Another embodiment according to the present disclosure is a medical device including: a tubular member with a longitudinal axis having a distal end and a proximal end including: a distal aspect terminating at the distal end with a helix formed by a helical cut terminating at the proximal side of the distal aspect; and a proximal aspect terminating at the proximal end; and a longitudinal displacer disposed within the tubular member and slidable relative to the tubular member and configured to impart longitudinal force on the distal helix. The distal cut width may be in a range of about 0.1 micrometers to about 30 millimeters, and the distal helical cut angle may be between about 10 and about 80 degrees. The tubular member may be made of one or more of: polyimide, polyurethane, polyether block amide, nylon, nickel titanium, stainless steel braiding, and hollow helical stranded tubing and wherein the coupling means comprises at least one of: 1) adhesive, 2) welding, 3) brazing, 4) soldering, and 5) mechanical linking. The longitudinal displacer may include a longitudinal member with an outer diameter, and the tubular member has inner diameter such that the inner diameter of the tubular member is greater than the outer diameter of the longitudinal member except for a portion between the distal end of the distal aspect and the junction where the inner diameter of the tubular member is reduced to less than the outer diameter of the longitudinal member such that longitudinal movement of the longitudinal member toward the distal end of the tubular member imparts longitudinal force on the distal aspect. The medical device may also include a cap disposed on the distal end of the tubular member obstructing forward movement of the longitudinal displacer. The longitudinal displacer may include a membrane configured to elongate when fluid is injected and longitudinally displace the distal end of the helical cut tubing. The distal helix may include at least one of: a shape memory alloy and a shape memory polymer; and further comprising: a first magnetic element disposed on one of the distal aspect and the proximal aspect of the tubular member; a second magnetic element disposed on the other of the distal aspect and the proximal of the tubular member; and a power source configured to energize at least one of the first and second magnetic elements; wherein the first magnetic element is one of: a magnet, an electret, a wire, and a coil configured to carrying current and generate a magnetic field; and wherein the second magnetic element is one of: a magnet, a ferromagnetic material, an electret, a wire, and a coil configured to carrying current and generate a magnetic field.

Another embodiment according to the present disclosure is a method for controlling the distal end of the a medical device that includes a tubular member with a longitudinal axis having a distal end and a proximal end comprising: a distal aspect terminating at the distal end with a distal helix formed by distal helical cut terminating at the proximal side of the distal aspect; a proximal aspect terminating at the proximal end with a proximal helix formed by proximal helical cut terminating at the distal side of the proximal aspect, wherein the proximal helical cut is one of right or left handed and the distal helical cut is the other of right and left handed; and a junction where the distal aspect and the proximal aspect are joined; a longitudinal displacer disposed within the tubular member and slidable relative to the tubular member; and a distal segment disposed around part of the tubular member and coupled to the tubular member at the junction. The method includes inserting the medical device into an endoluminal structure of a body; displaying an image of the medical device within the body; selecting a region of interest within the image; applying longitudinal force to displace the dual chirality helix causing rotation of the distal end; observing the change in position of the distal end on the display; and adjusting the amount of longitudinal displacement is adjusted to rotate the distal end the desired degree of rotation. The display may be in form of any imaging techniques for objects internal to the human body, including, but not limited to, x-ray fluoroscopy, ultrasound imaging, computed axial tomography (CAT) imaging, magnetic resonance imaging (MRI), and/or endoscopic imaging.

Another embodiment according to the present disclosure is a device including a tube with a distal end and a proximal end wherein a dual chirality helix is cut into the distal aspect of the tube, a wire, a slidable sleeve located coaxially over the wire, a distal segment that is coupled to the junction of the two helices of the dual chirality helix and a handle with controlled linear displacement. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal aspect of the tube in which the dual chirality helix is inscribed. The distal segment is coupled to the junction of the helices of the dual chirality helix. The tip of the distal segment can have an angulated tip so as to aid in improved navigation of the device. The tube has a shelf of a reduced luminal inner diameter distal to the dual chirality helix. The outer diameter of the sleeve is greater than the inner diameter of the shelf of the tube, but is less than the inner diameter of the tube proximal to said shelf. The sleeve slidably abuts and engages said shelf of the tube. Advancing the sleeve results in linear displacement of the dual chirality helix. The handle with controlled linear displacement enables controlled movement of the sleeve with respect to the long axis of the tube. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end wherein a dual chirality helix is cut into the distal aspect of the tube, a wire with a tapered distal end, a distal segment that is coupled to the junction of the two helices of the dual chirality helix and a handle with controlled linear displacement. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal aspect of the tube in which the dual chirality helix is inscribed. The distal segment is coupled to the junction of the helices of the dual chirality helix. The tip of the distal segment can have an angulated tip so as to aid in improved navigation of the device. The tube has a shelf of a reduced luminal inner diameter distal to the dual chirality helix. The diameter of the tapered portion of the wire is less than the inner diameter of the shelf. The outer diameter of the non-tapered portion of the wire is greater than the inner diameter of the shelf of the tube, but is less than the inner diameter of the tube proximal to said shelf. The non-tapered portion of the wire abuts and engages said shelf of the tube. Advancing the wire results in linear displacement of the dual chirality helix. The handle with controlled linear displacement enables controlled movement of the wire with respect to the long axis of the tube. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end wherein a dual chirality helix is cut into the distal aspect of the tube, a wire with a reversibly expandable member, a distal segment that is coupled to the junction of the two helices of the dual chirality helix and a handle with controlled linear displacement. The wire slidably engages the lumen of the tube. A reversibly expandable member is located along the distal aspect of the wire. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal end of the tube and is coupled to the junction of the left and right handed helices of the dual chirality helix. The tip of the distal segment can have an angulated tip so as better select branch vessels. With the expandable member collapsed, the outer diameter of the wire is less than the inner diameter of the hypotube and thus the wire is able to free move within the lumen of the tube. However, the outer diameter of the expandable member in its expanded state is greater than the inner diameter of the tube. When the reversibly expandable member is expanded, it engages the distal end of the tube. Subsequent advancement of the wire then results in linear displacement of the dual chirality helix. The handle with controlled linear displacement enables controlled movement of the wire with respect to the long axis of the tube. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end wherein a dual chirality helix is cut into the distal aspect of the tube and wherein the distal end is capped, a wire, a distal segment that is coupled to the junction of the two helices of the dual chirality helix and a handle with controlled linear displacement. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal aspect of the tube in which the dual chirality helix is inscribed. The distal segment is coupled to the junction of the helices of the dual chirality helix. The tip of the distal segment can have an angulated tip so as to aid in improved navigation of the device. The outer diameter of the wire is less than the inner diameter of the tube. The distal end of the wire abuts and engages the capped distal end of the tube. Advancing the wire results in linear displacement of the dual chirality helix. The handle with controlled linear displacement enables controlled movement of the wire with respect to the long axis of the tube. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end wherein a dual chirality helix is cut into the distal aspect of the tube and wherein the distal end is capped, a liner that encompasses the dual chirality helix, a distal segment that is coupled to the junction of the two helices of the dual chirality helix and a handle with controlled linear displacement. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal aspect of the tube in which the dual chirality helix is inscribed. The distal segment is coupled to the junction of the helices of the dual chirality helix. The tip of the distal segment can have an angulated tip so as to aid in improved navigation of the device. Injecting fluid into the lumen of the tube results in varying degrees of linear displacement of the dual chirality helix. This in turn results in rotation of the junction point of the left and right handed helices and subsequent rotation of the distal segment. The degree of rotation is proportional to the linear displacement of the dual chirality helix of the tube.

A handle can be applied to the proximal end of the sleeve or wire and the proximal end of the tube in order to provide more precise movement of the sleeve or wire with respect to elongated tube. This handle can be comprised of two coaxial tubes that capable of displacement with respect to one another along the long axis of the tubes. Means for translational motion with respect to one another include but are not limited to 1) manual displacement of the two coaxial tubes along the long axis of the tubes; 2) threaded portions of each tubes that are coaxially receivable such that rotation of the tubes along the threaded portions results in linear displacement of the tubes with respect to one another (similar mechanism to the linear movement of screwing a bolt into a nut.) The handle is able to coaxially receive the inner wire and elongated tube within the lumen of the gripper device. Fastening mechanisms can be located along each end of the handle so as to grip the sleeve or wire at one end and the tube at the other end. These fastening mechanisms can be permanently or reversibly fixed in place. These fastening mechanisms can also swivel about the sleeve or wire or elongated tube such the sleeve, wire or elongated tube do not undergo rotational motion while one or more of the coaxial tubes are being rotated.

Another embodiment according to the present disclosure is a device including a tube with a distal end and a proximal end wherein a dual chirality helix is cut into the distal aspect of the tube and wherein said elongated tube is comprised of material capable of undergoing a shape transformation in response to a change in the surrounding environment, a distal segment that is coupled to the junction of the two helices of the dual chirality helix, a means for causing the tube to undergo shape transformation and a means for counteracting the shape transformation of the tube. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal end of the tube and is coupled to the junction of the left and right handed helices of the dual chirality helix. The tip of the distal segment can have an angulated tip so as better select branch vessels. Alterations in environment including but not limited to temperature, electric field, pH, light, ion concentration result in shape transformation of the tube such that there is linear displacement of the dual chirality helix. This in turn results in rotation of the junction point of the left and right handed helices and subsequent rotation of the distal segment. The degree of rotation is proportional to the linear displacement of the dual chirality helix of the tube. A means for counteracting the shape transformation of the tube, including but not limited to coupling the conduit to the distal end of the tube. Varying amounts of tension can be applied to the conduit in order to counteract the linear displacement of the dual chirality helix.

Another embodiment according to the present disclosure is a device including a tube with a distal end and a proximal end wherein a dual chirality helix is cut into the distal aspect of the tube, a distal segment that is coupled to the junction of the two helices of the dual chirality helix, a means for linear displacement of the tube containing dual chirality cut wherein said means includes but is not limited to repulsion of electrical fields or repulsion of magnetic fields. By its nature, the junction of the left and right handed helices rotates when the ends of the dual chirality helix are linearly extended or retracted, resulting in the conversion of linear movement to rotational motion of the junction point of the two helices. The distal segment is located circumferentially around the distal end of the tube and is coupled to the junction of the left and right handed helices of the dual chirality helix. The tip of the distal segment can have an angulated tip so as better select branch vessels. Examples of means for applying opposing electrical or magnetic fields along or proximate to the region of the dual chirality helix include but are not limited to 1) applying a permanent electrical or magnetic charge on one end of the dual chirality helix and a variable, inducible charge on the opposite end of the dual chirality helix; 2) applying an inducible electrical or magnetic charge on one end of the dual chirality helix and a variable, inducible electrical or magnetic charge on the opposite end of the dual chirality helix; 3) applying an electrical or magnetic charge on one end of the dual chirality helix cut and an electrical or magnetic charge on a portion of guidewire proximate to the dual chirality helix. The opposing electrical or magnetic forces results in linear displacement of the dual chirality helix. This in turn results in rotation of the junction point of the left and right handed helices and subsequent rotation of the distal segment. The degree of rotation is proportional to the linear displacement of the dual chirality helix of the tube.

Another embodiment according to the present disclosure is a device including a tube with a distal end and a proximal end, a wire with two or more outer diameters, and a means for advancing the wire. A dual chirality helix is cut into the tube just proximal to the reduced luminal inner diameter of the tube. By its nature, the junction of the left and right handed helices rotates when the ends of the dual chirality helix are linearly extended or retracted, resulting in the conversion of linear movement to rotational motion of the junction point of the two helices. A means for engaging the wire, including but not limited to a tooth, is present on the junction point of the left and right handed helices. One or more grooves are located along the longitudinal axis of the wire along the tapered portion of the wire and the grooves extend slightly proximal to the transition the diameter of the wire. The tooth slidably engages one or more grooves along the distal aspect of the inner wire. The diameter of the distal aspect of the wire is less than the proximal diameter. The luminal inner diameter of the distal end of the tube is greater than the diameter of the distal aspect of the wire and less than the diameter of the proximal aspect of the wire. Advancing the wire into the tube results in linear displacement of the dual chirality helix. This in turn results in rotation of the junction point of the left and right handed helices and subsequent rotation of the distal aspect of the wire. The degree of rotation is proportional to the linear displacement of the dual chirality helix of the tube.

Another embodiment according to the present disclosure includes a medical device comprising: an outer sheath, a tube with a distal end and a proximal end wherein one or more helical or spiral cut(s) are imparted into the distal aspect of tube, and a slidable sleeve that is located within the lumen of the tube. By its nature, the portion of the tube that is distal to the helical or spiral cut(s) rotates when the helical or spiral cut(s) are linearly extended or retracted, resulting in the conversion of linear movement to rotational motion. The distal end of the helical/spiral cut tube can have an angulated tip so as to aid in improved navigation of the device. The tube can have a shelf of a reduced luminal inner diameter distal to the helical or spiral cut. The outer diameter of the sleeve is greater than the inner diameter of the shelf of the tube, but is less than the inner diameter of the tube proximal to said shelf. The sleeve slidably abuts and engages said shelf of the tube. Advancing the sleeve results in linear displacement of the cut portion of the tube. Alternatively, the sleeve can be coupled to the tube distal to the helical or spiral cut(s) by means including but not limited to: adhesives, soldering, welding, brazing and/or mechanical linkage. A handle with controlled linear displacement enables controlled movement of the sleeve with respect to the long axis of the tube. This in turn results in rotation of the distal end of the tube. The degree of rotation is proportional to the linear displacement of the helical or spiral cut portion of the tube. The tube is located within the lumen of the outer sheath such that the helical or spiral cut portion of the tube is disposed within the lumen of the outer sheath while the distal end of the tube can extend beyond the outer sheath (e.g., the total length of the tube is greater than the total length of the outer sheath, while the length from the proximal end of the tube to the distal most aspect of the cut portion of the tube is less than the total length of the outer sheath). The tube and slidable sleeve can be removed from the outer sheath such that the outer sheath may serve as a conduit for delivery of diagnostic and/or therapeutic agent(s) including but not limited to injection of contrast agent(s), medication(s), stents, embolic agents.

Another embodiment according to the present disclosure includes a medical device comprising: a tube with a distal end and a proximal end wherein one or more helical or spiral cut(s) are imparted into the distal aspect of tube, an outer layer around the tube, a slidable sleeve that is located within the lumen of the tube. By its nature, the portion of the tube that is distal to the helical or spiral cut(s) rotates when the helical or spiral cut(s) are linearly extended or retracted, resulting in the conversion of linear movement to rotational motion. The distal end of the helical/spiral cut tube can have an angulated tip so as to aid in improved navigation of the device. The tube can have a shelf of a reduced luminal inner diameter distal to the helical or spiral cut. The outer diameter of the sleeve is greater than the inner diameter of the shelf of the tube, but is less than the inner diameter of the tube proximal to said shelf. The sleeve slidably abuts and engages said shelf of the tube. Advancing the sleeve results in linear displacement of the cut portion of the tube. Alternatively, the sleeve can be coupled to the tube distal to the helical or spiral cut(s) by means including but not limited to: adhesives, soldering, welding, brazing and/or mechanical linkage. A handle with controlled linear displacement enables controlled movement of the sleeve with respect to the long axis of the tube. This in turn results in rotation of the distal end of the tube. The degree of rotation is proportional to the linear displacement of the helical or spiral cut portion of the tube. Around the outside of the tube is an outer layer that is coupled to the proximal and distal aspects of the tube. The outer layer is able to elongate as the tube undergoes linear displacement (elongation). The slidable sleeve can be removed from the tube may serve as a conduit for delivery of diagnostic and/or therapeutic agent(s) including but not limited to injection of contrast agent(s), medication(s), stents, embolic agents.

Another embodiment according to the present disclosure includes a medical device comprising: 1) a tube with a distal end and a proximal end wherein one or more helical or spiral cut(s) are imparted into the distal aspect of tube 2) a tubular member located coaxially around the helical or spiral cut tube and a 3) handle assembly. The distal end of the tubular member can be coupled to the tube distal to the helical or spiral cut(s) by means including but not limited to: adhesives, soldering, welding, brazing and/or mechanical linkage. The tubular member can be comprised of one or more elements including but not limited to: 1) coiled wire, 2) polymer, 3) hypotube. By its nature, the portion of the tube that is distal to the helical or spiral cut(s) rotates when the helical or spiral cut(s) are linearly extended or retracted, resulting in the conversion of linear motion to rotational motion. The distal aspect of the tubular member is able to undergo torsion strain when the distal end of the helical or spiral cut tube rotates. The distal end of the helical or spiral cut tube can have multiple configurations including but not limited to: 1) an angulated tip so as to aid in improved navigation of the device, 2) a beveled edge so as to aid in advancing the device past a severe stenosis or occlusion, 3) one or more flutes/grooves so as to aid in advancing the device past a severe stenosis or occlusion or advancing the device along a tortuous path, 4) one or more radio-opaque markers. The handle assembly is comprised of a proximal component and a distal component.

Another embodiment according to the present disclosure includes a medical device comprising: 1) a tube with a distal end and a proximal end wherein one or more helical or spiral cut(s) are imparted into the distal aspect of tube and 2) a tubular member located coaxially around the helical or spiral cut tube, wherein the outer diameter of the helical or spiral cut tube distal to the cut increase such that it is greater than the inner diameter of the tubular member. (Note the outer diameter of the helical or spiral cut tube from the proximal end to the helical or spiral cut is less than the inner diameter of the helical or spiral cut tube.) The tubular member can be comprised of one or more elements including but not limited to: 1) coiled wire, 2) polymer, 3) hypotube. Advancing the tubular member with respect to the helical or spiral cut tube results in elongation of the helical or spiral cut. By its nature, the portion of the tube that is distal to the helical or spiral cut(s) rotates when the helical or spiral cut(s) are linearly extended or retracted, resulting in the conversion of linear motion to rotational motion. The distal end of the tubular member and the distal end of the tube are able to rotate with respect to one another. The distal end of the helical or spiral cut tube can have multiple configurations including but not limited to: 1) an angulated tip so as to aid in improved navigation of the device, 2) a beveled edge so as to aid in advancing the device past a severe stenosis or occlusion, 3) one or more flutes/grooves so as to aid in advancing the device past a severe stenosis or occlusion or advancing the device along a tortuous path, 4) one or more radio-opaque markers.

Another embodiment according to the present disclosure includes a medical device comprising: 1) a tube with a distal end and a proximal end wherein one or more helical or spiral cut(s) are imparted into the distal aspect of tube, 2) a wire that is coupled to the proximal end of the helical or spiral cut tube and 3) a tubular member located coaxially around the helical or spiral cut tube. The distal end of the wire can be coupled to the proximal end of the helical or spiral cut tube by means including but not limited to: adhesives, soldering, welding, brazing and/or mechanical linkage. Also, the distal end of the tubular member can be coupled to the helical or spiral cut tube distal to the helical or spiral cut(s) by means including but not limited to: adhesives, soldering, welding, brazing and/or mechanical linkage. The tubular member can be comprised of one or more elements including but not limited to: 1) coiled wire, 2) polymer, 3) hypotube. By its nature, the portion of the tube that is distal to the helical or spiral cut(s) rotates when the helical or spiral cut(s) are linearly extended or retracted, resulting in the conversion of linear motion to rotational motion. The distal aspect of the tubular member is able to undergo torsion strain when the distal end of the helical or spiral cut tube rotates. The distal end of the helical or spiral cut tube can have multiple configurations including but not limited to: 1) an angulated tip so as to aid in improved navigation of the device, 2) a beveled edge so as to aid in advancing the device past a severe stenosis or occlusion, 3) one or more flutes/grooves so as to aid in advancing the device past a severe stenosis or occlusion or advancing the device along a tortuous path, 4) one or more radio-opaque markers.

Another embodiment according to the present disclosure includes a medical device comprising: 1) a tube with a distal end and a proximal end wherein one or more helical or spiral cut(s) are imparted into the distal aspect of tube, 2) a distendable layer that is located circumferentially around the helical or spiral cut tube, wherein the proximal and distal ends of the are coupled to the helical or spiral cut tube just proximal and just distal to helical or spiral cut(s), 3) a tubular member located within the lumen of the helical or spiral cut tube and a handle assembly. The distendable layer can be coupled to the helical or spiral cut tube by means including but not limited to: adhesives, soldering, welding, brazing and/or mechanical linkage. Also, the distal end of the tubular member can be coupled to the helical or spiral cut tube distal to the helical or spiral cut(s) by means including but not limited to: adhesives, soldering, welding, brazing and/or mechanical linkage. The tubular member can be comprised of one or more elements including but not limited to: 1) coiled wire, 2) polymer with or without reinforcement (braiding or coil reinforcement for example), 3) hypotube. By its nature, the portion of the tube that is distal to the helical or spiral cut(s) rotates when the helical or spiral cut(s) are linearly extended or retracted, resulting in the conversion of linear motion to rotational motion. The distal aspect of the tubular member is able to undergo torsion strain when the distal end of the helical or spiral cut tube rotates. The distal end of the helical or spiral cut tube can have multiple configurations including but not limited to: 1) an angulated tip so as to aid in improved navigation of the device, 2) a beveled edge so as to aid in advancing the device past a severe stenosis or occlusion, 3) one or more flutes/grooves so as to aid in advancing the device past a severe stenosis or occlusion or advancing the device along a tortuous path, 4) one or more radio-opaque markers.

A handle assembly can be applied to the proximal end of the tube or wire and the proximal end of the outer tubular member in order to provide more precise movement of the tube or wire with respect to outer tubular member. This handle can comprise two coaxial components that capable of displacement with respect to one another along the long axis of the components. Means for translational motion with respect to one another include but are not limited to 1) manual displacement of the two coaxial tubes along the long axis of the tubes; 2) threaded portions of each tubes that are coaxially receivable such that rotation of the tubes along the threaded portions results in linear displacement of the tubes with respect to one another (similar mechanism to the linear movement of screwing a bolt into a nut.) The handle assembly is able to coaxially receive the proximal end of the tube or wire and the outer tubular member. Fastening mechanisms can be located along both the proximal handle component and the distal handle component so as to grip the proximal end of the tube or wire and the proximal end of the outer tubular member. These fastening mechanisms can be permanently or reversibly fixed in place. These fastening mechanisms can also swivel about the proximal end of the tube or wire and the proximal end of the outer tubular member such the tube or wire and outer tubular member do not undergo rotational motion while one or more of the coaxial components are being rotated.

Another embodiment according to the present disclosure is a medical device including: a tubular member with a longitudinal axis having a distal end and a proximal end including: a distal aspect terminating at the distal end with a helix formed by a partial thickness helical cut terminating at the proximal side of the distal aspect; and a proximal aspect terminating at the proximal end; and a longitudinal displacer disposed within the tubular member and slidable relative to the tubular member and configured to impart longitudinal force on the distal helix. The partial thickness cut portion is elastic and can undergo elongation. The distal cut width may be in a range of about 0.1 micrometers to about 30 millimeters, and the distal helical cut angle may be between about 10 and about 80 degrees. The tubular member may be made of one or more of: polyimide, polyurethane, polyether block amide, nylon, nickel titanium, stainless steel braiding, and hollow helical stranded tubing and wherein the coupling means comprises at least one of: 1) adhesive, 2) welding, 3) brazing, 4) soldering, and 5) mechanical linking. The longitudinal displacer may include a longitudinal member with an outer diameter, and the tubular member has inner diameter such that the inner diameter of the tubular member is greater than the outer diameter of the longitudinal member except for a portion between the distal end of the distal aspect and the junction where the inner diameter of the tubular member is reduced to less than the outer diameter of the longitudinal member such that longitudinal movement of the longitudinal member toward the distal end of the tubular member imparts longitudinal force on the distal aspect. The medical device may also include a cap disposed on the distal end of the tubular member obstructing forward movement of the longitudinal displacer. The longitudinal displacer may include a membrane configured to elongate when fluid is injected and longitudinally displace the distal end of the helical cut tubing. The distal helix may include at least one of: a shape memory alloy and a shape memory polymer; and further comprising: a first magnetic element disposed on one of the distal aspect and the proximal aspect of the tubular member; a second magnetic element disposed on the other of the distal aspect and the proximal of the tubular member; and a power source configured to energize at least one of the first and second magnetic elements; wherein the first magnetic element is one of: a magnet, an electret, a wire, and a coil configured to carrying current and generate a magnetic field; and wherein the second magnetic element is one of: a magnet, a ferromagnetic material, an electret, a wire, and a coil configured to carrying current and generate a magnetic field.

Another embodiment according to the present disclosure includes a medical device comprising: an outer sheath, a tube with a distal end and a proximal end wherein one or more helical or spiral cut(s) are imparted into the distal aspect of tube. By its nature, the portion of the tube that is distal to the helical or spiral cut(s) rotates when the helical or spiral cut(s) are linearly extended or retracted, resulting in the conversion of linear movement to rotational motion. The distal end of the helical/spiral cut tube can have a deflectable distal end so as to aid in improved navigation of the device. Means for deflecting the distal end of the tube include but are not limited to: pull wire(s), slotted tube, shape memory alloys and/or shape memory polymers. The tube is located within the lumen of the outer sheath such that the helical or spiral cut portion of the tube is disposed within the lumen of the outer sheath while the distal end of the tube can extend beyond the outer sheath (e.g., the total length of the tube is greater than the total length of the outer sheath, while the length from the proximal end of the tube to the distal most aspect of the cut portion of the tube is less than the total length of the outer sheath). When the distal end of the tube is deflected, the distal end of the outer sheath slidably abuts and engages the deflected distal end of the tube. Advancing the outer sheath relative to the tube results in linear displacement (e.g., elongation) of the cut portion of the tube. A handle with controlled linear displacement enables controlled movement of the outer sheath with respect to the long axis of the tube. This in turn results in rotation of the distal end of the tube. The degree of rotation is proportional to the linear displacement of the helical or spiral cut portion of the tube. When the tube is not deflected (e.g., the distal end the of the tube is straight), the tube can be removed from the outer sheath such that the outer sheath may serve as a conduit for delivery of diagnostic and/or therapeutic agent(s) including but not limited to injection of contrast agent(s), medication(s), stents, embolic agents.

Another embodiment according to the present disclosure includes a medical device comprising: an outer sheath, a tube with a distal end and a proximal end wherein one or more helical or spiral cut(s) are imparted into the distal aspect of tube, a slidable sleeve that is located within the lumen of the tube. By its nature, the portion of the tube that is distal to the helical or spiral cut(s) rotates when the helical or spiral cut(s) are linearly extended or retracted, resulting in the conversion of linear movement to rotational motion. The tube is located within the lumen of the outer sheath such that the helical or spiral cut portion of the tube is disposed within the lumen of the outer sheath while the distal end of the tube can extend beyond the outer sheath (e.g., the total length of the tube is greater than the total length of the outer sheath, while the length from the proximal end of the tube to the distal most aspect of the cut portion of the tube is less than the total length of the outer sheath). The tube distal to the spiral cut portion of the tube can have a curved portion so as to aid in improved navigation of the device, wherein said curved portion has a lower modulus of rigidity (e.g., is more flexible) than the modulus of elasticity of the distal aspect of the outer sheath. As either the outer sheath is advanced distally over the curved portion of the tube or as the curved portion of the tube is retracted back into the outer sheath, the curved portion of the tube straightens. The degree in which the curved portion of the tube straightens is related to the amount of the curved portion of the tube that is disposed in the lumen of the outer sheath. When the curved portion of the tube is completely disposed in the lumen of the outer sheath, the curved portion of the tube is fully straightened (e.g., tip deflection angle is approximately 0 degrees relative to the longitudinal axis of the device). This can enable the user to selectively deflect the tip of the device. The tube can have a shelf of a reduced luminal inner diameter distal to the helical or spiral cut. The outer diameter of the sleeve is greater than the inner diameter of the shelf of the tube, but is less than the inner diameter of the tube proximal to said shelf. The sleeve slidably abuts and engages said shelf of the tube. Advancing the sleeve results in linear displacement of the cut portion of the tube. Alternatively, the sleeve can be coupled to the tube distal to the helical or spiral cut(s) by means including but not limited to: adhesives, soldering, welding, brazing and/or mechanical linkage. A handle with controlled linear displacement enables controlled movement of the sleeve with respect to the long axis of the tube. This in turn results in rotation of the distal end of the tube. The degree of rotation is proportional to the linear displacement of the helical or spiral cut portion of the tube. The tube and slidable sleeve can be removed from the tube may serve as a conduit for delivery of diagnostic and/or therapeutic agent(s) including but not limited to injection of contrast agent(s), medication(s), stents, embolic agents.

BRIEF DESCRIPTION OF THE DRAWINGS

For a detailed understanding of the present disclosure, reference should be made to the following detailed description of the embodiments, taken in conjunction with the accompanying drawings, in which like elements have been given like numerals, wherein:

FIG. 210 is a transverse cross sectional view of the distal aspect of the medical device in FIG. 21A through C-C' with no force applied to the distal end of the dual chirality helix;

FIG. 310 is a longitudinal cross sectional view of the distal aspect of another embodiment of the device wherein the expandable member of the sleeve has been collapsed by a straightening element;

FIG. 410 illustrates a transverse cross sectional view of the device of FIG. 41A through lines C-C';

Figure 3A:
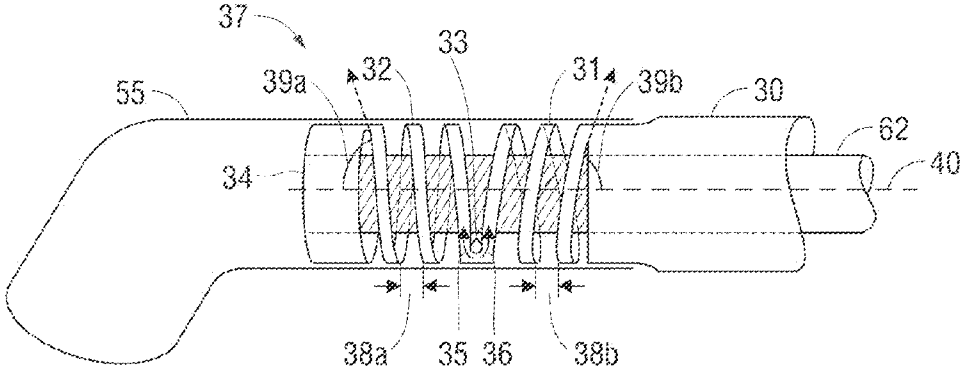
FIG. 3A is a diagram of the dual chirality helical cut into the tube with force vectors showing rotational forces during linear displacement of the distal end of the tube according to one embodiment of the present disclosure.
Figure 44A:
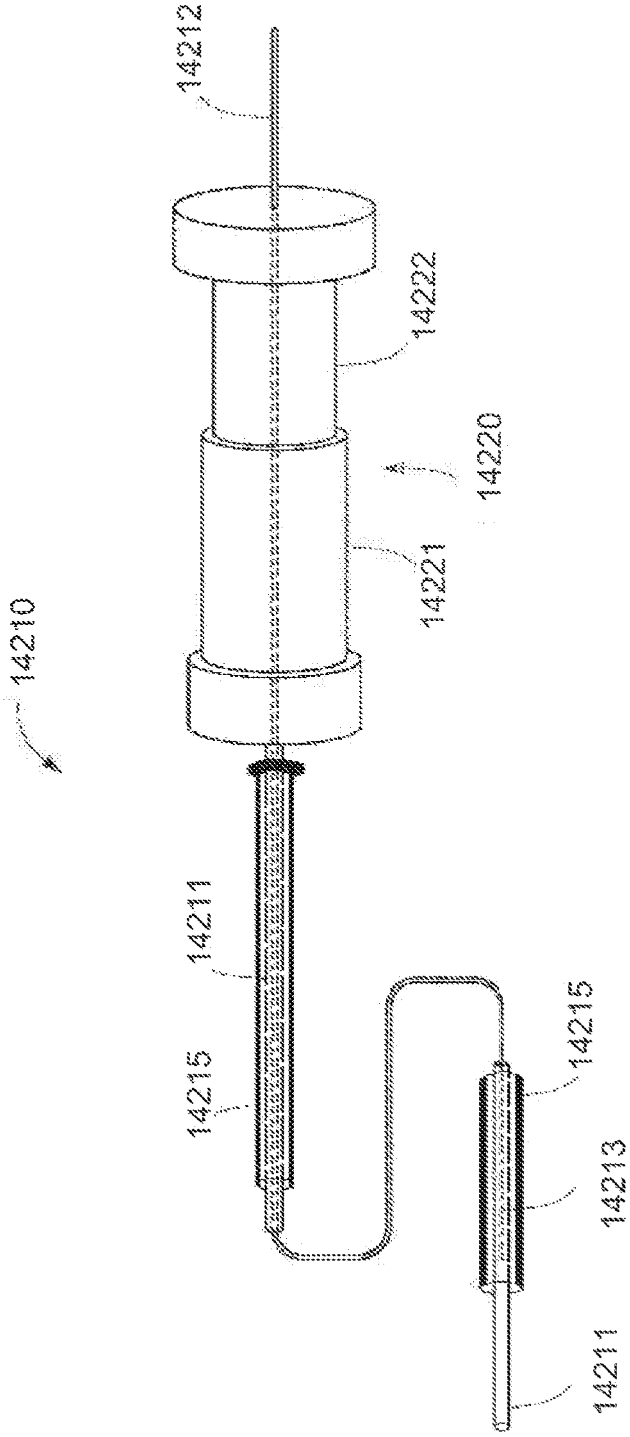
Figure 44B:
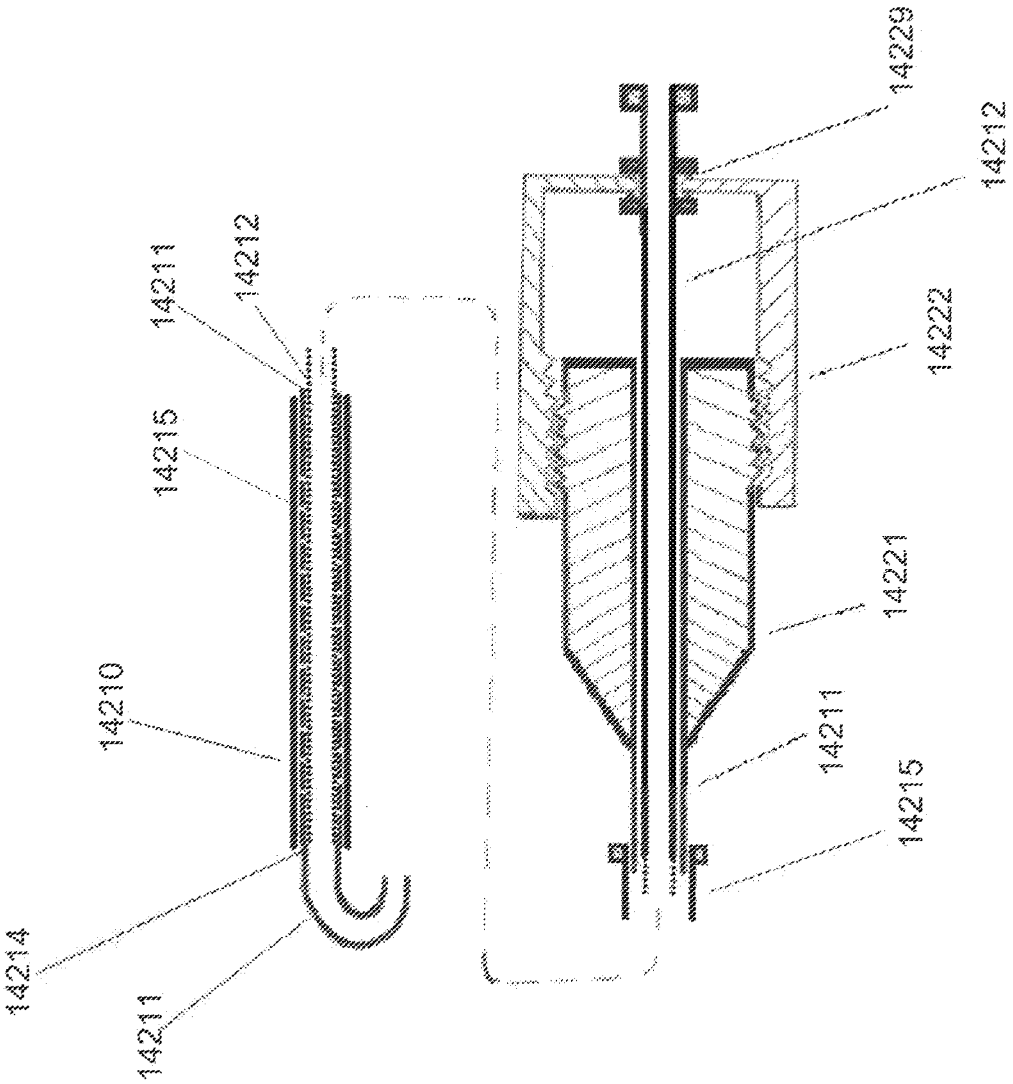
Figure 44C:
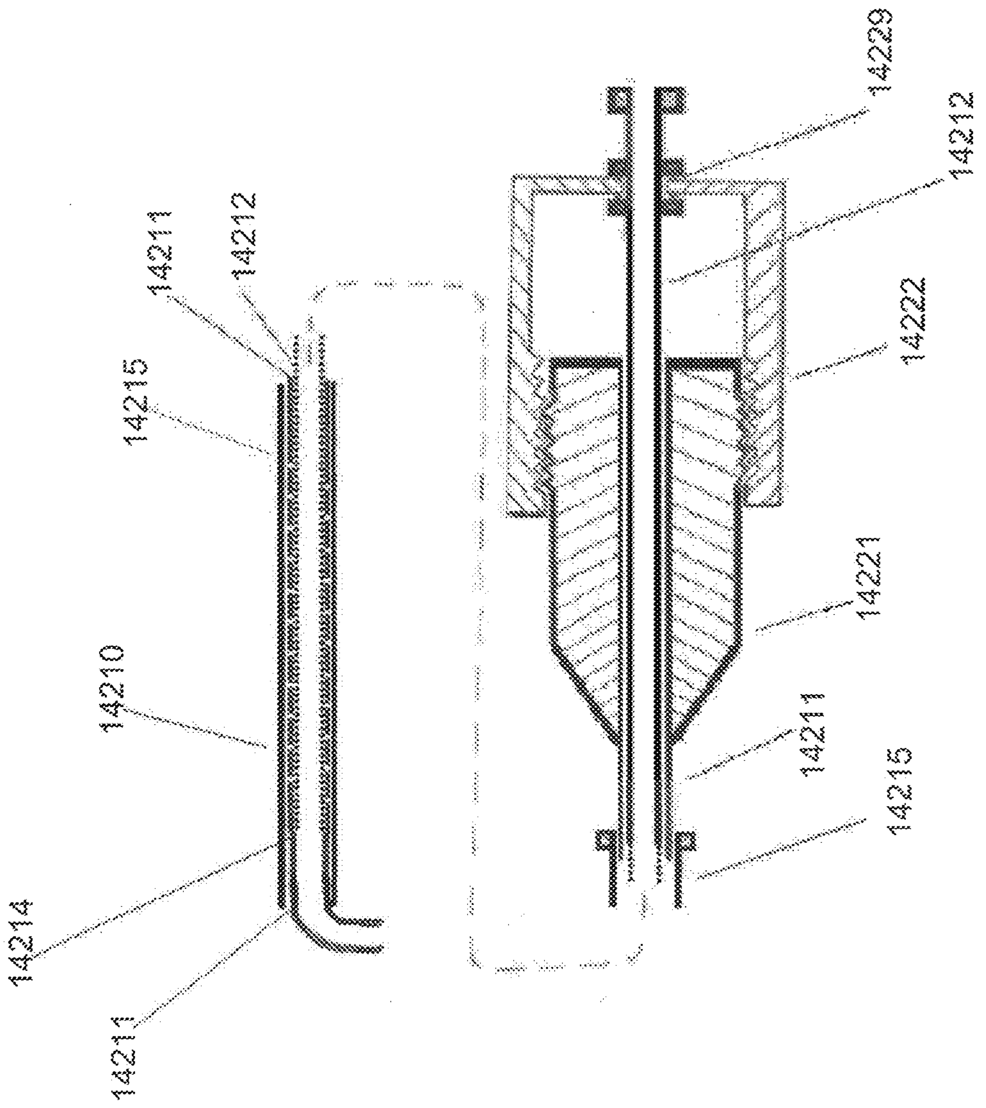
Figure 44D:
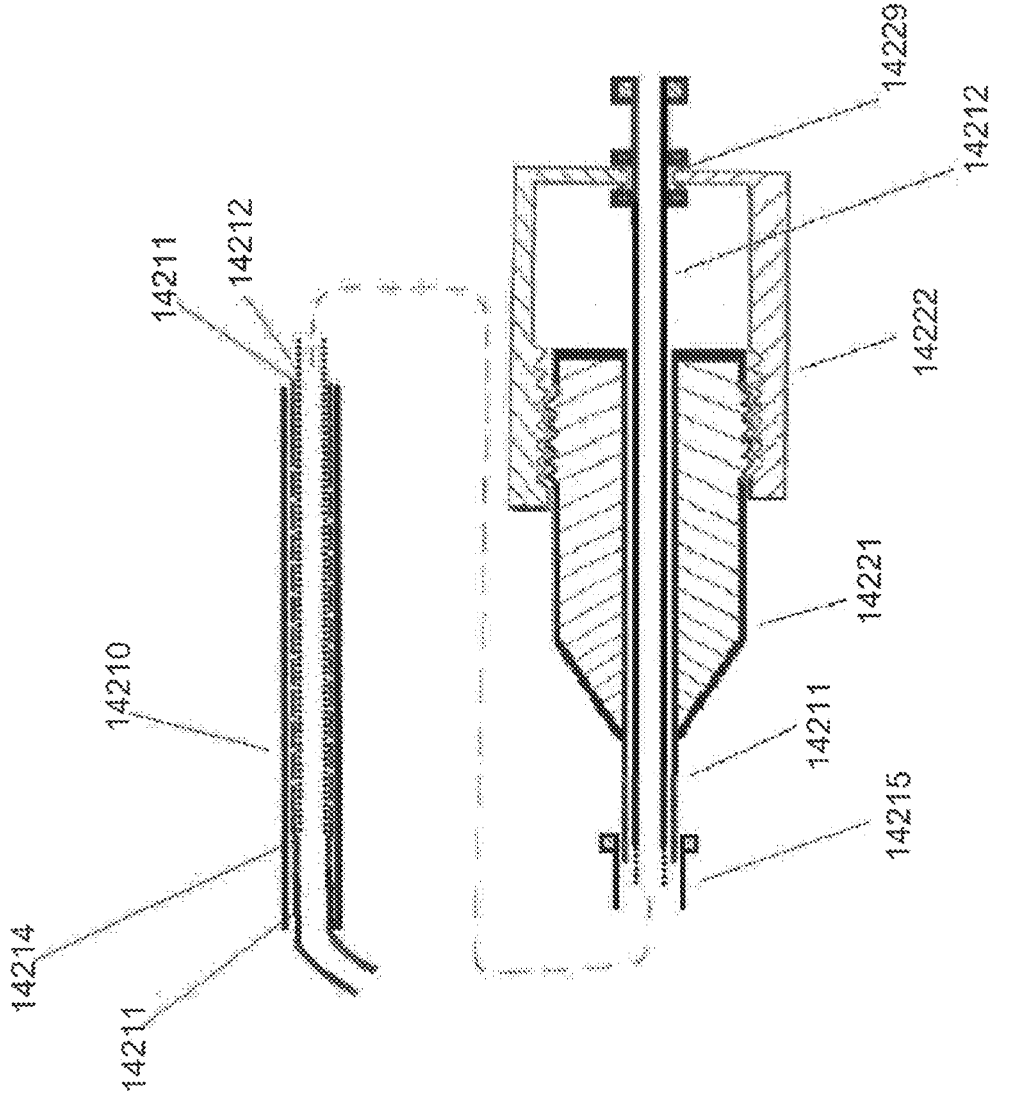
Figure 44E:
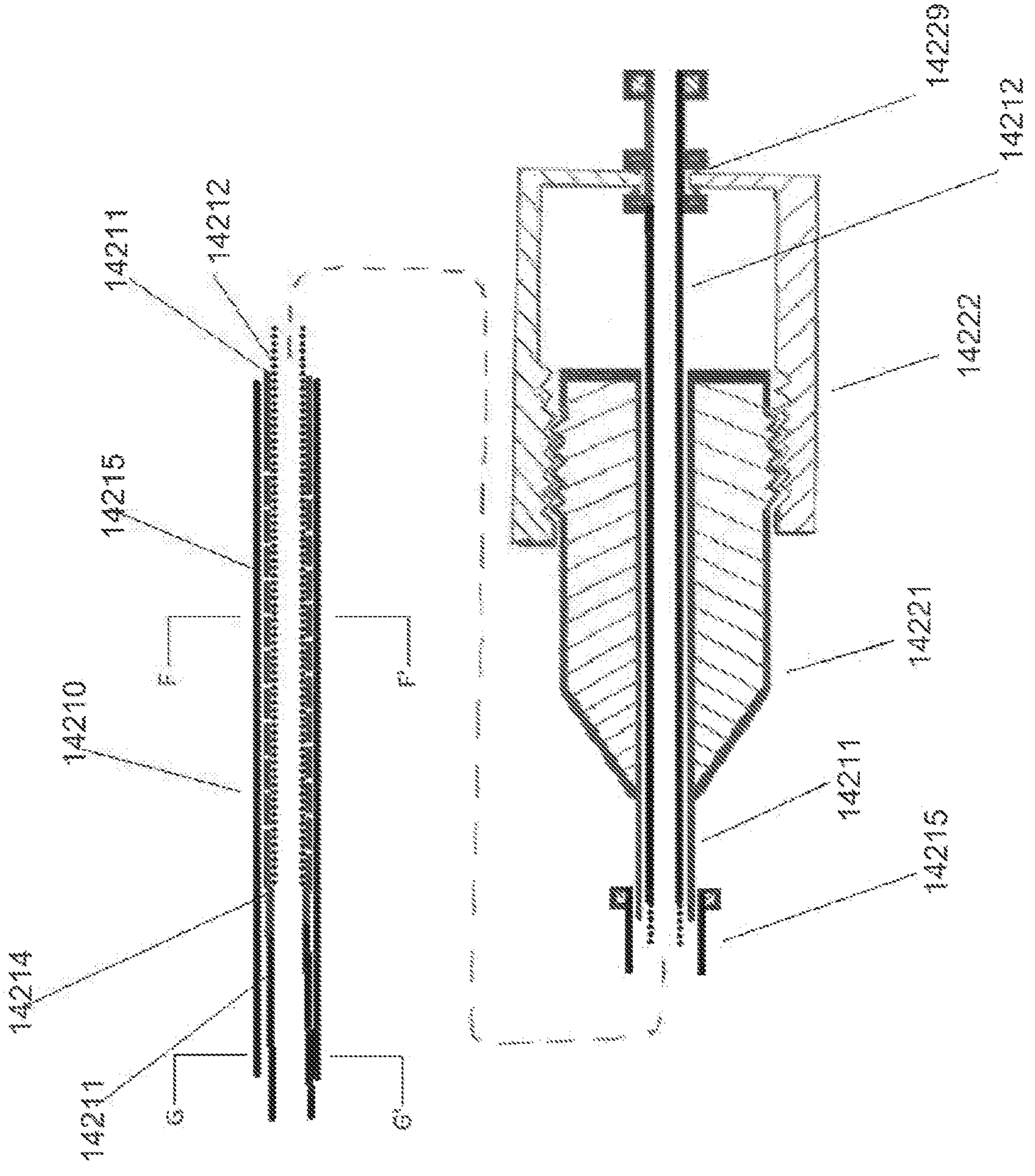
Figure 44F:
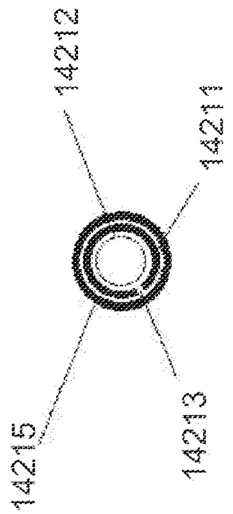
Figure 44G:
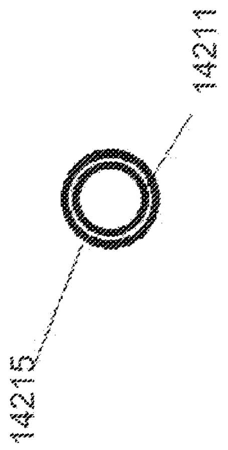
Figure 45:
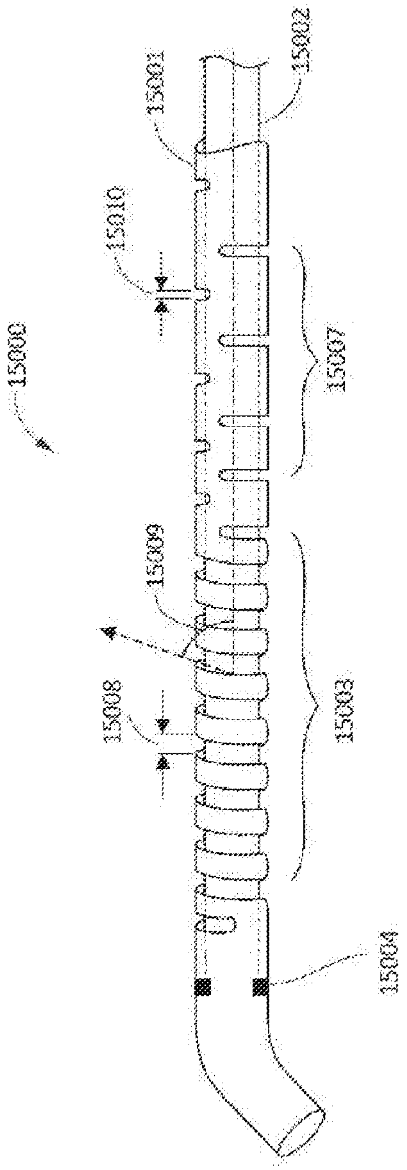
Figure 46A:
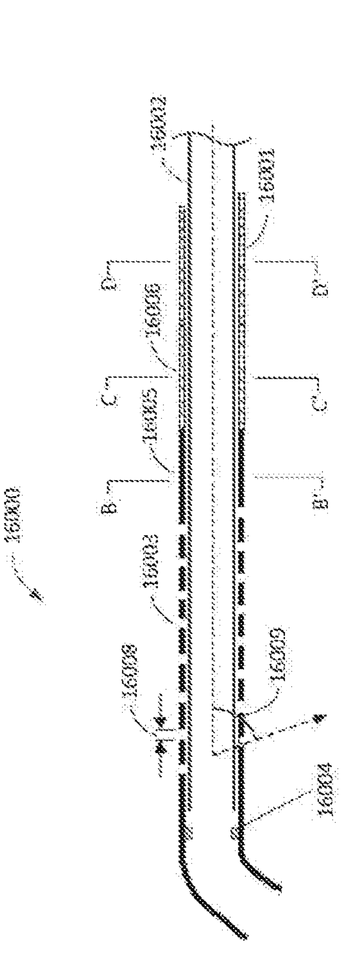
Figure 46B:
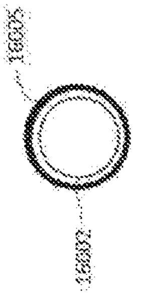
Figure 46C:
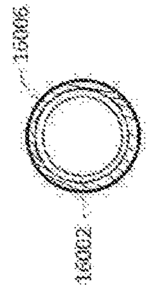
Figure 46D:
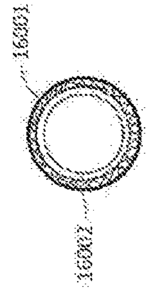
Figures 47A, 47B, 47C, 47D:
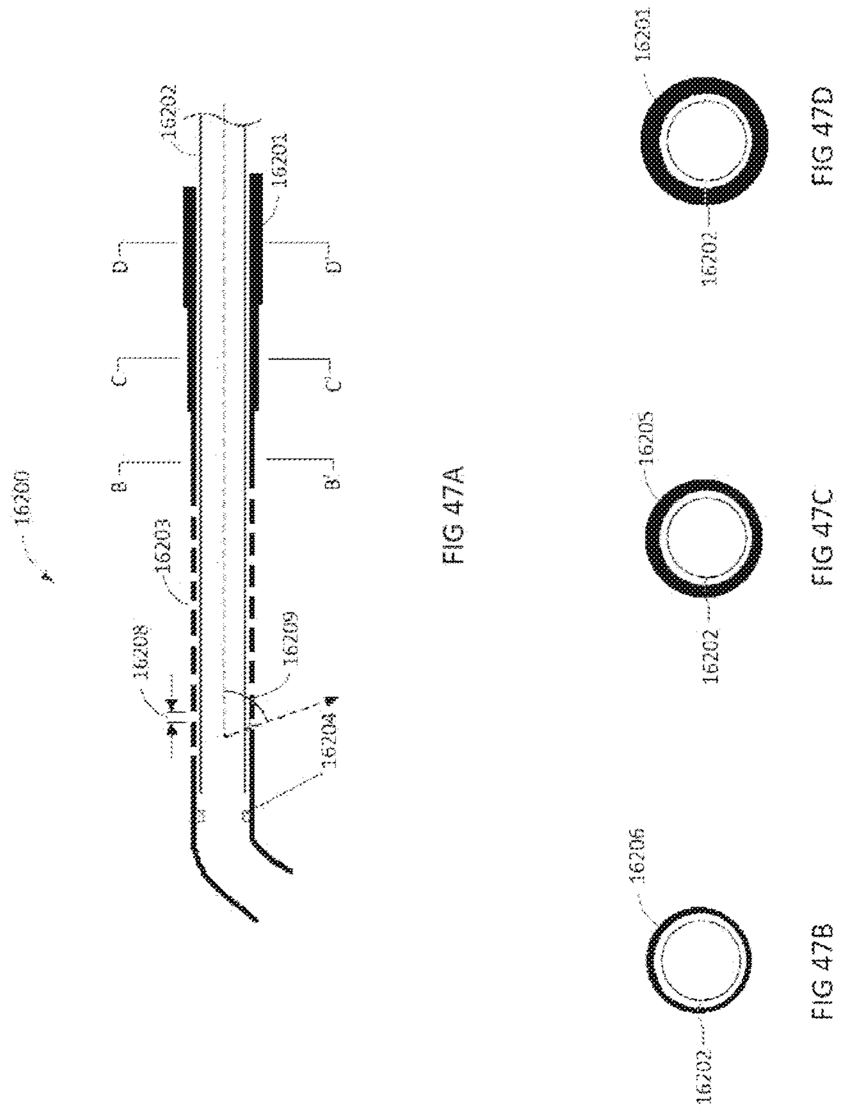
Figure 48A:
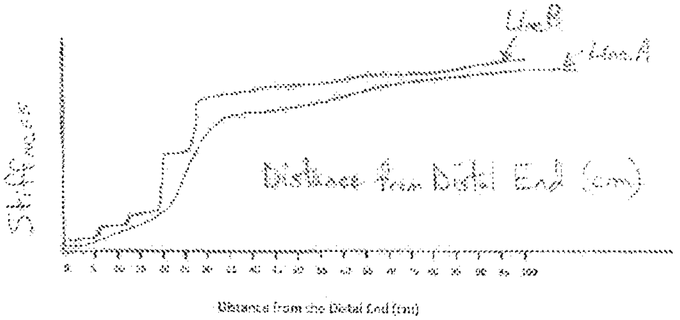
Figure 48B:
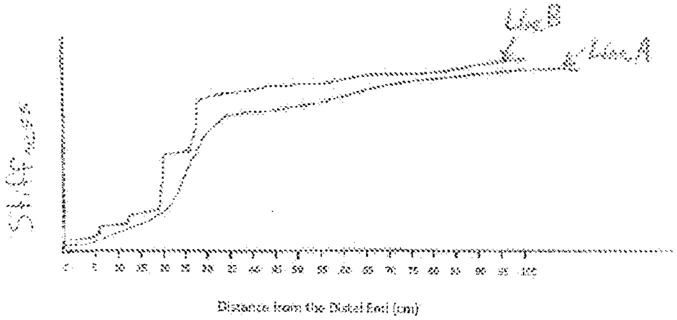
Figure 48C:
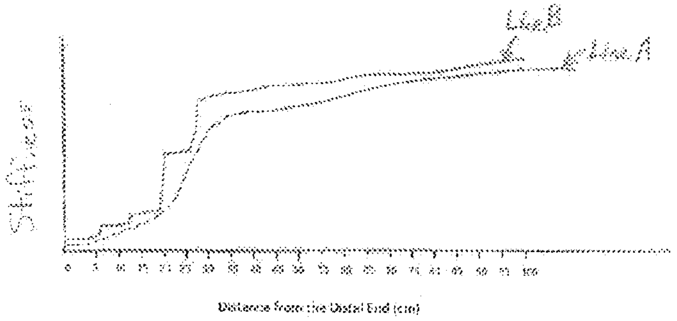
Figure 49:
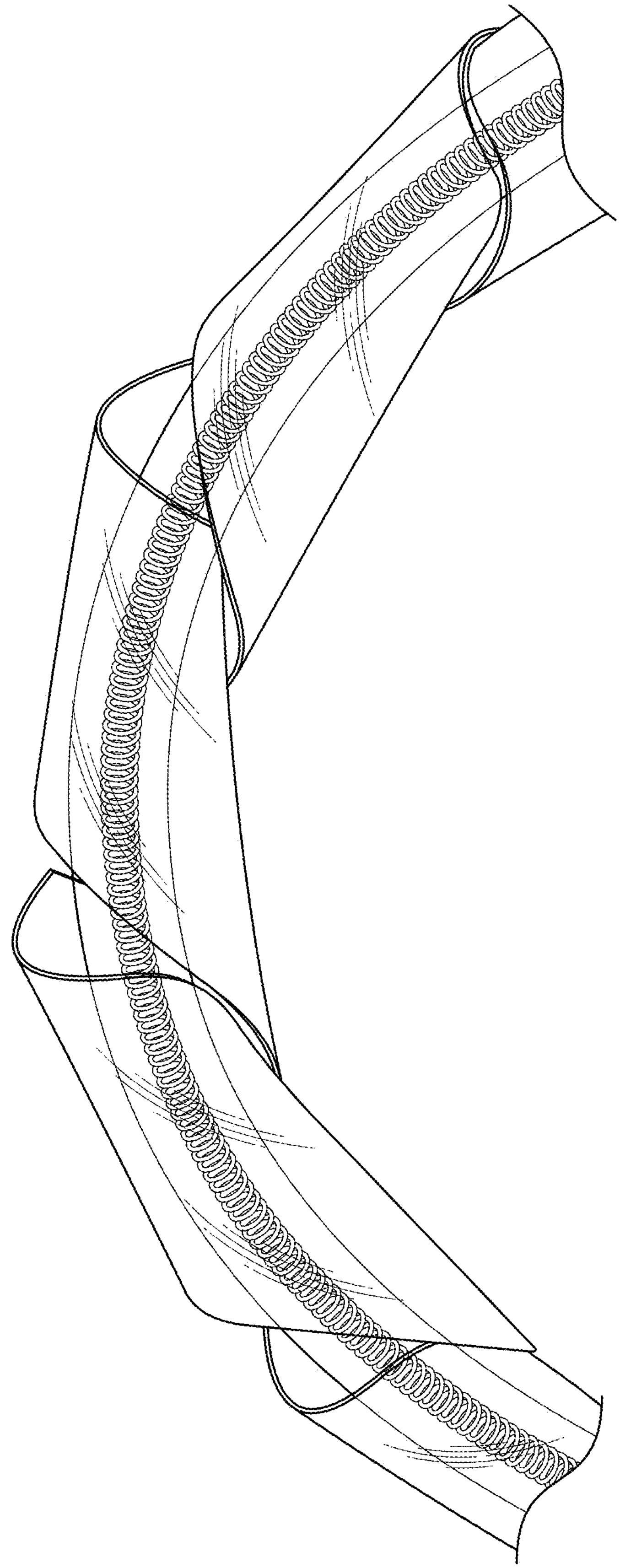
Figure 50A:
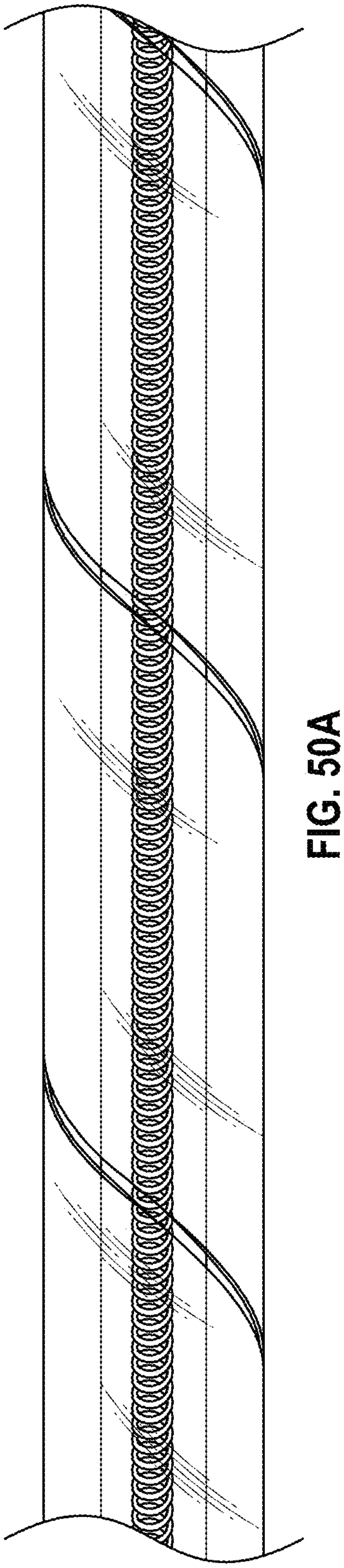
Figure 50B:
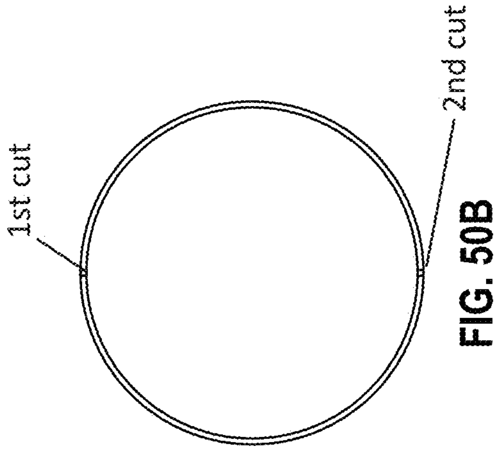
Figure 50C:
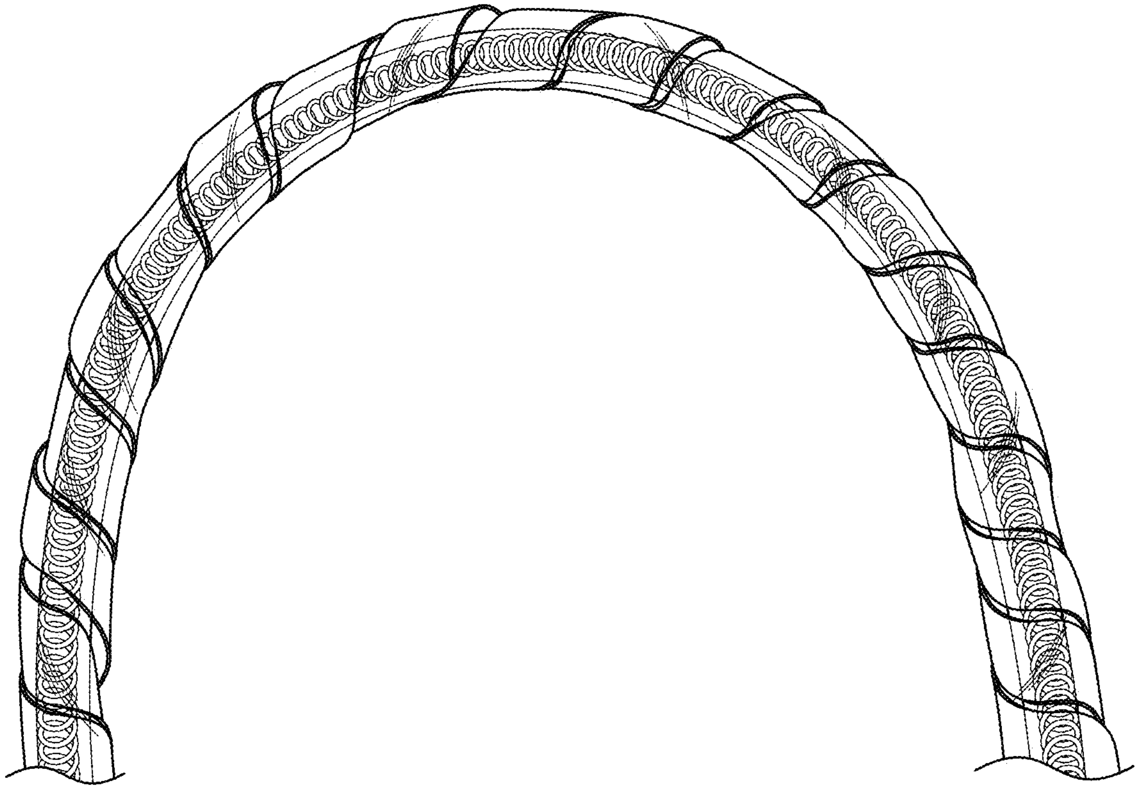

FIG. 44A schematically illustrates another embodiment of a medical device configured to convert linear motion to rotational motion along the distal aspect of the device;

FIG. 44B illustrates a longitudinal cross-sectional view of the distal end of the device of FIG. 44A wherein the outer sheath is not engaging the curved portion of the tube resulting in 180-degree curvature of distal aspect of the tube;

FIG. 44C illustrates a longitudinal cross-sectional view of the distal end of the device of FIG. 44A wherein the outer sheath partially engages the curved portion of the tube resulting in 90-degree curvature of distal aspect of the tube;

FIG. 44D illustrates a longitudinal cross-sectional view of the distal end of the device of FIG. 3A wherein the outer sheath further engages the curved portion of the tube resulting in 45-degree curvature of distal aspect of the tube;

FIG. 44E illustrates a longitudinal cross-sectional view of the distal end of the device of FIG. 44A wherein the outer sheath fully engages the curved portion of the tube resulting in straightening (0-degree curvature) of distal aspect of the tube;

FIG. 44F illustrates a transverse cross sectional view of the device of FIG. 44E through lines F-F';

FIG. 44G illustrates a transverse cross sectional view of the device of FIG. 44E through lines G-G';

FIG. 45 illustrates a side view of another embodiment of a medical device configured to be selectively rotated along the distal aspect of the device;

FIG. 46A schematically illustrates a longitudinal cross sectional view of a medical device configured to be selectively rotated along the distal aspect of the device;

FIG. 46B illustrates a transverse cross sectional view of the device of FIG. 46A through lines B-B';

FIG. 46C illustrates a transverse cross sectional view of the device of FIG. 46A through lines C-C';

FIG. 46D illustrates a transverse cross sectional view of the device of FIG. 46A through lines D-D';

FIG. 47A schematically illustrates a longitudinal cross sectional view of a medical device configured to be selectively rotated along the distal aspect of the device;

FIG. 47B illustrates a transverse cross sectional view of the device of FIG. 47A through lines B-B';

FIG. 47C illustrates a transverse cross sectional view of the device of FIG. 47A through lines C-C';

FIG. 47D illustrates a transverse cross sectional view of the device of FIG. 47A through lines D-D';

FIG. 48A is a graph of stiffness versus length for a device like the device illustrated in FIG. 45;

FIG. 48B is a graph of stiffness versus length for a device like the device illustrated in FIG. 46A;

FIG. 48C is a graph of stiffness versus length for a device like the device illustrated in FIG. 47A;

FIG. 49 illustrates a cut portion of the tubular member wherein a single cut is present and the cut portion is curved;

FIG. 50A illustrates a cut portion of the tubular member wherein two cuts are present such that the two cuts are out of phase with one another by 180 degrees;

FIG. 50B illustrates a transverse cross sectional view of the tubular membrane through B-B' in FIG. 49; and FIG. 50C illustrates a cut portion of the tubular member wherein two cuts are present such that the two cuts are out of phase with one another by 180 degrees and the cut portion is in a straight configuration.

Figure 50D:
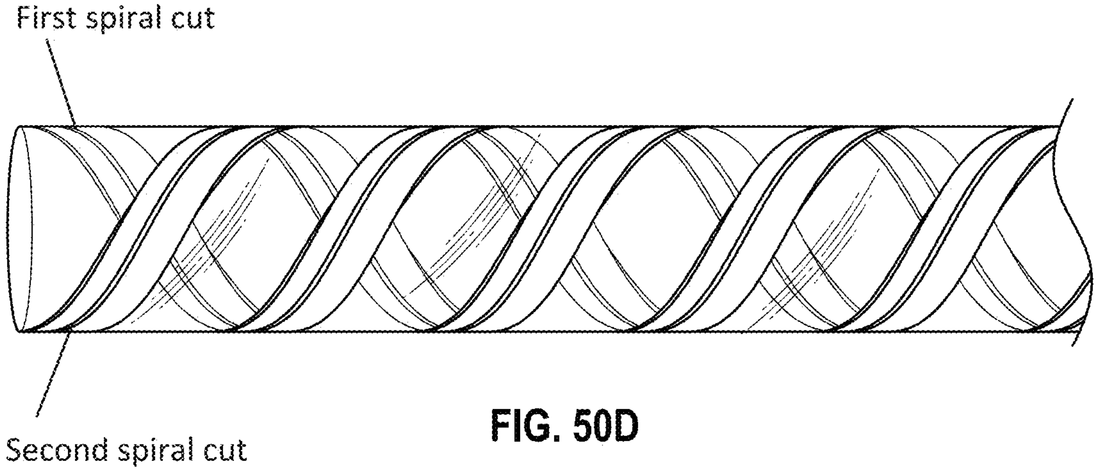

FIG. 50D illustrates a cut portion of the tubular member wherein two cuts are present such that the two cuts are out of phase with one another by 180 degrees and the cut portion is in a curved configuration.

Figure 51A:
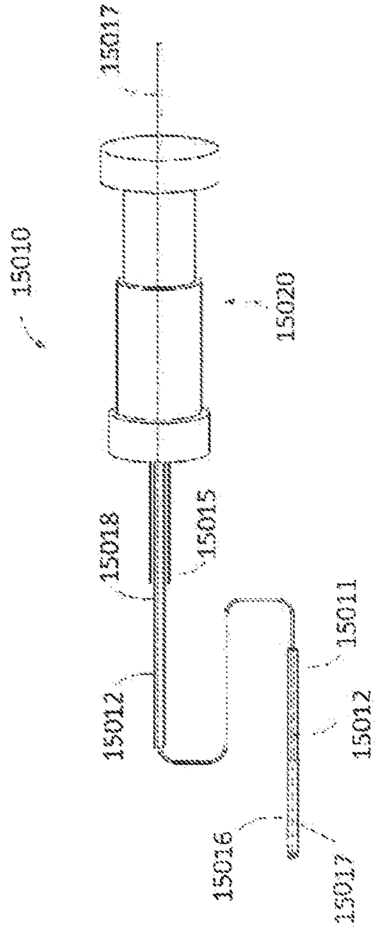
Figures 51B, 51D, 51E, 51F:
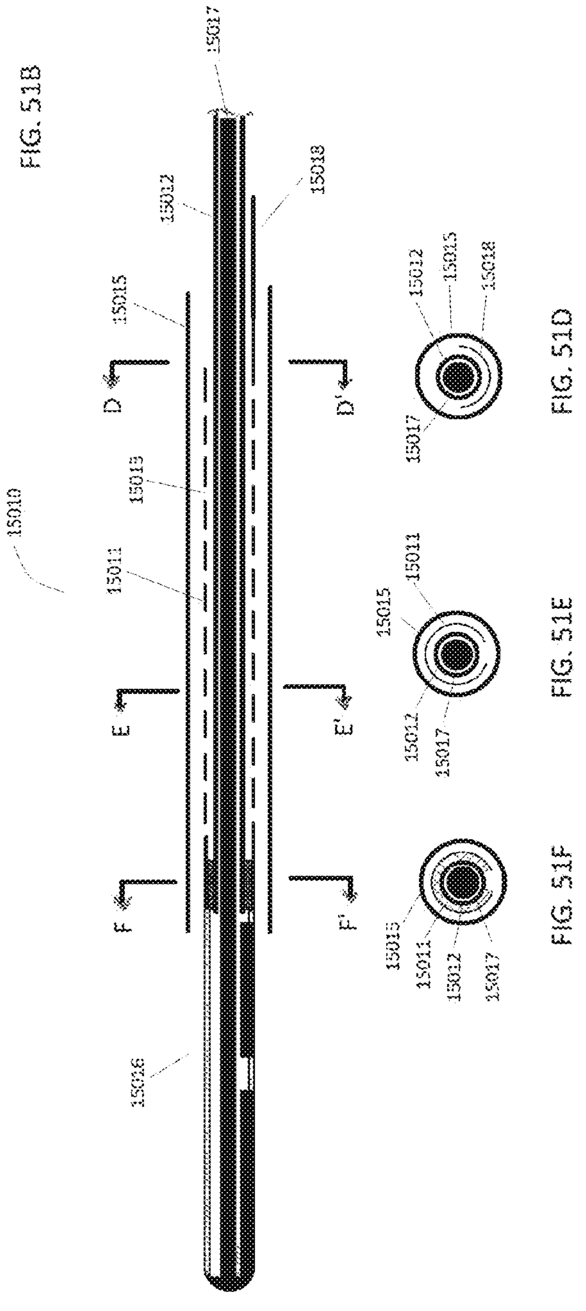
Figure 51C:
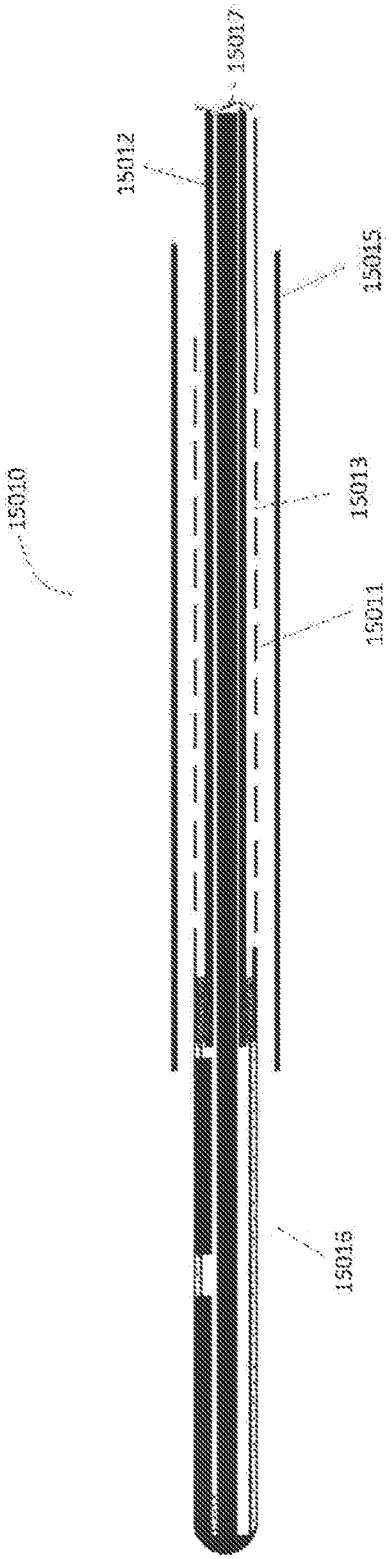
Figure 51G:
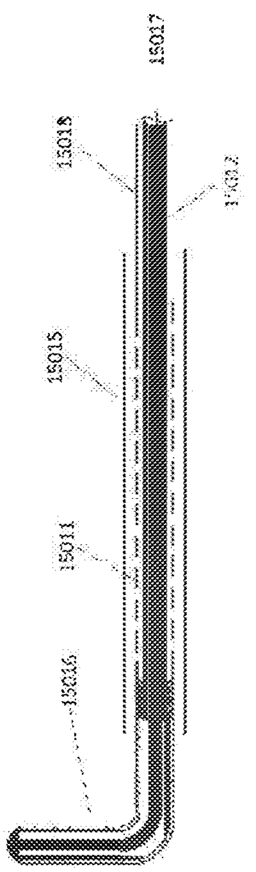
Figure 51H:
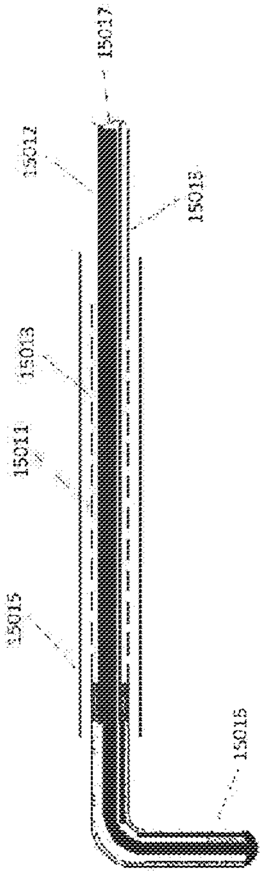
Figures 52A, 52B, 52C, 52D:
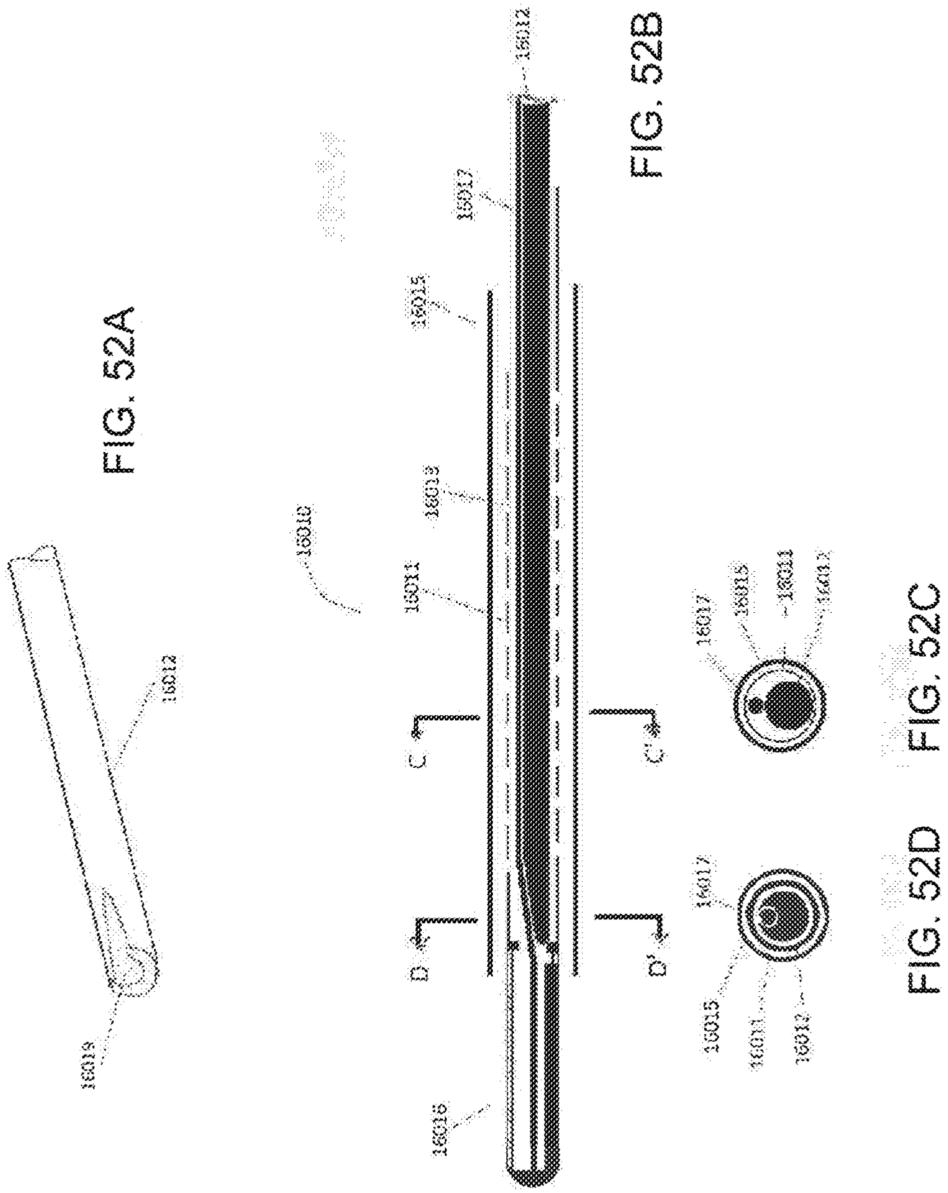
Figure 53A:
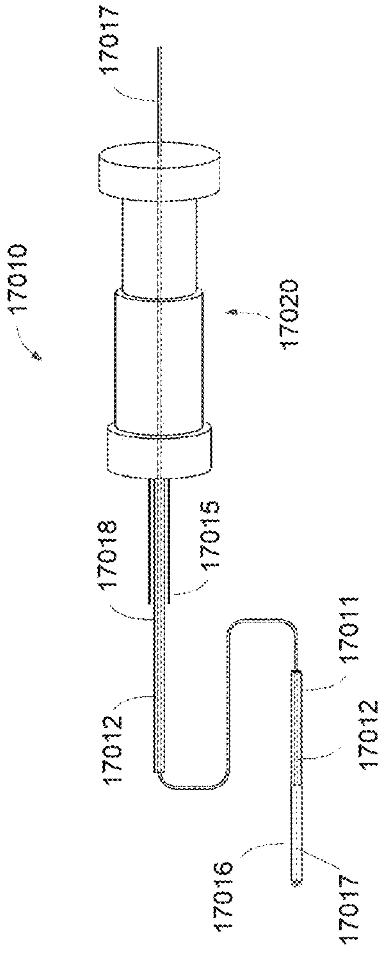
Figures 53B, 53C, 53D, 53E, 53F:
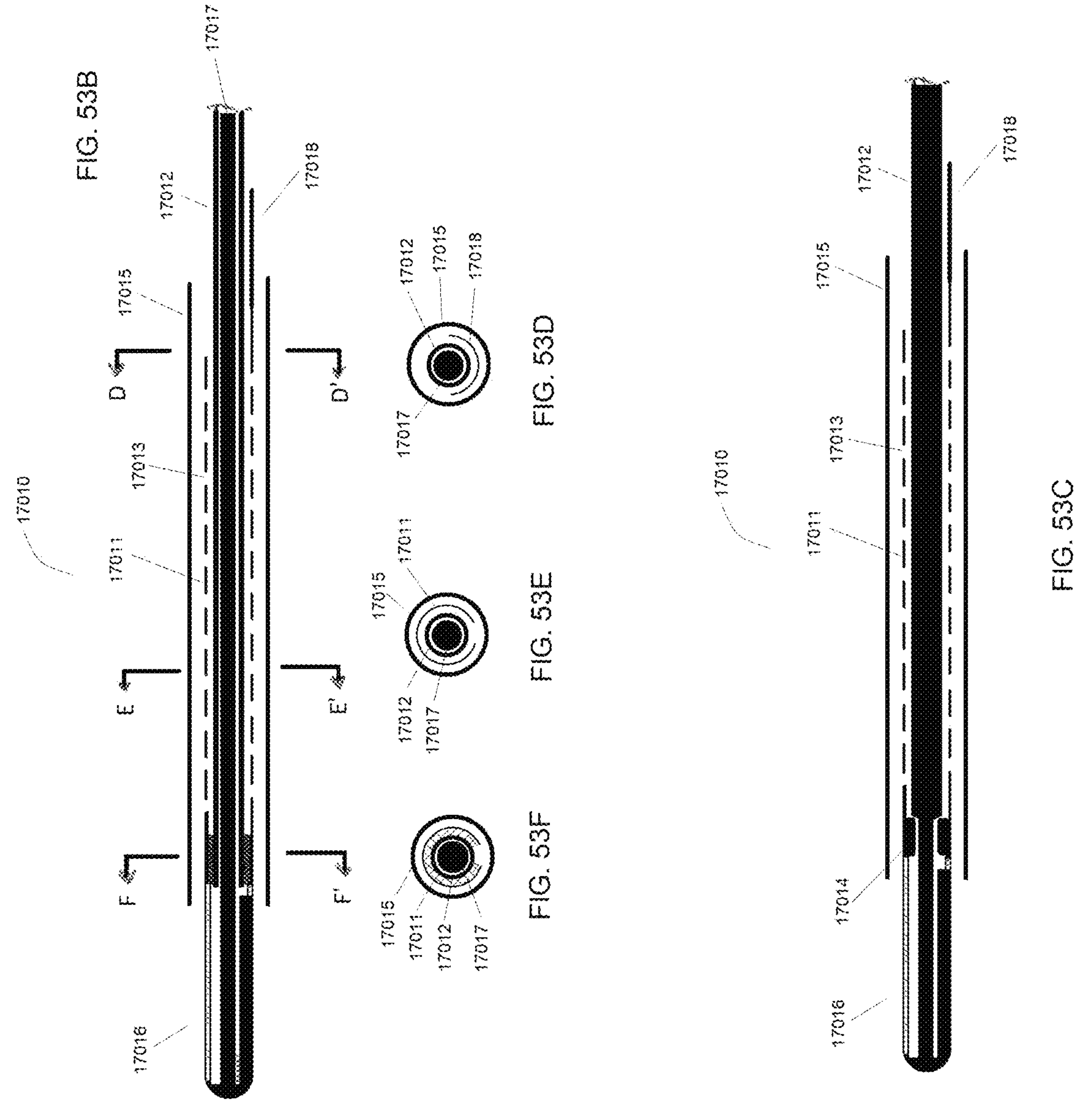
Figures 53G, 53H, 53I, 53J:
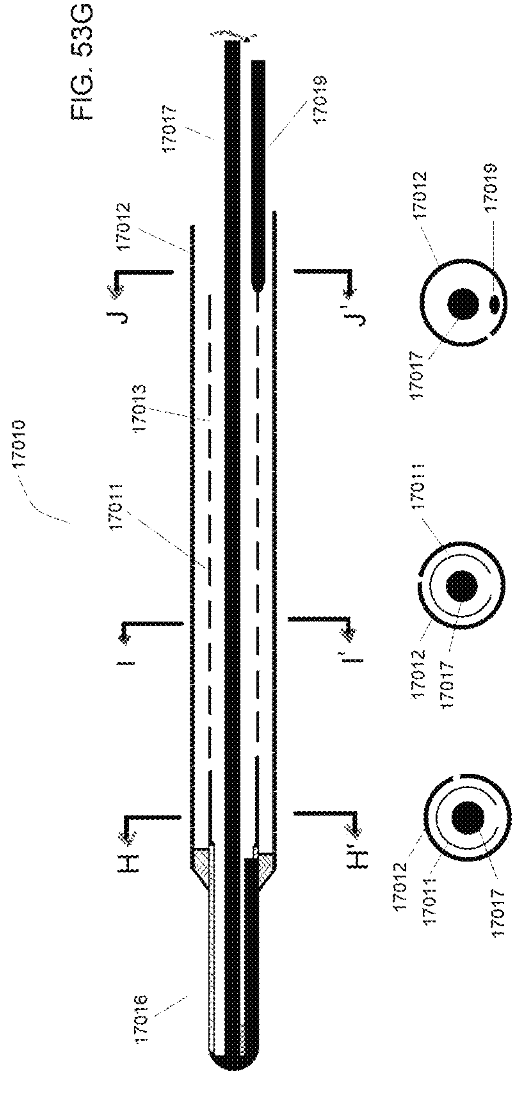
Figures 54A, 54B, 54C:
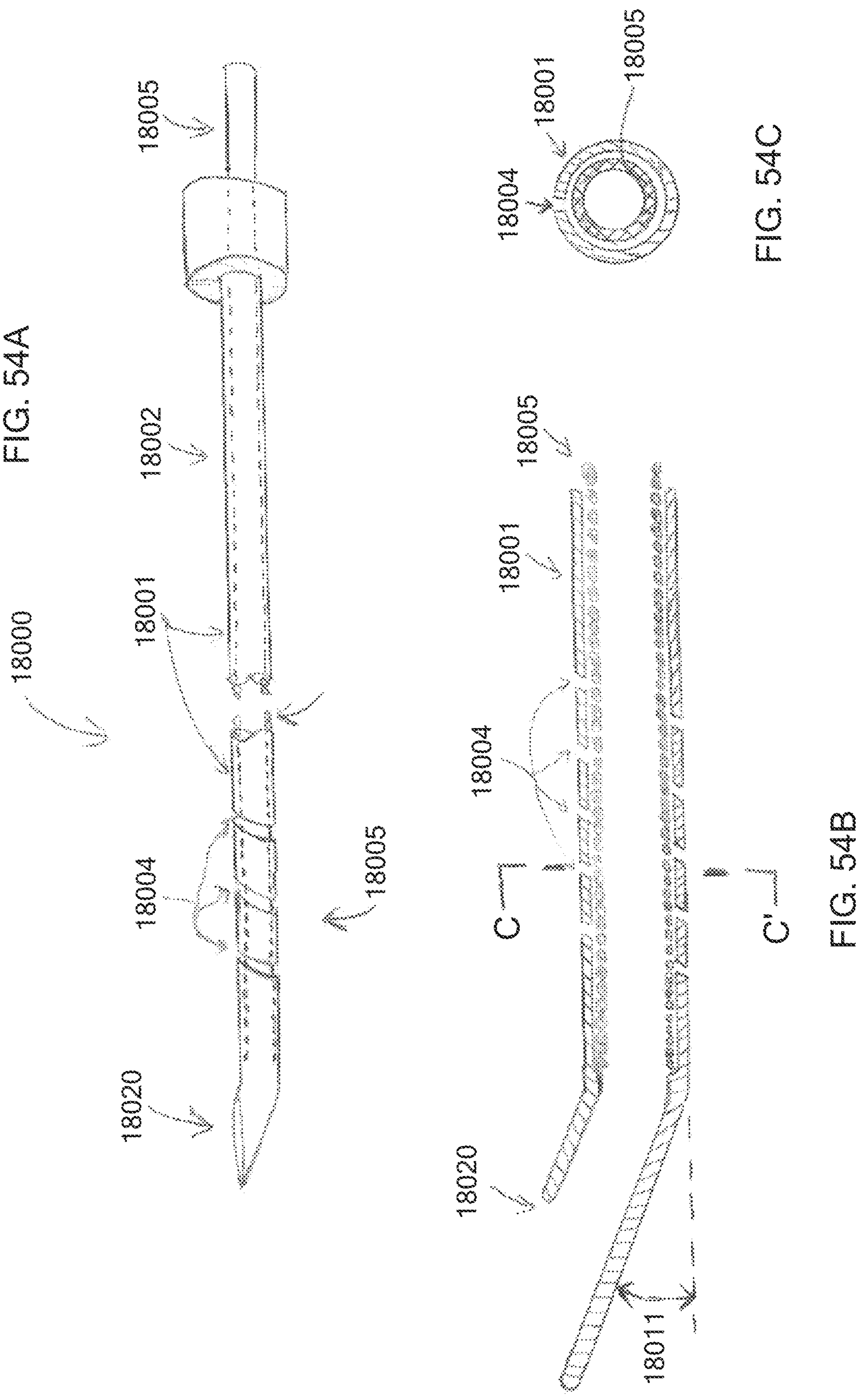
Figure 54D:
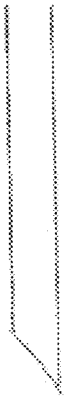
Figure 54E:
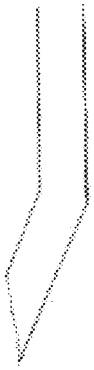
Figure 54F:
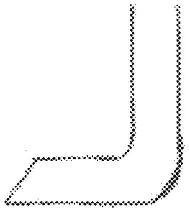
Figure 54G:
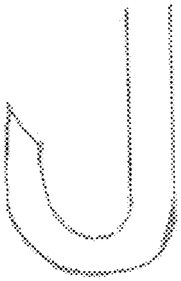
Figure 55:
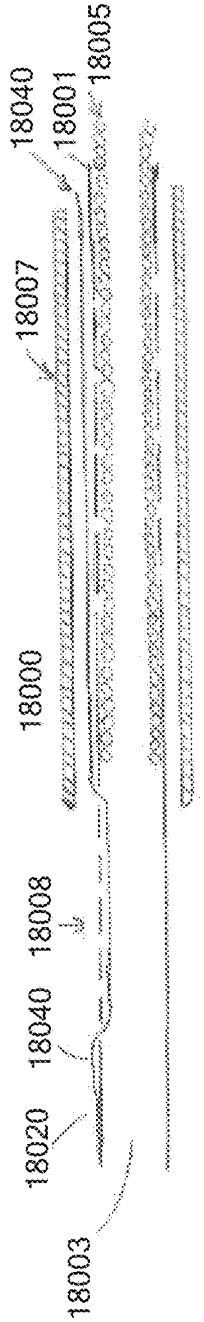
Figure 56B:
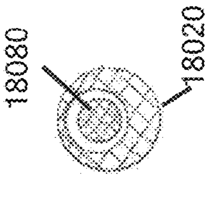
Figure 56A:
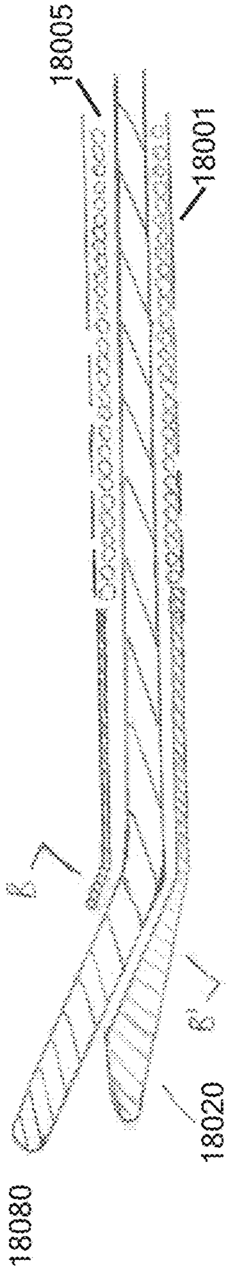
Figure 57:
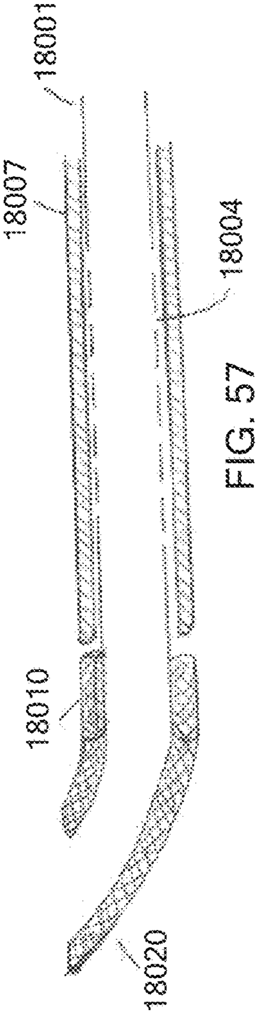
Figure 58:
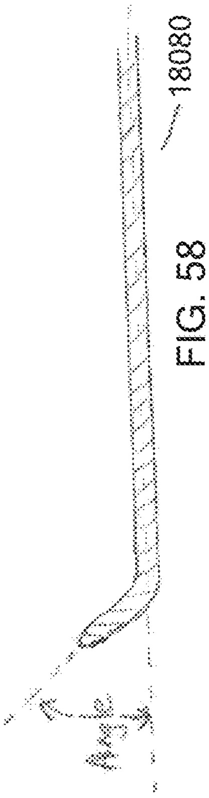
Figure 59A:
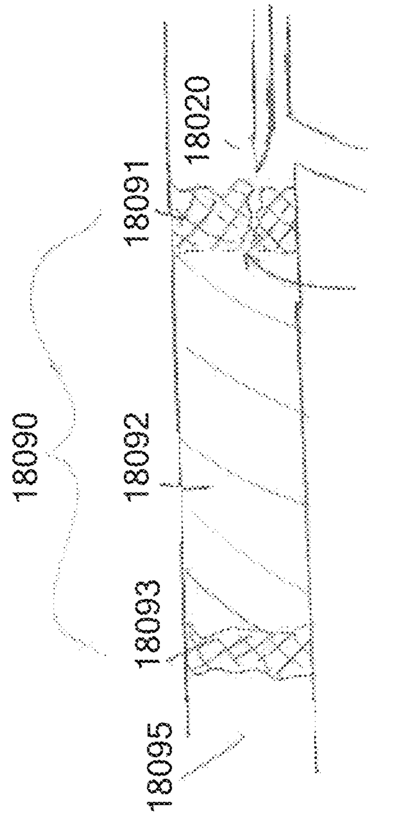
Figure 59B:
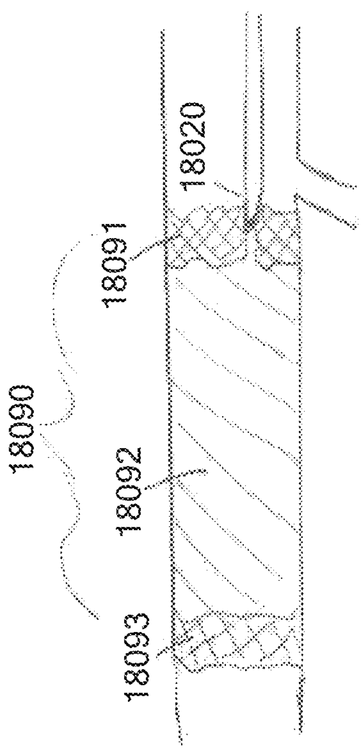
Figure 59C:
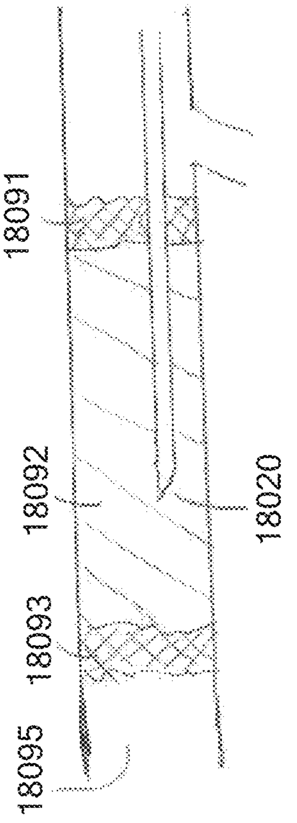
Figure 59D:
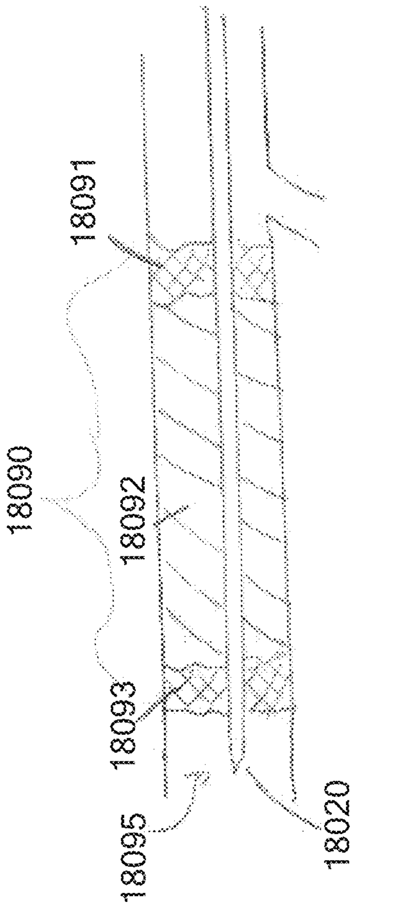
Figure 60A:
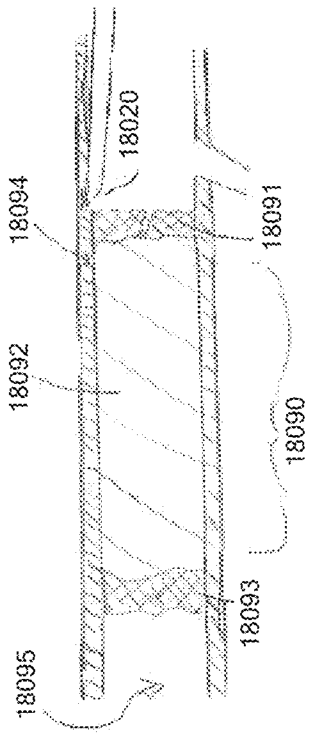
Figure 60B:
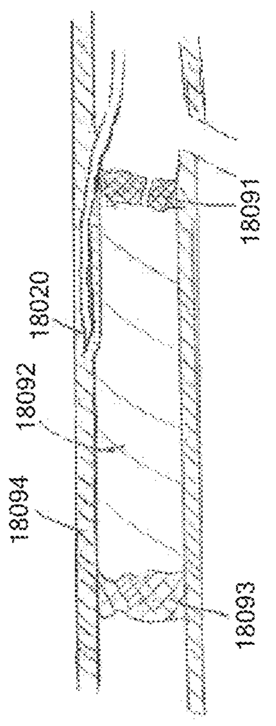
Figure 60C:
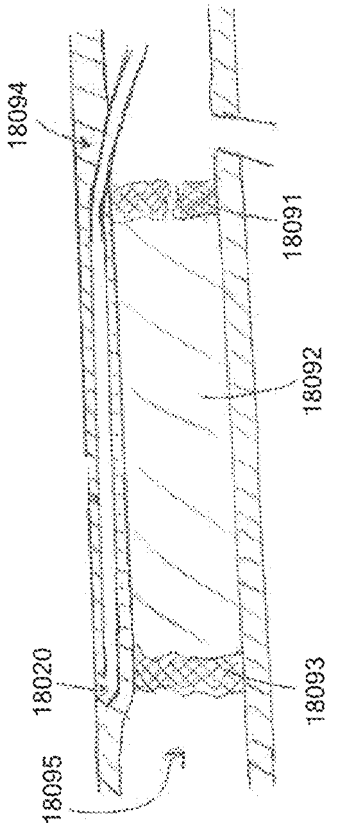
Figure 60D:
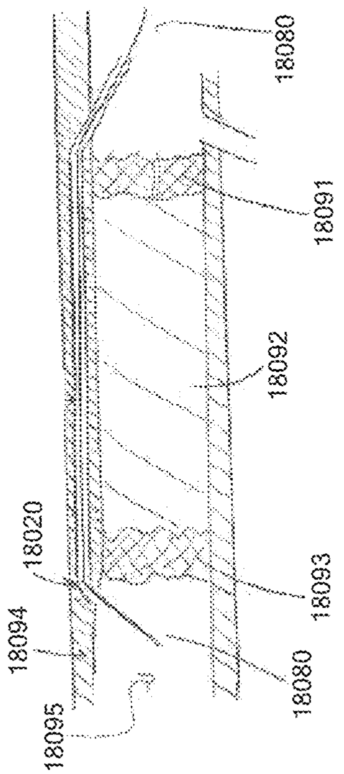

FIG. 51A illustrates a side view of another embodiment of a medical device configured to be selectively rotated along the distal aspect of the device with a tip deflecting mechanism;

FIG. 51B schematically illustrates a longitudinal cross sectional view of a medical device configured to be selectively rotated along the distal aspect of the device with a tip deflecting mechanism;

FIG. 510 schematically illustrates a longitudinal cross sectional view of a medical device configured to be selectively rotated along the distal aspect of the device with an alternative tip deflecting mechanism;

FIG. 51D illustrates a transverse cross sectional view of the device of FIG. 51B through lines D-D';

FIG. 51E illustrates a transverse cross sectional view of the device of FIG. 51B through lines E-E';

FIG. 51F illustrates a transverse cross sectional view of the device of FIG. 51B through lines F-F';

FIG. 51G schematically illustrates a longitudinal cross sectional view of a medical device configured to be selectively rotated along the distal aspect of the device with an alternative tip deflecting mechanism of FIG. 510, wherein the distal tip is deflected in one direction;

FIG. 51H schematically illustrates a longitudinal cross sectional view of a medical device configured to be selectively rotated along the distal aspect of the device with an alternative tip deflecting mechanism of FIG. 510, wherein the distal tip is deflected in opposite direction as that shown in FIG. 51G;

FIG. 52A illustrates a side view of another embodiment of an alternative force imparting mechanism wherein a groove or channel is located along the distal end of the force imparting mechanism;

FIG. 52B schematically illustrates a longitudinal cross sectional view of an alternative force imparting element wherein a groove or channel is located along the distal end of the force imparting mechanism;

FIG. 52C illustrates a transverse cross sectional view of the device of FIG. 52B through lines C-C';

FIG. 52D illustrates a transverse cross sectional view of the device of FIG. 52B through lines D-D';

FIG. 53A schematically illustrates one embodiment of a medical device herein relative movement of one member or portion relative to another member or portion of the device can advantageously create rotation along a distal end of the device;

FIG. 53B illustrates a longitudinal cross section of the distal aspect of a device configured to be selectively rotated along its distal portion;

FIG. 53C illustrates another embodiment of a device that is configured to be selectively rotated along its distal portion;

FIGS. 53D to 53F illustrate axial cross sectional views of the device of FIG. 53B;

FIG. 53G illustrates another embodiment of a device that is configured to be selectively rotated along its distal portion;

FIGS. 53H to 53J illustrate axial cross sectional views of the device of FIG. 53G;

FIG. 54A illustrates one embodiment of a medical device that can be used to treat vascular chronic total occlusions;

FIGS. 54B to 54L illustrate various embodiments and/or views related to the device of FIG. 54A;

FIG. 55 illustrates a cross sectional view through the longitudinal axis of one embodiment of a CTO device that also includes a pull wire;

FIG. 56A depicts a cross sectional view through the longitudinal axis of another embodiment of an intraluminal device, wherein the longitudinal axis of the distal tip is angulated relative to the longitudinal axis of the device;

FIG. 56B illustrates a cross-sectional view along a portion of the device of FIG. 56A;

FIG. 57 depicts a cross sectional view through the longitudinal axis of another embodiment of an intraluminal device, wherein the tube is disposed within the lumen of the outer sheath;

FIG. 58 provides a detailed view of the distal aspect or portion of a reentry wire according to one embodiment, wherein the distal tip of the reentry wire is tapered so as to aid in penetrating the intima of an organ of the subject;

FIG. 59A depicts one embodiment of the distal tip engaging the proximal cap of the CTO;

FIG. 59B depicts one embodiment of the distal tip engaged in a microchannel in the proximal cap of the CTO;

FIG. 59C depicts one embodiment of the distal tip in a microchannel in the body of the CTO;

FIG. 59D depicts one embodiment of the distal tip just distal to the distal cap of the CTO within the vessel lumen;

FIG. 60A illustrates another embodiment of a method of crossing a CTO, wherein the distal tip engages subintimal space at the level of the proximal cap of the CTO;

FIG. 60B depicts an embodiment of the distal tip in the subintimal space at the level of the body of the CTO;

FIG. 60C depicts one embodiment of the distal tip in the subintimal space just distal to the distal cap of the CTO; and FIG. 60D depicts the distal tip oriented towards the vessel lumen and the reentry wire being advanced through the tube lumen, penetrating the intima and reenters the vessel.

The figures are drawn for ease of explanation of the basic teachings of the present disclosure only; the extensions of the figures with respect to number, position, relationship, and dimensions of the parts to form the preferred embodiment will be explained or will be within the skill of the art after the following teachings of the present disclosure have been read and understood. Further, the exact dimensions and dimensional proportions to conform to specific force, weight, strength, and similar requirements will likewise be within the skill of the art after the following teachings of the present disclosures have been read and understood.

DETAILED DESCRIPTION

The present application is directed to a medical device comprising a distal portion, a proximal portion and a helical structure incorporated into the distal end of the device so as to convert linear motion to rotational motion (or otherwise create rotational motion) at the distal end of the device, such as a catheter (e.g., catheter, microcatheter, sheath, other intraluminal device, etc.). The helical structure may be a single helix or a dual chirality helix. In some embodiments, as discussed in greater detail herein, a dual chirality helix comprises a helix (e.g., having a first rotation, such as, a clockwise rotation) and a helix (e.g., having a second rotation opposite of the first rotation, such as, a counter-clockwise rotation). In some embodiments, the two helices intersect with one another. According to some embodiments, displacement (e.g., linear displacement or other movement) of the dual chirality helix along its long axis results in rotation of the junction of the two helices. While the medical device has application in human surgical and diagnostic procedures, the present disclosure contemplates the device having application and use in human and non-human medical procedures, as well as, non-medical applications for industrial and diagnostic procedures, such as inspections.

According to some embodiments, an intraluminal device comprises an outer member having at least one cut or feature that facilitates conversion of linear movement of an inner member relative to the outer member into rotation of a distal portion of the device. Such rotational movement can facilitate in maneuvering the distal end of the device through a vasculature or other intraluminal structure of a subject (e.g., to reach or approach a desired anatomical location), as desired or required. In some embodiments, as discussed in greater detail herein, the intraluminal device is configured to be directed to an intraluminal location (e.g., intravascular, other intraluminal, anatomical location (e.g., through the subject's airways, gastroenterological system, etc.), etc.).

As discussed in greater detail herein, the various embodiments disclosed herein can provide advantageous devices, systems and/or methods to manipulate the distal end of a medical device (e.g., catheter, microcatheter, sheath, other intraluminal device, etc.). In some embodiments, the device includes a tube or outer member comprising one or more cuts (e.g., partial or complete cuts through the wall of the tube or outer member). In some embodiments, the cuts or similar features extend throughout the entire thickness of the tube or outer member. However, in other embodiments, the cuts extend only partially through the tube or outer member, as desired or required.

In some embodiments, the distal portion of the tube or outer member comprises one or more cuts or other features. In some embodiments, such cuts are helical or spiral in shape. In some embodiments, such helical cuts have a constant or consistent orientation. However, in other arrangements, the cuts have two or more orientations (e.g., angles, pitches, etc.) relative to the longitudinal axis, opening sizes, spacing and/or other properties, as desired or required. For example, in some arrangements, the cut(s) comprises/comprise a dual helix or dual chirality helix design. However, in other embodiments, the cut comprises/comprise a single helix design (e.g., a cut having the same pitch, general direction of orientation, other properties and/or the like).

According to some embodiments, a device comprises a tube or outer member, a pusher member or other force imparting element and one or more cuts or other features along the distal end of the tube. In some embodiments, linear movement of the force imparting element relative to the tube or outer member causes rotational movement (e.g., rotation, twisting, turning, etc.) of a distal portion of the tube. Such movement can help maneuver and/or otherwise manipulate the device through the vasculature or other intraluminal system of a subject. In some embodiments, the tube or other member is secured to the pusher member or other force imparting element along one or more locations (e.g., the distal end of the device), using one or more securement (e.g., direct or indirect) methods, features, devices, technologies, etc.

In some embodiments, the cuts (e.g., partial or complete) through the tube or outer member comprise a helical or spiral shape. For example, in some embodiments, the cuts are angled relative to the longitudinal axis of the device (or a perpendicular axis of the longitudinal axis). For example, the helical angles can range from 10 to 80 degrees (e.g., 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the device. In some embodiments, the helical angle ranges from 15 to 75 degrees.

In some embodiments, the cuts are present only along or near the distal end of the tube or distal member. For example, the cut(s) is/are located along the distal 0 to 20 percent (e.g., 0-1, 1-2, 2-3, 3-4, 4-5, 5-6, 6-7, 7-8, 8-9, 9-10, 10-15, 15-20% of the tube and/or the device, percentages between the foregoing ranges and values, etc.).

According to some embodiments, the inner member, and thus the entire intraluminal device, is cannulated or otherwise comprises a lumen. In some embodiments, such a device can allow for the passage of one or more other devices, instruments and/or other members through its interior, as desired or required. In some embodiments, the devices disclosed herein comprise one or more external members, layers, coatings and/or other members.

Although several arrangements disclosed herein comprise a dual helix or dual chirality helix design, the conversion of linear to rotational movement can also be accomplished, and in certain embodiments can be preferred and/or otherwise offer certain advantages, relative to the dual helix configurations. Thus, any of the embodiments disclosed herein can be configured and/or otherwise adapted to include either a single or a multiple (e.g. dual chirality) helix design. Further, the medical devices disclosed herein can be adapted to perform the linear to rotational conversion using designs that do not include a helix, as discussed in greater detail in the present specification and illustrated in the accompanying drawings.

As discussed in greater detail herein, the embodiments disclosed herein can take the form of any one of various intraluminal devices, such as, for example, catheters, microcatheters, sheaths, other intraluminal devices and/or the like. In some embodiments, the diameter (e.g., the outer diameter) of any of the intraluminal devices disclosed herein can vary between 1 mm to 25 mm (e.g., 1-25, 1-5, 5-10, 1-10, 10-15, 15-20, 20-25, 10-20, 15-25, 10-25 mm, values between the foregoing ranges, etc.) or 1 French to 75 French (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75 French, French values between the foregoing, etc.), as desired or required. However, in other embodiments, the intraluminal device can comprise any other diameter or size, such as, for example and without limitation, a custom size that is below, above or in between the values provided above. Further, the length of the device can vary depending on the application or use. In some embodiments, the length of the device is between 10 and 500 cm (e.g., 50 to 100, 100 to 300, 10 to 20, 20 to 30, 30 to 40, 40 to 50, 50 to 60, 60 to 70, 70 to 80, 80 to 90, 90 to 100, 100 to 110, 110 to 120, 120 to 130, 130 to 140, 140 to 150, 150 to 160, 160 to 170, 170 to 180, 180 to 190, 190 to 200, 200 to 250, 250 to 300, 300 to 350, 350 to 400, 400 to 450, 450 to 500 cm, lengths between the foregoing, etc.).

According to some embodiments, the intraluminal devices disclosed herein can be used in a variety of applications and procedures. For example, the devices can be used to reach a particular organ or vasculature of a subject (e.g., heart or cardiac region, head and neck, liver, kidneys, hepatic vasculature, renal vasculature, extremities, etc.). Any other portion of the anatomy can also be reached and targeted using the device. The various embodiments disclosed herein can be particularly advantageous when a practitioner is attempting to reach and treat a portion of a subject's anatomy that is accessible through a tortious vascular or other intraluminal route (e.g., one that requires the intraluminal device to make several turns and directional changes). The various devices disclosed herein can be used for a variety of indications and procedures, such as, for example and without limitation, ablation procedures, stimulations or neuromodulation procedures, extractions, biopsies, aspirations, delivery of medicaments, fluids, energy (e.g., RF, ultrasound, cryogenic, etc.) and/or the like.

In some embodiments, imparting rotation on the distal portion at the distal end (e.g., as opposed to rotating the entire length of the medical device) can help reduce stress on the vasculature, improve the accuracy of the rotation of the medical device, reduce the risk of uncontrolled release of potential energy from the medical device and/or provide one or more additional advantages or benefits. These qualities can improve surgical efficiency, reduce overall time for the patient in the operating theater, reduce the time that the patient is required to be exposed to anesthesia, reduce the risk of surgical complications, reduce fatigue of the surgical staff during a medical procedure, reduce the exposure time of the patient to radiation (e.g., when a radiation source is required during the operation) and the like.

The terms "top," "bottom," "first," "second," "upper," "lower," "height," "width," "length," "end," "side," "horizontal," "vertical," and similar terms are used herein, it should be understood that these terms have reference only to the structures shown in the figures and are utilized only to facilitate describing embodiments of the disclosure. Features depicted some embodiments may be used in other embodiments disclosed herein as would be understood by a person of ordinary skill in the art.

Figure 1:
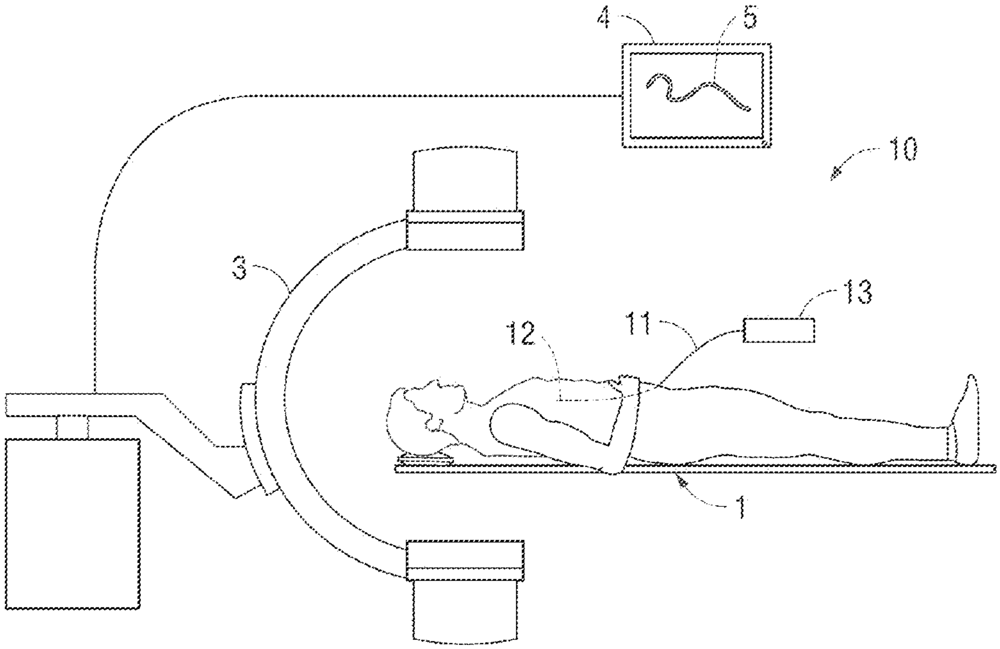
FIG. 1 is a diagram of a medical system including a medical device according to one embodiment of the disclosure.

FIG. 1 shows a system of imaging a medical device 10 within the human body 1 according to one embodiment. The depicted medical device includes a distal end 12 configured for use within the body 1, a proximal end 11 for use outside the body 1, and a handle 13. In operation, the device 10 can be monitored with an imaging device 3 which may project the medical device's image 5 onto a monitor 4. The handle 13 may be configured to control the operation of the distal end 12. The use of imaging (e.g., imaging devices, monitors, etc.), irrespective of whether they are included with or without the device, can be incorporated and synchronized with any of the embodiments disclosed herein.

Figure 2A:
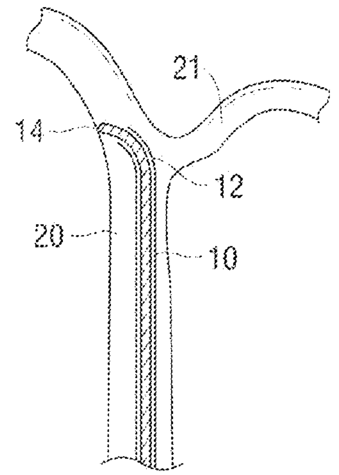
FIG. 2A is a diagram of a distal end of the medical device in an original orientation and disposed in branching segment of an endoluminal structure within the body prior to selection of a desired endoluminal structure.
Figure 2B:
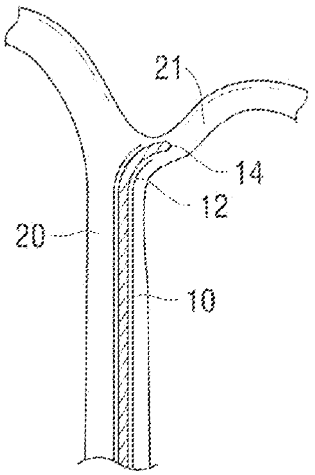
FIG. 2B is a diagram of the distal end of the medical device after selection of a branch within the branching endoluminal structure within the body.

FIGS. 2A-2B show the distal end 12 of the device 10 within an endoluminal structure 20 according to one embodiment. Endoluminal structures including but not limited to blood vessels, the heart, the gastrointestinal (GI) tract, genitourinary (GU) tract, peritoneal cavity, thoracic cavity, the mediastinum, bronchial passages, subarachnoidal spaces, and the intracranial ventricular system. In FIG. 2A, a guidewire 14 is shown in the device 10 with the distal end of the device 12 directed away from a desired endoluminal branch 21. In FIG. 2B, the distal end 12 and the guidewire 14 in the endoluminal structure 20 of FIG. 2A have been rotated to point towards the desired endoluminal branch 21.

FIG. 3A schematically illustrates a tube 30 with a dual chirality helix 37 formed by a proximal helical cut 31 and a distal helical cut 32, wherein the cuts 31, 32 are proximal and distal relative to a junction point 33. In the depicted embodiment, the distal cut 32 includes a cut width **38*a* and a helical angle 39*a*. Similarly, the proximal cut 31 has a cut width 38*b* and a helical angle 39*b*. The cut widths 38*a*, 38*b* can range from 0.1 micrometers to 10 millimeters (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10 millimeters, values between the foregoing, etc.). In some embodiments, the cut width ranges from 10 to 1000 microns. The helical angles 39*a*, 39*b* can range from 10 to 80 degrees (e.g., 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the device. In some embodiments, the helical angle ranges from 15 to 75 degrees. The cut widths 38*a*, 38*b* may be equal or different, and the helical angles 39*a*, 39*b* may have the same or different magnitudes. In some embodiments, when a force 34 is applied along a long axis 40 of the tube 30, the force is converted into a force along the distal helix 35 and a force along the proximal helix 36 that are exerted on the junction point 33. The cut widths 38*a*, 38*b* and the helical angles 39*a*, 39*b* change as the dual chirality helix 37** is elongated or reduced to impart rotational motion.

Figure 3B:
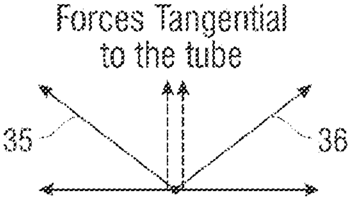
FIG. 3B is a free body diagram of the forces in FIG. 3A.

FIG. 3B shows a free body diagram of the force along the distal helix 35 and the force along the proximal helix 36 wherein the respective forces have been broken down into forces along the axis of the tube and forces tangential to the tube 30. This illustrates, in one embodiment, how the forces tangential to the tube 30 are additive and result in torqueing of the junction point 33.

Figure 4A:
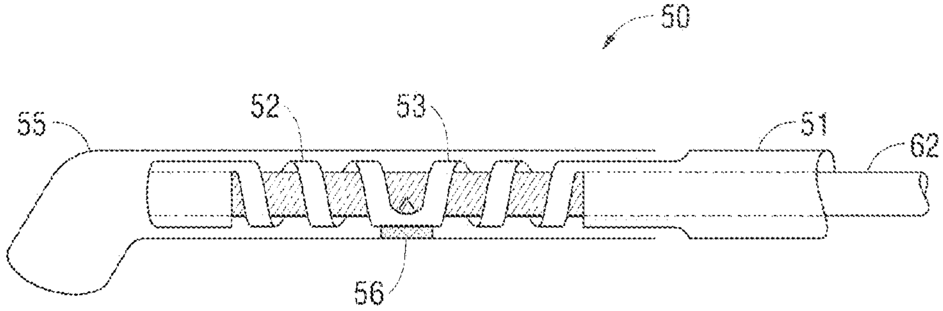
FIG. 4A is a cross sectional view along the long axis of a tube with a dual chirality helical cut without linear displacement of the distal end of the tube according to one embodiment of the present disclosure.
Figure 4B:
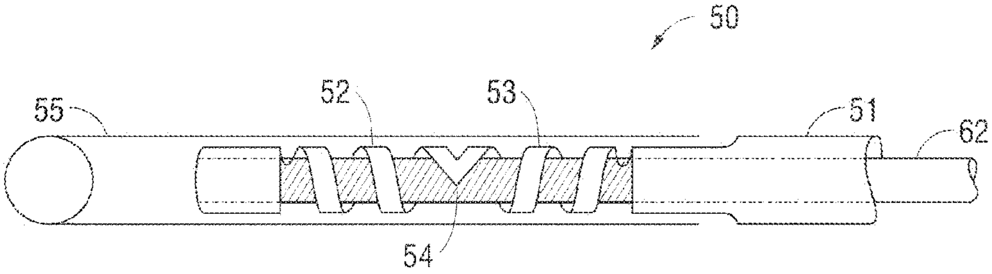
FIG. 4B is a cross sectional view along the long axis of the tube of FIG. 4A with linear displacement of the distal end of the tube.
Figure 4C:
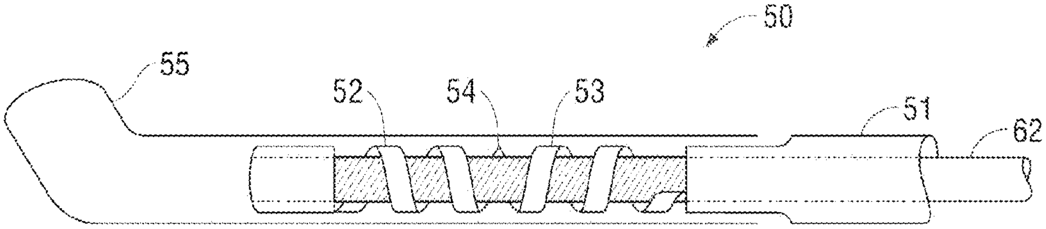
FIG. 4C is cross sectional view along the long axis of the tube of FIG. 4A with additional linear displacement of the distal end of the tube.

FIGS. 4A-4C illustrates the rotation of a junction point 54 between a proximal helical cut 53 and a distal helical cut 52 when the distal portion of the tube 51 is elongated, according to one embodiment. FIG. 4A shows the distal portion of the tube 51 not being elongated, while FIG. 4B shows the distal portion of the tube 51 in an elongated orientation (e.g., such that there is 90 degrees of rotation of the junction point 54 and distal segment 55 relative to their respective positions in FIG. 4A). FIG. 4C shows the distal portion of the tube 51 being elongated such that there is 180 degrees of rotation of the junction point 54 and distal segment 55 relative to their respective positions in FIG. 4A.

Figure 5:
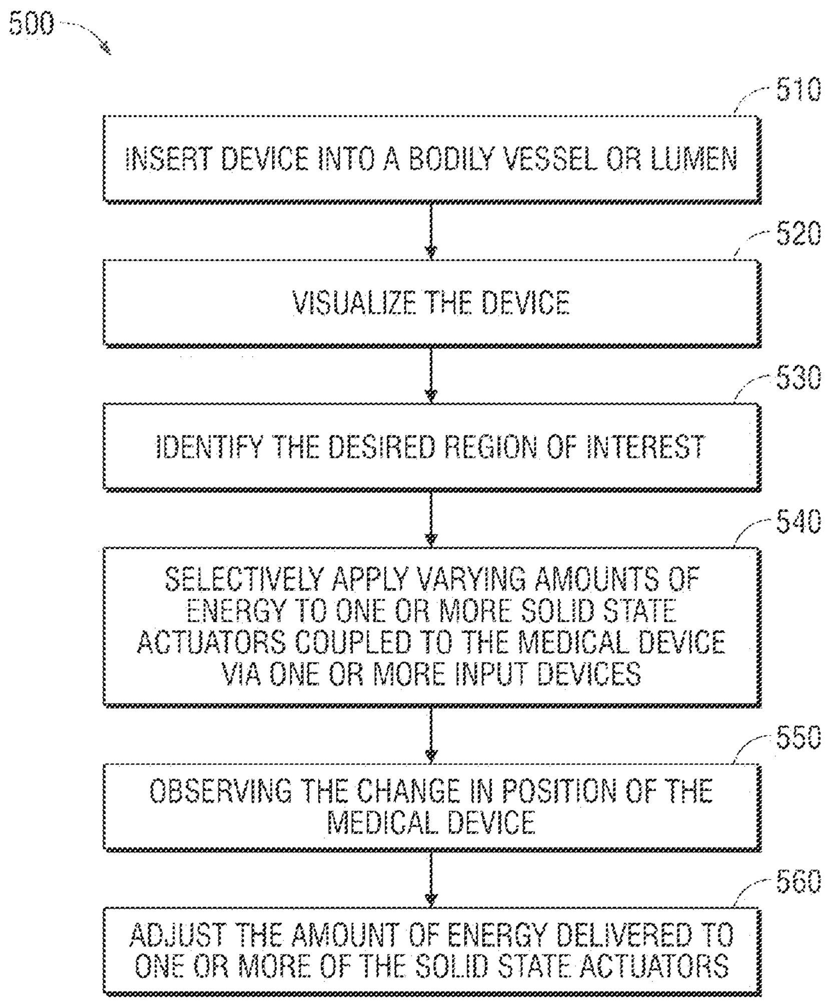
FIG. 5 is a flowchart of a method of imparting rotational motion to the distal end of the device by means of conversion of linear displacement to rotational motion via a dual chirality mechanism.
Figure 19A:
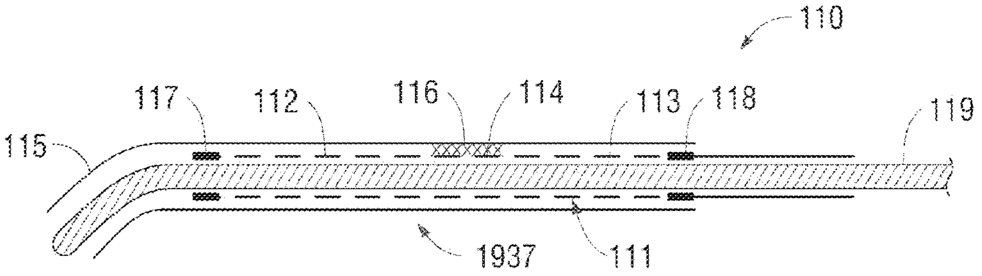
FIG. 19A is a longitudinal cross sectional view of the distal aspect of the medical device with a magnetic displacement mechanism in its resting state.

FIG. 5 shows a flow chart for one embodiment of a method 500 of controlling the distal end 12 of the device 10. In step 510, the device 10 is inserted into the endoluminal structure 20 of the body 1. In step 520, an image of the device 10 in the body 1 is displayed. The display may be in form of any imaging techniques for objects internal to the human body, including, but not limited to, x-ray fluoroscopy, ultrasound imaging, computed axial tomography (CAT) imaging, magnetic resonance imaging (MRI), and/or endoscopic imaging. In step 530, the region of interest is selected within the image. In step 540, longitudinal force and displacement are applied to the dual chirality helix 37 causing rotation of the distal end 12. The longitudinal force may be applied by manipulation of the sleeve 57 or wire 62. In some embodiments, the longitudinal force may be applied through the application of energy to one or more actuators coupled to the medical device, such as magnetic elements 117, 118 (FIG. 19A). In step 350, the change of position of the distal end 12 is observed on the display. In step 360, the amount of longitudinal displacement is adjusted to rotate the distal end 12 the desired degree of rotation by varying the amount of longitudinal force applied to the dual chirality helix 37 either via the sleeve 57/guidewire 62 or through energy applied to one or more actuators 117, 118.

Figure 6A:
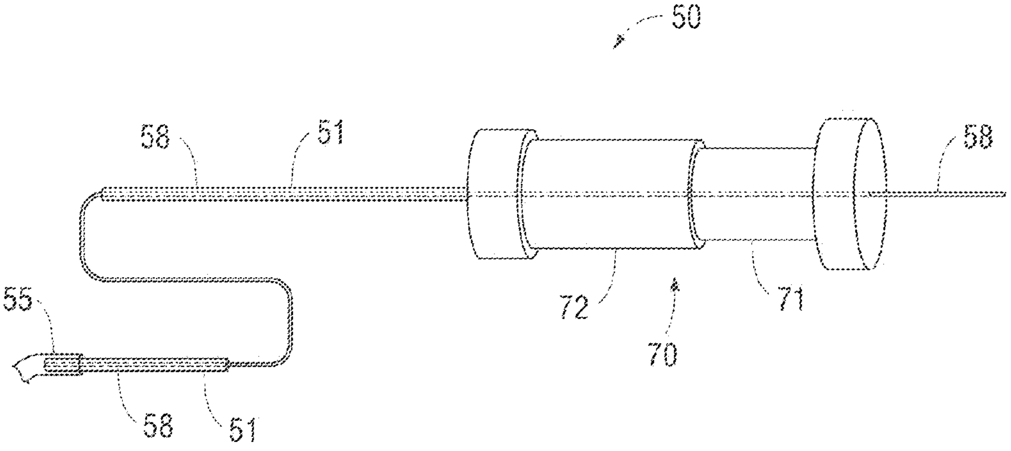
FIG. 6A is a diagram of the proximal end of the medical device according to one embodiment of the present disclosure.

FIG. 6A is a diagram of a medical device 50 according to one embodiment of the present disclosure. As shown, the device 50 includes a tube 51, a distal segment 55 coupled to the distal end of the tube 51, and a sleeve 58. The sleeve 58 is disposed within the lumen of the tube 51. The sleeve 58 can be advanced or retracted within the tube 51 to longitudinally displace the helices 52, 53. The device 50 also includes a handle 70, which is comprised of a proximal component 71 and a distal component 72 and is attached to the proximal end of the tube 51. The proximal component 71 and the distal component 72 each have cylindrical bodies, such that the proximal component 71 may be inserted into the distal component 72 and the sleeve 58 may be inserted into the proximal component 71. The proximal component 71 is reversibly coupled to the sleeve 58 and the distal component 72 is reversibly coupled to the tube 51. Each of the tube 51, the distal segment 55, and the sleeve 58 can be made of one or more of a variety of materials, including, but not limited to, polyimide, polyurethane, polyether block amides (such as Pebax®), nylon, nickel titanium (nitinol), stainless steel braiding, and hollow helical stranded tubing. In addition, the distal segment 55 may have, but is not limited to, a straight, angled, and reverse curved shape.

Figure 6B:
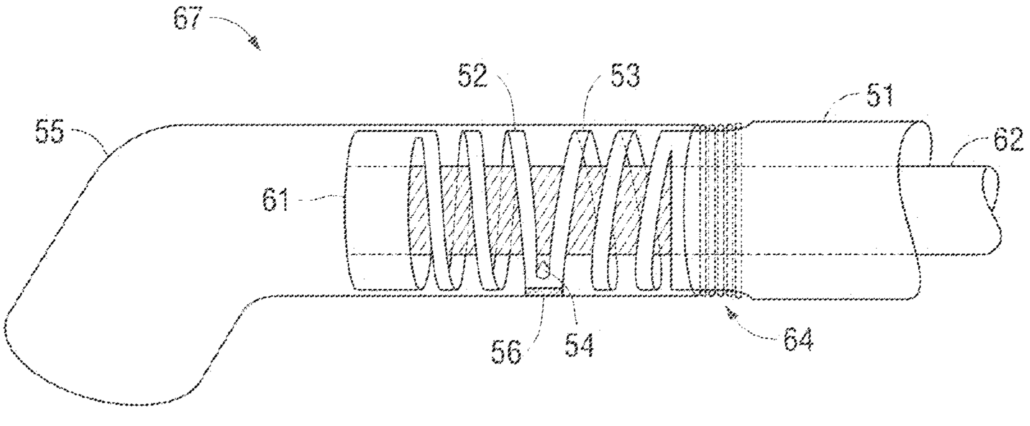
FIG. 6B is a diagram of the distal end of the medical device according to one embodiment of the present disclosure.

FIG. 6B is a close up of the distal segment and the distal end 51. As shown, a dual chirality helix 67 is formed by a distal helix 52 and a proximal helix 53 that are coupled at a junction 54. The distal and proximal helices 52, 53 are formed from the tube 51 by helical cuts, and the proximal helix 53 and the distal helix 52 converge at the junction point 54. The distal segment 55 is located circumferentially around the distal end of the tube 51 and is coupled to the junction point 54 via a coupling means 56. Suitable coupling means between the distal segment 55 and the junction 54 include, but are not limited to, one or more of: 1) adhesives (such as cyanoacrylate), 2) welding, 3) brazing, 4) soldering, and 5) mechanical linking; and additional suitable means are known by those of ordinary skill in the art. As shown, a wire 62 may be disposed within the lumen of the tube 51 and may be slidably advanced or withdrawn from the tube 51 along the long axis of the tube 51. When the wire 62 is advanced, it may abut a capped end 61 of the tube 51. Further advancement of the wire 62 after the wire abuts the capped end 61 may result in linear displacement of the dual chirality helix 67. The force associated with linear displacement of the dual chirality helix 67 produces rotational forces at the junction 54 that rotate the distal segment 55. As well known to one skilled in the art, a thin coil wire 64 can be wound around the proximal end of the distal segment 55 and coupled to the tube 51 to provide a smooth transition between the distal segment 55 and the tube 51. Advantageously, the linear motion is confined to the distal portion of the tube 51, specifically the dual chirality helix 67 and distal therefrom; thus, the entirety of the tube 51 does not require linear displacement.

Figure 7A:
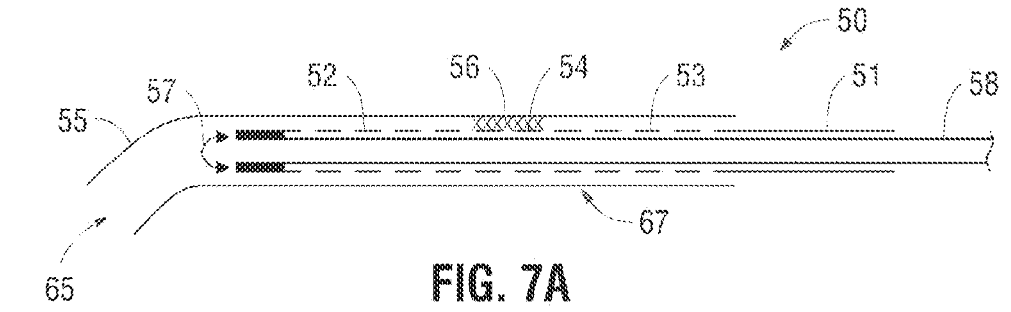
FIG. 7A is a longitudinal cross sectional view of the distal aspect of the device with an open distal end in its resting state according to one embodiment of the present disclosure.

FIG. 7A is a longitudinal cross sectional view of the device 50 with an open distal end 65 in the distal segment 55 in its resting state (i.e. no linear displacement of the dual chirality helix 67). The distal aspect of the device 50 is shown with the tube 51 wherein the dual chirality helix 67 is cut into the distal aspect of the tube 51 so as to form the proximal helix 53 and the distal helix 52. The cut section of the tube 51 may be cut entirely through the tube wall. The proximal helix 53 and the distal helix 52 are formed such that they have opposite orientations. For example, if the proximal helix 53 has a left handed orientation then the distal helix 52 has a right handed orientation or vice versa. The junction point 54 of the left and right handed helices rotates when the dual chirality helix 67 is linearly extended or compressed, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The distal segment 55 can have an angulated tip so as to aid in improved navigation of the device 50. The tube 51 may include of a reduced luminal inner diameter distal to the dual chirality helix 67 that forms a shelf 57. The outer diameter of the sleeve 58 is greater than the inner diameter of the shelf 57 of the tube 51 and is less than the inner diameter of the tube 51 proximal to the shelf 57. The sleeve 58 slide-ably contacts the shelf 57 of the tube 51.

Figure 7B:
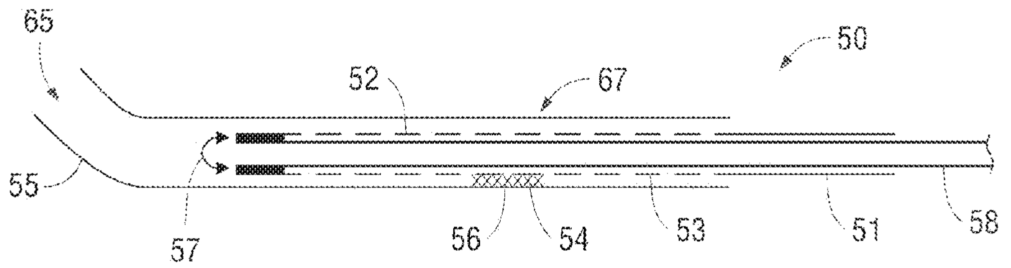
FIG. 7B is a longitudinal cross sectional view of the distal aspect of the device with an open distal end of FIG. 7A with linear displacement of the dual chirality helix via the sleeve abutting the shelf.

FIG. 7B shows the position of the distal end 65 after advancement of the sleeve 58, which linearly displaces the dual chirality helix 67. This in turn results in rotation of the junction point 54 of the proximal helix 53 and the distal helix 52 and subsequent rotation of the distal segment 55. The degree of rotation of the junction point 54 is proportional to the linear displacement of the dual chirality helix 67 of the tube 51. For illustration purposes, 180-degree rotation is shown in FIG. 7B, but different degrees of rotation may be achieved by increasing or decreasing the degree of linear displacement of the sleeve 58.

Figure 8A:
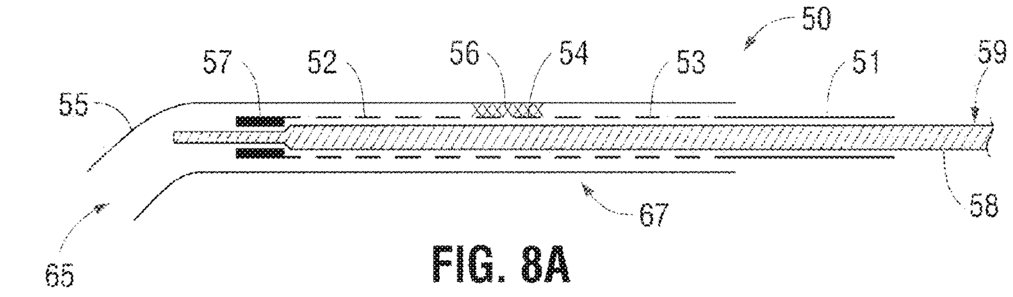
FIG. 8A is a longitudinal cross sectional view of the distal aspect of the device with an open distal end in its resting state, with an interior shelf and wire according to one embodiment of the present disclosure.

FIG. 8A shows a cross sectional view of another embodiment of the distal segment 55 of the device 50 in its resting state. The distal aspect of the device 50 is shown with the tube 51 with the distal end and the proximal end wherein the dual chirality helix 67 is cut into the distal aspect of the tube 51 so as to form the proximal helix 53 and the distal helix 52. The distal segment 55 that is coupled to the junction point 54 of the two helices of the dual chirality helix 67. The proximal helix 53 and the distal helix 52 are formed such that they have opposite orientations. For example, if the proximal helix 53 has a left handed orientation then the distal helix 52 has a right handed orientation or vice versa. By its nature, the junction point 54 of the left and right handed helices rotates when the ends of the dual chirality helix 67 are linearly extended or retracted, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The distal segment 55 can have an angulated tip so as to aid in improved navigation of the device 50. The tube 51 includes the shelf 57 with its reduced luminal inner diameter distal to the dual chirality helix 67. The outer diameter of the sleeve 58 is greater than the inner diameter of the shelf 57 of the tube 51 and is less than the inner diameter of the tube 51 proximal to said shelf 57. The device 50 also includes a wire 59. The wire 59 is disposed in the lumen of the tube 51 and a distal portion of the wire has a reduced diameter so that the distal portion of the wire 59 is dimensioned to pass through the reduced distal diameter of the shelf 57. The remainder of the wire 59, or at least the portion adjacent to the distal portion has a diameter that is greater than the inner diameter of the shelf 57. Thus, the wire 59 with reduced distal diameter slide-ably abuts and engages said shelf 57 of the tube 51.

Figure 8B:
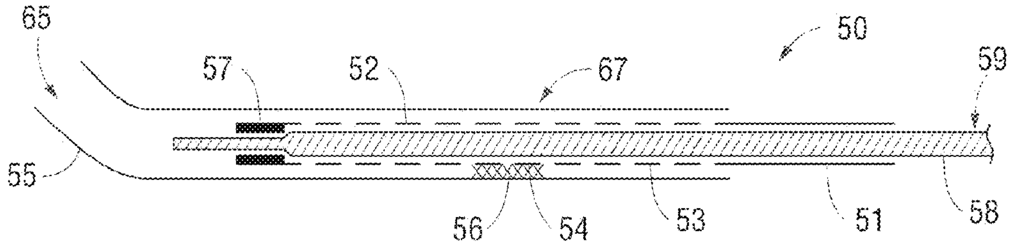
FIG. 8B is a longitudinal cross sectional view of the distal aspect of the device with an open distal end of FIG. 8A with linear displacement of the dual chirality helix via the nonreduced diameter of the wire abutting the shelf.

In FIG. 8B, the wire 59 is shown advanced in the tube 51 and linearly displacing the dual chirality helix 67 as depicted in FIG. 8B. The linear displacing causes rotation of the junction point 54 of the proximal helix 53 and the distal helix 52 and subsequent rotation of the distal segment 55. The degree of rotation of the distal segment 55 is proportional to the linear displacement of the dual chirality helix 67 of the tube 51. For illustration purposes 180-degree rotation is shown in FIG. 8B, but different degrees of rotation may be achieved by increasing or decreasing the degree of linear displacement of the wire 59.

Figure 9A:
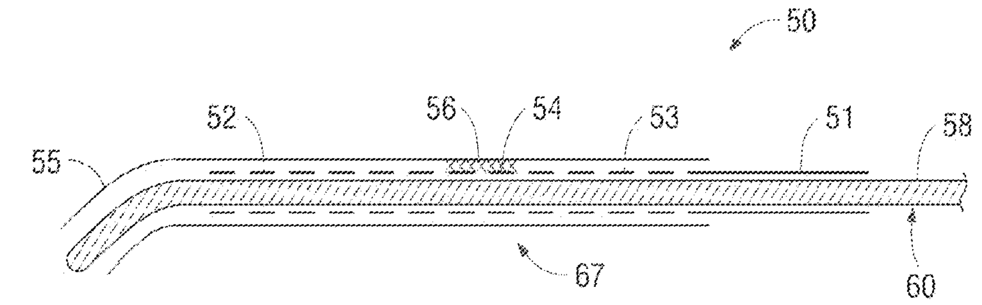
FIG. 9A is a longitudinal cross sectional view of the distal aspect of the device with an open distal end in its resting state with a wire with an expandable member.

FIG. 9A shows a cross sectional view of another embodiment of the distal segment 55 of the device 50 in its resting state with an open distal end 65. The distal aspect of the device 50 is shown with the tube 51 with its distal end and its proximal end wherein a dual chirality helix 67 is cut into the distal aspect of the tube 51 so as to form the proximal helix 53 and the distal helix 52. The distal segment 55 is coupled to the junction point 54 of the two helices of the dual chirality helix 67. The proximal helix 53 and the distal helix 52 are formed such that they have opposite orientations. For example, if the proximal helix 53 has a left handed orientation then the distal helix 52 has a right handed orientation or vice versa. By its nature, the junction point 54 of the left and right handed helices rotates when the ends of the dual chirality helix 67 are linearly extended or retracted, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The distal segment 55 can have an angulated tip so as to aid in improved navigation of the device 50. A wire 60 is disposed coaxially within the lumen of the tube 51, and the wire 60 is reversibly expandable.

Figure 9B:
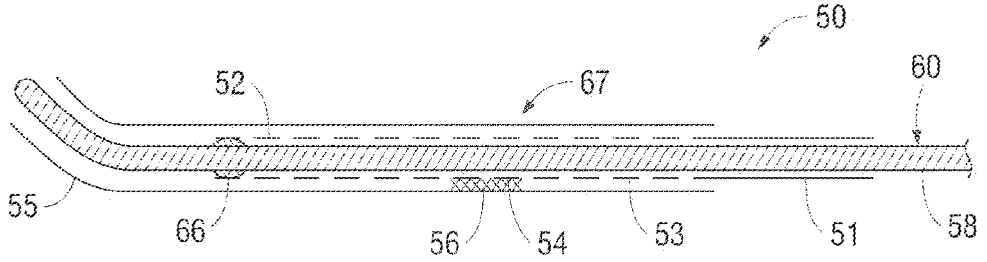
FIG. 9B is a longitudinal cross sectional view of the distal aspect of the device with an open distal end of FIG. 9A with linear displacement of the dual chirality helix via the expanded member of the wire abutting the distal end of the dual chirality helix.

FIG. 9B shows the device 50 of FIG. 9A with the wire 60 expanded so that the expandable member 66 is extended to or greater than the diameter of the tube 51. When the reversibly expandable member 66 is expanded, it engages the distal end of the tube 51. When the wire 60 is advanced while the reversibly expanded member 66 is in its expanded state, the wire 60 induces linear displacement in the dual chirality helix 67. This in turn results in rotation of the junction point 54 of the proximal helix 53 and the distal helix 52 and subsequent rotation of the distal segment 55. The degree of rotation is proportional to the linear displacement of the dual chirality helix 67 of the tube 51. For illustration purposes 180-degree rotation is shown in FIG.

9B, but different degrees of rotation may be achieved by increasing or decreasing the degree of linear displacement of the sleeve 58. When the reversibly expandable member 66 is collapsed, the outer diameter of the wire 60 is less than the inner diameter of the lumen of the tube 51 and thus the wire is able to move freely within the lumen of the tube 51, as shown in FIG. 9A.

Figure 10A:
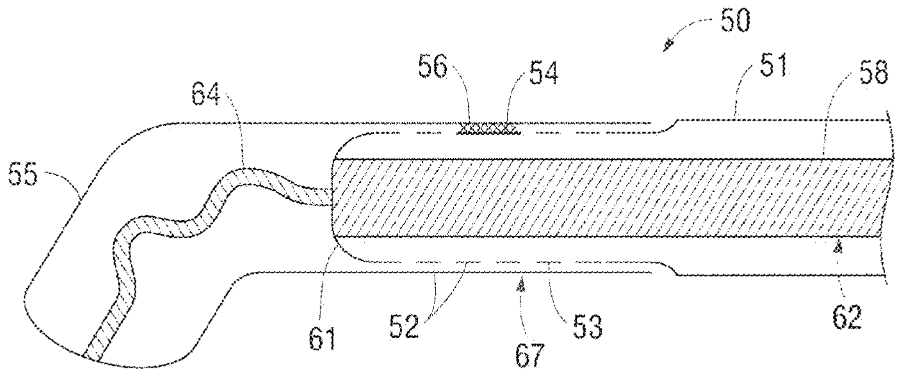
FIG. 10A is a longitudinal cross sectional view of the distal aspect of the medical device with a capped distal end in its resting state.
Figure 10B:
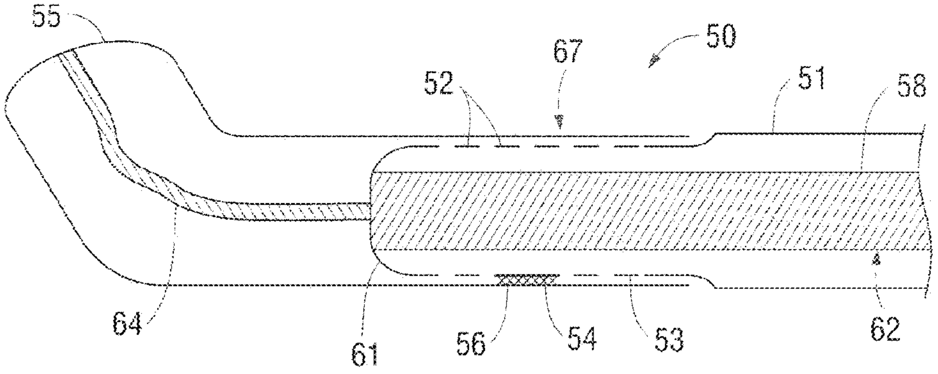
FIG. 10B is a longitudinal cross sectional view of the distal aspect of the medical device with a capped distal end of FIG. 10A with linear displacement of the dual chirality helix via the wire abutting the capped end.

FIG. 10A shows a cross sectional view of another embodiment of the distal aspect of the device 50 in its resting state that includes a capped end 61 on the tube 51. The distal aspect of the device 50 is shown with the tube 51 having the distal end and the proximal end wherein the dual chirality helix 67 is cut into the distal aspect of the tube 51 so as to form the proximal helix 53 and the distal helix 52. The distal segment 55 is coupled to the junction point 54 of the two helices of the dual chirality helix 67. The proximal helix 53 and the distal helix 52 are formed such that they have opposite orientations. For example, if the proximal helix 53 has a left handed orientation then the distal helix 52 has a right handed orientation or vice versa. By its nature, the junction point 54 of the left and right handed helices rotates when the ends of the dual chirality helix 67 are linearly extended or retracted, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The distal segment 55 can have an angulated tip so as to aid in improved navigation of the device 50. A wire 62 is disposed coaxially within the lumen of the tube 51. The wire 62 contacts the capped end 61, and advancing the wire 62 applies force against the capped end 61 and linearly displaces the dual chirality helix 67 as shown in FIG. 10B. This in turn results in rotation of the junction point 54 of the proximal helix 53 and the distal helix 52 and subsequent rotation of the distal segment 55. The degree of rotation is proportional to the linear displacement of the dual chirality helix 67 of the tube 51. For illustration purposes 180-degree rotation is shown in FIG. 10B, but different degrees of rotation may be achieved by increasing or decreasing the degree of linear displacement of the wire 62.

Figure 11A:
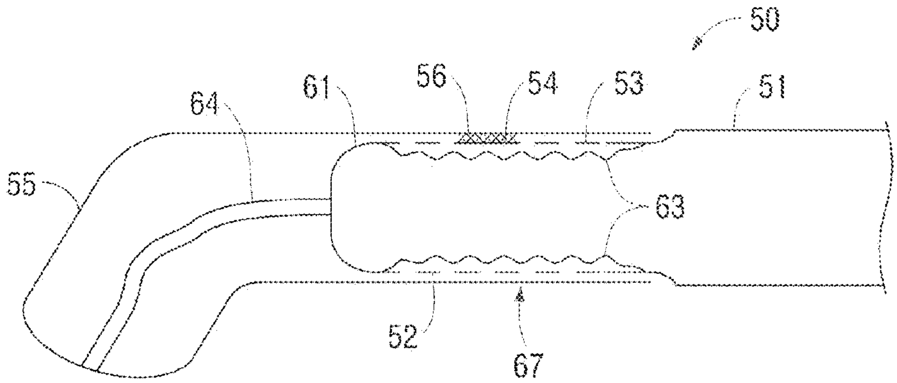
FIG. 11A is a longitudinal cross sectional view of the distal aspect of the device with a capped distal end in its resting state configured to receive an injection of fluid into the lumen of the tube.
Figure 11B:
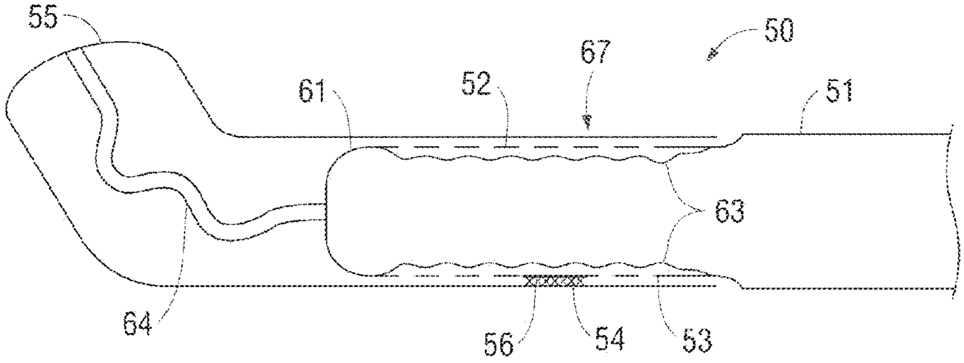
FIG. 11B is an enlarged longitudinal cross sectional view of the distal aspect of the device with a capped distal end of FIG. 11A with linear displacement of the dual chirality helix via the injection of fluid into the lumen of the tube.

FIG. 11A shows a cross sectional view of another embodiment of the distal aspect of the device 50 in its resting state with the capped end 61 of the tube 51. The distal aspect of the device 50 is shown with the tube 51 having the distal end and the proximal end wherein the dual chirality helix 67 is cut into the distal aspect of the tube 51 so as to form the proximal helix 53 and the distal helix 52, and the distal segment 55 is coupled to the junction point 54 of the two helices of the dual chirality helix 67. The proximal helix 53 and the distal helix 52 are formed such that they have opposite orientations. For example, if the proximal helix 53 has a left handed orientation then the distal helix 52 has a right handed orientation or vice versa. By its nature, the junction point 54 of the left and right handed helices rotates when the ends of the dual chirality helix 67 are linearly extended or retracted, resulting in the conversion of linear movement to rotational motion of the junction point 54 of the two helices. The distal segment 55 is located circumferentially around the distal aspect of the tube 51 in which the dual chirality helix 67 is cut. The distal segment 55 is coupled to the junction point 54 of the helices of the dual chirality helix 67 via a coupling means 56. The tip of the distal segment 55 can have an angulated tip so as to aid in improved navigation of the device 50. A membrane or liner 63 is disposed within the lumen of the tube 51. Injection of fluid within the lumen of the tube 51 expands the membrane 63, and imparts linear displacement on the dual chirality helix 67 as shown in FIG. 11B. This in turn results in rotation of the junction point 54 of the proximal helix 53 and the distal helix 52 and subsequent rotation of the distal segment 55. The degree of rotation is proportional to the linear displacement of the dual chirality helix 67 of the tube 51. The injection or withdrawal of fluid from the interior of the membrane 63 can be precisely controlled, which allows for fine adjustments to the rotation of the distal segment 55. The fine adjustments enable the medical device 100 to be used with vasculature that has small vessels and allowed for selections of specific branches with little risk of impacting the vascular walls due to whip or overshooting a selected branch during rotation of the distal segment 55. Additionally, the fine adjustments enable precision positioning of auxiliary equipment, such as a lamp for illumination of the interior of the body, where discrete and/or subtle adjustments in rotation angle are beneficial or necessary. It is noted that fine adjustments also reduce the buildup of potential energy in the distal segment 55 that could result in whip if release too suddenly. For illustration purposes 180-degree rotation is shown in FIG. 11B, but different degrees of rotation may be achieved by increasing or decreasing the degree of linear displacement dual chirality helix 67 with the inflation/deflation of the membrane 63. In some embodiments, the single helix 203 may be substituted for the dual chirality helix 67. See, e.g., FIGS. 23-25.

Figure 12A:
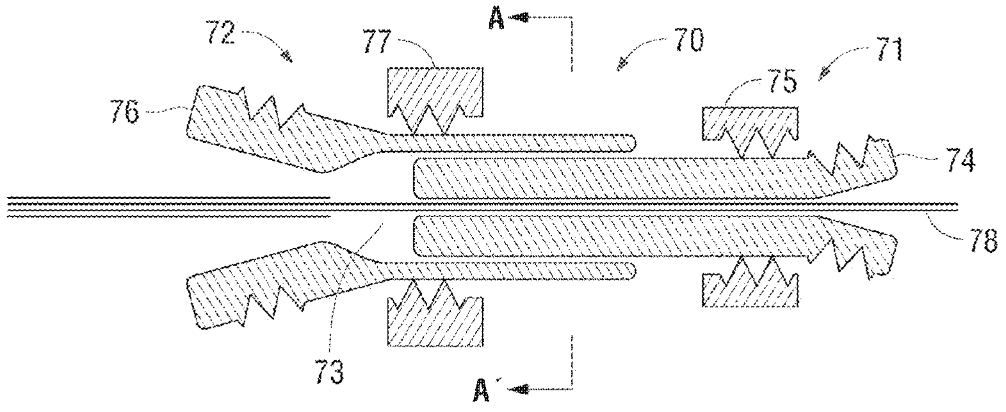
FIG. 12A is a longitudinal cross sectional view of the handle with controlled linear displacement in an open state.

FIG. 12A shows a cross sectional view of a handle 70 that is suitable as an embodiment of the handle 13 shown in FIG. 1 for grasping the proximal end 11 of the device 10. The handle 70 may include a proximal component 71 and a distal component 72, wherein the proximal component and 71 and a distal component 72 are coaxial with one another. The proximal component 71 and the distal component 72 may be made of one or more of a variety of materials, including, but not limited to, one or more of: polycarbonate and metal. The distal component 72 has a cylinder 73 which is configured to slidably receive the proximal aspect of the tube 51 and the sleeve 58 or a wire 78. The proximal component 71 and the distal component 72 configured to move relative to one another along the long axis of the handle 70.

Figure 12B:
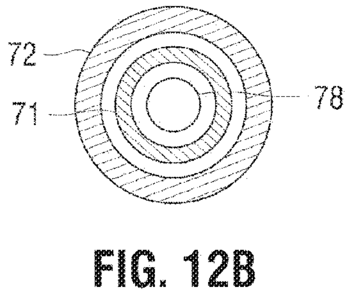
FIG. 12B is a transverse cross sectional view of the handle with controlled linear displacement through A-A' in FIG. 12A.

A distal fitting 76 is located on the distal end of the distal component 72. This distal fitting 76 is flared away from the lumen 73. A proximal fitting 74 is located on the distal end of the proximal end of the proximal component 71 and is also flared away from the cylinder 73. A distal compression nut 77 is fitted about the outer diameter of the distal component 72. The distal fitting 76 is threaded such that the threads mate with the distal compression nut 77. A proximal compression nut 75 is fitted about the outer diameter of the proximal component 71. The proximal fitting 74 is threaded such that the threads mate with the proximal compression nut 75. FIG. 12B shows a short axis cross section through line A-A'. The proximal component 71 and the distal component 72 are coaxial with each other and the wire 78.

Figure 13:
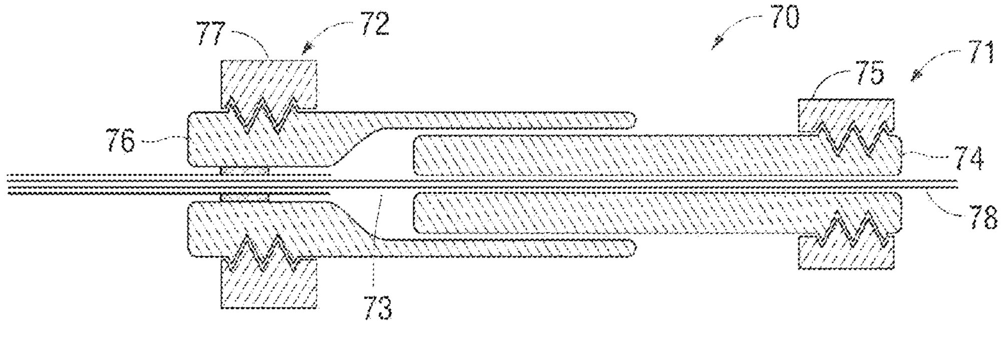
FIG. 13 is a longitudinal cross sectional view of the handle with controlled linear displacement in a closed state.

FIG. 13 shows a cross section through the longitudinal axis of the handle 70 with the proximal compression nut 75 and distal compression nut 77 engaged with the threaded portion of the proximal fitting 74 and the threaded portion of the distal fitting 76, respectively, such that the distal fitting 76 and the proximal fitting 74 are compressed towards the cylinder 73, rather than flared as in FIG. 12A.

Figure 14A:
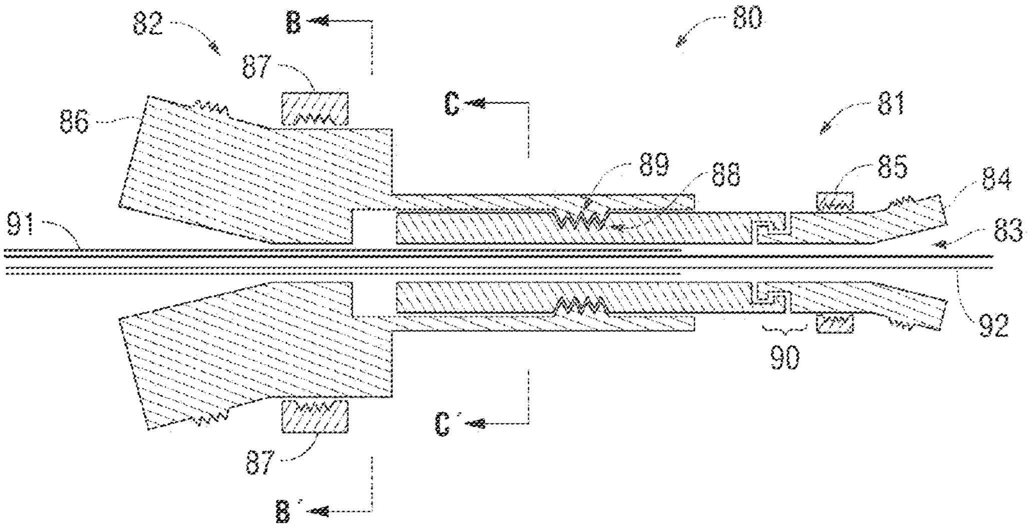
FIG. 14A is a longitudinal cross sectional view of the handle with controlled linear displacement in an open state.

FIGS. 14A-140 and FIGS. 15A-15C show a handle 80 that is suitable as another embodiment of the handle 13 shown in FIG. 1 for grasping the proximal end 11 of the device 10. FIG. 14A shows the handle 80 including a proximal component 81 and a distal component 82 wherein the proximal component 81 and a distal component 82 are coaxial with one another. The proximal component 81 and the distal component 82 may be made of one or more of a variety of materials, including, but not limited to, one or more of: polycarbonate and metal. The distal aspect of the proximal component 81 has a threaded portion herein referred to as proximal component threads 88 and the proximal portion of the distal component 82 has a threaded portion herein referred to as distal component threads 89. The proximal component 81 and the distal component 82 are capable of displacement with respect to one another along the long axis of the handle 80 via rotation of the proximal component 81 with respect to the distal component 82. A swivel 90 is disposed within the proximal component 81 such that the proximal fitting 84 and the proximal component 81 may be rotated relative to one another. The handle 80 has a lumen 83 that is dimensioned to receive the proximal aspect of a tube 91 and a sleeve or wire 92 that is disposed coaxially within the tube 91 for at least part of its length.

A distal fitting 86 is located on the distal end of the distal component 82. The distal end of the distal fitting 86 is flared away from the lumen 83. A proximal fitting 84 is located on the proximal end of the proximal component 81. The proximal end of the proximal fitting is flared away from the lumen 83. A distal compression nut 87 is fitted about an outer diameter of the distal component 82. The distal fitting 86 is threaded such that the threads mate with the distal compression nut 87. A proximal compression nut 85 is fitted about the outer diameter of the proximal component 81. The proximal fitting 84 is threaded such that the threads mate with the proximal compression nut 85.

Figure 14B:
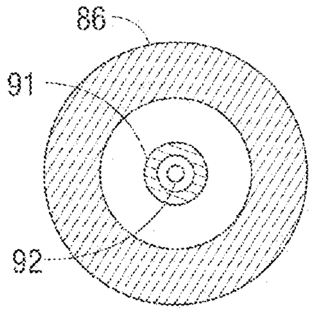
FIG. 14B is a transverse cross sectional view of the handle with controlled linear displacement through B-B' in FIG. 14A.
Figure 14C:
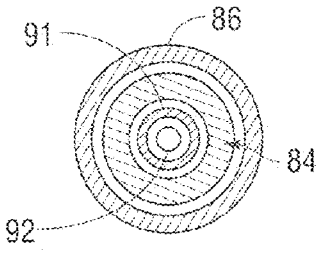
FIG. 14C is a transverse cross sectional view of the handle with controlled linear displacement through C-C' in FIG. 14A.

FIG. 14B shows a short axis cross section through line B-B' of FIG. 14A, which passes through the distal fitting 86. The longitudinal displacer, such as sleeve or wire 92, is shown coaxial with the tube 91, and both the sleeve or wire 92 and the tube 91 are coaxial with the distal fitting 86. Likewise, FIG. 14C shows a short axis cross section through line C-C' of FIG. 14A, which passes through the proximal fitting 84 where it overlaps the distal fitting 86. The sleeve or wire 92 is shown coaxial with the tube 91, as well as, the proximal fitting 84 and the distal fitting 86.

Figure 15A:
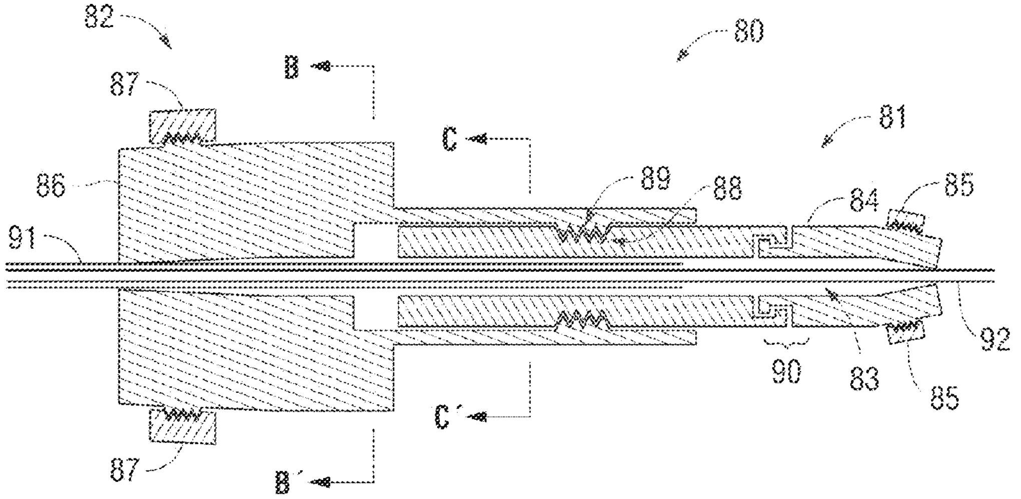
FIG. 15A is a longitudinal cross sectional view of the handle with controlled linear displacement in a closed state.
Figure 15B:
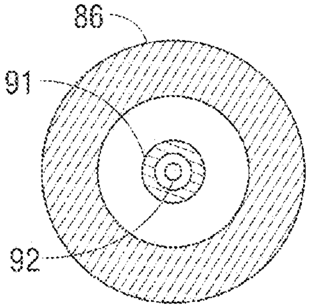
FIG. 15B is a transverse cross sectional view of the handle with controlled linear displacement through B-B' in FIG. 15A.
Figure 15C:
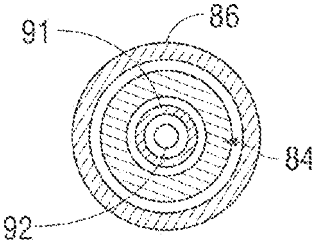
FIG. 15C is a transverse cross sectional view of the handle with controlled linear displacement through C-C' in FIG. 15A.

FIG. 15A shows a cross section through the longitudinal axis of the handle 80 with the proximal compression nut 85 and the distal compression nut 87 engaged with the threaded portion of the proximal fitting 84 and the threaded portion of the distal fitting 86, respectively, such that the distal fitting 86 and the proximal fitting 84 are compressed towards the lumen 83. FIG. 15B shows a short axis cross section through line B-B' of FIG. 15A, which passes through the distal fitting 86. The sleeve or wire 92 are shown coaxial with the tube 91, and both the sleeve or wire 92 and the tube 91 are coaxial with the distal fitting 86. Likewise, FIG. 15C shows a short axis cross section through line C-C' of FIG. 15A, which passes through the proximal fitting 84 where it overlaps the distal fitting 86. The sleeve or wire 92 is shown coaxial with the tube 91, as well as, the proximal fitting 84 and the distal fitting 86.

Figure 16:
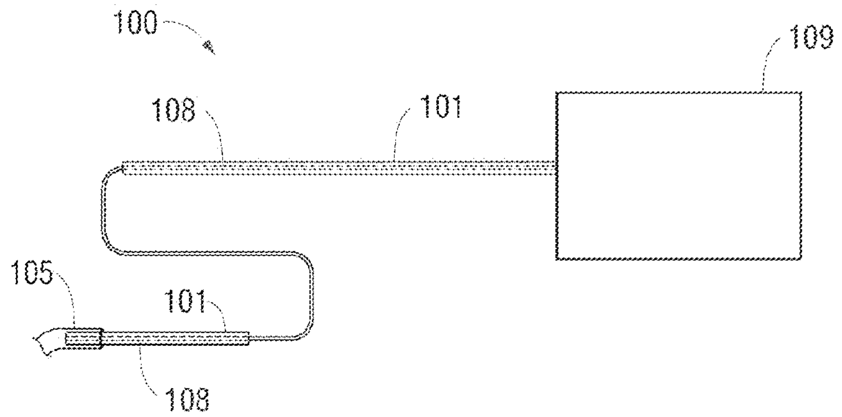
FIG. 16 is a diagram of a second embodiment of the medical device wherein the dual chirality helix is displaced via the tube undergoing a shape transformation in response to a change in the surrounding environment.

FIG. 16 is a diagram of another embodiment of the apparatus that includes a medical device 100 wherein a dual chirality helix 1709 (see FIG. 17A) is cut into the distal aspect of the tube 101. The tube 101 includes a material, including but not limited to nickel titanium (nitinol), selected to undergo a shape transformation in response to a change in the local environment, such that there is elongation of the dual chirality helix 1709. A conduit 108 is disposed within the tube 101. The conduit 108 may be connected to a source 109 for an agent for changing the local environment is located within the tube 101. Exemplary agents for changing the local environment may include, but are not limited to, one or more of: a battery for Joule heating or altering the magnetic field, a radiofrequency generator, a microwave generator, a heat source, a light source, and a chemical source of releasable ions. In one embodiment, the dual chirality helix 1709 may linearly elongate when exposed to an increase in temperatures. The elongation may take place over a temperature range of 40 degrees C. to 90 degrees C. In some embodiments, the temperature range for elongation may be between 40 degrees C. and 60 degrees C. A distal segment 105 is coupled to the distal aspect of the tube 101.

Figure 17A:
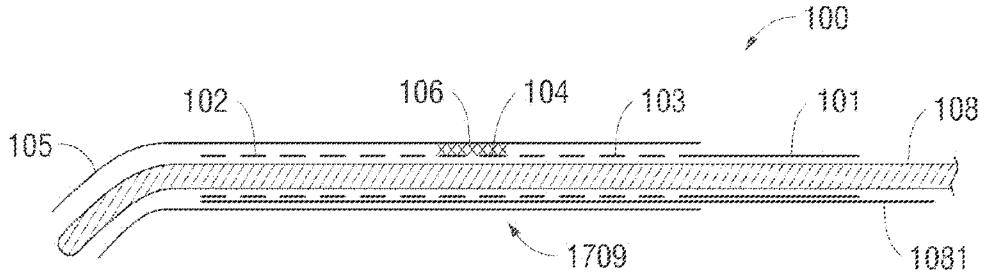
FIG. 17A is a longitudinal cross sectional view of the distal aspect of the device in its resting state according to another embodiment of the present disclosure.

FIG. 17A is a longitudinal cross sectional view of the distal aspect of one embodiment of the medical device 100 in its resting state where there is no linear displacement of the dual chirality helix 1709. The distal aspect of the medical device 100 is shown with the tube 101 with a distal end and a proximal end wherein the dual chirality helix 1709 is cut into the distal aspect of the tube 101 so as to form a proximal helix 103 and a distal helix 102. The conduit 108 is located coaxially within the lumen of the tube 101, and a distal segment 105 is coupled to the junction point 104 of the two helices 102, 103 of the dual chirality helix 1709. The proximal helix 103 and the distal helix 102 are formed such that they have opposite orientations. For example, if the proximal helix 103 has a left handed orientation then the distal helix 102 has a right handed orientation or vice versa.

By its nature, the junction point 104 of the left and right handed helices rotates when the ends of the dual chirality helix 1709 are linearly extended or retracted, resulting in the conversion of linear movement to rotational motion of the junction point 104 of the two helices 102, 103. The distal segment 105 is located circumferentially around the distal aspect of the tube 101 in which the dual chirality helix 1709 is cut. The distal segment 105 is coupled to the junction point 104 of the helices 102, 103 of the dual chirality helix 1709 via a coupling means 106 including, but not limited to, one or more of: 1) adhesives (such as cyanoacrylate), 2) welding, 3) brazing, 4) soldering, and 5) mechanical linkage. The distal segment 105 can have an angulated tip so as to aid in improved navigation of the medical device 100. Some embodiments may include an optional means for counteracting shape transformation of the tube 101, including, but not limited to, coupling the conduit 108 to the distal end of the tube 101. In one embodiment, the tube 101 has a distal diameter that is slightly greater than the rest of the tube 101 and a thin wire 1081 is run in the tube 101 adjacent to said conduit 108, such as in the annular space between the tube 101 and the conduit 108. When tension is applied to the conduit 108 with the thin wire 1081 in place, tension on the thin wire 1081 counteracts the linear displacement of the dual chirality helix 1709.

Figure 17B:
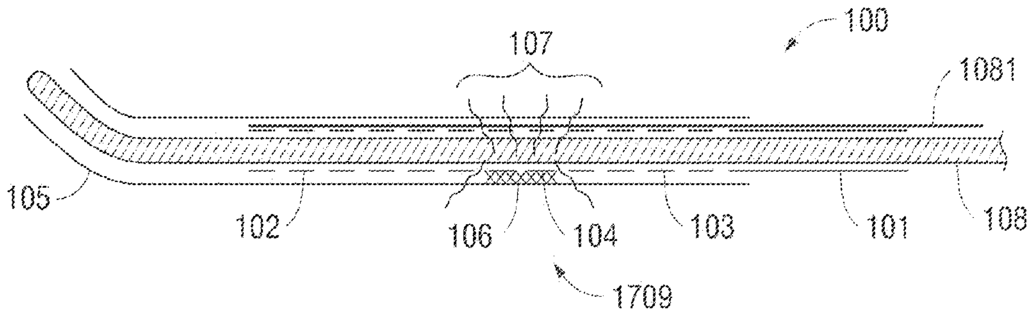
FIG. 17B is a longitudinal cross sectional view of the distal aspect of the medical device of FIG. 17A with linear displacement of the dual chirality helix secondary to shape transformation of the tube.

FIG. 17B shows a longitudinal cross sectional view of the distal aspect of the embodiment of FIG. 17A when a change in the local environment 107 is delivered to the environment around the dual chirality helix 1709, wherein local in proximity to the dual chirality helix 1709. An exemplary change in the local environment may be a change in local temperature that can cause part of the medical device 100 to undergo shape transformation due to heat expansion or contraction. The change in the local environment may include one or more of changes in temperature, pH, magnetic field strength, ion concentration, and light. The change in the local environment 107 may result in a shape transformation of the proximal helix 103 and distal helix 102 and cause linear displacement of the dual chirality helix 1709. The junction point 104 of the proximal helix 103 and the distal helix 102 rotates and, in turn, rotates the distal segment 105. The degree of rotation of the distal segment 105 is proportional to the linear displacement of the dual chirality helix 1709 of the tube 101. For illustration purposes 180-degree rotation is shown. In some embodiments, the distal helix 102 and the proximal helix 103 may be comprised of a shape member alloy (such as, but not limited to, nitinol) or a shape memory polymer (such as, but not limited to, block copolymer of polyethylene terephthalate (PET) and polyethyleneoxide (PEO)).

In some embodiments, the thin wire 1081 may be used to restrain the longitudinal movement of the junction point 104. Thus, the user, by releasing tension on the wire 1081 may allow the junction point 104 to extend longitudinally in a controlled fashion.

Figure 18:
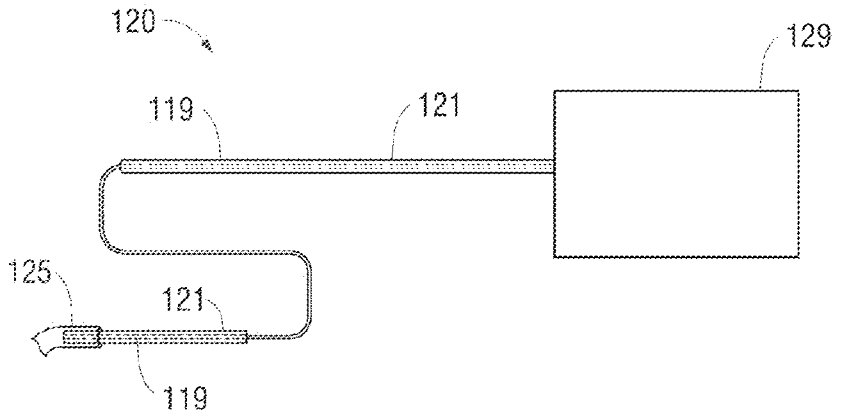
FIG. 18 is a diagram of another embodiment of the medical device wherein the dual chirality helix is displaced via magnetic forces.

FIG. 18 is a diagram of another embodiment of the apparatus that includes a medical device 120 wherein a dual chirality helix 1937 (see FIG. 19A) is cut into a distal aspect of a tube 121 and wherein another means for linear displacement of the tube containing a dual chirality helical cut is provided. The tube 212 can be made of one or more of a variety of materials, including, but not limited to, polyimide, polyurethane, polyether block amides (such as Pebax®), nylon, nickel titanium (nitinol), stainless steel braiding, coiled wire and hollow helical stranded tubing. The proximal end of the medical device 120 is connected to a source of electricity 129, such as a battery, wherein energy is able to be transmitted along the device via conductive elements, such as thin wires. A distal segment 125 is coupled to the distal aspect of the tube 121. The linear displacement means includes, but is not limited to, repulsion or attraction of electrical fields or magnetic fields between elements within or coupled to the distal end of the dual chirality helix 1937 that is capable of emitting a permanent or inducible magnetic field, and elements proximate to, but not in direct contact with the distal end of the dual chirality helix 1937 that is capable of emitting a permanent or inducible magnetic field. Examples of these elements include, but are not limited to, rare earth magnets, coiled wire capable of passage of electrical current, electret, and plate capacitor. Examples of methods for applying opposing electrical or magnetic fields along or proximate to the region of the dual chirality helix 1937 include but are not limited to 1) applying a permanent electrical or magnetic charge on one end of the dual chirality helix 1937 and a variable, inducible charge on the opposite end of the dual chirality helix 1937; 2) applying an inducible electrical or magnetic charge on one end of the dual chirality helix 1937 and a variable, inducible electrical or magnetic charge on the opposite end of the dual chirality helix 1937; 3) applying an electrical or magnetic charge on one end of the dual chirality helix 1937 and an electrical or magnetic charge on a portion of a guidewire 119 proximate to the dual chirality helix 1937.

FIG. 19A shows a longitudinal cross sectional view of the distal aspect of a medical device 110 suitable for use as an alternative for the distal aspect of the medical device 120 of FIG. 18 in its resting state. The distal aspect of the medical device 110 is shown with a tube 111 with a distal end and a proximal end wherein a dual chirality helix 1937 is cut into the distal aspect of the tube 111 so as to form a proximal helix 113 and a distal helix 112, a distal magnetic element 117, a proximal magnetic element 118, and a distal segment 115 that is coupled to the junction point 114 of the two helices 112, 113 of the dual chirality helix 1937. Each of the magnetic elements 117, 118 may be biocompatible. Exemplary magnetic elements 117, 118 may include rare earth magnets and coil-electromagnets. The types of electromagnets used for magnetic elements 117 and 118 may be the same or different. The magnetic elements 117, 118 are selected such that the force of attraction/repulsion between the magnetic elements 117, 118, when energized, is sufficient to overcome the spring force of the dual chirality helix 1937. The magnetic elements 117, 118 may be connected to the tube 111 in proximity to opposite ends of the dual chirality helix 1937, so that magnetic force between the magnetic elements 117, 118, when energized, will elongate or compress the dual chirality helix 1937 longitudinally, depending on the configuration of the magnetic elements 117, 118 (attractive or repulsive magnetic force). In this manner, the energizing of one or both of the magnetic elements 117, 118, by elongating or compressing the dual chirality helix 1937, imparts rotational force on the distal segment 115 without rotating the guidewire 119. Exemplary magnetic elements 117, 118 may include permanent magnets (such as rare earth magnets) and electromagnets. In some embodiments, one of the magnetic elements 117, 118 may be a ferromagnetic material that response to a magnetic field is not itself magnetic. The proximal helix 113 and the distal helix 112 are formed such that they have opposite orientations. For example, if the proximal helix 113 has a left handed orientation then the distal helix 112 has a right handed orientation or vice versa. By its nature, the junction point 114 of the left and right handed helices rotates when the ends of the dual chirality helix 1937 are linearly extended or retracted, resulting in the conversion of linear movement to rotational motion of the junction point 114 of the two helices. The distal segment 115 is located circumferentially around the distal aspect of the tube 111 in which the dual chirality helix 1937 is cut. The distal segment 115 is coupled to the junction point 114 of the helices 112, 113 of the dual chirality helix 1937 via a coupling means 116. The coupling means 116 may include, but is not limited to, one or more of: 1) adhesives (such as cyanoacrylate), 2) welding, 3) brazing, 4) soldering, and 5) mechanical linking. The distal segment 115 can have an angulated tip so as to aid in improved navigation of the medical device 110.

Figure 19B:
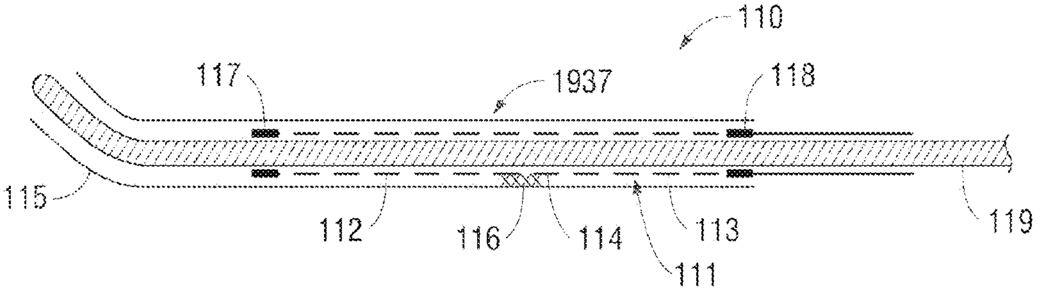
FIG. 19B is a longitudinal cross sectional view of the distal aspect of the medical device with the magnetic displacement mechanism of FIG. 19A with linear displacement of the dual chirality helix secondary magnetic forces imparted on the tube.

FIG. 19B shows a longitudinal cross sectional view of the distal aspect of the medical device 110 from FIG. 19A when the magnetic field at least one of the distal magnetic element 117 and the proximal magnetic element 118 is changed, which causes linear displacement of the dual chirality helix 1937. This in turn rotates the junction point 114 of the proximal helix 113 and the distal helix 112 and subsequent rotation of the distal segment 115. The degree of rotation is proportional to the linear displacement of the dual chirality helix 1937 of the tube 111. For illustration purposes 180-degree rotation is shown.

In some embodiments, a single helix 203 (see, e.g., FIGS. 23-25) can be used as an alternative to the dual chirality helix 1937 in the medical device 110, such that the magnetic elements 117, 118 may be disposed on or in the tube 111 in contact with opposite ends of the single helix 203 to realize elongation or compression of the single helix 203 to impart rotational motion on the distal segment 115 and/or the distal end of the tube 111. Similarly, this rotational motion may be imparted to the distal end of the tube 201 in FIGS. 25A and 25B when magnetic elements 117, 118 are disposed in the device 200 in substantially or identically the same position as in FIGS. 19A and 19B.

Figure 20A:
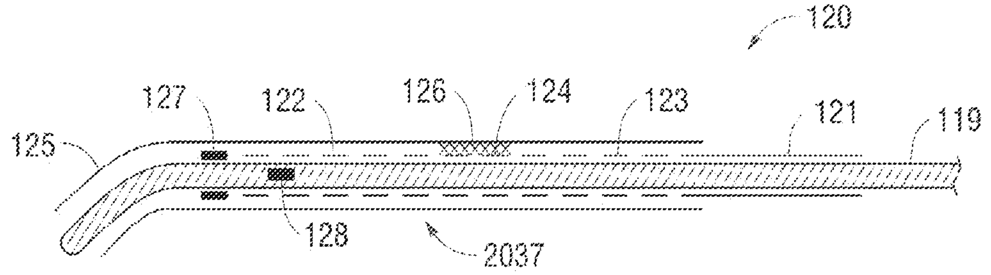
FIG. 20A is a longitudinal cross sectional view of the distal aspect of another embodiment of the medical device with a magnetic displacement mechanism in its resting state where one of the magnetic forces is provided via shaft with a magnetic element.

FIG. 20A is a longitudinal cross sectional view of the distal aspect of an embodiment of the medical device 120 in its resting state. The distal aspect of the medical device 120 is shown with a tube 121 with a distal end and a proximal end (wherein a dual chirality helix 2037 is cut into the distal aspect of the tube 121 to form a proximal helix 123 and a distal helix 122), a tube magnetic element 127, a guidewire magnetic element 128, and a distal segment 125 that is coupled to the junction point 124 of the two helices 122, 123 of the dual chirality helix 2037. The proximal helix 123 and the distal helix 122 are formed such that they have opposite orientations. For example, if the proximal helix 123 has a left handed orientation then the distal helix 122 has a right handed orientation or vice versa. By its nature, the junction point 124 of the left and right handed helices rotates when the ends of the dual chirality helix 2037 are linearly extended or retracted, resulting in the conversion of linear movement to rotational motion of the junction point 124 of the two helices. The distal segment 125 is located circumferentially around the distal aspect of the tube 121 in which the dual chirality helix 2037 is cut. The distal segment 125 is coupled to the junction 124 of the helices 122, 123 of the dual chirality helix 2037 via a coupling means 126. The distal segment 125 may have an angulated tip so as to aid in improved navigation of the medical device 120. The magnetic elements 127, 128 may include one or more of: a permanent magnet and an electromagnet. In some embodiments, one or both of the magnetic elements 127, 128 may be a rare earth magnet. The tube magnetic element 127 may comprise the same or a different magnetic element as the guidewire magnetic element 128. The magnetic elements 127, 128 may be configured to impart attractive or repulsive force between each other to impart linear displacement on the dual chirality helix 2037.

Figure 20B:
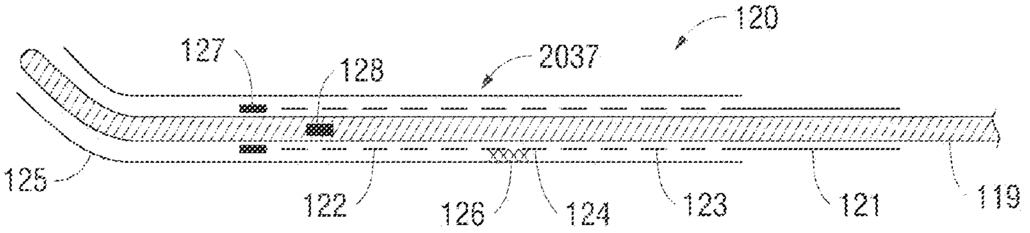
FIG. 20B is a longitudinal cross sectional view of the distal aspect of the medical device with the magnetic displacement mechanism of FIG. 20A with linear displacement of the dual chirality helix secondary magnetic forces imparted on the tube via shaft with a magnetic element.

FIG. 20B demonstrates linear displacement of the dual chirality helix 2037 when there is either 1) a change in the magnetic field of the either the tube magnetic element 127 or the guidewire magnetic element 128 or 2) a change in the distance between the tube magnetic element 127 and the guidewire magnetic element 128. The linear displacement causes the rotation of the junction point 124 of the proximal helix 123 and the distal helix 122 and subsequent rotation of the distal segment 125. The degree of rotation is proportional to the linear displacement of the dual chirality helix 2037 of the tube 121. For illustration purposes, 180-degree rotation is shown.

Figure 21A:
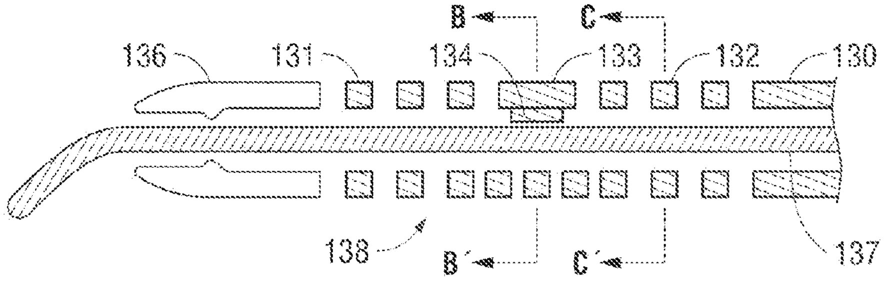
FIG. 21A is a longitudinal cross sectional view of the distal aspect of the medical device with a tooth-gear interface between a guidewire and the tube with no force applied to the distal end of the dual chirality helix.
Figure 21B:
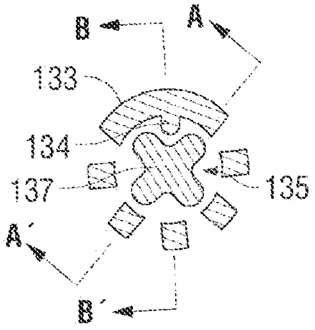
FIG. 21B is a transverse cross sectional view of the distal aspect of the medical device in FIG. 21A through B-B' with no force applied to the distal end of the dual chirality helix.
Figure 21C:
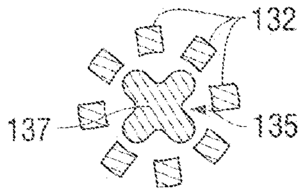

FIG. 21A is a longitudinal cross sectional view of the distal aspect of another embodiment of the device in its resting state. The distal aspect of the device is shown with a tube 130 with a distal end and a proximal end, wherein a dual chirality helix 138 is cut into the distal aspect of the tube 130 to form a proximal helix 132 and a distal helix 131, and a guidewire 137 located within the lumen of the tube 130. The tube 130 can be made of one or more of a variety of materials, including, but not limited to, polyimide, polyurethane, polyether block amides (such as Pebax®), nylon, nickel titanium (nitinol), stainless steel braiding, coiled wire and hollow helical stranded tubing. The proximal helix 132 and the distal helix 131 are formed such that they have opposite orientations. For example, if the proximal helix 132 has a left handed orientation then the distal helix 131 has a right handed orientation or vice versa. By its nature, the junction point 133 of the left and right handed helices 131, 132 rotates when the ends of the dual chirality helix 138 are linearly extended or retracted, resulting in the conversion of linear movement to rotational motion of the junction point 133 of the two helices. The tube 130 has a reduced inner diameter 136 along its distal aspect. The distal aspect of the guidewire 137 has a reduced diameter. The inner diameter of the distal end of the tube 130 is greater than the diameter of the distal aspect of the guidewire 137 but less than the non-reduced diameter of the guidewire 137. The guidewire 137 may include one or more grooves 135 that located along the longitudinal axis of the guidewire 137. An engagement means 134 for engaging the guidewire 137, such as a tooth 134 is disposed between the guidewire 137 and the tube 130 at the junction point 133 of the dual chirality helix 138. The tooth 134 slidably engages one or more of the grooves 135 along the distal aspect of the guidewire 137. FIG. 21B shows a short axis cross section through line B-B' of FIG. 21A, which passes through the tube at the junction point 133. The tooth 134 is shown protruding from the tube 130 at the junction point 133 and meshing with one of the grooves 135 in the guidewire 137. FIG. 210 shows a short axis cross section through line C-C' of FIG. 21A, which passes through the proximal helix 132 of the tube 130. Advancing the guidewire 137 into the tube 130 results in linear displacement of the dual chirality helix 138. This in turn results in rotation of the junction point 133 and tooth 134 and subsequent rotation of the distal aspect of the guidewire 137 as depicted in FIGS. 22A and 22B.

Figure 22A:
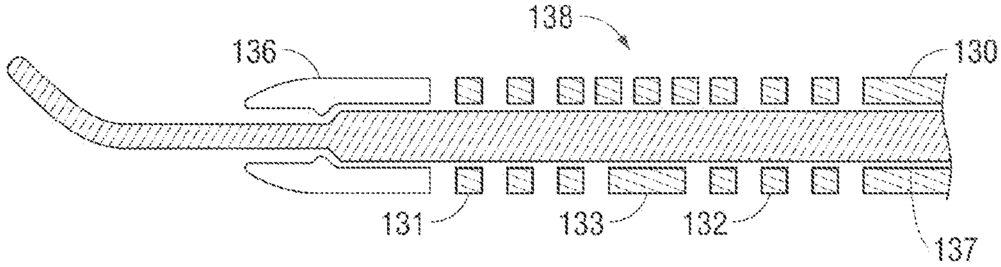
FIG. 22A is a longitudinal cross sectional view of the distal aspect of the guidewire at the level of the tooth-gear interface when the dual chirality helix undergoes longitudinal displacement.
Figure 22B:
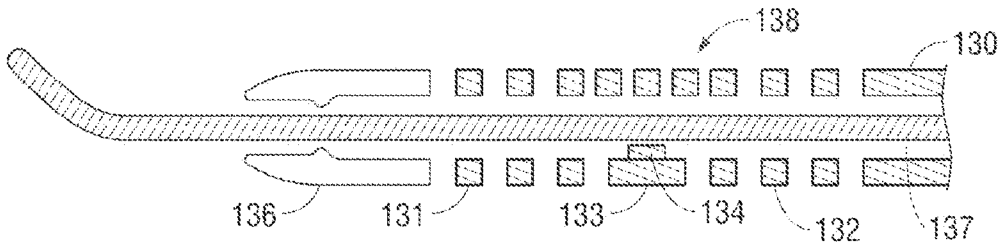
FIG. 22B is a longitudinal cross sectional view of the distal aspect of the guidewire at the level of the tooth-gear interface when the dual chirality helix undergoes longitudinal displacement.

FIG. 22A shows a longitudinal cross sectional view through line A-A' in FIG. 21B when the dual chirality helix 138 is displaced. FIG. 22B shows a longitudinal cross sectional view through line B-B' in FIG. 21B when the dual chirality helix 138 is displaced. The degree of rotation is proportional to the displacement of the dual chirality helix 138 of the tube 130.

Figure 23A:
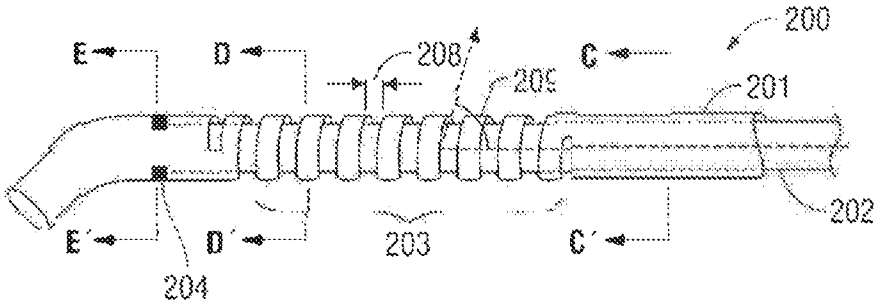
FIG. 23A is a diagram of a catheter with a single helix formed from a tube according to one embodiment of the present disclosure.
Figure 23B:
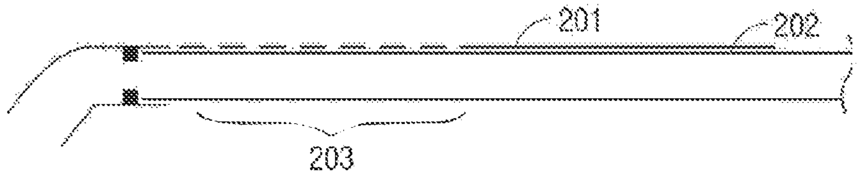
FIG. 23B is a cross-sectional view of FIG. 23A.
Figure 23C:
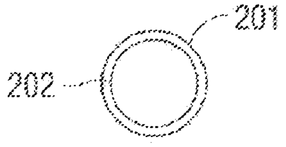
FIG. 23C is a transverse cross section of FIG. 23A through lines C-C'.
Figure 23D:
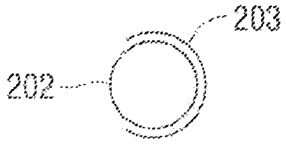
FIG. 23D is a transverse cross section of FIG. 23A through lines D-D'.
Figure 23E:
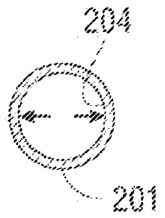
FIG. 23E is a transverse cross section of FIG. 23A through lines E-E'.
Figure 23F:
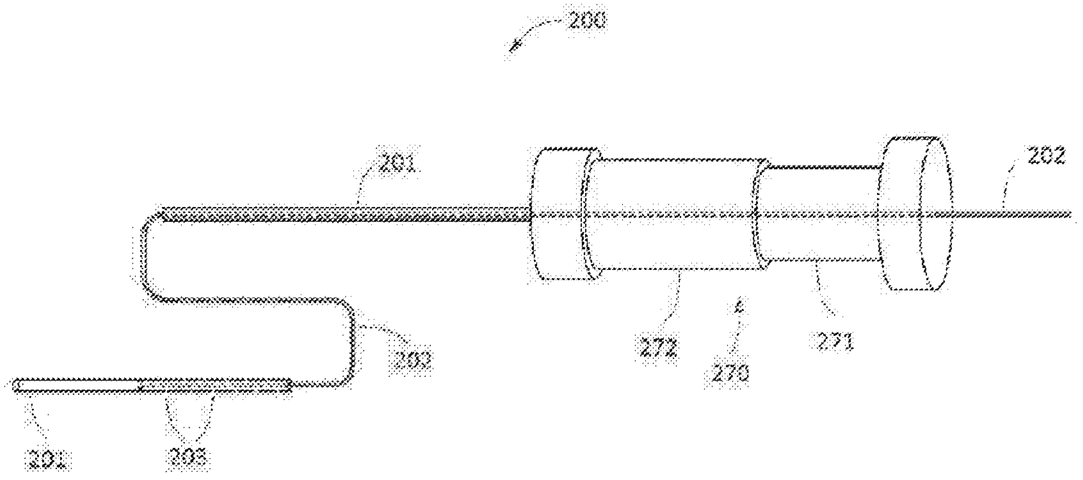
FIG. 23F is a diagram of a handle connected to the catheter of FIG. 23A.

FIG. 23A illustrates a medical device 200 according to another embodiment of the present application. As shown, the device 200 can include a tube 201, a longitudinal displacer, such as, for example, a sleeve 202, and a handle 270 that is attached to the proximal end of the tube 201. In some embodiments, a helical or spiral cut 203 is present in the distal aspect of the tube 201 wherein the helical or spiral cut 203 has a cut width 208 and helical angle 209. The end of the tube 201 distal to the helical cut 203 may include a curve to aid in navigating the medical device 200 through the vasculature. The cut width 208 can range from 0.1 micrometers to 30 millimeters. In some embodiments, the cut width may range from about 0.1 millimeters to about 10 millimeters. The helical angle can range from 10 to 80 degrees relative to the longitudinal axis of the tube 201. In some embodiments, the helical angle range from 15 to 75 degrees. The sleeve 202 is disposed within the lumen of the tube 201. The tube 201 may have a reduced inner diameter on the distal end to form a shelf 204 that prevents forward movement of the sleeve 202. In some embodiments, the sleeve 202 may abut the shelf 204 to transmit longitudinal force from the sleeve 202 to the tube 201. In some embodiments, the sleeve 202 may be coupled to the tube 201 at a point distal to the helical or spiral cut 203, such as at the shelf 204, and can be advanced or retracted within the tube 201 wherein advancement or retraction of the sleeve 202 results in advancement or retraction of the tube 201 distal to the helical or spiral cut 203. In some embodiments, the coupling means may be reversible, such as a solder connection that can be melted by application of electric current or heat to release the sleeve 202 from the tube 201. Means of coupling the sleeve 202 and tube 201 include, but are not limited to, one or more of: 1) frictional fit, 2) adhesives (such as cyanoacrylate), 3) welding, 4) brazing, 5) soldering, and 6) mechanical linking. As depicted in FIG. 23F the device 200 also includes a handle 270, which is comprised of a proximal component 271 and a distal component 272 and is attached to the proximal end of the tube 201. The proximal component 271 and the distal component 272 each have cylindrical bodies, such that the proximal component 271 may be inserted into the distal component 272 and the sleeve 202 may be inserted into the proximal component 271. The proximal component 271 is reversibly coupled to the sleeve 202 and the distal component 272 is reversibly coupled to the tube 201. Each of the tube, 201 and the sleeve 202 can be made of one or more of a variety of materials, including, but not limited to, polyimide, polyurethane, polyether block amides (such as Pebax®), nylon, nitinol, stainless steel braiding, coiled wire and hollow helical stranded tubing. The lumen of the tube 201 and outer surface of the sleeve 202 preferentially have a low coefficient of friction, including but not limited to PTFE or a hydrophilic coating. In addition, the distal aspect of the tube 201 may have, but is not limited to, a straight, angled, and reverse curved shape. FIG. 23C is an axial cross section through line C-C' in FIG. 23A. FIG. 23D is an axial cross section through line D-D' in FIG. 23A. FIG. 23B is a longitudinal cross section of the device 200 in FIG. 23A. FIG. 23E is an axial cross section through line E-E' in FIG. 23A.

Figure 24A:
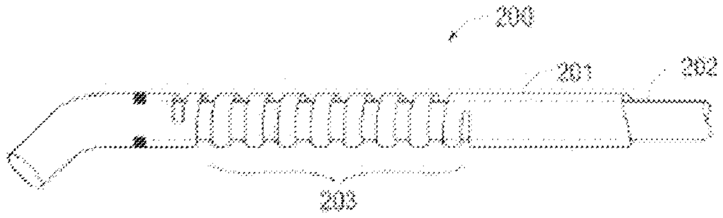
FIG. 24A is a diagram of the catheter of FIG. 23A at rest (no longitudinal force) with a distal member.
Figure 24B:
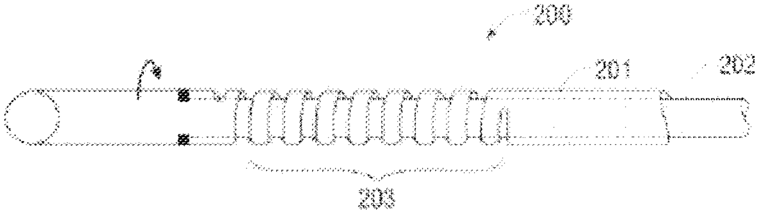
FIG. 24B is a diagram of the catheter of FIG. 23A with longitudinal force at the proximal end causing a rotation of the distal end by 90 degrees.
Figure 24C:
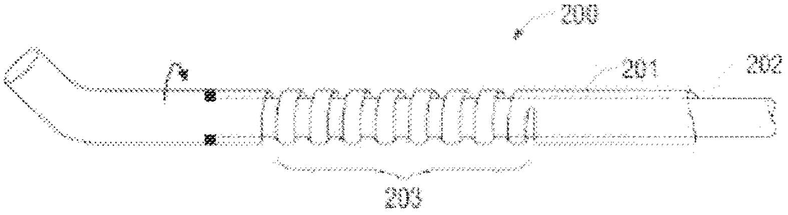
FIG. 24C is a diagram of the catheter of FIG. 23A with longitudinal force at the proximal end causing a rotation of the distal end by 180 degrees.
Figure 24D:
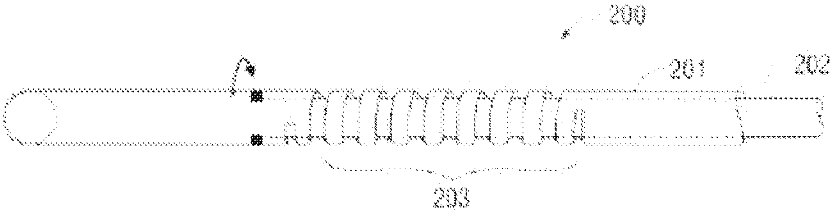
FIG. 24D is a diagram of the catheter of FIG. 23A with longitudinal force at the proximal end causing a rotation of the distal end by 270 degrees.

FIG. 24A shows the device 200 wherein the device 200 is in its resting state (no longitudinal displacement) of the distal end of the tube 201. FIG. 24B shows the device 200 wherein there is longitudinal displacement of the distal end of the tube 201 by advancement of the sleeve 202 such that the distal end of the tube 201 results in 90 degrees of rotation relative to the position of the distal end of the tube 201 in FIG. 24A. FIG. 24C shows the device 200 wherein there is further longitudinal displacement of the distal end of the tube 201 by advancement of the sleeve 202 such that the distal end of the tube 201 results in 180 degrees of rotation relative to the position of the distal end of the tube 201 in FIG. 24A. FIG. 24*d* shows the device 200 wherein there is further longitudinal displacement of the distal end of the tube 201 by advancement of the sleeve 202 such that the distal end of the tube 201 results in 270 degrees of rotation relative to the distal position of the tube 201 in FIG. 24A.

Figure 25A:
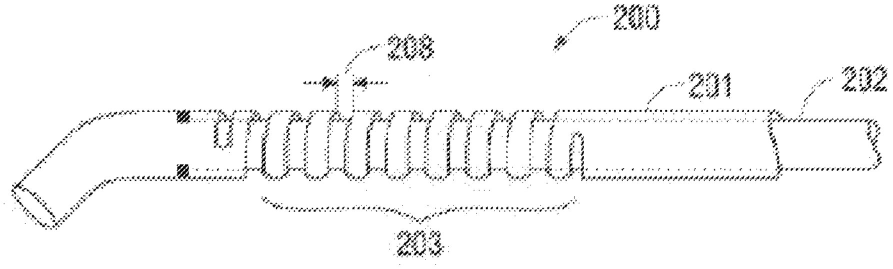
FIG. 25A is a diagram of the catheter of FIG. 23A while in its resting state (0 degrees of rotation)
Figure 25B:
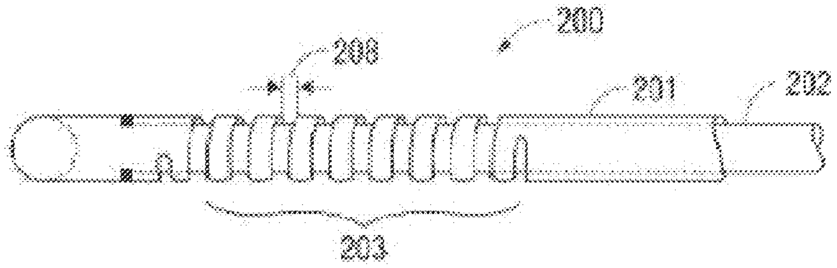
FIG. 25B is a diagram of the catheter of FIG. 23A when the sleeve is retracted to reverse the rotation of the distal end to −90 degrees.

FIG. 25A shows the device 200 wherein the device 200 is in its resting state (no longitudinal displacement) of the distal end of the tube 201. FIG. 25B shows the device 200 wherein there is longitudinal displacement of the distal end of the tube 201 by retraction of the sleeve 202 such that the distal end of the tube 201 results in −90 degrees of rotation.

Figure 26A:
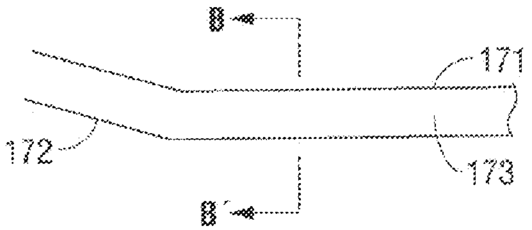
FIGS. 26A and 26B schematically illustrate a chronic total occlusion crossing device embodiment of the distal segment.
Figure 26B:

FIG. 26A is a longitudinal cross sectional view of a chronic total occlusion crossing device embodiment 170 of the distal segment 171 wherein the distal segment 171 and a lumen 173. In one embodiment the distal segment 171 has a beveled tip 172. FIG. 26B is a short axis view through line B-B' in FIG. 26A.

Figure 27A:
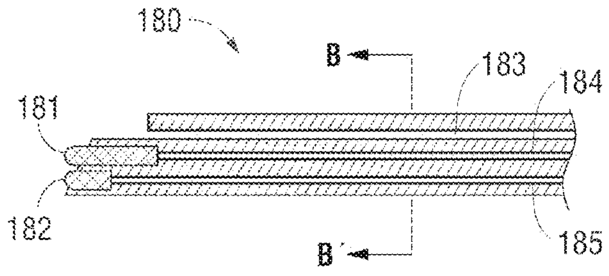
FIGS. 27A and 27B illustrate an endoscope embodiment of the distal segment.
Figure 27B:
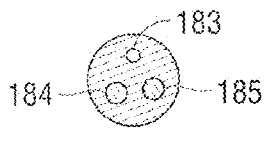

FIG. 27A is a longitudinal cross sectional view of an endoscope embodiment 180 of the distal segment wherein a camera 181 and a light source 182 are located at the distal end. There is a conduit 184 for the camera (fiber optics or wiring) for transmission of information to the proximal end of the device, and a conduit for the light source 185 (fiber optics or wiring) for transmission of energy (such as light or electrical current) to the light source 182. Additional this embodiment 180 can have a working channel for passage of instruments or delivery or aspiration of fluid. FIG. 27B is a short axis view through line B-B' in FIG. 27A.

Figure 28:
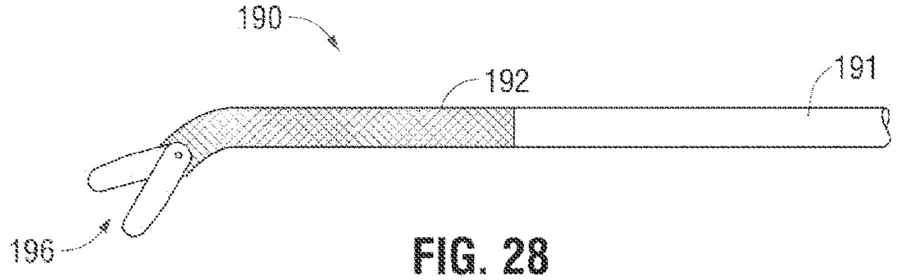
FIG. 28 is a diagram of an endoscopic grasping tool embodiment of the distal segment.

FIG. 28 is a longitudinal cross sectional view of an endoscopic instrument embodiment 190 wherein there is a hollow portion 191, a solid portion 192 and a grasper 196.

Figure 29:
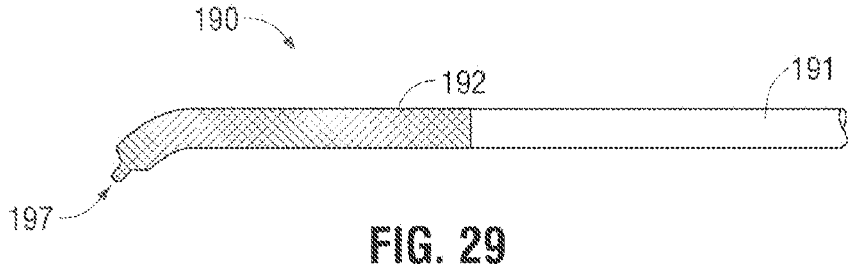
FIG. 29 is a diagram of an endoscopic cauterizing tool embodiment of the distal segment.

FIG. 29 is a longitudinal cross sectional view of an endoscopic instrument embodiment 190 wherein there is a hollow portion 191, a solid portion 192 and a cautery 197.

Figure 30A:
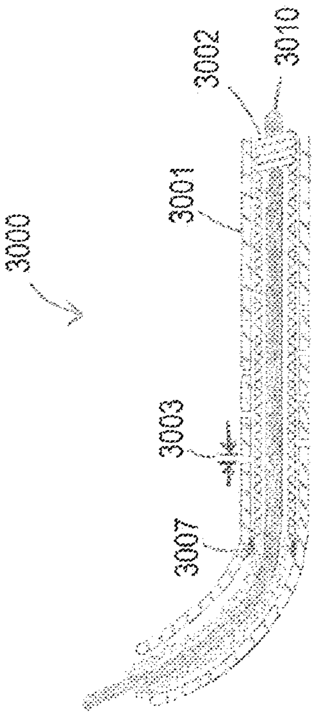
FIG. 30A is a longitudinal cross sectional view of the distal aspect of another embodiment of the medical device wherein the sleeve and the tube has a shelf within its lumen distal to the helical cut.
Figure 30B:
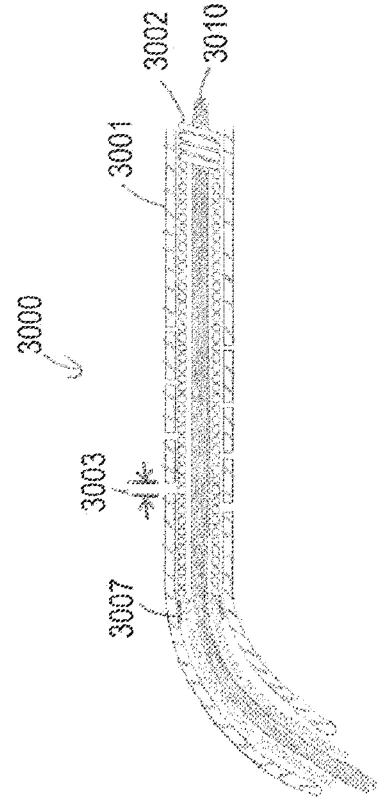
FIG. 30B is a longitudinal cross sectional view of the distal aspect of another embodiment of the medical device wherein the sleeve displaces the shelf resulting in a 180-degree rotation relative to FIG. 30A.
Figure 30C:
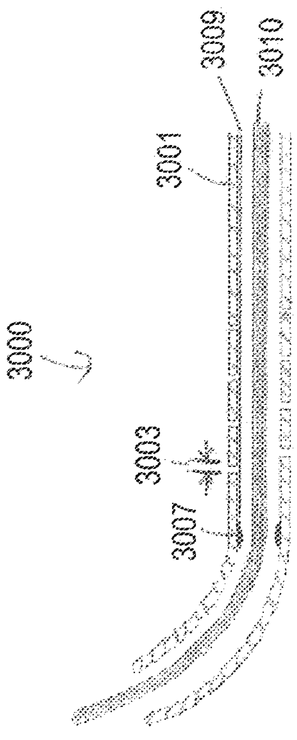
FIG. 30C is a longitudinal cross sectional view of the distal aspect of another embodiment of the medical device wherein the sleeve as shown in FIG. 30A has been replaced by a liner resulting greater luminal diameter of the device.

FIG. 30A shows a longitudinal cross section of the distal end of a device 3000 wherein the device 3000 is in its resting state (no longitudinal displacement). The device 3000 includes a tube 3001 and a longitudinal displacer such as a sleeve 3002. A helical or spiral cut 3003 is present in the distal aspect of the tube 3001. The sleeve 3002 is disposed within the lumen of the tube 3001. The sleeve 3002 is coupled to the tube 3001 distal to the helical or spiral cut 3003, and the sleeve 3002 may be advanced or retracted within the tube 3001 wherein advancement or retraction of the sleeve 3002 causes advancement or retraction of the tube 3001 distal to the helical or spiral cut 3003. Said advancement or retraction of the tube 3001 results in rotation of the tube 3001 distal to the helical or spiral cut 3003 wherein the amount of rotation is proportional to the amount of advancement or retraction of the tube 3001. Means of coupling the sleeve 3002 and tube 3001 include, but are not limited to, one or more of: 1) frictional fit, 2) adhesives (such as cyanoacrylate), 3) welding, 4) brazing, 5) soldering, 6) mechanical linking, and 7) direct linkage by a member that can undergo electrolysis, or other suitable means understood by a person of ordinary skill in the art. In addition, the tube 3001 may include of a reduced luminal inner diameter distal to the helical or spiral cut 3003 that forms a shelf 3007. The outer diameter of the sleeve 3002 is greater than the inner diameter of the shelf 3007 of the tube 3001, and the outer diameter of the sleeve 3002 is less than the inner diameter of the tube 3001 proximal to the shelf 3007. The sleeve 3002 slide-ably contacts the shelf 3007 of the tube 3001. FIG. 30*b* shows the device 3000 with a longitudinal displacement of the distal end of the tube 3001 due to advancement of the sleeve 3002 such that the distal end of the tube 3001 results in a 180-degree rotation relative to the position of the distal end of the tube 3001 in FIG. 30*a*. While a rotation of 180 degrees are shown, this is illustrative and exemplary only, as adjustment of the linear displacement may adjust the amount of rotation to less than or more than 180 degrees. FIG. 30*c* shows the device 3000 wherein the sleeve 3002 has been removed and a liner 3009 has been inserted coaxially within the tube 3001. The ability to remove and or replace the sleeve 3002 enables a user to modify the properties of the devices, such as pushability, trackability, or increase the luminal diameter. For example, replacing the sleeve 3002 (such as a coiled wire) with a thin walled liner 3009 (such as a thin walled polyimide tubing) provides a larger luminal diameter through which therapeutic agents such as embolic materials (for example: coils, particles, liquid embolics) can be delivered. Alternatively, if improved pushability or trackabilty is desired, a coiled wire or braided tube can be employed. As depicted in FIGS. 30*a* and 30*b* the sleeve 3002 is comprised of a coiled wire such distal aspect of the coiled wire has a reduced outer diameter that is less than the inner diameter of the shelf 3007. This provides a taper or smooth transition between the guidewire 3010 and the distal tip of the tube 3001. The outer diameter of the sleeve 3002 proximal to the shelf 3007 is greater than the inner diameter of the shelf 3007.

Figures 31A, 31B, 31C:
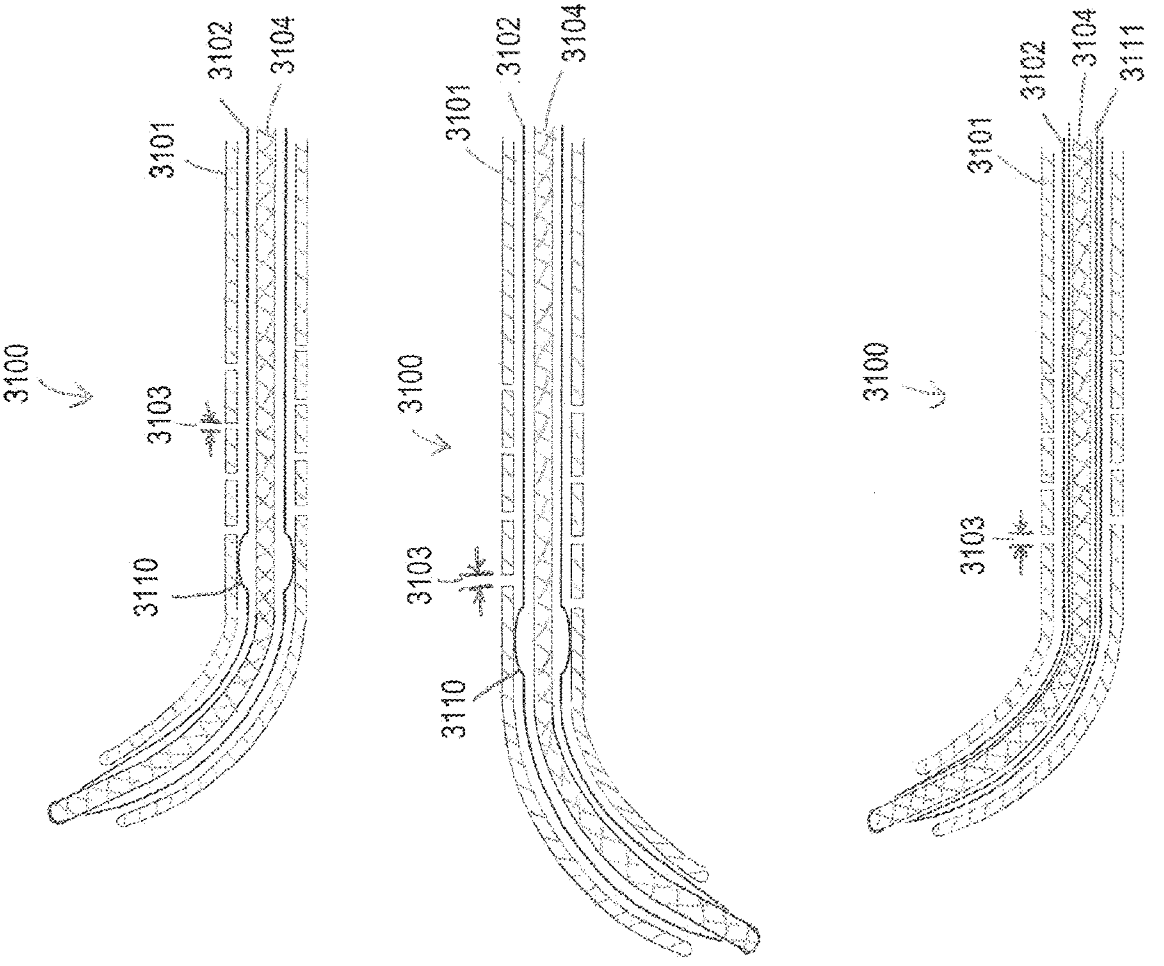
FIG. 31A is a longitudinal cross sectional view of the distal aspect of another embodiment of the device in its resting state with a sleeve with an expandable member.
FIG. 31B is a longitudinal cross sectional view of the distal aspect of another embodiment of the device wherein there is longitudinal displacement of the distal end of the tube by advancement of the sleeve.

FIG. 31A shows a longitudinal cross section of the distal end of a device 3100 wherein the device 3100 is in its resting state (no longitudinal displacement). The device 3100 includes a tube 3101 and a longitudinal displacer such as a sleeve 3102. A helical or spiral cut 3103 is present in the distal aspect of the tube 3101. The sleeve 3102 is disposed within the lumen of the tube 3101. A guidewire 3104 is disposed within the lumen of the sleeve 3102. The sleeve 3102 has a radially expanded portion 3110 such that the radially expanded portion 3110 abuts the tube 3101 distal to the helical or spiral cut 3103. The radially expanded portion 3110 can be comprised of a Malecot type tube or braided material or other suitable radially expandable material as would be understood by a person of ordinary skill in the art. The sleeve 3102 can be advanced or retracted within the tube 3101 wherein advancement or retraction of the sleeve 3102 causes advancement or retraction of the tube 3101 distal to the helical or spiral cut 3103. Said advancement or retraction of the tube 3101 results in rotation of the tube 3101 distal to the helical or spiral cut 3103 where the amount of rotation is proportional to the amount of advancement or retraction of the tube 3101. FIG. 31B shows the device 3100 wherein there is longitudinal displacement of the distal end of the tube 3101 by advancement of the sleeve 3102 such that the distal end of the tube 3101 results in a 180-degree rotation relative to the position of the distal end of the tube 3101 in FIG. 31A, though it is contemplated that adjusting the longitudinal displacement allows to use to adjust the amount of rotation to more or less than 180 degrees. FIG. 310 shows a collapse of the radially expanded portion 3110 by advancing a straightening element 3111 within the lumen of the sleeve 3102 to create tension on the radially expanded portion 3110 and thus collapse the radially expanded portion 3110.

Figure 32A:
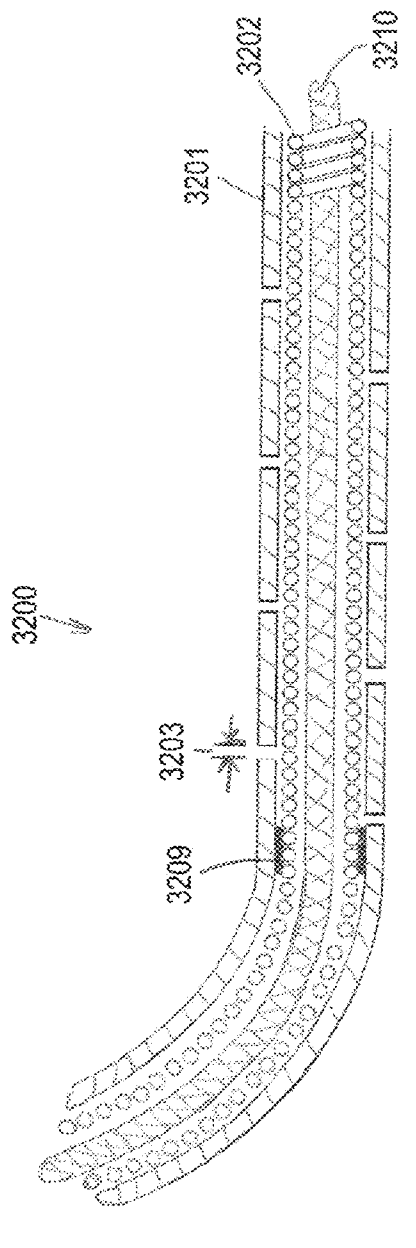
FIG. 32A is a longitudinal cross sectional view of the distal aspect of another embodiment of the device in its resting state wherein the sleeve is coupled to the tube distal to the helical cut.
Figure 32B:
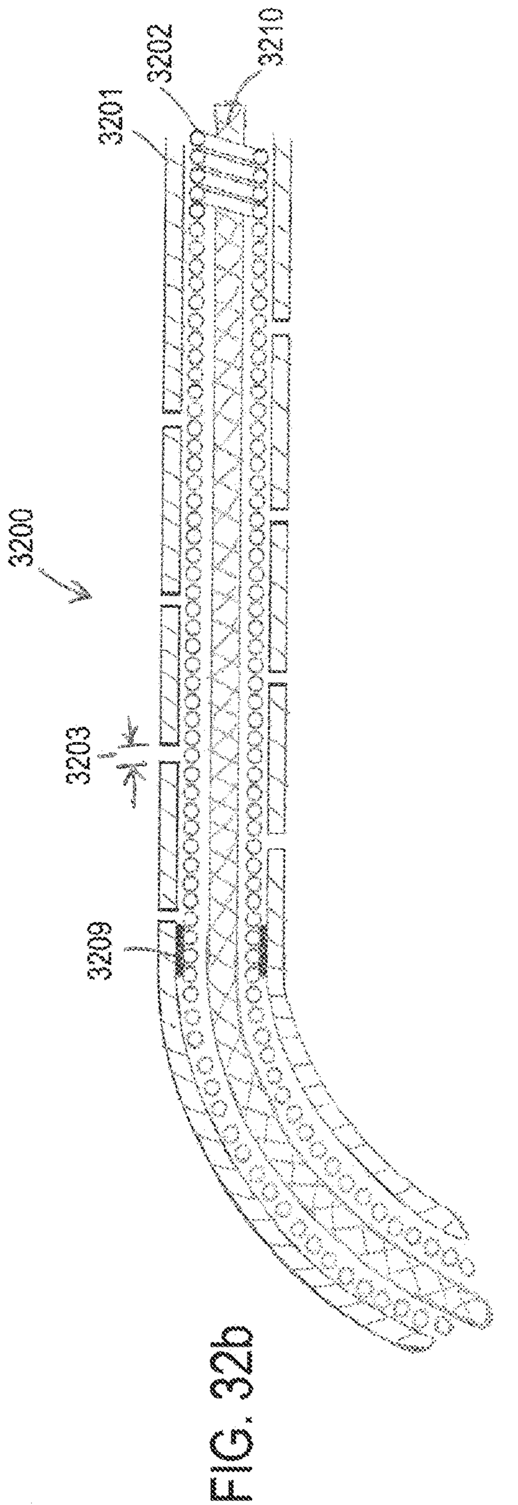
FIG. 32B is a longitudinal cross sectional view of the distal aspect of another embodiment of the device wherein there is longitudinal displacement of the distal end of the tube by advancement of the sleeve.
Figure 32C:
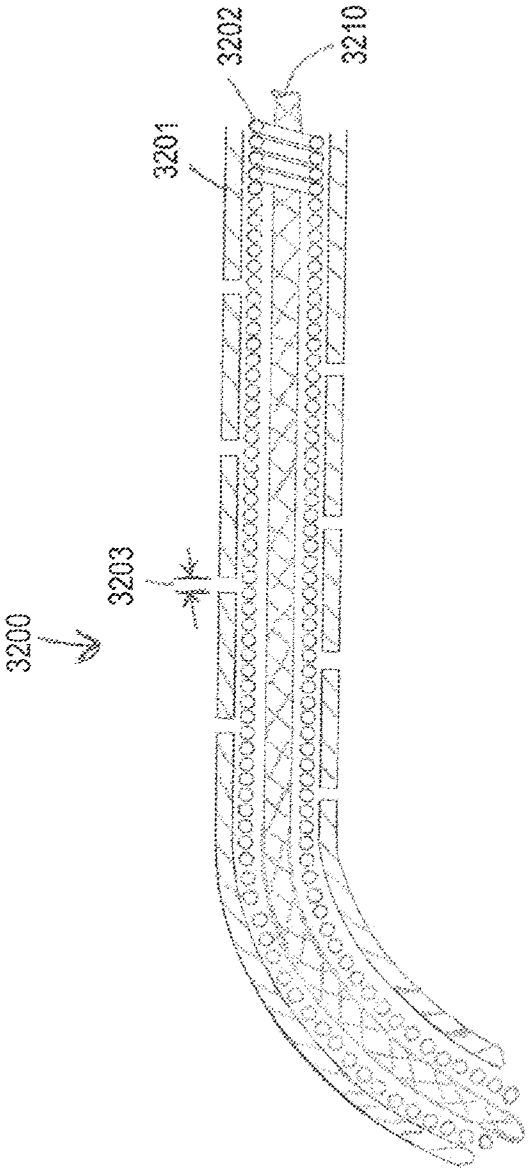
FIG. 32C is a longitudinal cross sectional view of the distal aspect of another embodiment of the device wherein the coupling has been removed.

FIG. 32A shows a longitudinal cross section of the distal end of a device 3200 wherein the device 3200 is in its resting state (no longitudinal displacement). The device 3200 includes a tube 3201 and a longitudinal displacer such as a sleeve 3202. A helical or spiral cut 3203 is present in the distal aspect of the tube 3201. The sleeve 3202 is disposed within the lumen of the tube 3201. A guidewire 3210 is disposed within the lumen of the sleeve 3202. The sleeve 3202 is coupled to the tube 3201 distal to the helical or spiral cut 3203 and can be advanced or retracted within the tube 3201 wherein advancement or retraction of the sleeve 3202 results in advancement or retraction of the tube 3201 distal to the helical or spiral cut 3203. Said advancement or retraction of the tube 3201 causes rotation of the tube 3201 distal to the helical or spiral cut 3203 where the amount of rotation is proportional to the amount of advancement or retraction of the tube 3201. Means of coupling 3209 the sleeve 3202 and tube 3201 include, but are not limited to, one or more of: 1) frictional fit, 2) adhesives (such as cyanoacrylate), 3) welding, 4) brazing, 5) soldering, 6) mechanical linking, and 7) direct linkage by a member that can undergo electrolysis, or other suitable means understood by a person of ordinary skill in the art. FIG. 32B shows the device 3200 wherein there is longitudinal displacement of the distal end of the tube 3201 by advancement of the sleeve 3202 such that the distal end of the tube 3201 results in a 180 degree relative to the position of the distal end of the tube 3201 in FIG. 32A, though this degree of rotation may be adjusted to greater or less than 180 degrees by adjusting the linear displacement. FIG. 32*c* shows the device 3200 wherein the coupling 3209 has been removed which enables the sleeve 3202 to be removed. The ability to remove and or replace the sleeve 3202 enables a user to modify the properties of the devices, such as pushability, trackability, or increase the luminal diameter.

Figure 33A:
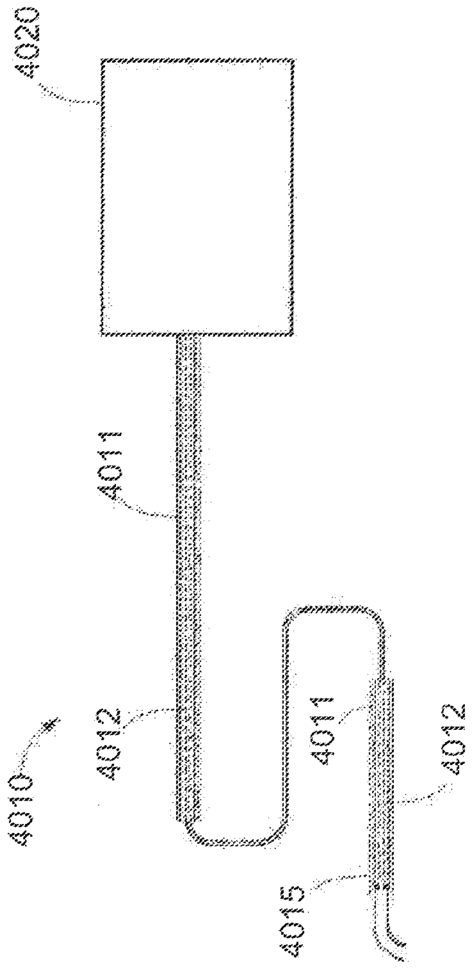
FIG. 33A illustrates a diagram of a medical device for converting linear motion to rotational motion along the distal aspect of the device that comprises an outer sheath, tube with one or more helical or spiral cuts and a slidable sleeve disposed within the lumen of said tube according to one embodiment of the present disclosure.

FIG. 33A schematically illustrates a medical device 4010 according to another embodiment of the present disclosure. As depicted, the device 4010 includes a tube 4011, an outer sheath 4015, a sleeve 4012 and a handle assembly 4020. In the illustrated arrangement, the sleeve 4012 is disposed within the lumen of the tube 4011. In the illustrated embodiment, the tube 4011 is disposed within the lumen of the outer sheath 4015. Each of the tube 4011, the outer sheath 4015, and the sleeve 4012 can comprise one or more of a variety of materials, including, but not limited to, polyimide, polyurethane, polyether block amides (such as Pebax®), nylon, nickel titanium (Nitinol), stainless steel, stainless steel braiding, and hollow helical stranded tubing. In addition, the distal end of the tube 4011 may have, but is not limited to, a straight, angled, and reverse curved shape. In some embodiments, the tube 4011 is located within the lumen of the outer sheath 4015 such that the one or more helical or spiral cut(s) 4013 in the distal aspect of the tube 4011 are disposed within the lumen of the outer sheath 4015 while the distal end of the tube 4011 extends beyond the outer sheath 4015 (e.g., the total length of the tube is greater than the total length of the outer sheath, while the length from the proximal end of the tube to the distal most aspect of the cut portion of the tube is less than the total length of the outer sheath).

Figures 33B, 33C, 33D, 33E, 33F:
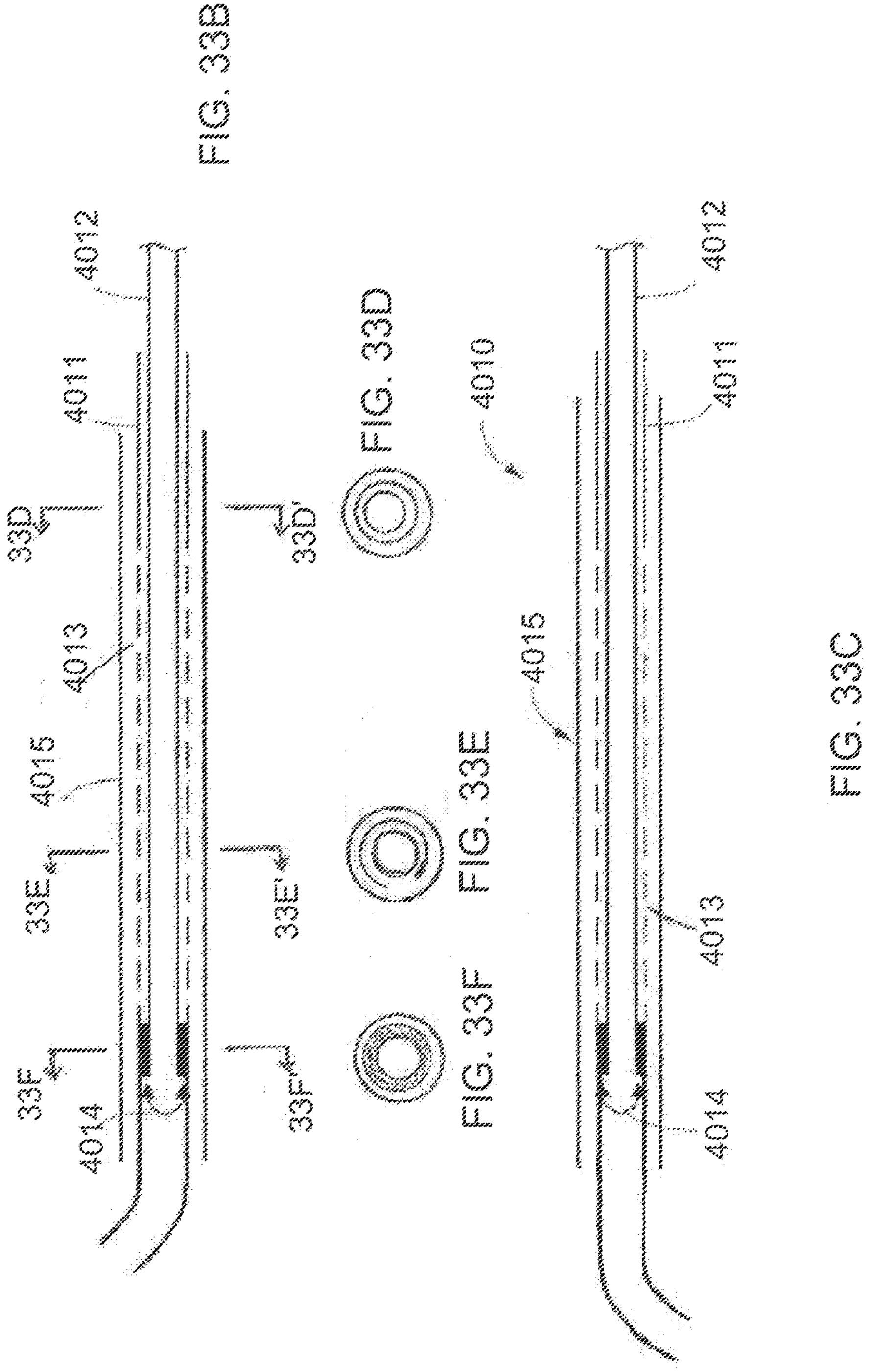
FIG. 33B illustrates a longitudinal cross-sectional view of the distal end of the device in FIG. 33A while in its resting state (e.g., 0 degrees of rotation), according to one embodiment.
FIG. 33C illustrates a longitudinal cross-sectional view of the distal end of the device in FIG. 33A with longitudinal force at the proximal end causing a rotation of the distal end by 180 degrees, according to one embodiment.
FIG. 33D illustrates a transverse cross section of FIG. 33B through lines 33D-33D'.
FIG. 33E illustrates a transverse cross section of FIG. 33B through lines 33E-33E'.
FIG. 33F illustrates a transverse cross section of FIG. 33B through lines 33F-33F'.

FIG. 33B illustrates a longitudinal cross section of a close up of the distal aspect of the device 4010. In the depicted arrangement, one or more helical or spiral cut(s) 4013 are present in the distal aspect of the tube 4011 wherein the one or more helical or spiral cut(s) 4013 has a cut width and helical angle. The end of the tube 4011 distal to the one or more helical or spiral cut(s) 4013 may include a curve to aid in navigating the device 4010 through the vasculature. However, in other embodiments, the end of the tube 4011 (both for the arrangement illustrated in FIGS. 33A and 33B, as well as any other arrangements disclosed herein, or variations thereof) is straight (not curved) and/or includes some other feature or characteristic (e.g., tapered, flared, etc.), as desired or required. In some embodiments, the helical or spiral cuts extend throughout the entire wall thickness or depth of the tube 4011; however, in alternative embodiments, the cuts extend only partially through the wall, as desired or required. Thus, the cuts can be recessed or scored portions of the tube, wherein a certain amount (e.g., but less than all, e.g., 5-10, 10-25, 25-50, 50-75, 75-99% of the material has been removed or was never there relative to adjacent portions of the wall in the first place). These features or characteristics of the cuts can be applied to any of the embodiments disclosed herein. Further, in some embodiments, helical or spiral cuts, as used herein, is configured to connote an orientation that is angled both a longitudinal axis of the tube and a radial or transverse angle of the tube (e.g., angled relative to the perpendicular axis of the longitudinal axis).

In some arrangements, the cut width can range from 0.1 micrometers to 30 millimeters, depending on the size of the device, the materials used, the desired level and rotation response and/or one or more other factors or considerations. In some embodiments, the cut width may range from about 0.1 millimeters to about 10 millimeters (e.g., 0.1-0.2, 0.2-0.5, 0.5-1, 1-2, 2-3, 3-4, 4-5, 5-6, 6-7, 7-8, 8-9, 9-10 millimeters, values between the foregoing ranges, etc.), as desired or required. The helical angle can range from 10 to 80 degrees (e.g., 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the tube 4011. In some embodiments, the helical angle can range from 15 to 75 degrees. The sleeve 4012 is disposed within the lumen of the tube 4011. The tube 4011 may have a reduced inner diameter on the distal end to form a shelf 4014 that prevents or at least partially limits forward movement of the sleeve 4012. In some embodiments, the sleeve 4012 may abut the shelf 4014 to transmit longitudinal force from the sleeve 4012 to the tube 4011. In some embodiments, the sleeve 4012 may be coupled to the tube 4011 at a point distal to the one or more helical or spiral cut(s) 4013, such as at the shelf 4014, and can be advanced or retracted within the tube 4011 wherein advancement or retraction of the sleeve 4012 results in advancement or retraction of the tube 4011 distal to the one or more helical or spiral cut(s) 4013. In some embodiments, the coupling means may be reversible, such as a solder connection that can be melted by application of electric current or heat to release the sleeve 4012 from the tube 4011. Means of coupling the sleeve 4012 and tube 4011 include, but are not limited to, one or more of: 1) frictional fit, 2) adhesives (such as cyanoacrylate), 3) welding, 4) brazing, 5) soldering, and 6) mechanical linking.

With further attention to the embodiments of FIGS. 33A and 33B, each of the tube, 4011 and the sleeve 4012 can be made of one or more of a variety of materials, including, but not limited to, polyimide, polyurethane, polyether block amides (such as Pebax®), nylon, Nitinol, stainless steel, stainless steel braiding, coiled wire, hollow helical stranded tubing, any or any other suitable material, as desired or required. The lumen of the tube 4011 and outer surface of the sleeve 4012 preferentially have a low coefficient of friction, including but not limited to PTFE or a hydrophilic coating. In addition, the distal aspect of the tube 4011 may have, but is not limited to, a straight, angled, and reverse curved shape. FIG. 33C is a longitudinal cross-sectional view of the distal end of the device in FIG. 33A with longitudinal force at the proximal end causing a rotation of the distal end (e.g., by 180 degrees). FIG. 33D is an axial cross section through line 33D-33D' in FIG. 33A. FIG. 33E is an axial cross section through line 33E-33E' in FIG. 33A. FIG. 33F is an axial cross section through line 33F-33F' in FIG. 33A.

Figure 34A:
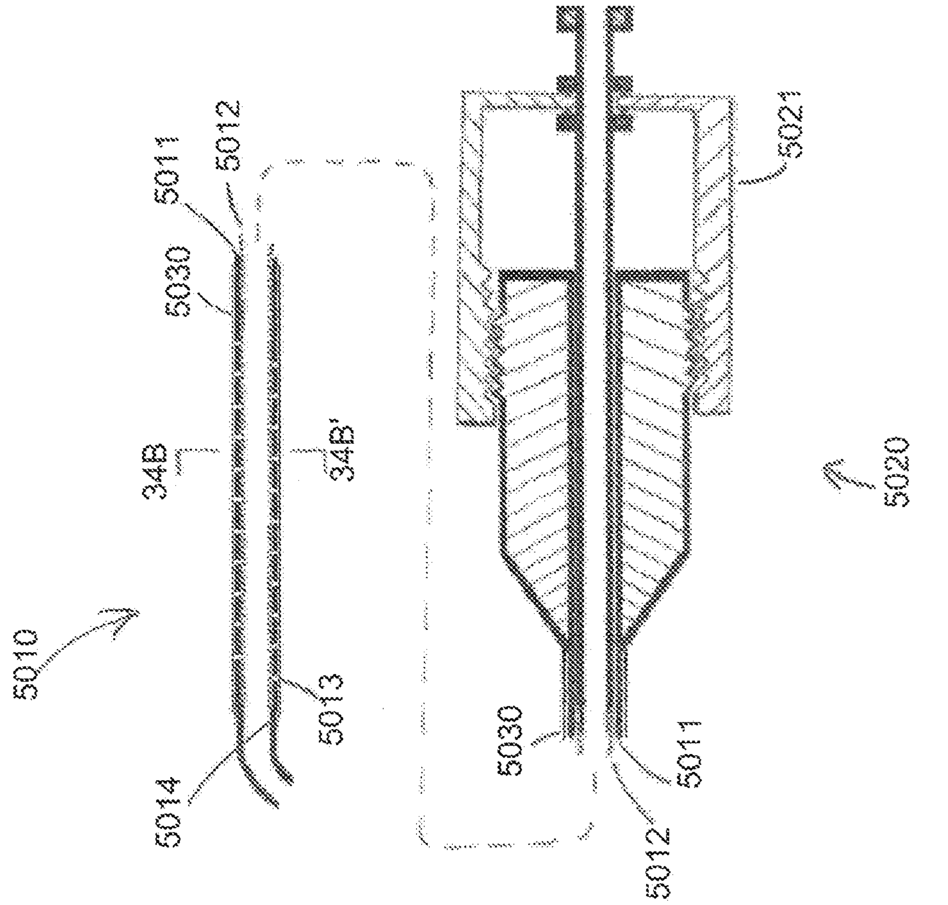
FIG. 34A illustrates a longitudinal cross-sectional view of a medical device for converting linear motion to rotational motion along the distal aspect of the device that comprises a tube with one or more helical or spiral cuts, a slidable sleeve disposed within the lumen of said tube and an outer layer disposed around said tube according to another embodiment of the present disclosure.

FIG. 34A illustrates a longitudinal cross section of a medical device 5010 according to another embodiment of the present disclosure. As illustrated, the device 5010 can include a tube 5011, an outer layer 5030, a sleeve 5012 and a handle assembly 5020. The handle assembly 5020 is comprised of a proximal component or portion 5021 and a distal component or portion 5022. The distal component or portion 5022 is coupled to the proximal end of the tube 5011. In the illustrated embodiment, the proximal component 5021 is coupled to the proximal end of the sleeve 5012. The proximal component 5021 and the distal component 5022 can each have cylindrical bodies, such that the proximal component 5021 may be inserted into the distal component 5022. However, as with any other embodiments disclosed herein, these components can any other cross-sectional shape (e.g., rectangular, oval, irregular, other non-circular, etc.), as desired or required. Each of the tube 5011 and the sleeve 5012 can comprise one or more of a variety of materials, including, but not limited to, polyimide, polyurethane, polyether block amides (such as Pebax®), nylon, nickel titanium (Nitinol), stainless steel, stainless steel braiding, and hollow helical stranded tubing. One or more helical or spiral cut(s) 5013 are present in the distal aspect of the tube 5011. The cut width can range from 0.1 micrometers to 30 millimeters. In some embodiments, the cut width may range from about 0.1 millimeters to about 10 millimeters. The helical angle of the cut(s) 5013 can range from 10 to 80 degrees relative to the longitudinal axis of the tube 5011. In some embodiments, the helical angle can range from 15 to 75 degrees. In addition, the distal end of the tube 11 may have, but is not limited to, a straight, angled, and reverse curved shape.

In some embodiments, a sleeve 5012 is disposed within the lumen of the tube 5011. The tube 5011 may have a reduced inner diameter on the distal end to form a shelf 5014 that prevents forward movement of the sleeve 5012. In some embodiments, the sleeve 5012 may abut the shelf 5014 to transmit longitudinal force from the sleeve 5012 to the tube 5011. In some embodiments, the sleeve 5012 may be coupled to the tube 5011 at a point distal to the one or more helical or spiral cut(s) 5013, such as at the shelf 5014, and can be advanced or retracted within the tube 5011 wherein advancement or retraction of the sleeve 5012 results in advancement or retraction of the tube 5011 distal to the one or more helical or spiral cut(s) 5013. In some embodiments, the coupling means may be reversible, such as a solder connection that can be melted by application of electric current or heat to release the sleeve 5012 from the tube 5011. Means of coupling the sleeve 5012 and tube 5011 include, but are not limited to, one or more of: 1) frictional fit, 2) adhesives (such as cyanoacrylate), 3) welding, 4) brazing, 5) soldering, and 6) mechanical linking. Each of the tube 5011 and the sleeve 5012 can comprise one or more of a variety of materials, including, but not limited to, polyimide, polyurethane, polyether block amides (such as Pebax®), nylon, Nitinol, stainless steel, stainless steel braiding, coiled wire and hollow helical stranded tubing. The lumen of the tube 5011 and outer surface of the sleeve 5012 preferentially have a low coefficient of friction, including but not limited to PTFE or a hydrophilic coating. The outer layer 5030 is disposed around the outer surface of tube 5011. The distal end of the outer layer 5030 is coupled to the tube 5011 distal to the one or more helical or spiral cut(s) 5013. The proximal end of the outer layer 5030 is coupled to the tube 5011 proximal to the one or more helical or spiral cut(s) 5013. The portion of the tube 5011 containing the one or more helical or spiral cut(s) 5013 is able to move along the longitudinal axis with respect to the outer layer 5030.

Figure 34B:
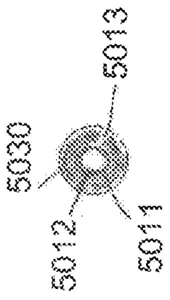
FIG. 34B illustrates a transverse cross sectional view of FIG. 34A through lines 34B-34B'.

In some embodiments, the outer layer 5030 or at least a portion of the outer layer is able to undergo elongation as the portion of the tube 5011 containing the one or more helical or spiral cut(s) 5013 undergoes elongation. The outer layer 5030 can comprise one or more of a variety of materials, including, but not limited to, thin walled PET tubing, polyimide, polyurethane, polyether block amides (such as Pebax®), nylon, Nitinol, stainless steel, stainless steel braiding, coiled wire and hollow helical stranded tubing. FIG. 34B is an axial cross section through line 34B-34B' in FIG. 34A.

Figure 35A:
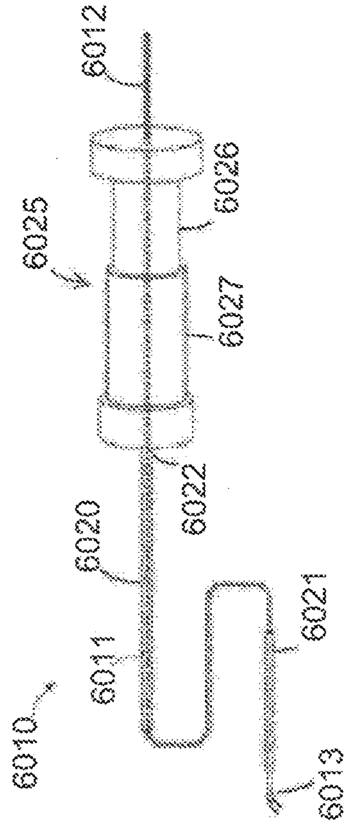
FIG. 35A schematically illustrates one embodiment of a medical device for converting linear motion to rotational motion along the distal aspect of the device.

FIG. 35A illustrates a diagram of medical device 6010 according to one embodiment of the present disclosure. The device includes a tube 6011, an outer tubular member 6020 and a handle assembly 6025. In the illustrated embodiment, the handle assembly 6025 comprises a proximal handle component 6026 and a distal handle component 6027. The proximal handle component 6026 and the distal handle component 6027 can be coaxial with one another and slidably engage with one another. As shown, the proximal handle component 6026 can be coupled to the proximal end of tube 6012, and the distal handle component 6027 is coupled to the proximal end of the outer tubular member 6022.

Figure 35B:
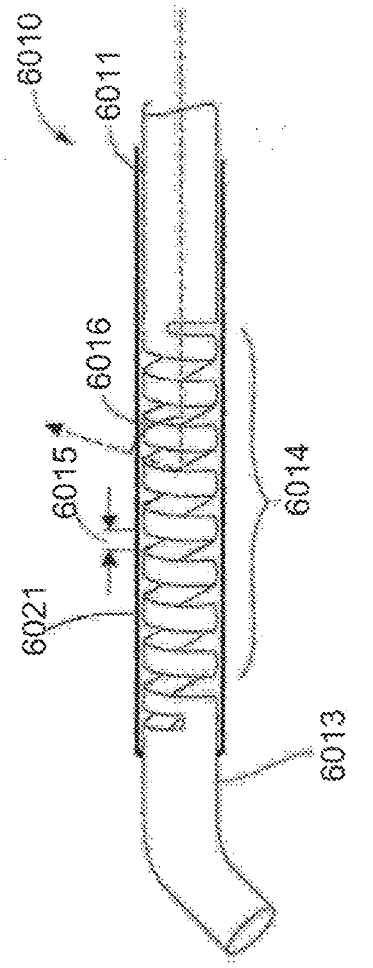
FIG. 35B is a detailed view of the distal aspect of the device of FIG. 35A.

FIG. 35B provides a detailed view of the distal aspect of the device 6010 of FIG. 35A. One or more helical or spiral cuts 6014 can be located along the distal aspect of the tube 6011 as depicted in FIG. 35B. In some embodiments, the tube 6011 is disposed within the outer tubular member lumen 6023. In some embodiments, each of the tube 6011 and the outer tubular member 6020 comprise one or more of a variety of materials, including, but not limited to, polyimide, polyurethane, polyether block amides (such as Pebax®), nylon, nickel titanium (Nitinol), stainless steel, stainless steel braiding, coiled wire and hollow helical stranded tubing. In some embodiments, the outer tubular member lumen 6023 and outer surface of the tube 6011 advantageously have a low coefficient of friction via, including but not limited to, PTFE, a hydrophilic coating, other relatively low friction coatings or materials and/or the like. The distal end of the tube 6013 may have, but is not limited to, a straight, angled, and reverse curved shape to aid in navigating the device 6010 through the human body. In addition, the distal end of the tube 13 can have one or more malleable elements such that the distal end of the tube 13 can be manually shaped by the operator at the time of use.

According to some embodiment, one or more helical or spiral cut(s) 6014 are present in the distal aspect of the tube 6011. In some arrangements, the one or more helical or spiral cut(s) 6014 has a cut width 6015 and a helical angle 6016. In some embodiments, the cut width 6015 can range from 0.1 micrometers to 30 millimeters. In some embodiments, the cut width 6015 may range from about 0.1 millimeters to about 10 millimeters. In some configurations, the helical angle 6016 can range from 10 to 80 degrees relative to the longitudinal axis of the tube 6011. In some embodiments, the helical angle 6016 can range from 15 to 75 degrees. In some embodiments, the distal end of the outer tubular member 6021 is coupled to the tube 6011 distal to the one or more helical or spiral cut(s) 6014. Means of coupling the distal end of the outer tubular member 6021 and tube 6011 include, but are not limited to, one or more of: 1) frictional fit, 2) adhesives (such as cyanoacrylate), 3) welding, 4) brazing, 5) soldering, and 6) mechanical linking.

Figures 35C, 35D, 35E, 35F, 35G, 35H:
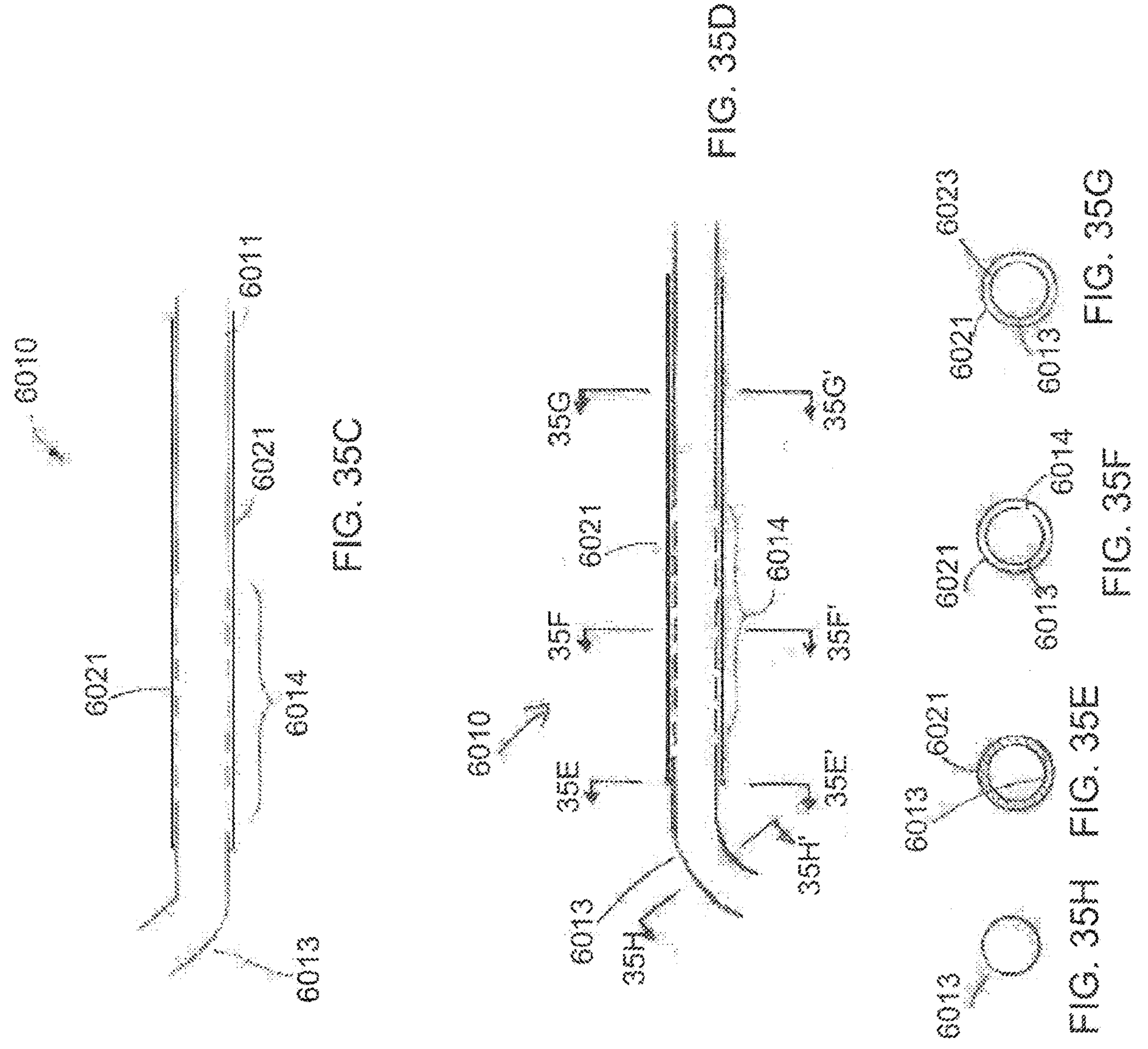
FIG. 35C illustrates a longitudinal cross-sectional view of the distal end of the device in FIG. 35A with longitudinal force at the proximal end causing a rotation of the distal end.
FIG. 35D illustrates a longitudinal cross-sectional view of the distal end of the device in FIG. 35A while in its resting state (e.g., 0 degrees of rotation)
FIG. 35E illustrates a transverse cross section of FIG. 35D through lines 35E-35E'.
FIG. 35F illustrates a transverse cross section of FIG. 35D through lines 35F-35F'.
FIG. 35G illustrates a transverse cross section of FIG. 35D through lines 35G-35G'.
FIG. 35H illustrates a transverse cross section of FIG. 35D through lines 35H-35H'.

FIG. 35C illustrates a close up of a longitudinal cross-sectional view of the distal end of the device in FIG. 35A. As noted herein, in some embodiments, advancement of the outer tubular member 6020 relative to the tube 6011 results in displacement of the helical or spiral cut(s) causing rotation of the distal end (e.g., by 180 degrees or some other desired angle). FIG. 35D illustrates a close up of a longitudinal cross-sectional view of the distal end of the device in FIG. 35A while in its resting state (e.g., 0 degrees of rotation). Further, FIG. 35E illustrates an axial cross section through line 35E-35E' in FIG. 35D, FIG. 1F illustrates an axial cross section through line 35F-35F' in FIG. 35D, and FIG. 35H illustrates an axial cross sectional view through line 35H-35H' in FIG. 35D.

Figure 36A:
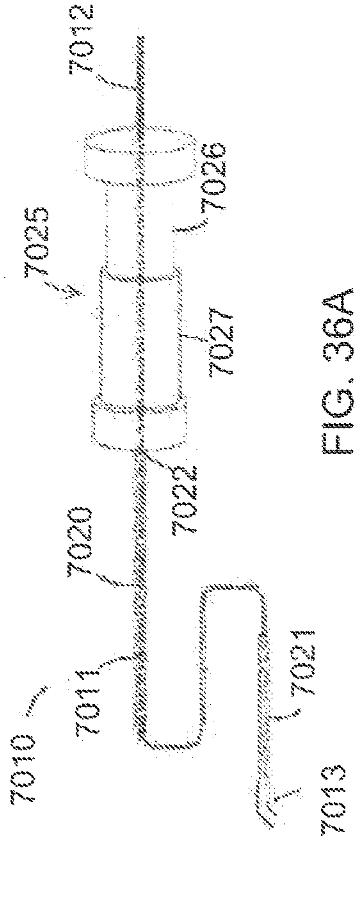
FIG. 36A illustrates one embodiment of a medical device for converting linear motion to rotational motion along the distal aspect of the device.
Figure 36B:
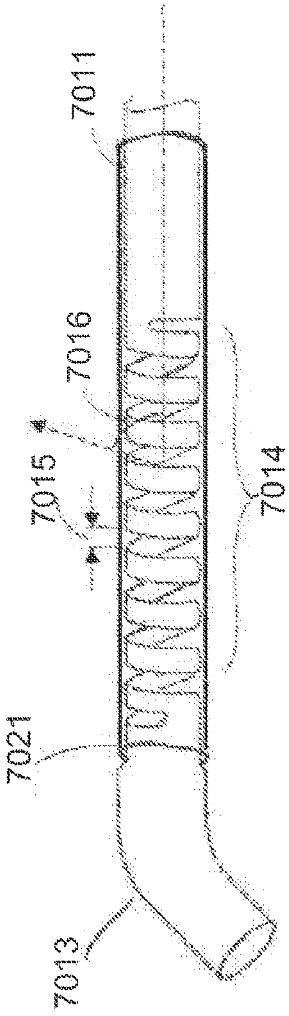
FIG. 36B illustrates a detailed view of the distal aspect of the device of FIG. 36A.

FIG. 36A schematically illustrates another embodiment of a medical device 7010 that is configured to facilitate rotation of a distal end or portion. As shown, the device can include a tube 7011, an outer tubular member 7020 and a handle assembly 7025. FIG. 36B illustrates a detailed view of the distal portion or aspect of the device 7010. As with other embodiments disclosed herein, the illustrated device can include one or more helical or spiral cuts 7014 are located along the distal aspect of the tube 7011. In some embodiments, the tube 7011 is disposed within the outer tubular member lumen 7023. The depicted tube 7011 comprises two or more outer diameters, wherein the outer diameter of the distal end of the tube 7013 is greater than the outer tubular member lumen 7023, while the outer diameter from the proximal end of the tube up to and including the helical or spiral cuts 7014 is less than the outer tubular member lumen 7023.

With continued attention to FIG. 36A, the handle assembly 7025 of the device 7010 comprises a proximal handle component 7026 and a distal handle component 7027. In some embodiments, the proximal handle component 7026 and the distal handle component 7027 are coaxial with one another and slidably engage with one another. The proximal handle component 7026 can be coupled to the proximal end of tube 7012, and the distal handle component 7027 can be coupled to the proximal end of the outer tubular member 7022. Each of the tube 7011 and the outer tubular member 7020 can comprise one or more of a variety of materials, including, but not limited to, polyimide, polyurethane, polyether block amides (such as Pebax®), nylon, nickel titanium (Nitinol), stainless steel, stainless steel braiding, coiled wire and hollow helical stranded tubing. In some embodiments, the outer tubular member lumen 7023 and outer surface of the tube 7011 advantageously have a low coefficient of friction (e.g., via the use of materials, such as, for example, PTFE, one or more hydrophilic coatings and/or the like).

According to some arrangements, the distal end of the tube 7013 may have, but is not limited to (and/or does not need to have), a straight, angled, and reverse curved shape to aid in navigating the device 7010 through the human body. In addition, the distal end of the tube 7013 can have one or more malleable elements such that the distal end of the tube 7013 can be manually shaped by the operator at the time of use. Such shaping features can be implanted into any of the embodiments disclosed herein. In some embodiments, one or more helical or spiral cut(s) 7014 are present in the distal aspect of the tube 7011. By way of example, and without limitation, one or more of the helical or spiral cut(s) 14 can comprise a cut width 7015 and a helical angle 7016. The cut width 7015 can range from 0.1 micrometers to 30 millimeters. In some embodiments, the cut width 7015 may range from about 0.1 millimeters to about 10 millimeters. The helical angle 7016 can range from 10 to 80 degrees relative to the longitudinal axis of the tube 7011. In some embodiments, the helical angle 7016 can range from 15 to 75 degrees.

In some configurations, the distal end of the tube 7013 transitions to a greater outer diameter distal to the helical or spiral cut(s) 7014. The distal end of the outer tubular member 7021 may abut the distal end of the tube 7013 where it transitions to a greater diameter. In some arrangements, the relative advancement of the outer tubular member 7020 results in elongation of the helical or spiral cut(s) 7014, and thus, rotation of the distal end of the tube 7013. In some embodiments, the distal end of the tube 7013 is able to rotate freely or substantially freely with respect to the distal end of the outer tubular member 7021.

Figures 36C, 36D, 36E, 36F, 36G:
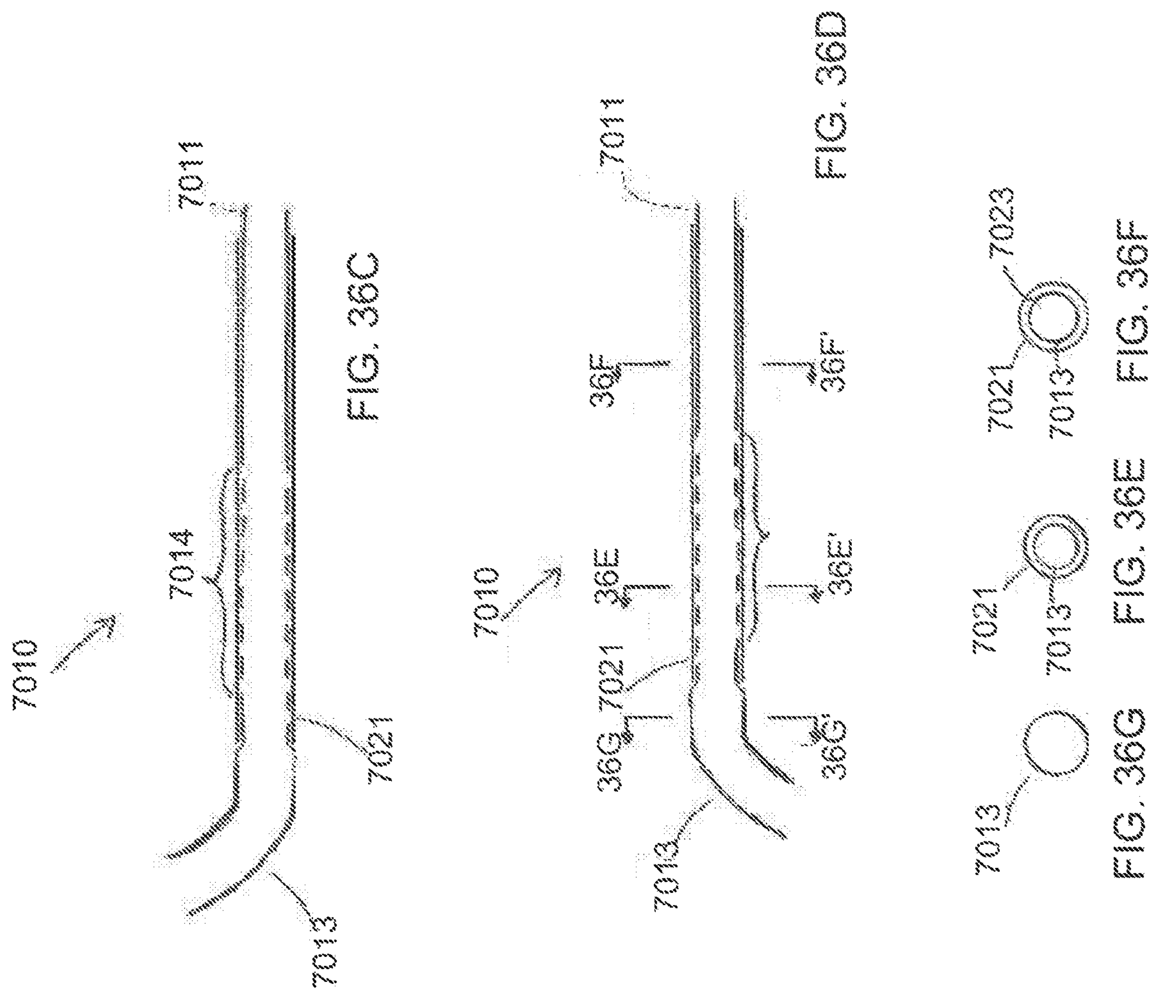
FIG. 36C illustrates a longitudinal cross-sectional view of the distal end of the device in FIG. 36A with longitudinal force at the proximal end causing a rotation of the distal end by 180 degrees.
FIG. 36D illustrates a longitudinal cross-sectional view of the distal end of the device in FIG. 36A while in its resting state (0 degrees of rotation)
FIG. 36E illustrates a transverse cross section of FIG. 36D through lines 36E-36E'.
FIG. 36F illustrates a transverse cross section of FIG. 36D through lines 36F-36F'.
FIG. 36G illustrates a transverse cross section of FIG. 36D through lines 36G-36G'.

FIG. 36C illustrates a longitudinal cross-sectional view of the distal end of the device in FIG. 36A. As noted herein, in some embodiments, advancement of the outer tubular member 7020 relative to the tube 7011 results in displacement of the helical or spiral cut(s), thereby causing rotation of the distal end (e.g., by 180 degrees or some other desired angle). Such rotation of the device illustrated in FIGS. 36A-36F, and/or any other devices disclosed in the present application, can facilitate advancing an intraluminal device (e.g., guidewire, microcatheter, catheter, sheath, endoscope, etc.) within the anatomy of the subject being treated. Further, FIG. 36D illustrates a longitudinal cross section of a close up of the distal aspect of the device 7010 while in its resting state (0 degrees of rotation), FIG. 36E illustrates an axial cross section through line 36E-36E' in FIG. 36D, FIG. 36F illustrates an axial cross section through line 36F-36F' in FIG. 2D, and FIG. 2G illustrates an axial cross sectional view through line 36G-36G' in FIG. 36D.

Figure 37A:
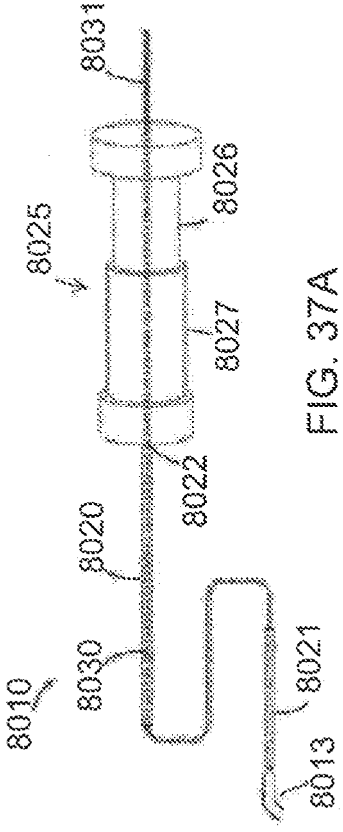
FIG. 37A illustrates one embodiment of a medical device for converting linear motion to rotational motion along the distal aspect of the device.
Figure 37B:
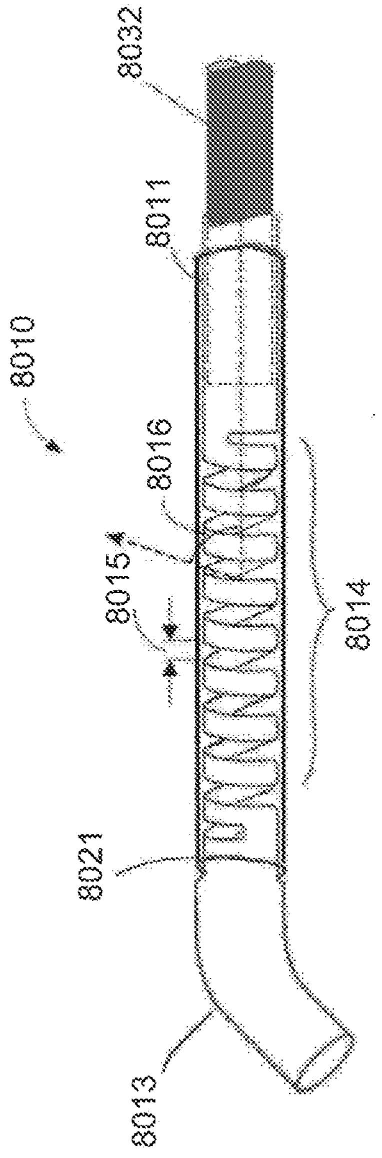
FIG. 37B illustrates a detailed view of the distal aspect of the device of FIG. 37A.

FIG. 37A illustrates an intraluminal device 8010 according to another embodiment of the present disclosure. As shown, the device 8010 comprises a tube 8011, a core wire 8030, an outer tubular member 8020 and a handle assembly 8025. FIG. 37B illustrates a detailed view of the distal aspect or portion of the device 8010 of FIG. 37A. As with other embodiments disclosed herein, one or more helical or spiral cuts 8014 can be located along the tube 8011. The proximal end of the tube 8012 can be coupled to the distal end of the core wire 8032. Means of coupling include, but are not limited to, one or more of: 1) frictional fit, 2) adhesives (such as cyanoacrylate), 3) welding, 4) brazing, 5) soldering, and 6) mechanical linking. The core wire 30, proximal end of the tube 8012 and the portion of the tube 8011 containing the helical or spiral cut(s) 14 can be disposed within the lumen of the outer tubular member 8023. In some embodiments, the tube 8011 includes two or more outer diameters, wherein the outer diameter of the distal end of the tube 13 is greater than the outer tubular member lumen 8023, while the outer diameter from the proximal end of the tube 8011 up to and including the helical or spiral cuts 8014 is less the outer tubular member lumen 8023. In some arrangements, the outer diameter of the core wire 8030 is less than the outer tubular member lumen 8023 (e.g., such that the outer tubular member 8020 can slide coaxially along the core wire 8030).

With continued reference to FIG. 37A, the handle assembly 25 can comprise a proximal handle component 8026 and a distal handle component 8027. In some embodiments, the proximal handle component 8026 and the distal handle component 8027 are coaxial with one another and slidably engage with one another. The proximal handle component 8026 can be coupled to the proximal end of core wire 31, and the distal handle component 8027 can be coupled to the proximal end of the outer tubular member 8022. Each of the tube 8011 and the outer tubular member 8020 can comprise one or more of a variety of materials, including, but not limited to, polyimide, polyurethane, polyether block amides (such as Pebax®), nylon, nickel titanium (Nitinol), stainless steel, stainless steel braiding, coiled wire, hollow helical stranded tubing and/or the like.

In some embodiments, the lumen of the outer tubular member 8023 and outer surface of the tube 8011 advantageously have a low coefficient of friction (e.g., via the use of PTFE, a hydrophilic coating and/or other materials or features with a relatively low coefficient of friction). The distal end of the tube 8013 may have, but is not limited to, a straight, angled, and reverse curved shape to aid in navigating the device 8010 through the human body. In addition, the distal end of the tube 8013 can have one or more malleable elements such that the distal end of the tube 8013 can be manually shaped by the operator at the time of use. In some embodiments, one or more helical or spiral cut(s) 8014 are present in the distal aspect of the tube 8011. The one or more helical or spiral cut(s) 8014 can have a cut width 8015 and a helical angle 8016. The cut width 8015 can range from 0.1 micrometers to 30 millimeters. In some embodiments, the cut width 8015 may range from about 0.1 millimeters to about 10 millimeters. The helical angle 8016 can range from 10 to 80 degrees relative to the longitudinal axis of the tube 8011. In some embodiments, the helical angle 8016 can range from 15 to 75 degrees. In some configurations, the distal end of the tube 8013 transitions to a greater outer diameter distal to the helical or spiral cut(s) 8014. The distal end of the outer tubular member 8021 may abut the distal end of the tube 8013 where it transitions to a greater diameter, wherein relative advancement of the outer tubular member 8020 results in elongation of the helical or spiral cut(s) 8014 and thus rotation of the distal end of the tube 8013. In some embodiments, the distal end of the tube 8013 is configured to rotate freely or substantially freely with respect to the distal end of the outer tubular member 8021.

Figures 37C, 37D, 37E, 37F, 37G:
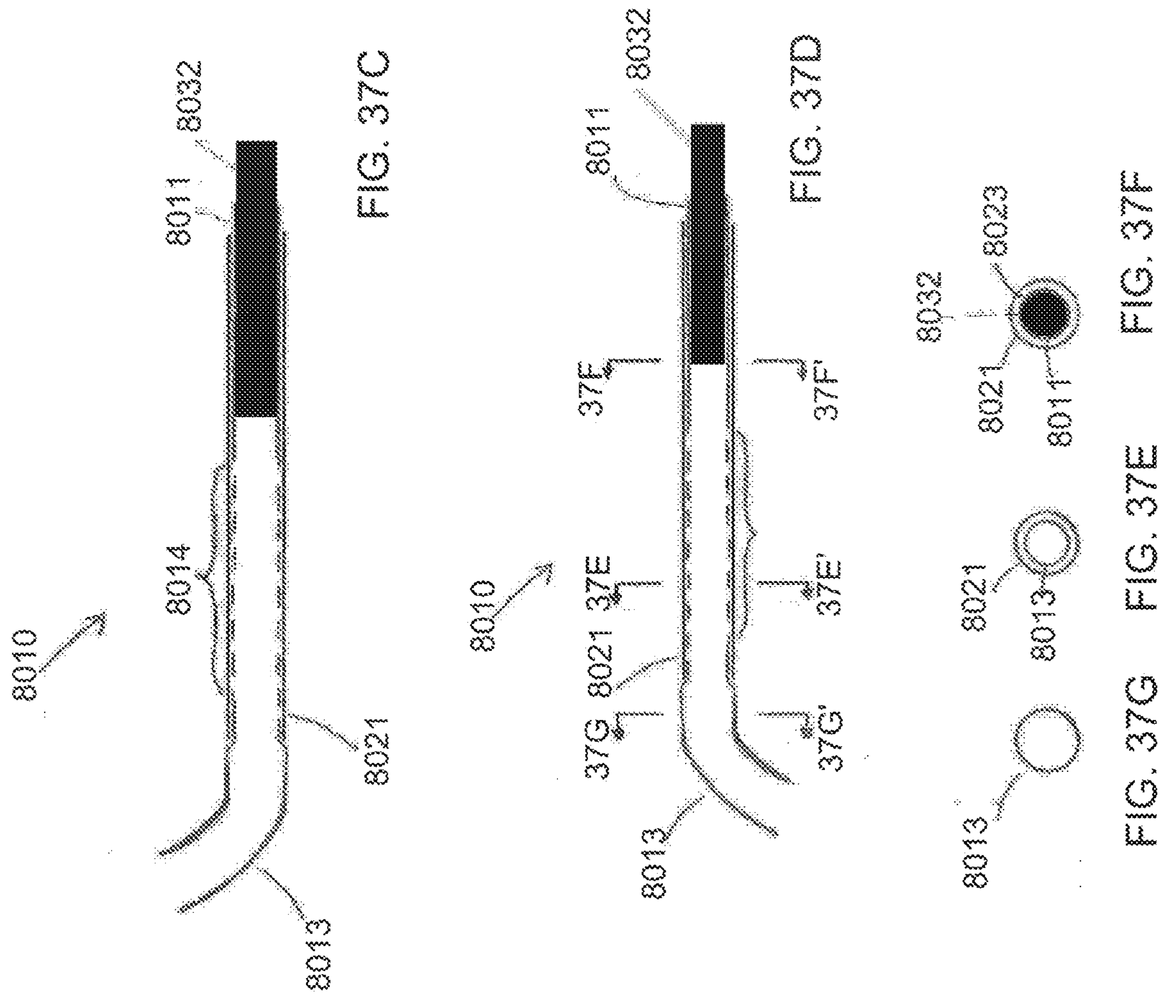
FIG. 37C illustrates a longitudinal cross-sectional view of the distal end of the device in FIG. 37A with longitudinal force at the proximal end causing a rotation of the distal end by 180 degrees.
FIG. 37D illustrates a longitudinal cross-sectional view of the distal end of the device in FIG. 37A while in its resting state (0 degrees of rotation)
FIG. 37E illustrates a transverse cross section of FIG. 37D through lines 37E-37E'.
FIG. 37F illustrates a transverse cross section of FIG. 37D through lines 37F-37F'.
FIG. 37G illustrates a transverse cross section of FIG. 37D through lines 37G-37G'.

FIG. 37C illustrates a longitudinal cross-sectional view of the distal end of the device in FIG. 37A. As noted herein, in some embodiments, advancement of the outer tubular member 8020 relative to the tube 8011 results in displacement of the helical or spiral cut(s) causing rotation of the distal end (e.g., by 180 degrees, other desired angles, etc.). FIG. 37D illustrates a detailed longitudinal cross sectional view of the distal aspect of the device 8010, FIG. 3E illustrates an axial cross sectional view through line 37E-37E' in FIG. 37D, FIG. 37F illustrates an axial cross sectional view through line 37F-37F' in FIG. 37D, and FIG. 37G illustrates an axial cross sectional view through line 37G-37G' in FIG. 37D.

Figures 38A, 38B:
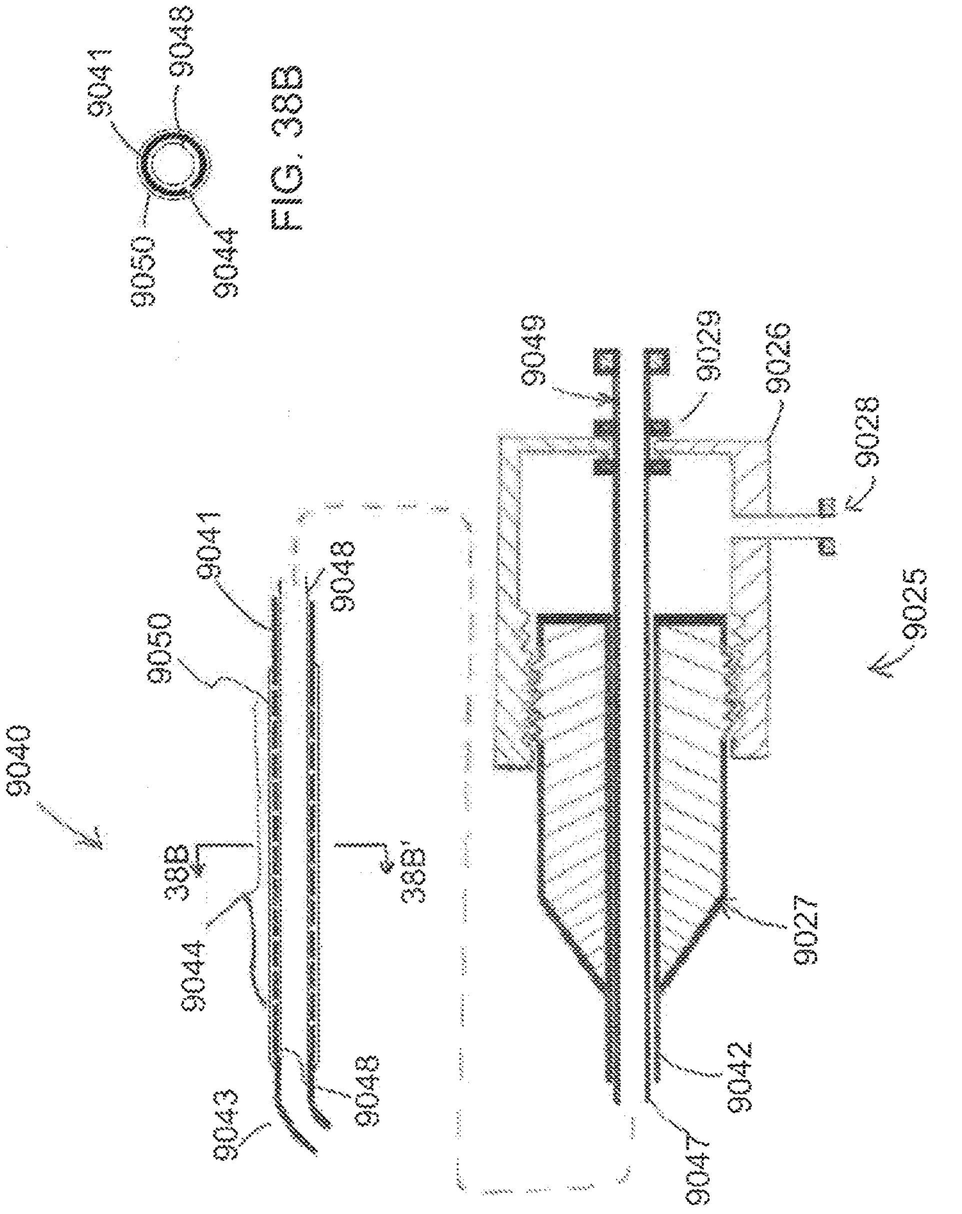
FIG. 38A illustrates a longitudinal cross-sectional view of another embodiment of a medical device configured to convert linear motion to rotational motion along the distal aspect of the device.
FIG. 38B illustrates a transverse cross section of FIG. 38A through lines 38B-38B'.

FIG. 38A illustrates a longitudinal cross-sectional view of another embodiment of an intraluminal medical device 9040. As shown, the device includes a tube 9041, an inner tubular member 9047, a distendable layer or member (e.g., balloon, other expandable member, etc.) 50 along the outer surface of the cut portion of the tube 9041 and a handle assembly 9025. In some embodiments, the handle assembly 9025 comprises a proximal handle component 9026 and a distal handle component 9027. In some embodiments, the proximal handle component 9026 and the distal handle component 9027 are coaxial with one another and can engage with one another via multiple means, such as, for example and without limitation, corresponding threaded components. In some embodiments, the proximal handle component 9026 is coupled to the proximal end of the inner tubular member 9049 via a swivel or other movable portion 9029, and the distal handle component 9027 is coupled to the proximal end of the tube 9042.

With continued reference to FIG. 38A, the proximal handle component 9026 comprises an inflation port 9028 for injection of fluid so as to distend the distendable or expandable member 9050 (e.g., balloon). In some embodiments, as shown, one or more helical or spiral cuts 9044 are located along the distal aspect of the tube 9041. The inner tubular member 9047 can be disposed within the lumen of the tube 9041. The tube 9041 and the inner tubular member 9047 can comprise one or more of a variety of materials, including, but not limited to, polyimide, polyurethane, polyether block amides (such as Pebax®), nylon, nickel titanium (Nitinol), stainless steel, stainless steel braiding, coiled wire and hollow helical stranded tubing. In some embodiments, the lumen of the tube 9041 and outer surface of the inner tubular member 9047 advantageously have a low coefficient of friction, e.g., via including using materials such PTFE, hydrophilic coatings and/or the like. In some embodiments, the distal end of the tube 9043 has, but is not limited to, a straight, angled, and reverse curved shape to aid in navigating the device 9040 through the human body. In addition, the distal end of the tube 9043 can have one or more malleable elements such that the distal end of the tube 9043 can be manually shaped by the operator at the time of use. In some embodiments, the helical or spiral cut(s) 9044 are present in the distal aspect of the tube 9041, wherein the one or more helical or spiral cut(s) 9044 has a cut width and a helical angle, as described. The cut width can range from 0.1 micrometers to 30 millimeters. In some embodiments, the cut width may range from about 0.1 millimeters to about 10 millimeters. The helical angle can range from 10 to 80 degrees relative to the longitudinal axis of the tube 9041. In some embodiments, the helical angle can range from 15 to 75 degrees. The distal end of the inner tubular member 9048 is coupled to the tube 9041 distal to the one or more helical or spiral cut(s) 9044. Means of coupling the distal end of the inner tubular member 9048 and tube 9041 include, but are not limited to, one or more of: 1) frictional fit, 2) adhesives (such as cyanoacrylate), 3) welding, 4) brazing, 5) soldering, and 6) mechanical linking. As shown, the distendable layer 9050 can be located along the outer surface of the cut portion of the tube 9041.

Figure 38D:
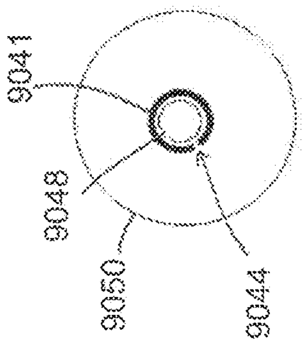
FIG. 38D illustrates a transverse cross section of FIG. 38C through lines 38C-38C'.
Figure 38C:
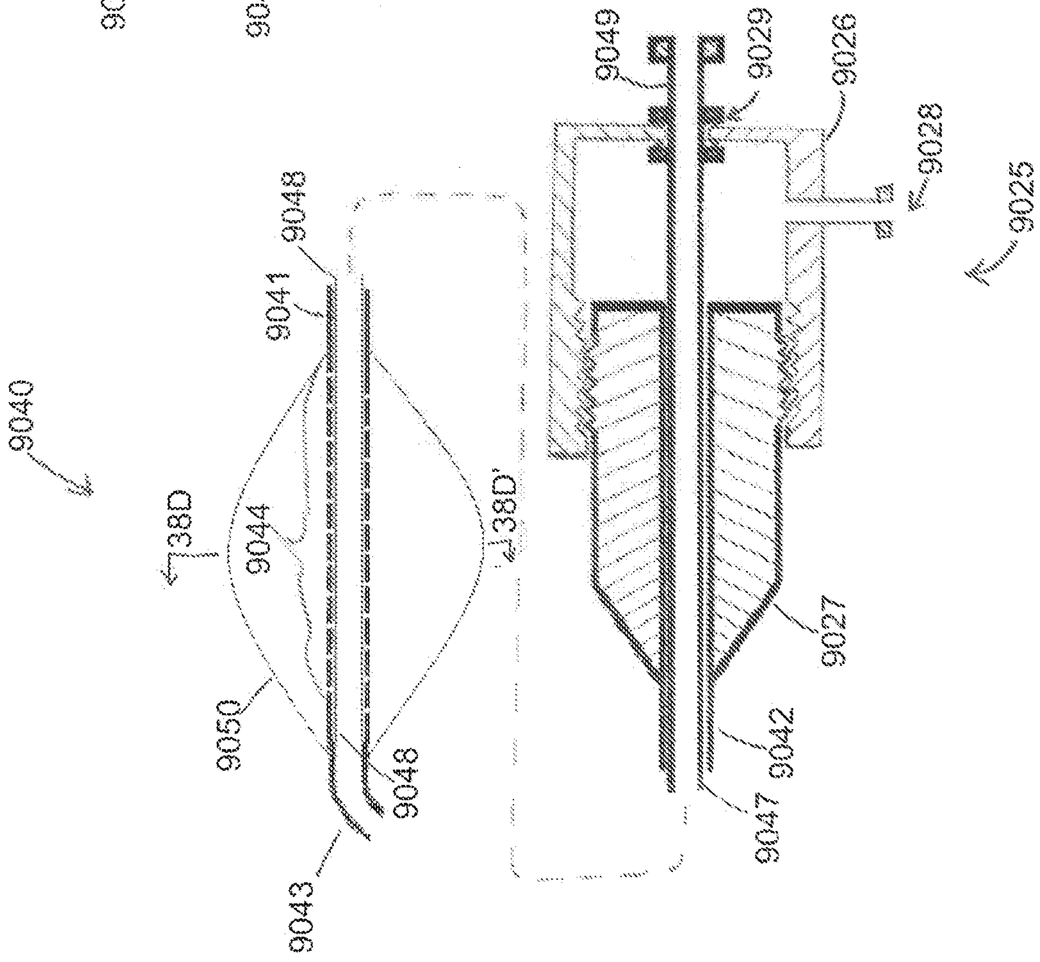
FIG. 38C illustrates a longitudinal cross-sectional view of one embodiment of a medical device for converting linear motion to rotational motion along the distal aspect of the device.

FIG. 38B illustrates a transverse cross section of FIG. 38A through lines 38B-38B'. The distendable layer 9050 can be distended as depicted in FIG. 38C (e.g., by injection of fluid through the inflation port 29). The injected fluid (e.g., water, saline, other liquids, gases, etc.) is able to travel within the space between the tube 9041 and the inner tubular member 9047. The fluid can subsequently travel through the one or more helical or spiral cut(s) 9044 into the space between the cut portion of the tube 9041 and the distendable member 9050. FIG. 38D is a transverse cross section of FIG. 38C through lines 38C-38C'. These configurations can be beneficial in preventing reflux and nontarget embolization during delivery of embolic material including but limited to radioembolic particles (e.g., Y-90).

Figure 39:
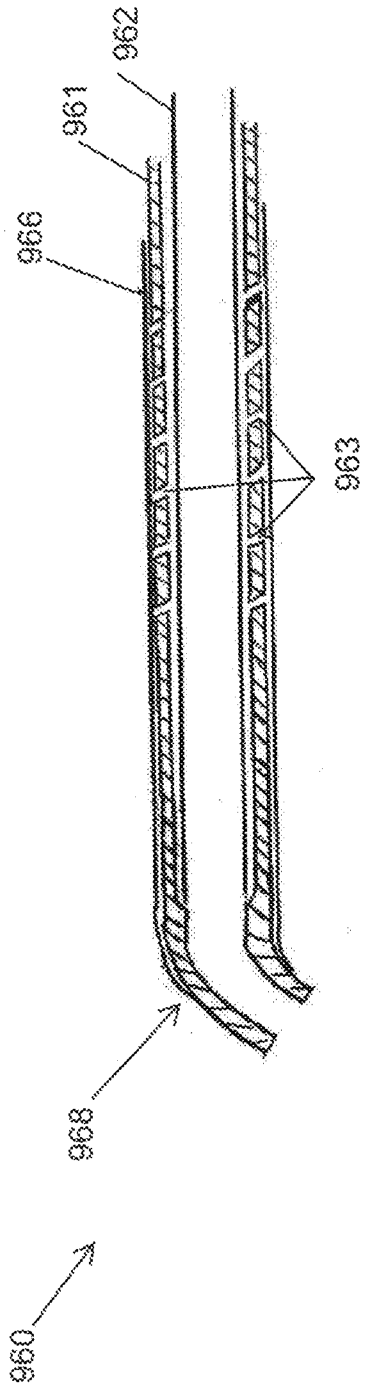
FIG. 39 illustrates a longitudinal cross-sectional view of another embodiment of a medical device configured to convert linear motion to rotational motion along the distal aspect of the device.

FIG. 39 illustrates another embodiment of an intraluminal device 960. As with other embodiments disclosed herein, the device 960 is configured to advantageously use longitudinal movement of one member or component (e.g., relative to another member or component) to create predictable, reliable and responsive rotation of the distal portion of the device. For example, in the illustrated arrangement, the pusher member, inner member and/or any other force imparting element 962 is sized, shaped and otherwise configured to slidably move within a lumen of a tube or outer member 961 positioned along the outside of the force imparting element 962. In the illustrated arrangement, the force imparting element 962 is configured to abut a flanged or shoulder portion formed along an interior of the tube 961 along the device's distal portion. As discussed herein with reference to other embodiments, advancing the pusher member, inner member or any other force imparting element 962 once the distal end of the pusher contacts the interior shoulder portion of the tube causes the distal portion of the tube or outer member 961 to rotate. In some embodiments, this results from the presence, configuration and other details of the cut(s) 963 (e.g., helical or spiral cuts) located along the distal end of the tube. In the embodiment of FIG. 39, the pusher 962 is not attached to the tube 961. Thus, the force imparting element (e.g., pusher member, inner member, etc.) 962 can be partially or completely removable from the tube (and thus, from the rest of the device). As shown, the device can include one or more outer layers, coatings, portions, components and/or the like 966 along the exterior of the tube 961. Such layers or portions 966 can be secured to the tube 961 and/or other portions of the device 960 (e.g., using adhesives, friction fit connections, etc.).

Figure 40:
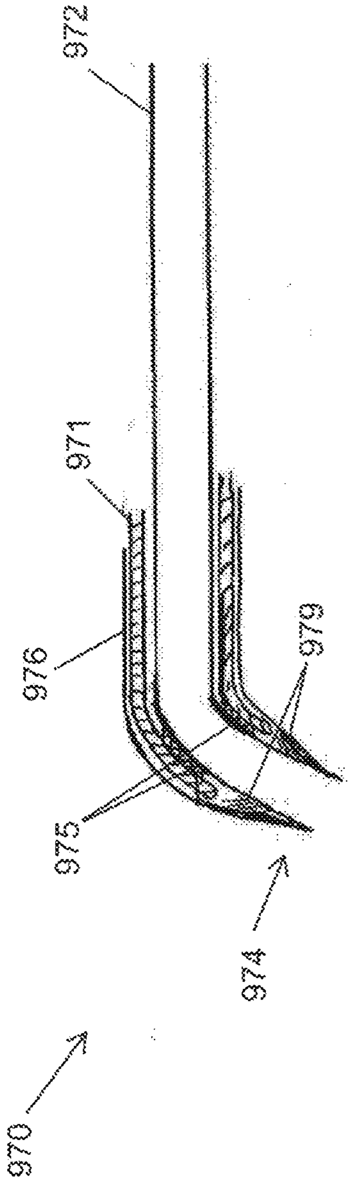
FIG. 40 illustrates a longitudinal cross-sectional view of another embodiment of a medical device configured to convert linear motion to rotational motion along the distal aspect of the device.

FIG. 40 illustrates an embodiment of an intraluminal device 970 similar to the one depicted in FIG. 39; however, in the device 970 of FIG. 40, the pusher member, inner member or other force imparting element 972 is attached or otherwise coupled (e.g., directly or indirectly) to the tube 971 (as well as one or more other layers or portions of the device, e.g., the outer layer positioned along the exterior of the device). As shown in FIG. 40, in some embodiments, the force imparting element 972 is secured to tube 971 along the distal end 974 of the device 970. In some embodiments, the distal end 974 of the device 970 can include a tapered tip (or other portion having a reduced diameter or other cross-sectional size). This can assist in positioning the distal end 974 of the device in a desired portion of a subject's anatomy and such a feature can be incorporated into any of the embodiments disclosed herein, even if not discussed or illustrated specifically in connection with such embodiments.

With continued reference to FIG. 40, the outer layer, coating or other outer portion 976 can also be secured or otherwise coupled or disposed relative to the tube 971 at one or more attachment sites. In some embodiments, such an attachment site or sites 979 is/are located at or near the distal end 974 of the device. However, the outer layer 976 and the tube 971 can be secured (e.g., directly or indirectly (using, for example, one or more intermediate members or features)) continuously or intermittently at one or more locations of the device, either in lieu of or in addition to the distal end 974 of the device 970, as desired or required. As noted above, such an outer member, coating or other member 976 can be incorporated into any of the embodiments disclosed herein.

In any of the embodiments disclosed in the present application, including the devices illustrated in FIGS. 39 and 40, one or more components of the device can include a wire (e.g., thin coil wire) that is wound (e.g., about a base member, about itself, etc.). For example, the pusher member, inner member or other force imparting element 962, 972 in FIG. 39 or 40 can include such a wound member, as can any other embodiments disclosed herein or equivalents thereof. For any embodiments disclosed herein, a force imparting element (e.g., pusher or inner member) can be sized to provide a desired amount of clearance between the outer diameter or other cross-sectional dimension of the pusher and the inner diameter or other dimension of the tube (e.g., to permit the pusher to freely slidably move relative to the tube without binding, sticking or other problems). Such wound members can provide the desired rigidity to the pusher and/or other components or portions of the device without buckling or encountering other problems.

Likewise, the outer or exterior layer of the device (e.g., the outer layer or coating 976 in the embodiment depicted in FIG. 40) can include one or more layers of a wound wire, coil or other member, either alone or in combination of another coating or member (e.g., layer of a thermoplastic, metallic member, etc.). Such an outer member can shield and protect the tube (e.g., the cut section of the tube), provide a smoother outer surface of the device and/or provide additional benefits or advantages.

Figure 41A:
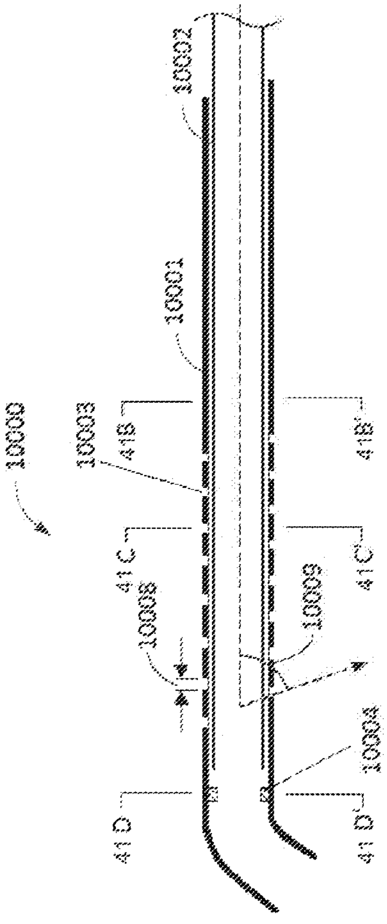
FIG. 41A illustrates a longitudinal cross-sectional view of another embodiment of a medical device comprising a single helix.
Figure 41B:
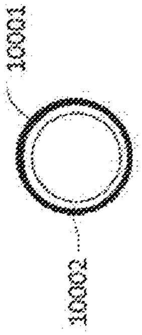
FIG. 41B illustrates a transverse cross sectional view of the device of FIG. 41A along lines B-B'.
Figure 41C:
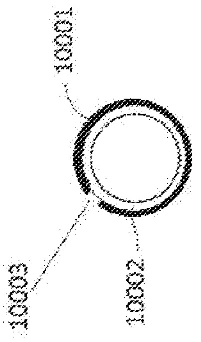
FIG. 41D illustrates a transverse cross sectional view of the device of FIG. 41A through lines D-D'.
Figure 41D:
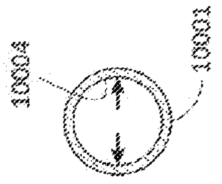

FIG. 41A illustrates a medical device 10000 according to another embodiment of the present application. As shown, the device 10000 can include a tube 10001, a longitudinal displacer, pusher or other inner member 10002, and a handle (not shown) that is attached to the proximal end of the tube 10001. In the depicted embodiment, a partial thickness helical or spiral cut 10003 is included at or along the distal portion of the tube 10001. In some embodiments, the partial thickness helical or spiral cut 10003 includes a cut width 10008 and helical angle 10009. The cut width 10008 and/or helical angle 10009 can be identical or similar to any of the embodiments disclosed herein, including for example and without limitation, the embodiments illustrated and disclosed with reference to FIG. 3A.

In some embodiments, the partial thickness cut 10003 extends only partially through the wall of the tube 10001. Such a partial thickness cut 10003 can be incorporated into any of the embodiments disclosed herein. For example, in any of the arrangements disclosed herein, including without limitation the device illustrated in FIG. 41A, the cut 10003 extends 10 to 90% (e.g., 10-15, 15-20, 20-25, 25-30, 30-35, 35-40, 40-45, 45-50, 50-55, 55-60, 60-65, 65-70, 70-75, 75-80, 80-85, 85-90%, percentages between the foregoing ranges, etc.) of the overall thickness of the wall of the tube 10001, as desired or required.

With continued reference to FIG. 41A, the end of the tube 10001 distal to the partial thickness helical cut 10003 can comprise a curve to aid in navigating the medical device 10000 through the vasculature. For example, such a configuration can help the user manipulate the device 10000 through various curves and turns to access a desired portion or location of the subject's anatomy. In some embodiments, the cut width 10008 is between 0.1 micrometers and 30 millimeters (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-15, 15-20, 20-30, 30-40, 40-50, 50-60, 60-70, 70-80, 80-90, 90-100, 100-150, 150-200, 200-250, 250-300, 300-400, 400-500, 500-600, 600-700, 700-800, 800-900 micrometers, 900 micrometers to 1 millimeters, 1-2, 2-3, 3-4, 4-5, 5-6, 6-7, 7-8, 8-9, 9-10, 10-15, 15-20, 20-25, 25-30 millimeters, widths between the foregoing values, etc.). In some embodiments, the cut width ranges from 0.1 millimeters to 10 millimeters (e.g., 0.5-5 millimeters). In other configurations, the cut width is less than 0.1 micrometers or greater than 30 millimeters (e.g., 30-40, 40-50, 50-100, values between the foregoing, greater than 100 millimeters), as desired or required for a particular application or use.

In some embodiments, including for the arrangement illustrated in FIG. 41A, as well as any other arrangements disclosed herein or equivalents thereof, the helical angle 10009 of the cut ranges from 10 to 80 degrees (e.g., 10-15, 1-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the tube 10001. In some embodiments, the helical angle 10009 ranges from 15 to 75 degrees (e.g., 20 to 70 degrees, 30 to 60 degrees, 15 to 30 degrees, 25 to 40 degrees, 40 to 60 degrees, 60 to 75 degrees, etc.).

According to some embodiments, as with other arrangements disclosed herein, the sleeve 10002 is disposed within the lumen of the tube 10001. In some configurations, the tube 10001 has a smaller diameter (e.g., inner diameter) at or along the distal end to form a shelf 10004 that prevents forward movement of the sleeve 10002 relative to the tube 10001. However, any other configuration can be used that prevents forward movement of the sleeve relative to the tube. For example, the sleeve and the tube can be coupled (e.g., via one or more attachment methods or devices, directly or indirectly) along the distal end, using, for instance and without limitation, adhesives, welds or other welding procedures, brazing, soldering, other heat based methods or technologies, mechanical linking and/or the like. Alternatively, the sleeve 10002 and the tube 10001 can have one or more elements that interact with an electromagnetic field, wherein said elements may be one of: a magnet, a ferromagnetic material, an electret, a material capable of holding an electrical charge, a wire, and a coil configured to carry current and generate a magnetic field. In some embodiments, the sleeve 10002 abuts the shelf 10004 to transmit longitudinal force from the sleeve 10002 to the tube 10001. In some embodiments, the sleeve 10002 may be coupled to the tube 10001 at a point distal to the helical or spiral cut 10003 (e.g., the partial thickness cut), such as, for instance, at the shelf 10004, and can be selectively advanced and/or retracted within the tube 10001. As noted herein, in some embodiments, such advancement and retraction of the sleeve 10002 results in advancement or retraction of the tube 10001 relative to the sleeve distal to the partial thickness helical or spiral cut 10003.

In some embodiments, the coupling means or mechanism between the sleeve 10002 and the tube 10001 can be reversed. For instance, a solder connection can be melted or severed by application of electric current or heat to release the sleeve 10002 from the tube 10001. Means of coupling the sleeve 10002 and tube 10001 include, but are not limited to, one or more of: frictional fit, adhesives (e.g., acrylic-based adhesives (e.g., cyanoacrylate), epoxies, silicone, thermosetting resins, polyurethanes, other suitable adhesives, etc.), welding, brazing, soldering, mechanical linking or coupling and/or the like.

According to some configurations, the tube, 10001 and/or the sleeve 10002 can comprise one or more of a variety of materials, including, without limitation, polyimide, polyurethane, polyether block amides (such as Pebax®), nylon, other polymers, nitinol, stainless steel braiding, coiled wire, hollow helical stranded tubing, other metals and/or alloys and/or any other natural or synthetic materials, as desired or required.

In some embodiments, the partial thickness cut 10003 is elastic and can undergo elongation and/or contraction. In some configurations, in light of the relative decreased thickness as compared to the rest of the tube 10001, the partial thickness cut 10003 preferentially undergoes elongation. The lumen of the tube 10001 and outer surface of the sleeve 10002 preferentially have a low coefficient of friction. For example, in some embodiments, the surfaces and/or components that contact each other can include relatively low friction materials, coatings, layers, etc., such as for example, PTFE, hydrophilic materials, other polymeric materials, etc. In addition, the distal aspect of the tube 10001 may have, but is not limited to, a straight, angled, and reverse curved shape.

Figure 42A:
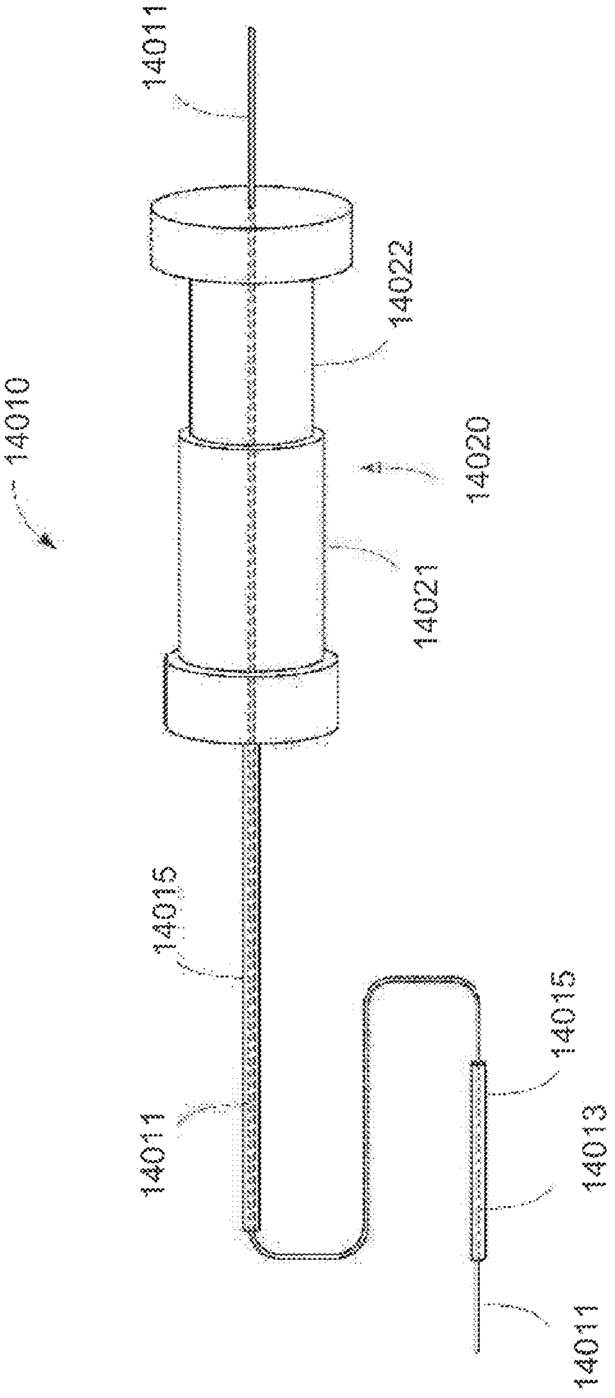
FIG. 42A schematically illustrates another embodiment of a medical device configured to convert linear motion to rotational motion along the distal aspect of the device.

FIG. 42A schematically illustrates a medical device 14010 according to another embodiment of the present application. In some embodiments, as illustrated, the device 14010 comprises a tube 14011, an outer sheath 14015 and a handle assembly 14020. As shown in FIG. 42A, the handle assembly 14020 can comprise a proximal component or portion 14021 and a distal component or portion 14022. In some embodiments, the distal component or portion 14022 is coupled to the proximal end of the tube 14011, and the proximal component or portion 14021 is coupled to the proximal end of the tube 14011. The distal component 14022 can be coupled to the proximal end of the outer sheath 14015.

With continued reference to FIG. 42A, the proximal component or portion 14021 and the distal component or portion 14022 each have cylindrical bodies, such that the proximal component or portion 14021 can be inserted (e.g., slidably) into or otherwise relative to the distal component or portion 14022. Thus, the cross-sectional shape of the components 14201, 14022 can be circular or round. In other embodiments, however, the proximal and distal components can include any other cross-sectional shape (e.g., square or rectangular, other polygonal, oval, irregular, etc.), as desired or required. Regardless of their exact shape, size and other characteristics, the proximal and distal components or portions 14021, 14022 can be slidably or otherwise movable relative to each other.

In the illustrated embodiment, the tube 14011 is disposed within the lumen of the outer sheath 14015. Each of the tube 14011 and the outer sheath 14015 can comprise one or more of a variety of materials, including, but not limited to, polyimide, polyurethane, polyether block amides (such as Pebax®), nylon, other polymers, nickel titanium (Nitinol), stainless steel, stainless steel braiding, hollow helical stranded tubing, other metals or alloys, other composites or natural materials and/or the like, as desired or required. The tube 14011 can be located within the lumen of the outer sheath 14015 such that the one or more helical or spiral cut(s) 14013 in the distal aspect or portion of the tube 14011 are disposed within the lumen of the outer sheath 14015 while the distal end of the tube 14011 extends beyond (e.g., distally beyond) the outer sheath 14015. Therefore, in some embodiments, the total length of the tube 14011 is greater than the total length of the outer sheath 14015, while the length from the proximal end of the tube to the distal most aspect of the cut portion of the tube is less than the total length of the outer sheath.

In addition, in any of the embodiments disclosed herein, as illustrated for example in FIGS. 42B to 42E, a pull wire 14016 can be coupled or otherwise secured to the tube 14011. In the depicted configuration, the pull wire 14016 is coupled distal to the one or more helical or spiral cut(s) 14013. However, in other embodiments, the pull wire can be secured to any other part and/or any other location of the tube 14011. In yet other embodiments, any other feature or method can be used to assist in the bending or other manipulation of the device. For example, the use of shape memory materials, e.g., as discussed herein with reference to FIGS. 43A-43E, can be used and/or any other method, device, feature and/or technology, as desired or required.

Figure 42B:
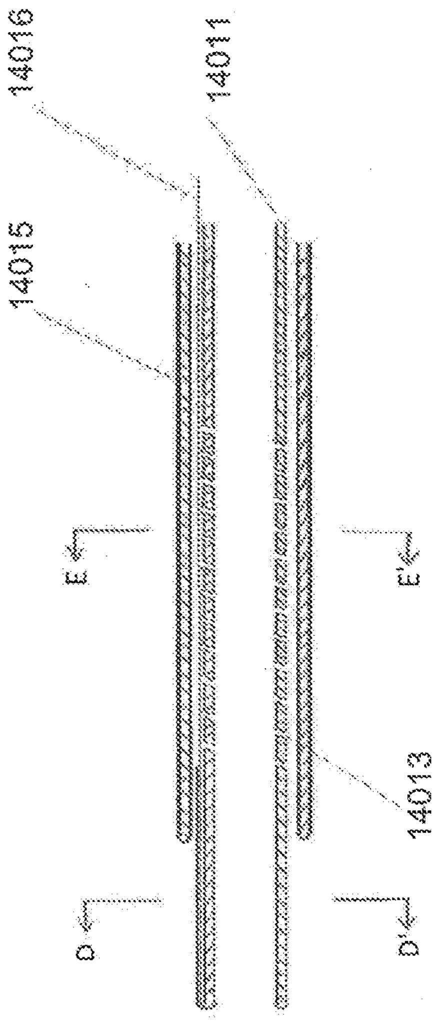
FIG. 42B illustrates a longitudinal cross-sectional view of the distal end of the device of FIG. 42A in a first orientation.

FIG. 42B illustrates a longitudinal cross-sectional view of the distal end of the device 14010 of FIG. 42A. In the depicted arrangement, no tension is being applied to the distal end of the tube 14011 via the pull wire 14016 such that the distal aspect of the tube 14011 is in a straight position (e.g., 0 degrees of tip deflection relative to the longitudinal axis of the device). As shown and discussed herein with other embodiments, the tube 14011 comprises one or more cuts 14013 (e.g., helical or spiral cuts) at or along the distal aspect or portion of the tube. In some arrangements, the helical or spiral cut(s) 14013 has or have a cut width and helical angle. Accordingly, the end of the tube 14011 distal to the one or more helical or spiral cuts 14013 may include a curve to aid in navigating the device 14010 through the vasculature. For example, such a configuration can help the user manipulate the device 14010 through various curves and turns to access a desired portion or location of the subject's anatomy.

In some embodiments, the cut width is between 0.1 micrometers and 30 millimeters (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-15, 15-20, 20-30, 30-40, 40-50, 50-60, 60-70, 70-80, 80-90, 90-100, 100-150, 150-200, 200-250, 250-300, 300-400, 400-500, 500-600, 600-700, 700-800, 800-900 micrometers, 900 micrometers to 1 millimeters, 1-2, 2-3, 3-4, 4-5, 5-6, 6-7, 7-8, 8-9, 9-10, 10-15, 15-20, 20-25, 25-30 millimeters, widths between the foregoing values, etc.). In some embodiments, the cut width ranges from 0.1 millimeters to 10 millimeters (e.g., 0.5-5 millimeters). In other configurations, the cut width is less than 0.1 micrometers or greater than 30 millimeters (e.g., 30-40, 40-50, 50-100, values between the foregoing, greater than 100 millimeters), as desired or required for a particular application or use.

In some embodiments, including for the arrangement illustrated in FIGS. 42A to 42E, as well as any other arrangements disclosed herein or equivalents thereof, the helical angle of the cut ranges from 10 to 80 degrees (e.g., 10-15, 1-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the tube 14011. In some embodiments, the helical angle ranges from 15 to 75 degrees (e.g., 20 to 70 degrees, 30 to 60 degrees, etc.).

With continued reference to the embodiment illustrated in FIGS. 42A to 42E, adjacent or contacting surfaces of the lumen or opening of the outer sheath 14015 and the tube 14011 comprise a low coefficient of friction. For example, these components can include contacting surfaces with relatively low-friction materials or coatings, such as, without limitation PTFE, hydrophilic coatings or materials (e.g., and without limitation, from companies such as BioCoat, DSM Medical, Surmodics, AST Products, Hydromer, Surface Solutions Labs, Harland Medical, Bayer Material Science, Medi-Solve, AdvanSource Biomaterials (e.g. HYDAK®, Comfortcoat™, LubriLast®, Aquacoat, Lubricient®, Baymedix CL, Hydromer) and/or the like.

Figure 42D:
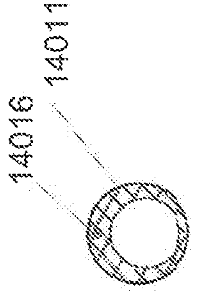
FIG. 42D illustrates a transverse cross sectional view of the device of FIG. 42B through lines D-D'.
Figure 42E:
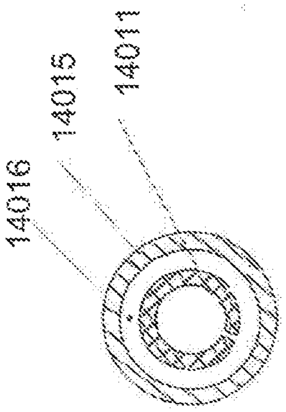
FIG. 42E illustrates a transverse cross sectional view of the device of FIG. 42B through lines E-E'.
Figure 42C:
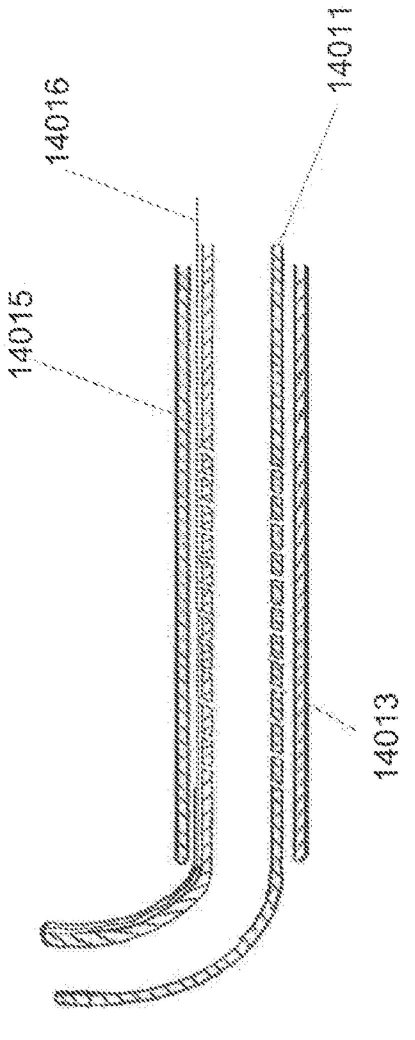
FIG. 42C illustrates a longitudinal cross-sectional view of the distal end of the device in FIG. 42A in a second orientation.

FIG. 42C illustrates a longitudinal cross-sectional view of the distal end of the device in FIG. 42A. In the depicted orientation, tension is being applied to the pull wire 14016 such that the distal aspect or portion of the tube 14011 is deflected 90 degrees or approximately 90 degrees relative to the longitudinal axis of the tube 14011. In some embodiments, the distal end of the tube 14011 can be deflected at any of a variety of angles relative to the longitudinal axis of the tube 14011, including without limitation angles between 0 and 270 degrees (e.g. 0-30 degrees, 0-45 degrees, 0-60 degrees, 0-90 degrees, 0-120 degrees, 0-150 degrees, 0-180 degrees, 0-210 degrees, 0-240 degrees, 0-270 degrees, 15-30 degrees, 15-45 degrees, 15-60 degrees, 15-90 degrees, 15-120 degrees, 15-150 degrees, 15-180 degrees, 15-210 degrees, 15-240 degrees, 15-270 degrees, 30-45 degrees, 30-60 degrees, 30-90 degrees, 30-120 degrees, 30-150 degrees, 30-180 degrees, 30-210 degrees, 30-240 degrees, 30-270 degrees, 45-60 degrees, 45-90 degrees, 45-120 degrees, 45-150 degrees, 45-180 degrees, 45-210 degrees, 45-240 degrees, 45-270 degrees, 60-90 degrees, 60-120 degrees, 60-150 degrees, 60-180 degrees, 60-210 degrees, 60-240 degrees, 60-270 degrees, 75-90 degrees, 75-120 degrees, 75-150 degrees, 75-180 degrees, 75-210 degrees, 75-240 degrees, 75-270 degrees, 90-120 degrees, 90-150 degrees, 90-180 degrees, 90-210 degrees, 90-240 degrees, and 90-270 degrees). FIG. 42D illustrates a transverse cross section of FIG. 42B through lines D-D', while FIG. 42F illustrates a transverse cross section of FIG. 42B through lines E-E'.

Figure 43A:
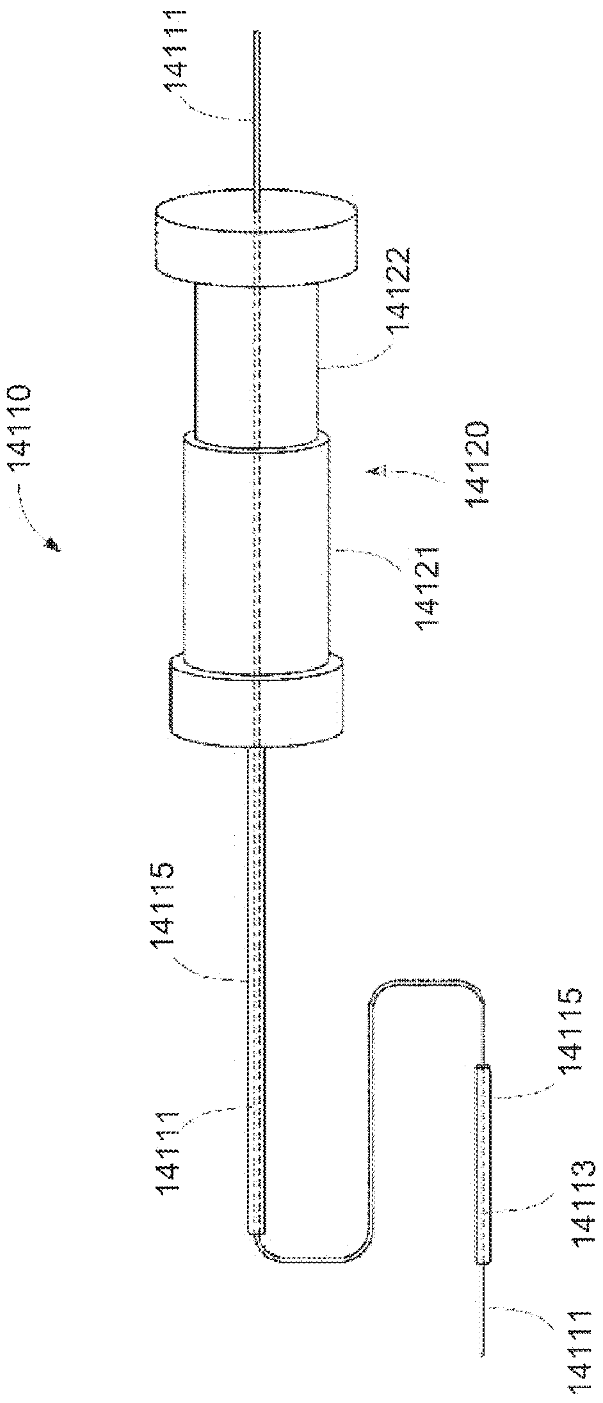
FIG. 43A schematically illustrates another embodiment of a medical device configured to convert linear motion to rotational motion along the distal aspect of the device.

FIG. 43A schematically illustrates a medical device 14110 according to another embodiment of the present application. As with other arrangements disclosed herein, the depicted device 14110 includes a tube 14111, an outer sheath 14115 and a handle assembly 14120. The handle assembly 14120 can include a proximal component or portion 14121 and a distal component or portion 14122. The distal component 14122 can be coupled to the proximal end of the tube 14111. The proximal component 14121 can be coupled or otherwise secured to the proximal end of the tube 14111. In some embodiments, the distal component 14122 is coupled or otherwise secured to the proximal end of the outer sheath 14115.

With continued reference to FIG. 43A, the proximal component or portion 14121 and the distal component or portion 14122 each have cylindrical bodies, such that the proximal component or portion 14121 can be inserted (e.g., slidably) into or otherwise relative to the distal component or portion 14122. Thus, the cross-sectional shape of the components 14121, 14122 can be circular or round. In other embodiments, however, the proximal and distal components can include any other cross-sectional shape (e.g., square or rectangular, other polygonal, oval, irregular, etc.), as desired or required. Regardless of their exact shape, size and other characteristics, the proximal and distal components or portions 14121, 14122 can be slidably or otherwise movable relative to each other.

The tube 14111 and the outer sheath 14115 can comprise one or more of a variety of materials, including, but not limited to, polyimide, polyurethane, polyether block amides (such as Pebax®), nylon, other polymers, nickel titanium (Nitinol), stainless steel, stainless steel braiding, hollow helical stranded tubing, other metals or alloys and/or any other material, as desired or required.

In some embodiments, the tube 14111 is located within the lumen of the outer sheath 14115 such that the one or more cuts 4113 (e.g., helical or spiral cuts) in the distal aspect of the tube 14111 are disposed or otherwise positioned within the lumen of the outer sheath 14115 while the distal end of the tube 14111 extends beyond the outer sheath 14115. Therefore, in some arrangements, the total length of the tube 14111 is greater than the total length of the outer sheath 14115, while the length from the proximal end of the tube to the distalmost aspect of the cut portion of the tube is less than the total length of the outer sheath.

In addition, according to some configurations, a shape memory element 14116 can be coupled or otherwise secured to the tube 14111 distal to the one or more cuts 14113 (e.g., helical or spiral cuts). The shape memory element 14116 can include, but is not limited to, one or more shape memory alloys and/or other materials or configurations, such as, for example, Nitinol, other shape memory polymers, etc. In one embodiment, the shape memory element 14116 can be under phase/shape transformation via Joule heating, wherein the shape memory element 14116 is coupled to two or more wires 14117 and 14119. In such configurations, one wire 14117 can be coupled to the proximal end of the shape memory element 14116 and a second wire 14119 is coupled to an electrically conductive band 14118. In some embodiments, the electrically conductive band 14118 is coupled or otherwise secured (e.g., directly or indirectly) to the distal end of the shape memory element 14116. The electrically conductive band 14118 can comprise, but is not limited to, one or more materials, such as, for example, platinum, gold, palladium, stainless steel and/or any other metal and/or alloy. In some embodiments, the electrically conductive band 14118 can advantageously serve as a radiopaque marker during use of the device within the anatomy.

Figure 43B:
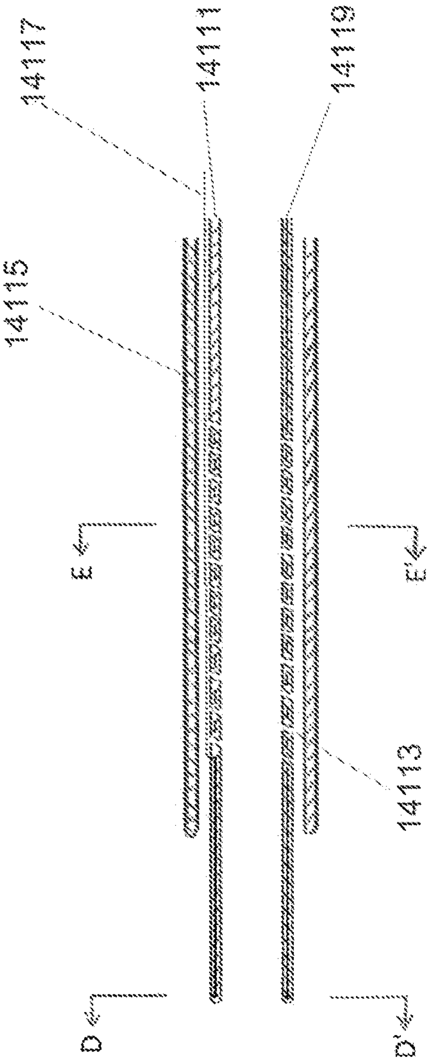
FIG. 43B illustrates a longitudinal cross-sectional view of the distal end of the device of FIG. 43A with the distal end of the tube in a first orientation.

FIG. 43B illustrates a longitudinal cross-sectional view of the distal end of the device 14110 of FIG. 43A when the shape memory element 14116 is applied to the distal end of the tube 14111 such that the distal aspect of the tube 14111 is in a straight position (e.g., 0 degrees of tip deflection relative to the longitudinal axis of the device). In the depicted arrangement, one or more helical or spiral cut(s) 14113 are present in the distal aspect or portion of the tube 14111. As discussed with reference to other embodiments herein, the cuts 14113 include a cut width and helical angle.

In some embodiments, the cut width is between 0.1 micrometers and 30 millimeters (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-15, 15-20, 20-30, 30-40, 40-50, 50-60, 60-70, 70-80, 80-90, 90-100, 100-150, 150-200, 200-250, 250-300, 300-400, 400-500, 500-600, 600-700, 700-800, 800-900 micrometers, 900 micrometers to 1 millimeters, 1-2, 2-3, 3-4, 4-5, 5-6, 6-7, 7-8, 8-9, 9-10, 10-15, 15-20, 20-25, 25-30 millimeters, widths between the foregoing values, etc.). In some embodiments, the cut width ranges from 0.1 millimeters to 10 millimeters (e.g., 0.5-5 millimeters). In other configurations, the cut width is less than 0.1 micrometers or greater than 30 millimeters (e.g., 30-40, 40-50, 50-100, values between the foregoing, greater than 100 millimeters), as desired or required for a particular application or use.

In some embodiments, including for the arrangement illustrated in FIG. 43A, as well as any other arrangements disclosed herein or equivalents thereof, the helical angle of the cut ranges from 10 to 80 degrees (e.g., 10-15, 1-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the tube 14111. In some embodiments, the helical angle ranges from 15 to 75 degrees (e.g., 20 to 70 degrees, 30 to 60 degrees, etc.).

Figure 43E:
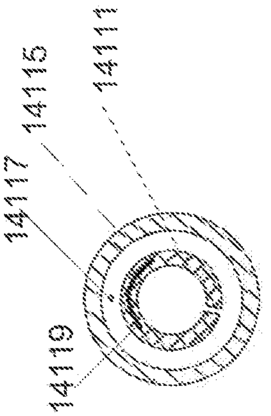
FIG. 43E illustrates a transverse cross sectional view of the device of FIG. 43B through lines E-E'.
Figure 43D:
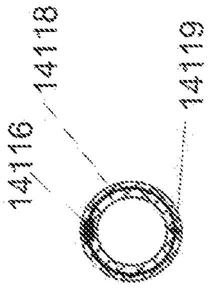
FIG. 43D illustrates a transverse cross sectional view of the device of FIG. 43B through lines D-D'.
Figure 43C:
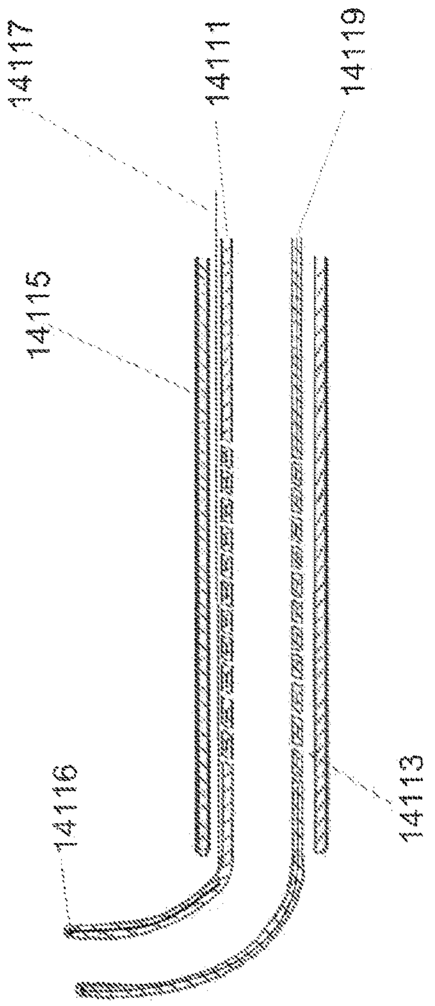
FIG. 43C illustrates a longitudinal cross-sectional view of the distal end of the device of FIG. 43A with the distal end of the tube in a second orientation.

In some embodiments, adjacent contacting surfaces of the lumen of the outer sheath 14115 and the tube 14111 can advantageously have a low coefficient of friction, including but not limited to having materials or coating with relatively low friction properties, such as, e.g., PTFE, hydrophilic coatings or materials (e.g., from companies such as, for instance and without limitation, BioCoat, DSM Medical, Surmodics, AST Products, Hydromer, Surface Solutions Labs, Harland Medical, Bayer Material Science, Medi-Solve, AdvanSource Biomaterials (e.g. HYDAK®, Comfortcoat™, LubriLast®, Aquacoat, Lubricient®, Baymedix CL, Hydromer)) and/or the like. FIG. 43C illustrates a longitudinal cross-sectional view of the distal end of the device in FIG. 43A. In the depicted orientation, current is being applied to the shape memory element 14116 via the wires 14117 and 14119 such that the distal aspect or portion of the tube 14111 is deflected by 90 degrees (e.g., or approximately 90 degrees) relative to the longitudinal axis of the tube 14111. FIG. 43D illustrates a transverse cross sectional vie of the device of FIG. 43B through lines D-D', while FIG. 43E illustrates a transverse cross sectional view of the device through lines E-E'. In some embodiments, the distal end of the tube 14111 can be deflected at any of a variety of angles relative to the longitudinal axis of the tube 14111, including, for example, and without limitation, angles between 0 and 270 degrees (e.g. 0-30 degrees, 0-45 degrees, 0-60 degrees, 0-90 degrees, 0-120 degrees, 0-150 degrees, 0-180 degrees, 0-210 degrees, 0-240 degrees, 0-270 degrees, 15-30 degrees, 15-45 degrees, 15-60 degrees, 15-90 degrees, 15-120 degrees, 15-150 degrees, 150-180 degrees, 15-210 degrees, 15-240 degrees, 15-270 degrees, 30-45 degrees, 30-60 degrees, 30-90 degrees, 30-120 degrees, 30-150 degrees, 30-180 degrees, 30-210 degrees, 30-240 degrees, 30-270 degrees, 45-60 degrees, 45-90 degrees, 45-120 degrees, 45-150 degrees, 45-180 degrees, 45-210 degrees, 45-240 degrees, 45-270 degrees, 60-90 degrees, 60-120 degrees, 60-150 degrees, 60-180 degrees, 60-210 degrees, 60-240 degrees, 60-270 degrees, 75-90 degrees, 75-120 degrees, 75-150 degrees, 75-180 degrees, 75-210 degrees, 75-240 degrees, 75-270 degrees, 90-120 degrees, 90-150 degrees, 90-180 degrees, 90-210 degrees, 90-240 degrees, and 90-270 degrees).

FIG. 44A illustrates a diagram of a medical device 14210 according to another embodiment of the present application. As shown and as discussed herein with reference to other embodiments, the device 14210 comprises a tube 14211, an outer sheath 14215, a sleeve 14212 and a handle assembly 14220. The handle assembly 14220 can include a proximal component or portion 14221 and a distal component or portion 14222. The distal component 14222 can be coupled to the proximal end of the tube 14211. The proximal component 14221 can be coupled to the proximal end of the sleeve 14212.

With continued reference to FIG. 44A, the proximal component 14221 can comprise a swivel member or portion 14229 that extends circumferentially around the proximal end of the sleeve 14212. In such embodiments, the proximal component 14221 can rotate independent of the sleeve 14212. In some arrangements, the proximal component 14221 and the distal component 14222 each have cylindrical bodies, such that the proximal component 14221 may be inserted into the distal component 14222. The tube 14211 can be disposed or otherwise positioned within the lumen of the outer sheath 14215. The tube 14211, the sleeve 14212, the outer sheath 14215 and/or any other portion or component of the device can comprise one or more of a variety of materials, including, but not limited to, polyimide, polyurethane, polyether block amides (such as Pebax®), nylon, other polymer, nickel titanium (Nitinol), stainless steel, stainless steel braiding, hollow helical stranded tubing, other metals or alloys and/or any other material.

In some embodiments, the distal end of the tube 14211 can include, but is not limited to, one or more angled or reverse curved shapes. In the depicted arrangement, the tube 14211 is located within the lumen of the outer sheath 14215, such that the one or more helical or spiral cut(s) 14213 (and/or any other cuts or features) in the distal aspect of the tube 14211 are disposed within the lumen of the outer sheath 14215. The distal end of the tube 14211 can extend beyond the outer sheath 14215. In some embodiments, therefore, the total length of the tube is greater than the total length of the outer sheath, while the length from the proximal end of the tube to the distal most aspect of the cut portion of the tube is less than the total length of the outer sheath.

In some embodiments, a sleeve 14212 is disposed within the lumen of the tube 14211. The tube 14211 can have a reduced inner diameter on the distal end to form a shelf 14214 that prevents or otherwise limits forward movement of the sleeve 14212. In some embodiments, the sleeve 14212 abuts the shelf 14214 to transmit longitudinal force from the sleeve 14212 to the tube 14211. In some embodiments, the sleeve 14212 is coupled or otherwise secured to the tube 14211 at a point distal to the one or more helical or spiral cut(s) 14213, such as at the shelf 14214, and can be advanced or retracted within the tube 14211. In some configurations, advancement or retraction of the sleeve 14212 results in advancement or retraction of the tube 14211 distal to the one or more cut 14213. In some embodiments, the coupling means may be reversible, such as a solder connection that can be melted by application of electric current or heat to release the sleeve 14212 from the tube 14211. Means of coupling the sleeve 14212 and tube 14211 include, but are not limited to, one or more of the following: frictional fit, press fit, adhesives (e.g., acrylic based adhesives (e.g. cyanoacrylate), epoxies, silicone, thermosetting resins, polyurethanes and/or the like), welding, brazing, soldering, mechanical linking and/or any other coupling method, device and/or technology, as desired or required.

According to some embodiments, the lumen of the tube 14211 and outer surface of the sleeve 14212 preferentially have a low coefficient of friction. For example, adjacent contacting surfaces of the tube 14211 and the sleeve 14212 can comprise PTFE, hydrophilic materials/coatings from companies such as, for example and without limitation, BioCoat, DSM Medical, Surmodics, AST Products, Hydromer, Surface Solutions Labs, Harland Medical, Bayer Material Science, Medi-Solve, AdvanSource Biomaterials (e.g. HYDAK®, Comfortcoat™, LubriLast®, Aquacoat, Lubricient®, Baymedix CL, Hydromer) and/or the like.

FIG. 44B illustrates a longitudinal cross-sectional view of the device of FIG. 44A. In the depicted orientation, the outer sheath is not engaging the curved portion of the tube, resulting in a 180 degree (e.g., or approximately a 180 degree) curvature of distal aspect or portion of the tube relative to the longitudinal axis. FIG. 44C illustrates a longitudinal cross-sectional view of the distal end of the device of FIG. 44A. In the depicted orientation, the outer sheath partially engages the curved portion of the tube resulting in a 90 degree (e.g., approximately a 90 degree) curvature of distal aspect of the tube relative to the longitudinal axis of the device. FIG. 44D illustrates a longitudinal cross-sectional view of the distal end of the device of FIG. 44A. In the depicted orientation, the outer sheath further engages the curved portion of the tube resulting in a 45 degree (e.g., approximately a 45 degree) curvature of distal aspect of the tube relative to the longitudinal axis. Further, FIG. 44E illustrates a longitudinal cross-sectional view of the distal end of the device of FIG. 44A. In the depicted orientation, the outer sheath fully engages the curved portion of the tube resulting in straightening (0 degree curvature relative to the longitudinal axis) of distal aspect of the tube. FIG. 44F illustrates a transverse cross section of FIG. 44E through lines F-F', while FIG. 44G illustrates a transverse cross section of FIG. 44E through lines G-G'. In some embodiments, the curve in the distal end of the tube 14211 can be have a variety of angles relative to the longitudinal axis of the tube 14211, including without limitation angles between 10 and 270 degrees (e.g., 60 to 180, 90 to 145, 10 to 45, 30 to 90, 30 to 60, 45 to 90, 90 to 100, 100 to 110, 110 to 120, 120 to 130, 130 to 140, 140 to 150, 150 to 160, 160 to 170, 170 to 180, 180 to 190, 190 to 200, 200 to 210, 210 to 220, 220 to 230, 230 to 240, 240 to 250, 250-260, 260 to 270, ranges between the foregoing, etc.).

According to some embodiments, the degree of stiffness can very along the longitudinal axis of the device, such that the stiffness increases in continuous fashion, graduated stepwise fashion or a combination of the two, wherein said variable stiffness results in improved delivery/navigation of the device through the subject's anatomy. This variable stiffness can be achieved by multiple mechanisms including but not limited to 1) multiple transverse cuts with variable spacing between the cuts; 2) varying the modulus of elasticity of one or more portions of the device between the one or more spiral or helical cuts and the noncut portion of the device; 3) varying the thickness of one or more portions of the device between the one or more spiral or helical cuts and the noncut portion of the device; 4) a combination of the above mechanisms. With regards to varying the modulus of elasticity and/or the thickness of one or more portions of the device between the one or more spiral or helical cuts and the noncut portion of the device, said portions with a variable the modulus of elasticity can include but are not limited to: 1) the tubular member with one or more at least partial spiral or helical cuts; 2) the force imparting element; and/or 3) the outer tube. This variable longitudinal stiffness enables the push-ability of the proximal end while providing the flexible along the distal end of the device such that the device is able to navigate tortuous anatomy.

In some embodiments, a medical device can include, among other things, a medical device having multiple transverse cuts with variable spacing between the cuts to create variable flexibility. For example, FIG. 45 schematically illustrates another embodiment of a medical device configured to have one or more cuts or partial cuts between the one or more helical or spiral cuts and the non-cut portion of the tubular member, wherein the one or more partial cuts are not contiguous with the one or more helical or spiral cuts resulting in varying stiffness between the helical or spiral cut section of the tubular member and the non-cut section of the tubular member.

FIG. 45 illustrates the distal aspect or portion of a medical device 15000 according to another embodiment of the present application. As shown, the device 15000 can include a tube or other elongate member 15001, a longitudinal displacer or force imparting element, such as, for example, a sleeve 15002. The sleeve 15002 can include a sleeve, another cannulated or otherwise one or more openings through it.

With further attention to FIG. 45, in some embodiments, one or more helical or spiral cuts or features 15003 are included along the distal aspect of the tube 15001. As depicted, the helical or spiral cut 15003 can have a cut width 15008 and a helical angle 15009. The cut width 15008 can range from 0.1 micrometers to 30 millimeters (e.g., 0.1-0.2 0.2-0.3, 0.3-0.4, 0.4-0.5, 0.5-0.6, 0.6-0.7, 0.7-0.8, 0.8-0.9, 0.9-1, 0.2-0.8, 0.3-0.7, 0.1 to 1, 1-2, 2-3, 3-4, 4-5, 5-10, 10-15, 15-20, 20-25, 25-30, 1-30, 10-20 millimeters, values between the foregoing ranges, etc.). In one embodiment, the cut width 15008 may range from about 0.1 millimeters to about 10 millimeters. The helical angle 15009 can range from 10 to 80 degrees (e.g., 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the tube 15001. In some embodiments, the helical angle range from 15 to 75 degrees.

In some arrangements, the sleeve 15002 is disposed within (e.g., at least partially, fully, etc.) the lumen of the tube 15001. The tube 15001 can have a reduced inner diameter on the distal end to form a shelf 15004 that prevents or otherwise limits forward movement of the sleeve 15002 relative to the tube 15001.

In some embodiments, the device 15000 is configured so that the sleeve 15002 can abut a shelf or other abutting feature or portion 15004 of the tube 15001. Such abutment or other contact can transmit a longitudinal force from the sleeve 15002 to the tube 15001 (e.g., with continued advancement of the sleeve 15002 relative to the tube 15001 after contact or abutment).

In some embodiments, the sleeve 15002 is at least partially coupled to the tube 15001 at a location similar to and/or distal to the helical or spiral cut 15003, such as at the shelf 15004, and can be advanced or retracted relative to (e.g., within) the tube 15001. Advancement or retraction of the sleeve 15002 can result in advancement or retraction of the tube 15001 distal to the helical or spiral cut 15003. In some embodiments, the coupling of the sleeve 15002 and the tube 15001 is at least partially reversible. In some arrangements, for instance, the connection comprises a solder connection that can be melted or otherwise compromised (e.g., by application of electric current and/or heat to release the sleeve 15002 from the tube 15001). Technologies, methods and/or means of coupling the sleeve 15002 and tube 15001 can include, but are not limited to, one or more of the following: frictional fit, glues and/or other adhesives (e.g., cyanoacrylate), welding, brazing, soldering, frictional fit, other mechanical linking and/or the like.

In some embodiments, the device 15000 comprises one or more slots and/or other openings or features 15007 at one or more locations proximal to the spiral cut 15003. The slots 15007 can include a cut width 15010. The cut width 15010 can range from 0.1 micrometers to 30 millimeters. In some embodiments, the cut width 15010 may range from about 0.1 millimeters to about 10 millimeters (e.g., 0.1-0.2 0.2-0.3, 0.3-0.4, 0.4-0.5, 0.5-0.6, 0.6-0.7, 0.7-0.8, 0.8-0.9, 0.9-1, 0.2-0.8, 0.3-0.7, 0.1 to 1, 1-2, 2-3, 3-4, 4-5, 5-6, 6-7, 7-8, 8-9, 9-10, 1-10, 2-8, 3-7, 4-6 millimeters, values between the foregoing ranges, etc.).

According to some embodiments, the spacing/distance between two or more of the slots 15007 can vary, as desired or required. In some embodiments, the distance between successive slots (or every second, third, fourth, etc. successive slot) 15007 increases in a proximal direction along the tube 15001. Each of the tube, 15001 and the sleeve 15002 can comprise one or more of a variety of materials, including, but not limited to, polyimide, polyurethane, polyether block amides (such as Pebax®), ChronoPrene, PolyBlend, latex, nylon, other polymeric materials, nitinol, other shape memory materials, stainless steel braiding, other metals and/or alloys, coiled wire, hollow helical stranded tubing and/or the like.

In some embodiments, interior surfaces or portions (e.g., surfaces along the lumen) of the tube 15001 and outer surfaces or portions of the sleeve 15002 comprise a low coefficient of friction. For example, such surfaces can include, among other things, one or more PTFE, FEP, hydrophilic materials, thermoplastics with lubricious additives, including but not limited to EverGlide®, PEBASlide, ProPell S™, and Mobilize, etc. and/or the like. In some arrangements, the coefficient of friction of such surfaces or portions can be less than 0.3 (e.g., 0.01 to 0.1, 0.01 to 0.02, 0.02 to 0.03, 0.03 to 0.04, 0.04 to 0.05, 0.05 to 0.06, 0.06 to 0.07, 0.07 to 0.08, 0.08 to 0.09, 0.09 to 0.1, 0.01 to 0.1, 0.02 to 0.08, 0.03 to 0.07, 0.04 to 0.06, 0.1 to 0.15, 0.15 to 0.2, 0.2 to 0.25, 0.25 to 0.3, values between the foregoing ranges, less than 0.01, etc.).

The distal aspect, end or portion of the tube 15001 can have a straight, angled, reverse curved and/or any other shape, as desired or required. For example, in some embodiments, the distal end of the tube 15001 (and thus, the entire device 15000) has a desired shape for facilitating advancement of the device through an anatomical intraluminal network (e.g., the vasculature) of a subject. In some embodiments, at least a portion of the tube 15001 distal to the helical cut 15003 may include a curve, a bend, an angle or other feature to aid in navigating the medical device 15000 through the vasculature.

FIG. 46A schematically illustrates an embodiment of a medical device configured to have one or more areas of varying modulus of elasticity. For example, such areas or regions of varying or different modulus of elasticity can be along the tubular member and/or the force imparting element, between the one or more helical or spiral cuts and the non-cut (or non-compromised) portion of the tubular member, and/or any other member or portion of the device. Such varying modulus of elasticity along one or more portions or regions of the device can result in varying stiffness between the helical or spiral cut section of the tubular member and the non-cut (or non-compromised) section of the tubular member. The material of the tubular member and/or the force imparting element can help create the variable flexibility is such embodiments.

With continued reference to FIG. 46A, the device 16000 can include a tube 16001, a force imparting element (e.g., longitudinal displacer, pusher, other inner member, etc.) 16002, and a handle (not shown) that is attached to the proximal end of the tube 16001. In the depicted embodiment, one or more helical or spiral cuts 16003 are included at or along the distal portion of the tube 16001. In some embodiments, the helical or spiral cut 16003 includes a cut width 16008 and helical angle 16009. The cut width 16008 and/or helical angle 16009 can be identical or similar to any of the embodiments disclosed herein, including for example and without limitation, the embodiments illustrated and disclosed with reference to FIG. 3A.

In some embodiments, as noted above, the tube 16001 has a variable modulus of elasticity along one or more portions or lengths of the tube 16003, resulting in variable stiffness along the length of the tube 16001. As illustrated in FIG. 46A to 46D, the device 16000 can have one or more transition zone sections, for example 16005 and 16006 along the length of the tube 16001, wherein the modulus of elasticity of the transition zone sections 16005 and 16006 differs from one another and/or differs from the modulus of elasticity of the tube 16001. In some embodiments the modulus of elasticity of one portion 16005 of the tube is less than the modulus of elasticity of another portion 16006 of the tube. In some arrangements, the modulus of elasticity for these two section is less than the modulus of elasticity of the other portions (e.g. proximal portions) of tube 16001, resulting in a graduated stiffness of the device 16000, wherein the distal end is less stiff than the proximal end.

In some embodiments the modulus of elasticity of the distal to the spiral or helical cuts 16003 can range from 0.003 to 0.03 and the modulus of elasticity of 16006 can range from 0.01 to 0.3. The modulus of elasticity of 16005 can range from 0.17 to 5. The modulus of elasticity of 16001 can range from 1 to 250.

With continued reference to FIG. 46A, the portion (e.g., end) of the tube 16001 located distal to the helical or spiral cut 16003 can comprise a curve or bend (e.g., a shape that is angled or offset from the longitudinal axis of the device) to aid in navigating the medical device 16000 through the body, including but not limited to the vasculature and other intraluminal structures. For example, such a configuration can help the user manipulate the device 16000 through various curves and turns to access a desired portion or location of the subject's anatomy.

In some embodiments, the cut width 16008 is between 0.1 micrometers and 30 millimeters (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-15, 15-20, 20-30, 30-40, 40-50, 50-60, 60-70, 70-80, 80-90, 90-100, 100-150, 150-200, 200-250, 250-300, 300-400, 400-500, 500-600, 600-700, 700-800, 800-900 micrometers, 900 micrometers to 1 millimeters, 1-2, 2-3, 3-4, 4-5, 5-6, 6-7, 7-8, 8-9, 9-10, 10-15, 15-20, 20-25, 25-30 millimeters, widths between the foregoing values, etc.). In some embodiments, the cut width ranges from 0.1 millimeters to 10 millimeters (e.g., 0.5-5 millimeters). In other configurations, the cut width is less than 0.1 micrometers or greater than 30 millimeters (e.g., 30-40, 40-50, 50-100 millimeters, values between the foregoing, greater than 100 millimeters), as desired or required for a particular application or use.

In some embodiments, including for the arrangement illustrated in FIG. 46A, as well as any other arrangements disclosed herein or equivalents thereof, the helical angle 16009 of the cut ranges from 5 to 80 degrees (e.g., 5-10, 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the tube 16001. In some embodiments, the helical angle 16009 ranges from 15 to 75 degrees (e.g., 20 to 70 degrees, 30 to 60 degrees, 15 to 30 degrees, 25 to 40 degrees, 40 to 60 degrees, 60 to 75 degrees, etc.).

According to some embodiments, as with other arrangements disclosed herein, the sleeve 16002 is disposed within the lumen of the tube 16001. In some configurations, the tube 16001 has a smaller diameter or other cross-sectional dimension (e.g., inner diameter) at or along the distal end to form a shelf 16004 that prevents forward movement of the sleeve 16002 relative to the tube 16001. However, any other configuration can be used that prevents forward movement of the sleeve relative to the tube. For example, the sleeve 16002 and the tube 16001 can be coupled (e.g., via one or more attachment methods or devices, directly or indirectly) along the distal end, using, for instance and without limitation, adhesives, welds or other welding procedures, brazing, soldering, other heat based methods or technologies, mechanical linking and/or the like.

According to some embodiments, the sleeve 16002 and the tube 16001 can have one or more elements that interact with an electromagnetic field, wherein said elements can include one or more of the following: a magnet, a ferromagnetic material, an electret, a material capable of holding an electrical charge, a wire, a coil configured to carry current and generate a magnetic field and/or the like. In some embodiments, the sleeve 16002 abuts the shelf 16004 to transmit longitudinal force from the sleeve 16002 to the tube 16001. In some embodiments, the sleeve 16002 may be coupled to the tube 16001 at a point distal to the helical or spiral cut 16003, such as, for instance, at the shelf 16004, and can be selectively advanced and/or retracted within the tube 16001. As noted herein, in some embodiments, such advancement or retraction of the sleeve 16002 results in advancement or retraction of the tube 16001 relative to the sleeve distal to the helical or spiral cut 16003.

In some embodiments, the coupling means or mechanism between the sleeve 16002 and the tube 16001 can be reversed. For instance, a solder connection can be melted or severed by application of electric current or heat to release the sleeve 16002 from the tube 16001. Means of coupling the sleeve 16002 and tube 16001 include, but are not limited to, one or more of the following: a frictional fit, adhesives (e.g., acrylic-based adhesives (e.g., cyanoacrylate), epoxies, silicone, thermosetting resins, polyurethanes, other suitable adhesives, etc.), welding, brazing, soldering, mechanical linking or coupling and/or the like.

According to some configurations, the tube, 16001 and/or the sleeve 16002 can comprise one or more of a variety of materials, including, without limitation, polyimide, polyurethane, polyether block amides (such as Pebax®), nylon, other polymers, nitinol, stainless steel braiding, coiled wire, hollow helical stranded tubing, other metals and/or alloys and/or any other natural or synthetic materials, as desired or required.

In some embodiments, the helical or spiral cut 16003 is elastic and/or has elastic properties and can undergo elongation and/or contraction (e.g., with the application of forces, moments, etc.). In some configurations, in light of the relative decreased thickness as compared to the rest of the tube 16001, the partial thickness cut 16003 undergoes elongation. The lumen of the tube 16001 and outer surface of the sleeve 16002 can have a relatively low coefficient of friction. In some arrangements, the coefficient of friction of such surfaces or portions can be less than 0.3 (e.g., 0.01 to 0.1, 0.01 to 0.02, 0.02 to 0.03, 0.03 to 0.04, 0.04 to 0.05, 0.05 to 0.06, 0.06 to 0.07, 0.07 to 0.08, 0.08 to 0.09, 0.09 to 0.1, 0.01 to 0.1, 0.02 to 0.08, 0.03 to 0.07, 0.04 to 0.06, 0.1 to 0.15, 0.15 to 0.2, 0.2 to 0.25, 0.25 to 0.3, values between the foregoing ranges, less than 0.01, etc.). For example, in some embodiments, the surfaces and/or components that contact each other can include relatively low friction materials, coatings, layers, etc., such as for example, PTFE, FEP, hydrophilic materials, other polymeric materials with lubricious additives, including but not limited to EverGlide®, PEBASlide, ProPell S™, and Mobilize, etc. and/or the like. In addition, the distal aspect of the tube 16001 may have, but is not limited to, a straight, angled, and reverse curved shape.

FIG. 47A schematically illustrates another embodiment of a medical device configured to have one or more areas of varying wall thickness of the tubular member and/or force imparting element, between the one or more helical or spiral cuts and the non-cut portion of the tubular member. Such embodiments can result in varying stiffness between the helical or spiral cut section of the tubular member and the non-cut section of the tubular member. In some embodiments, the wall thickness of the tubular member and/or the force imparting element help create the variable flexibility in such embodiments.

With continued reference to FIG. 47A, the device 16000 can include a tube 16201, a force imparting element (e.g., a longitudinal displacer, pusher, other inner member, etc.) 16202, and a handle (not shown) that is attached to the proximal end of the tube 16201. In the depicted embodiment, helical or spiral cut 16203 is included at or along the distal portion or end of the tube 16201.

In some embodiments, the helical or spiral cut 16203 includes a cut width 16208 and helical angle 16209. The cut width 16208 and/or helical angle 16209 can be identical or similar to any of the embodiments disclosed herein, including for example and without limitation, the embodiments illustrated and disclosed with reference to FIG. 3A. In some embodiments, the tube 16201 has variable modulus of elasticity along one or more areas or portions along the length of the tube 16203, resulting in variable stiffness along the length of the tube 16201.

As depicted in FIG. 47A to 47D, the device 16200 can have one or more transition zone sections, for example sections 16205 and 16206 along the length of the tube 16201. In some embodiments, the wall thickness of the transition zone sections 16205 and 16206 differs from one another and differs from the wall thickness of the tube 16201. In some embodiments the wall thickness of 16205 is less than the wall thickness of 16206, which is less than the wall thickness of the tube 16201, resulting in a graduated stiffness of the device 16200, wherein the distal end is less stiff than the proximal end.

With continued reference to FIG. 47A, the end of the tube 16201 distal to the helical or spiral cut 16203 can comprise a curve to aid in navigating the medical device 16200 through the body, including but not limited to the vasculature and other intraluminal structures or networks. For example, such a configuration can help the user manipulate the device 16200 through various curves and turns to access a desired portion or location of the subject's anatomy. In some embodiments, the cut width 16208 is between 0.1 micrometers and 30 millimeters (e.g., 0.1-0.2, 0.2-0.3, 0.3-0.4, 0.4-0.5, 0.5-0.6, 0.6-0.7, 0.7-0.8, 0.8-0.9, 0.9-1, 1-2, 2-3, 3-4, 4-5, 5-6, 6-7, 7-8, 8-9, 9-10, 10-15, 15-20, 20-30, 30-40, 40-50, 50-60, 60-70, 70-80, 80-90, 90-100, 100-150, 150-200, 200-250, 250-300, 300-400, 400-500, 500-600, 600-700, 700-800, 800-900 micrometers, 900 micrometers to 1 millimeters, 1-2, 2-3, 3-4, 4-5, 5-6, 6-7, 7-8, 8-9, 9-10, 10-15, 15-20, 20-25, 25-30 millimeters, widths between the foregoing values, etc.). In some embodiments, the cut width ranges from 0.1 millimeters to 10 millimeters (e.g., 0.5-5 millimeters). In other configurations, the cut width is less than 0.1 micrometers or greater than 30 millimeters (e.g., 30-40, 40-50, 50-100 millimeters, values between the foregoing, greater than 100 millimeters), as desired or required for a particular application or use.

In some embodiments, including for the arrangement illustrated in FIG. 47A, as well as any other arrangements disclosed herein or equivalents thereof, the helical angle 16209 of the cut ranges from 5 to 80 degrees (e.g., 5-10, 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the tube 16001. In some embodiments, the helical angle 16209 ranges from 15 to 75 degrees (e.g., 20 to 70 degrees, 30 to 60 degrees, 15 to 30 degrees, 25 to 40 degrees, 40 to 60 degrees, 60 to 75 degrees, etc.).

According to some embodiments, as with other arrangements disclosed herein, the sleeve 16202 is disposed within the lumen of the tube 16201. In some configurations, the tube 16201 has a smaller diameter (e.g., inner diameter) at or along the distal end to form a shelf 16204 that prevents forward movement of the sleeve 16202 relative to the tube 16201. However, any other configuration can be used that prevents forward movement of the sleeve relative to the tube. For example, the sleeve 16202 and the tube 16201 can be coupled (e.g., via one or more attachment methods or devices, directly or indirectly) along the distal end, using, for instance and without limitation, adhesives, welds or other welding procedures, brazing, soldering, other heat based methods or technologies, mechanical linking and/or the like.

In some arrangements, the sleeve 16202 and the tube 16201 can have one or more elements that interact with an electromagnetic field, wherein the can include one or more of the following: a magnet, a ferromagnetic material, an electret, a material capable of holding an electrical charge, a wire, a coil configured to carry current and generate a magnetic field and/or the like. In some embodiments, the sleeve 16202 abuts the shelf 16204 to transmit longitudinal force from the sleeve 16202 to the tube 16201. In some embodiments, the sleeve 16202 may be coupled to the tube 16201 at a point distal to the helical or spiral cut 16203, such as, for instance, at the shelf 16204, and can be selectively advanced and/or retracted within the tube 16201. As noted herein, in some embodiments, such advancement or retraction of the sleeve 16202 results in advancement or retraction of the tube 16201 relative to the sleeve distal to the helical or spiral cut 16203.

In some embodiments, the coupling means or mechanism between the sleeve 16202 and the tube 16201 can be reversed. For instance, a solder connection can be at least partially melted, severed and/or otherwise compromised by application of electric current or heat to release the sleeve 16202 from the tube 16201. Means of coupling the sleeve 16202 and tube 16201 include, but are not limited to, one or more of: frictional fit, adhesives (e.g., acrylic-based adhesives (e.g., cyanoacrylate), epoxies, silicone, thermosetting resins, polyurethanes, other suitable adhesives, etc.), welding, brazing, soldering, mechanical linking or coupling and/or the like.

According to some configurations, the tube, 16201 and/or the sleeve 16202 can comprise one or more of a variety of materials, including, without limitation, polyimide, polyurethane, polyether block amides (such as Pebax®), nylon, other polymers, nitinol, stainless steel braiding, coiled wire, hollow helical stranded tubing, other metals and/or alloys and/or any other natural or synthetic materials, as desired or required.

In some embodiments, the helical or spiral cut 16203 is elastic and can undergo elongation and/or contraction. In some configurations, in light of the relative decreased thickness as compared to the rest of the tube 16201, the partial thickness cut 16203 preferentially undergoes elongation. The lumen of the tube 16201 and outer surface of the sleeve 16202 have a relatively low coefficient of friction. In some arrangements, the coefficient of friction of such surfaces or portions can be less than 0.3 (e.g., 0.01 to 0.1, 0.01 to 0.02, 0.02 to 0.03, 0.03 to 0.04, 0.04 to 0.05, 0.05 to 0.06, 0.06 to 0.07, 0.07 to 0.08, 0.08 to 0.09, 0.09 to 0.1, 0.01 to 0.1, 0.02 to 0.08, 0.03 to 0.07, 0.04 to 0.06, 0.1 to 0.15, 0.15 to 0.2, 0.2 to 0.25, 0.25 to 0.3, values between the foregoing ranges, less than 0.01, etc.). For example, in some embodiments, the surfaces and/or components that contact each other can include relatively low friction materials, coatings, layers, etc., such as for example, PTFE, FEP, hydrophilic materials, other polymeric materials with lubricious additives, including but not limited to EverGlide®, PEBASlide, ProPell S™, and Mobilize, etc. and/or the like. In addition, the distal aspect of the tube 16201 may have, but is not limited to, a straight, angled, and reverse curved shape.

FIG. 48A illustrates a graph of the stiffness of the device 15000 with respect to the long or horizontal axis. In some embodiments, the stiffness of the distal aspect or portion of the device 15000 is less than the stiffness of the proximal aspect of the device 15000, and the change in stiffness decreases in a continuous fashion as depicted by line A. In some embodiments, the stiffness of the distal aspect of the device 15000 is less than the stiffness of the proximal aspect of the device 15000 and the change in stiffness decreases in a step wise fashion as depicted by line B.

FIG. 48B illustrates a graph of the stiffness of the device 16000 with respect to the long or horizontal axis. In some embodiments, the stiffness of the distal aspect or portion of the device 16000 is less than the stiffness of the proximal aspect of the device 16000 and the change in stiffness decreases in a continuous fashion as depicted by line A. In some embodiments, the stiffness of the distal aspect of the device 15000 is less than the stiffness of the proximal aspect of the device 16000 and the change in stiffness decreases in a step wise fashion as depicted by line B.

FIG. 48C illustrates a graph of the stiffness of the device 16200 with respect to the long or horizontal axis. In some embodiments, the stiffness of the distal aspect or portion of the device 16200 is less than the stiffness of the proximal aspect of the device 16200 and the change in stiffness decreases in a continuous fashion as depicted by line A. In some embodiments, the stiffness of the distal aspect of the device 15000 is less than the stiffness of the proximal aspect of the device 16200 and the change in stiffness decreases in a step wise fashion as depicted by line B.

For any of the embodiments disclosed herein or equivalents thereof, FIG. 49 illustrates a cut portion of the tubular member wherein a single cut is present and the cut portion is curved.

For any of the embodiments disclosed herein, a device can comprise a cut portion of the tubular member that includes multiple (e.g., two or more) cuts are out of phase with one another. In some embodiments, such cuts are out of phase by 180 degrees. FIG. 50A, for example, illustrates a cut portion of the tubular member wherein two cuts are present such that the two cuts are out of phase with one another by 180 degrees. FIG. 50B illustrates a transverse cross sectional view of the tubular membrane through B-B' in FIG. 49. FIG. 50C illustrates the distal end of the cut portion of the tubular member wherein two cuts are present such that the two cuts are out of phase with one another by 180 degrees. Further, FIG. 50C illustrates a cut portion of the tubular member wherein two cuts are present such that the two cuts are out of phase with one another by 180 degrees and the cut portion is at least partially curved (e.g., curved, bent, angled, etc. relative to the longitudinal axis of the device).

For any of the embodiments disclosed herein, a device can comprise a deflectable segment that is control by a deflecting actuator mechanism, wherein in some embodiments the deflectable segment can be manipulated independent of the rotation of the device. The deflecting mechanism can comprise one or more of the following, including, but not limited to, mechanical coupling mechanisms, hydraulic mechanisms, pneumatic mechanisms, mechanisms incorporating electromagnetic element(s), mechanisms incorporating shape memory element(s), such as a shape memory material including but not limited to nitinol, cobalt chromium, shape memory polymers, and the like and/or the combination of above. Mechanical coupling mechanisms can comprise one or more of the following, including, but not limited to, direct coupling of one or more mechanical element(s), including but not limited to wire(s), tubular element(s) and/or the like, wherein displacement of the one or more mechanical element(s), results in deflection of the device. Hydraulic mechanisms can comprise one or more of the following, including, but not limited to, displacement of a fluid, including but not limited to water, sterile saline, lactated ringer's solution, contrast agents such as Iohexol, Omnipaque 240, Omnipaque 300, Omnipaque 350, Visipaque 320, D5W, and the like, wherein said fluid displacement results in preferential elongation of one aspect, side or portion of tubular member relative to the opposing aspect/side which in turn results in deflection of the device. Pneumatic mechanisms can comprise one or more of the following, including, but not limited to, displacement of a compressible fluid, including but not limited to room air, carbon dioxide, oxygen, nitrogen, and the like, wherein said fluid displacement results in preferential elongation of one aspect, side or portion of tubular member relative to the opposing aspect/side which in turn results in deflection of the device. The degree of deflection is related to the amount of displacement. Mechanisms incorporating electromagnetic element(s) can comprise one or more of the following, including, but not limited to, permanent magnetics, materials capable of inducing an electromagnetic field as a result of flow of electrical current through one or more element(s), and/or inducing an electrical charge in one or more element(s), wherein a corresponding portion of the device is able to interact with said electromagnetic element(s). Deflection can result via one or more of the following, including, but not limited to, displacement of said electromagnetic element(s) relative to the corresponding portion of the device, altering the induced electromagnetic field and/or a combination of the two. Mechanisms incorporating shape memory element(s), such as shape memory elements, including but not limited to nitinol, cobalt chromium, shape memory polymers, and the like and/or the combination of above, wherein the shape memory element(s) can undergo a change in shape as a result of an external stimulus, including but not limited to temperature, pH, light, electrical charge, electrical current. This change in shape as a result of an external stimulus results in deflection of a portion of the device.

FIG. 50D illustrates a cut portion of the tubular member wherein two cuts are present such that the two cuts are out of phase with one another by 180 degrees and the cut portion is in a curved configuration.

FIG. 51A schematically illustrates a medical device 15010 according to another embodiment of the present disclosure. As depicted, the device 15010 includes, among other things, a cut tube 15011, an elongate member 15018 that is coupled (e.g., directly or indirectly) to the cut tube 15011, an outer tube 15015, a longitudinal displacing or force imparting element 15012, a deflectable segment 15016, a deflecting actuator 15017 and a handle assembly 15020. In the illustrated arrangement, the longitudinal displacing element 15012 is disposed within the lumen of the cut tube 15011, and the cut tube 15011 is disposed within the lumen of the outer tube 15015.

Each of the cut tube 15011, the elongate member 15018, the outer tube 15015, the longitudinal displacing element 15012, the deflectable segment 15016, and the deflecting actuator 15017 can comprise one or more of a variety of materials, including, but not limited to, polyimide, polyimide-PTFE blend, polyurethane, polyether block amides (such as Pebax®), nylon, other polymeric materials, nickel titanium (Nitinol), stainless steel, other metals or alloys, closed loop coil, coiled wire, stainless steel braiding, hollow helical stranded tubing and/or the like.

In some embodiments, each of the cut tube 15011, the elongate member 15018, the outer tube 15015, the longitudinal displacing element 15012, the deflectable segment 15016, and the deflecting actuator 15017 can comprise one or more of a variety of radio-opaque materials, including but not limited to platinum, palladium, gold, tungsten, barium and/or the like.

With continued reference to FIG. 51A, one or more helical or spiral cut(s) 15013 are present in the distal aspect or portion of the cut tube 15011. Such helical or spiral cut(s) 15013 can have a cut width and a helical angle. In addition, in some arrangements, the distal end of the cut tube 15011 may include, but is not limited to, a straight, angled shape, reverse curved shape, shapeable tip, a variable shape and/or other shape. The distal aspect or end can be controlled by a deflecting mechanism.

According to some embodiments, the distal aspect or portion of the longitudinal displacing or force imparting element 15012, the outer tube 15015, the deflectable segment 15016, and/or the deflecting actuator 15017 may have, but are not limited to, a straight, angled, reverse curved and/or any other shape, as desired or required.

In some embodiments, the cut tube 15011 is located, at least partially, within the lumen of the outer tube 15015 such that the one or more helical or spiral cut(s) 15013 in the distal aspect or portion of the cut tube 15011 are disposed within the lumen of the outer tube 15015, while the distal end of the cut tube 15011 and deflectable segment 15016 extend beyond the distal end of the outer tube 15015. Thus, in some arrangements, the total length of the cut tube 15011 and deflectable segment 15016 is greater than the total length of the outer tube 15015, while the length from the proximal end of the cut tube 15011 to the distal most aspect of the cut portion of the cut tube 15011 is less than the total length of the outer tube 15015.

According to some configurations, the elongate member 15018 includes, but is not limited to, one or more strips, wires, curvilinear member and/or the like. The cut tube 15011 and the elongate member 15018 can be coupled to one another proximal to the one or more spiral cut(s) 15013. Such a coupling can be permanent or temporary (e.g., reversible). By way of example, potential coupling technologies include, but are not limited, frictional fit, glues or other adhesives (e.g., cyanoacrylate), welding, brazing, soldering, mechanical linking and/or the like.

FIG. 51B illustrates a close-up, longitudinal cross sectional view along the distal aspect or portion of the device 15010. In the depicted arrangement, one or more helical or spiral cut(s) 15013 are present in the distal aspect of the cut tube 15011 wherein the one or more helical or spiral cut(s) 15013 has a cut width and helical angle. The end of the cut tube 15011 distal to the one or more helical or spiral cut(s) 15013, as well as the distal aspect or portion of the longitudinal displacing element 15012, the outer tube 15015, the deflectable segment 15016, and/or the deflecting actuator may include a non-linear (e.g., curved, rounded or other shape).

In some embodiments, the distal aspect or portion of the device 15010 can have a tip deflection mechanism within the deflectable segment 15016. For example, such a device can comprise a pull wire mechanism or vertebrated tube and/or any other component or feature to aid in navigating the device 15010 through the endoluminal (e.g., intravascular, gastrointestinal tract, respiratory tract, genitourinary tract) network. The deflectable segment 15016 is coupled to a deflecting actuator 15017. Potential coupling means include, but are not limited to, one or more of: 1) frictional fit, 2) adhesives (such as cyanoacrylate), 3) welding, 4) brazing, 5) soldering, and 6) mechanical linking. As illustrated in FIG. 51C, FIG. 51G and FIG. 51H, the advancement of the deflecting actuator 15017 results in deflection the deflectable segment 15016 in one direction, FIG. 51G, while, retraction of the deflecting actuator 15017 results in deflection of the deflectable segment 15016 in the opposite direction, FIG. 51H, so as to enable the user to tip controllably, deflect the tip of the device 15010. The deflecting actuator 15017 can be disposed within the longitudinal displacement element 15012, wherein the longitudinal displacement element 15012 is comprised of a tubular member, such as a closed loop coil and/or tubing. This enables the user to move the longitudinal displacement element 15012 and the deflecting actuator 15017 independent of one another, which in turns enables the user to rotate the device 15010 independent of tip deflection, as well as tip deflect the device 15010 independent of rotation.

In certain embodiments, the distal aspect or portion of the cut tube 15011, as well as the distal aspect or portion of the longitudinal displacing element 15012, the deflectable segment 15016, and/or the deflecting actuator 15017 (both for the arrangement illustrated in FIG. 51A and FIG. 51B, as well as any other arrangements disclosed herein, or variations thereof) can be straight or substantially straight (e.g., not curved) and/or can include one or more features or characteristics (e.g., tapered, flared, etc.), as desired or required.

In some embodiments, the helical or spiral cuts extend throughout the entire wall thickness or depth of the cut tube 15011; however, in alternative embodiments, the cuts extend only partially through the wall, as desired or required. Thus, the cuts can be recessed or scored portions of the tube, wherein a certain amount (e.g., but less than all, e.g., 5-10, 10-25, 25-50, 50-75, 75-99% of the material has been removed or was never there relative to adjacent portions of the wall in the first place). These features or characteristics of the cuts can be applied to any of the embodiments disclosed herein. Further, in some embodiments, helical or spiral cuts, as used herein, is configured to connote an orientation that is angled both a longitudinal axis of the tube and a radial or transverse angle of the tube (e.g., angled relative to the perpendicular axis of the longitudinal axis).

In some arrangements, the cut width can range from 0.1 micrometers to 30 millimeters, depending on the size of the device, the materials used, the desired level and rotation response and/or one or more other factors or considerations. In some embodiments, the cut width may range from about 0.01 millimeters to about 10 millimeters (e.g., 0.01-0.03, 0.03-0.05, 0.05-0.1, 0.1-0.2, 0.2-0.5, 0.5-1, 1-2, 2-3, 3-4, 4-5, 5-6, 6-7, 7-8, 8-9, 9-10 millimeters, values between the foregoing ranges, etc.), as desired or required. The helical angle can range from 10 to 80 degrees (e.g., 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the cut tube 15011. For instance, in one embodiment, the helical angle can range from 5 to 75 degrees.

According to some embodiments, the longitudinal displacing or force imparting element 15012 is disposed within the lumen of the cut tube 15011. In some embodiments, the longitudinal displacing or force imparting element 15012 is coupled to and/or abuts, at least partially, the cut tube 15011 distal to or near the one or more helical or spiral cut(s) 15013 and the longitudinal displacing element 15012. The cut tube 15011 can be configured to undergo relative longitudinal displacement with respect to one another, wherein relative longitudinal displacement of the longitudinal displacing element 15012 with respect to the cut tube 15011 results in rotation of the distal end of the cut tube 15011 as well as the deflectable segment 15016.

The longitudinal displacing or force imparting element 15012 or a portion of the longitudinal displacing element 15012 can be configured to undergo rotational deformation/torsional strain when the distal end of the cut tube 15011 rotates. In some embodiments, the coupling between the longitudinal displacing or force imparting element 15012 and the cut tube 15011 is permanent or temporary. The coupling method or technology can be reversible, using, for example, a solder connection that can be melted by application of electric current or heat to release the longitudinal displacing element 15012 from the cut tube 15011. Methods and other technologies for coupling the longitudinal displacing element 15012 and cut tube 15011 include, but are not limited to, one or more of the following: frictional fit, glues or other adhesives (e.g., cyanoacrylate), welding, brazing, soldering, mechanical linking, other mechanical connections and/or the like.

With further attention to the embodiments of FIGS. 51A and 51B, each of the lumen of the cut tube 15011, the outer surface of the longitudinal displacing element 15012, the lumen of the longitudinal displacing element 15012, lumen of the outer tube 15015, outer surface of the deflecting actuator 15017 can include a relatively low coefficient of friction. In some arrangements, the coefficient of friction of such surfaces or portions can be less than 0.3 (e.g., 0.01 to 0.1, 0.01 to 0.02, 0.02 to 0.03, 0.03 to 0.04, 0.04 to 0.05, 0.05 to 0.06, 0.06 to 0.07, 0.07 to 0.08, 0.08 to 0.09, 0.09 to 0.1, 0.01 to 0.1, 0.02 to 0.08, 0.03 to 0.07, 0.04 to 0.06, 0.1 to 0.15, 0.15 to 0.2, 0.2 to 0.25, 0.25 to 0.3, values between the foregoing ranges, less than 0.01, etc.). For example, in some embodiments, the surfaces and/or components that contact each other can include relatively low friction materials, coatings, layers, etc., such as for example, PTFE, FEP, hydrophilic materials, other polymeric materials with lubricious additives, including but not limited to EverGlide®, PEBASlide, ProPell S™, and Mobilize, etc. and/or the like.

In some arrangements, the distal aspect or portion of the cut tube 15011 includes, but is not limited to, a straight, angled, and reverse curved shape. The portion of the inner tube 15011 proximal to the one or more helical or spiral cut(s) 15013 can be at least partially cut or otherwise undermined (e.g., scored) so as to provide an open configuration.

FIG. 51O illustrates a longitudinal cross-sectional view of the distal end of the device in FIG. 51A with longitudinal force at the proximal end causing a rotation of the distal end (e.g., by 180 degrees). FIG. 51D illustrates an axial cross sectional view through line D-D' in FIG. 51B. FIG. 51E illustrates an axial cross sectional view through line E-E' in FIG. 51B. FIG. 51F illustrates an axial cross sectional view through line F-F' in FIG. 51B.

According to some embodiments, the cut tube 15011 or a portion or portions of the cut tube 15011 proximal to the one or more helical or spiral cut(s) 15013, can have one or more aperture(s) and/or other opening(s). Such features can help reduce the frictional forces between the cut tube 15011 and the longitudinal displacement element 15012. As illustrated in FIGS. 51B, 51D, 51E and 51F, the deflecting actuator 15017 can be at least partially disposed or otherwise located within the lumen of longitudinal displacement element 15012, such that the deflecting actuator 15017 can be moved along the longitudinal axis of the longitudinal displacement element 15012.

FIG. 51G illustrates a longitudinal cross-sectional view of the distal end of the device in FIG. 51A wherein the deflecting actuator 15017 has been retracted so as to cause the deflectable segment 15016 to bend. FIG. 51H illustrates a longitudinal cross-sectional view of the distal end of the device in FIG. 51A wherein the deflecting actuator 15017 has been advanced so as to cause the deflectable segment 15016 to bend in the opposite direction as in FIG. 51G.

FIG. 52A illustrates an alternative embodiment of the distal aspect or portion of the longitudinal displacement or force imparting element 16012. As shown, a groove or channel 16019 can be included in or near the distal aspect or portion of the longitudinal displacement element 16012 such that the deflecting actuator 16017 is configured to slidably pass through the groove or channel 16019.

FIG. 52B illustrates a longitudinal cross sectional view of FIG. 52A that also includes the cut tube 16011, the deflecting actuator 16017, the deflectable segment 16016 and the outer tube 16015. FIG. 52C depicts an axial cross sectional view through line C-C' in FIG. 52B. FIG. 52D depicts an axial cross sectional view through line D-D' in FIG. 52B.

FIG. 53A schematically illustrates another embodiment of a medical device 17010 wherein relative movement of one member or portion relative to another member or portion of the device can advantageously create rotation along a distal end of the device. As depicted, the device 17010 includes an inner tube 17011, an outer tube 17015 and a longitudinal displacing element 17012. The device 17010 can include one or more additional components or members, such as, for example, a handle assembly 17020. In the illustrated arrangement, the longitudinal displacing element 17012 is disposed within the lumen, opening or passage of the inner tube 17011, and the inner tube 17011 is disposed within the lumen, opening or passage of the outer tube 17015. In some embodiments, each of the inner tube 17011, the outer tube 17015 and the longitudinal displacing element 17012 comprises one or more of a variety of materials, including, but not limited to, polyimide, polyimide-PTFE blend, polyurethane, polyether block amides (such as Pebax®), nylon, nickel titanium (Nitinol), stainless steel, stainless steel braiding, and hollow helical stranded tubing.

With continued reference to FIG. 53A, one or more helical or spiral cut(s) 17013 are present in the distal aspect of the inner tube 17011. The one or more helical or spiral cut(s) 17013 can include a cut width and helical angle. In addition, in some embodiments, the distal end of the inner tube 17011 includes a straight, angled shape, reverse curved shape, shapeable tip, or a tip deflection mechanism, as desired or required. Further, the distal aspect of the longitudinal displacing element 17012 may have, but is not limited to, a straight, angled, and reverse curved shape. However, the device can include any other type of shape or feature along its distal end.

In some embodiments, the inner tube 17011 is located within the lumen of the outer tube 17015 such that the one or more helical or spiral cut(s) 17013 in the distal aspect of the inner tube 17011 are disposed within (e.g., completely, partially, etc.) the lumen of the outer tube 17015 while the distal end of the inner tube 17011 extends beyond the distal end of the outer tube 17015 (e.g., the total length of the inner tube 17011 is greater than the total length of the outer tube 17015, while the length from the proximal end of the inner tube 17011 to the distal most aspect of the cut portion of the inner tube 17011 is less than the total length of the outer tube 17015). Also, in some embodiments, one or more apertures or other openings are present along the inner tube 17011 proximal to the one or more spiral cut(s) 17013. This can help reduce potential frictional forces between the inner tube 17011 and the longitudinal displacing element 17012.

FIG. 53B illustrates a longitudinal cross section of the distal aspect of the device 17010. In the depicted arrangement, one or more helical or spiral cut(s) 17013 are present in the distal portion or aspect of the inner tube 17011. The helical or spiral cut(s) 17013 can include a cut width and helical angle. In some arrangements, the end of the inner tube 17011 distal to the one or more helical or spiral cut(s) 17013 and the distal aspect of the longitudinal displacing element 17012 distal to the one or more helical or spiral cut(s) 17013 include a nonlinear shape (e.g., a curved shape) and/or a tip deflection component. However, in other embodiments, the distal portion or aspect of the device can be linear or substantially linear, as desired or required.

In some arrangements, where tip defection is desired or required, a tip deflection component can include, but is not limited to, a pull wire 17017 mechanism or vertebrated (or slotted) tube. Such configurations can assist with navigating the device 17010 through an endoluminal network (e.g., a subject's intravascular network). However, as noted above, in other embodiments, the distal aspect of the inner tube 17011, as well as the distal aspect of the longitudinal displacing element 17012 (e.g., both for the arrangement illustrated in FIGS. 53A and 53B, as well as any other arrangements disclosed herein or variations thereof), is straight or substantially straight or linear (e.g., not curved).

In some embodiments, regardless of whether the distal portion or aspect of the device is linear, substantially linear or non-linear, the device can include one or more other features or characteristics to assist with the advancement and/or other manipulation of the device during use. For instance, the device can include a tapered and/or flared distal portion or aspect, as desired or required. This can apply to any of the embodiments disclosed herein. In some configurations, the helical or spiral cuts extend throughout the entire wall thickness or depth of the inner tube 17011. However, in alternative embodiments, the cuts extend only partially through the wall, as desired or required. Thus, the cuts can be recessed or scored portions of the tube, wherein a certain amount (e.g., but less than all, e.g., 5-10, 10-25, 25-50, 50-75, 75-99% of the material has been removed or was never there relative to adjacent portions of the wall in the first place). These features or characteristics of the cuts can be applied to any of the embodiments disclosed herein. Further, in some embodiments, helical or spiral cuts, as used herein, is configured to connote an orientation that is angled both a longitudinal axis of the tube and a radial or transverse angle of the tube (e.g., angled relative to the perpendicular axis of the longitudinal axis).

In some arrangements, the cut width can range from 0.1 micrometers to 30 millimeters, depending on the size of the device, the materials used, the desired level and rotation response and/or one or more other factors or considerations. In some embodiments, the cut width may range from about 0.1 millimeters to about 10 millimeters (e.g., 0.1-0.2, 0.2-0.5, 0.5-1, 1-2, 2-3, 3-4, 4-5, 5-6, 6-7, 7-8, 8-9, 9-10 millimeters, values between the foregoing ranges, etc.), as desired or required. The helical angle can range from 10 to 80 degrees (e.g., 10-15, 15-20, 20-25, 25-30, 30-35, 35-40, 40-45, 45-50, 50-55, 55-60, 60-65, 65-70, 70-75, 75-80 degrees, angles between the foregoing ranges, etc.) relative to the longitudinal axis of the inner tube 17011. In some embodiments, the helical angle can range from 15 to 75 degrees.

According to some arrangements, the longitudinal displacing element 17012 is disposed within the lumen of the inner tube 17011. In some embodiments, the longitudinal displacing element 17012 may be coupled to the inner tube 17011 distal to the one or more helical or spiral cut(s) 17013 and can be advanced or retracted within the inner tube 17011 wherein advancement or retraction of the longitudinal displacing element 17012 results in advancement or retraction of the inner tube 17011 distal to the one or more helical or spiral cut(s) 17013. In some embodiments, the coupling means or mechanism is reversible, such as a solder connection that can be melted by application of electric current or heat to release the longitudinal displacing element 17012 from the inner tube 17011. Means of coupling the longitudinal displacing element 17012 and inner tube 17011 include, but are not limited to, one or more of the following: frictional fit, glues or other adhesives (e.g., cyanoacrylate, other medically-approved adhesives, etc.), welding, brazing, soldering, mechanical linking and/or the like.

With further attention to the embodiments of FIGS. 53A and 53B, each of the tube 17011 and the longitudinal displacing element 17012 can include one or more of a variety of materials, including, but not limited to, polyimide, polyurethane, polyether block amides (such as Pebax®), nylon, other polymeric materials, nickel titanium (e.g., Nitinol), other shape memory materials, stainless steel, stainless steel braiding, other metals or alloys, coiled wire, hollow helical stranded tubing, any or any other suitable material, as desired or required.

In some embodiments, an interface between the lumen of the inner tube 17011 and outer surface of the longitudinal displacing element 17012 advantageously comprises a low coefficient of friction, including but not limited to PTFE or a hydrophilic coating. For example, the coefficient of friction, in some embodiments, is (e.g. 0.005-0.5 (e.g., 0.005 to 0.01, 0.01 to 0.02, 0.02 to 0.03, 0.03 to 0.04, 0.04 to 0.05, 0.05 to 0.075, 0.075 to 0.1, 0.1 to 0.2, 0.2 to 0.3, 0.3 to 0.4, 0.4 to 0.5, values between the foregoing ranges or values, etc.). In addition, the distal tip 17016 of the inner tube 17011 may include, for example, a straight, angled or reverse curved shape, in accordance with a desired or required configuration. In some embodiments, at least a portion of the inner tube 17011 proximal to the one or more helical or spiral cut(s) 17013 has been cut (or includes a similar configuration, e.g., as a result of manufacturing) so as to provide a skive, lip or similar opened feature or configuration 17018.

As noted above and understood from the FIG. 53B, FIG. 53D is an axial cross sectional view through line D-D' in FIG. 53B, FIG. 53E is an axial cross sectional view through line E-E' in FIG. 53B, and FIG. 53F is an axial cross sectional view through line F-F' in FIG. 53B.

FIG. 53C illustrates an alternative embodiment, wherein the inner tube 17011 includes a reduced inner diameter at or along the distal end of the device. As illustrated, such a feature can form a shelf 17014 that prevents or at least partially limits forward movement of the longitudinal displacing element 17012 relative to the inner tube. The distal end of the longitudinal displacing element 17012 can include a reduced outer diameter such that this reduced distal outer diameter is less than the inner diameter of the shelf 17014. In some embodiments, the longitudinal displacing element 17012 may abut or otherwise contact (e.g., contact that prevents or otherwise limits further movement, axially) the shelf 17014 to transmit longitudinal force from the longitudinal displacing element 17012 to the inner tube 17011.

According to some arrangements, at least a portion of the longitudinal displacing element 17012 with the reduced diameter can extend distally to the distal end of the inner tube 17011. The longitudinal displacing element 17012 and inner tube 17011 can be located within the lumen of the outer tube 17015 such that the one or more helical or spiral cut(s) 17013 in the distal aspect of the inner tube 17011 are disposed within (e.g., partially or completely) the lumen of the outer tube 17015 while the distal end of the longitudinal displacing element 17012 extends beyond the distal end of the outer tube 17015. Thus, in some embodiments, the total length of the longitudinal displacing element 17012 is greater than the total length of the outer tube 17015, while the length from the proximal end of the inner tube 17011 to the distal most aspect of the cut portion of the inner tube 17011 is less than the total length of the outer tube 17015).

FIG. 53G illustrates another embodiment of an intraluminal device, wherein the proximal end of the inner tube 17011 is coupled to an elongated member 17019. In some arrangements, the elongated member 17019 includes, but is not limited to, one or more of the following: a round wire, a flat wire, a strip, hypotubing, other tubing, a stranded wire, any or any other suitable component or feature, as desired or required. Means of coupling the elongated member 17019 and inner tube 17011 include, but are not limited to, one or more of the following: frictional fit, glues or other adhesives (e.g., cyanoacrylate, other medically-accepted or approved adhesives, etc.), welding, brazing, soldering, mechanical linking and/or the like.

As noted above and reflected in FIG. 53G, FIG. 53H illustrates an axial cross sectional view through line H-H' in FIG. 53G, FIG. 53I illustrates an axial cross sectional view through line I-I' in FIG. 53G, and FIG. 53J illustrates an axial cross sectional view through line J-J' in FIG. 53G.

FIG. 54A illustrates one embodiment of a medical device 18000 that can be used to treat vascular chronic total occlusions (CTO). As shown, the device 18000 can comprise a tube 18001 and a longitudinal displacing element 18005. The tube 18001 can include a proximal segment 18002, a distal segment 18010 and a distal tip 18020. As shown in FIGS. 54B and 54C, in some embodiments, the distal segment 18010 of the tube 18000 comprises one or more cuts 18004 or other features. In some embodiments, such cuts 18004 are helical or spiral in shape (e.g., when viewing the device as a whole). In some embodiments, helical cuts 18004 included in the device have a constant or consistent orientation. In other words, the spacing and/or angle (e.g., relative to the longitudinal axis of the device) between adjacent cuts can be consistent or substantially constant or consistent.

In other embodiments, however, a medical device can include cuts 18004 that have two or more orientations (e.g., angles, pitches, etc.) relative to the longitudinal axis, opening sizes, spacing and/or other properties, as desired or required. For example, in some arrangements, the cut(s) 18004 comprises/comprise a dual helix or dual chirality helix design. However, in other embodiments, the cut(s) 18004 comprises/comprise a single helix design (e.g., a cut having the same pitch, general direction of orientation, other properties and/or the like). In other embodiments, the cut(s) 18004 comprises/comprise a multi-helical design (e.g., cuts having the same pitch, general direction of orientation, other properties and/or the like, wherein said cuts are out of phase with one another, such as two spiral cuts with the same pitch but are out of phase with one another by a certain angle (e.g., 180 degrees)).

With further reference to FIG. 54A, in some configurations, a distal tip 18020 can be situated or otherwise positioned distal to the cuts 18004. The angle of the distal tip 18011 relative to the longitudinal axis can include multiple (e.g., two, three, more than three, etc.) configurations. For example, the distal tip can be straight or substantially straight or linear relative to the longitudinal axis of the device (e.g., 0 to 5 degrees, 0 to 2 degrees, etc. relative to the longitudinal axis). In other embodiments, however, the distal tip can be angled relative to the longitudinal axis of the device. For instance, the distal tip can be acutely angled (e.g., 0 to 89 degrees) relative to the device's longitudinal axis. In some embodiments, the distal tip is angles at or substantially at a right angle (e.g., 90 degrees) relative to the longitudinal axis of the device. In yet other arrangements, the distal end reverse curved relative to the longitudinal axis (e.g., wherein the relative angle is greater than 90 degrees), as illustrated in FIGS. 54D, 54E, 54F and 54G.

Figure 54H:
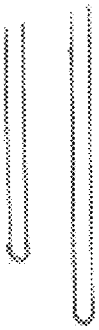
Figure 54I:
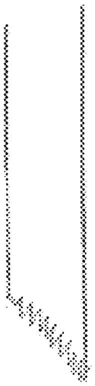
Figure 54J:
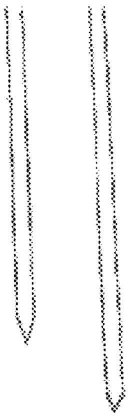
Figure 54K:
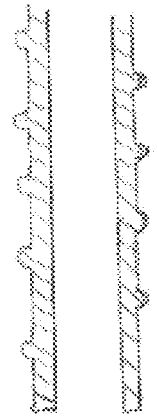
Figure 54L:
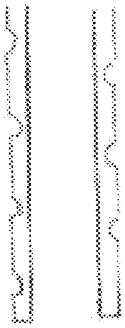

According to some embodiments, the edge or end of the distal tip 18020 can include one or more of the following configurations: a blunt edge, a serrated edge, a sharpened edge and/or the like, as illustrated in FIGS. 54H, 54I and 54J, as desired or required. Further, the distal tip 18020 can include a beveled or chamfered edge or configuration 18021 (e.g., such that the edge or end is not at a 90 degree angle) or a non-beveled edge 18022 (e.g., one that is or substantially is a 90 degree angle). The distal tip 18020 can, in some arrangements, also contain features on the outer surface such as ridges and/or grooves as illustrated in FIGS. 54K and 54L. Potential benefits of the above features of the edge of the distal tip 18020 include improved penetration through the occlusion or stenosis as well as improved visibility under ultrasound imaging, among others.

FIG. 55 illustrates a cross sectional view through the longitudinal axis of one embodiment of a CTO device 18000 that also includes a pull wire 18040. The pull wire (or similar feature) can allow or otherwise enable for deflection to undergo lateral deflection (e.g., bending) of the device (e.g., along the distal aspect or portion) when the pull wire 18040 is manipulated (e.g., tension is applied to the pull wire). The pull wire 18040 can be coupled to the distal tip 18020 via suitable coupling means, such as, for example, one or more of the following: glue or other adhesives (e.g., cyanoacrylate), welding, brazing, soldering, mechanical linking; other fasteners or mechanical features and/or the like.

According to one embodiment, the pull wire 18040 passes, at least partially, through the slotted portion of the tube 18008 such that the pull wire is located in the tube lumen 18003. In another embodiment, the pull wire 18040 passes through the distal aspect of the slotted portion of the tube 18008 such that the pull wire is located in the tube lumen 18003. The pull wire can then pass back through the slotted portion of the tube 18008 such that the pull wire 18040 is located between the outer sheath 18007 and the tube 18001.

In some arrangements, the outer sheath 18007, the tube 18001 and/or the inner member 18005 comprise(s) one or more of a variety of materials, including, but not limited to, polyimide, polyurethane, polyether block amides (such as Pebax®), nylon, nickel titanium alloy (Nitinol), stainless steel braiding, hollow helical stranded tubing, other polymeric materials, other metals and/or alloys and/or the like. In one embodiment, the inner member 18005 is disposed, at least partially (e.g., partially or completely), within the lumen of the tube 18001. The inner member 18005 can be advanced or retracted within the tube 18001 to longitudinally displace the cut portion of the tube 18001.

As illustrated in FIG. 55, the distal segment 18010 and inner member 18005 can be coupled to one another, either directly or indirectly, as desired or required. Suitable coupling means between the distal segment 18010 and the inner member 18005 include, but are not limited to, one or more of the following: glues or other adhesives (e.g., cyanoacrylate), welding, brazing, soldering, mechanical linking and/or the like. As shown, the inner member 18005 may be slidably advanced or withdrawn from the tube 18001 along the long axis of the tube 18001. In some arrangements, when the inner member 18005 is advanced relative to the tube, the cut portion of the distal segment 18010 undergoes longitudinal displacement, which in turn results in rotation of the distal tip 18020 and the distal segment 18010 distal to the cut(s) 18004. Advantageously, the linear and rotational motion is dependent upon the degree of longitudinal displacement, which results in fine controlled movements of the distal tip 18020. Such configurations can help decrease the risk of trauma or other harm to the subject (e.g., vascular trauma). Further, in some embodiments, the linear and rotational motion is confined to the distal segment 18010 and the distal tip 18020. Consequently, in some arrangements, the entirety of the tube 18001 does not require linear displacement or rotational motion.

FIG. 56A depicts a cross sectional view through the longitudinal axis of another embodiment of an intraluminal device, wherein the longitudinal axis of the distal tip 18020 is angulated relative to the longitudinal axis of the device 18000. In other words, the distal tip is curved or angled relative to the longitudinal axis and the distal tip 18020 has a beveled edge. In addition, as shown, the distal most aspect or portion of the distal tip 18020 can be flared. For example, the cross sectional radius of the distal most aspect of the distal tip 18020 can be greater than the cross sectional radius of the device 18000. Further, the wall thickness of the outer curvature of the flared portion of the distal tip 18020 can be greater than the wall thickness of the inner curvature of the flared portion of the distal tip 18020. Such configurations can provide one or more advantages and/or benefits, such as, for example and without limitation, the beveled edge of the distal tip 18020 has a shovel or spade-like configuration that enables the distal tip 18020 to better engage and cross the CTO 18090; the distal tip 18020 has a relatively small turning radius which decreases the risk for vessel perforation; the angled trajectory of the reentry wire 18080 compared to the distal tip 18020 can enable the reentry wire 18080 to probe a wider swath compared to the beveled edge 18021, a softer tip reentry wire 18080 (such as angled or "J" tip) to deflect and redirect the beveled edge to differing areas of the vessel and/or CTO 18090, the increased angulation of the trajectory of the reentry wire 18080 combined with fine rotational control of the distal tip 18020 can facilitate reentering the vessel lumen 18095, especially when a subintimal approach to treating a CTO 18090 is used.

FIG. 57 depicts a cross sectional view through the longitudinal axis of another embodiment of an intraluminal device, wherein the tube 18001 is disposed within the lumen of the outer sheath 18007. As shown, the outer diameter of the distal segment 18010 that is distal to the at least one cut or similar features 18004 can be greater than the inner diameter of the outer sheath 18007. In some embodiments, during use, when the outer sheath 18007 is advanced relative to the tube 18001, the cut portion of the distal segment 18010 undergoes longitudinal displacement which in turn results in rotation in combination with slight longitudinal displacement of the distal tip 18020 and the distal segment 18010 distal to the cut(s) 18004. When the proximal portion of tube 18001 is retracted relative to the outer sheath 18007, the cut portion of the tube 18001 undergoes longitudinal displacement which in turn results in only rotation of the distal tip 18020 and the distal segment 18010 distal to the cut(s) 18004.

FIG. 58 provides a detailed view of the distal aspect or portion of a reentry wire 18080 according to one embodiment, wherein the distal tip of the reentry wire is tapered so as to aid in penetrating the intima of a blood vessel of the subject. In addition, in some embodiments, the distal aspect or portion of the reentry wire 18080 is angled, wherein said angle of the distal aspect of the reentry wire 18080 relative to longitudinal axis of the reentry wire 18080 ranges from 1 to 80 degrees (e.g., 1 to 10, 10 to 20, 20 to 30, 30 to 40, 40 to 50, 50 to 60, 60 to 70, 70 to 80, 1 to 80, 1 to 20, 20 to 40, 40 to 80, 40 to 60, 60 to 80 degrees, values or ranges between the foregoing, etc.).

FIG. 59A depicts one embodiment of the distal tip 18020 engaging the proximal cap 18091 of the CTO 18090. In some arrangements, as the cut portion of the distal segment undergoes longitudinal displacement, the distal tip 18020 both rotates and advances longitudinally. This combined longitudinal and rotational motion of the distal tip 18020 can aid in penetrating the proximal cap 18091 of the CTO 18090. Further, the rotational motion can help decrease the frictional forces exerted on the distal tip 18020. This can also assist in selecting a microchannel within the CTO 18090, while the longitudinal motion aids in the distal tip 18020 advancing through the CTO 18090.

FIG. 59B depicts one embodiment of the distal tip 18020 engaged in a microchannel in the proximal cap 18091 of the CTO 18090. Further, FIG. 59C depicts one embodiment of the distal tip 18020 in a microchannel in the body of the CTO 18092, and FIG. 59D depicts one embodiment of the distal tip 18020 just distal to the distal cap 18093 of the CTO 18090 within the vessel lumen 18095.

FIG. 60A illustrates another embodiment of a method of crossing a CTO 18090, wherein the distal tip 18020 engages subintimal space 18094 at the level of the proximal cap 18091 of the CTO 18090. In some embodiments, as the cut portion of the distal segment 18010 undergoes longitudinal displacement, the distal tip 18020 both rotates and advances longitudinally. The rotational motion can help decrease the frictional forces exerted on the distal tip 18020, while the longitudinal motion aids in the distal tip 18020 advancing through the subintimal space 18094 of the CTO 18090.

FIG. 60B depicts an embodiment of the distal tip 18020 in the subintimal space 18094 at the level of the body of the CTO 18092. Further, FIG. 60C depicts one embodiment of the distal tip 18020 in the subintimal space 18094 just distal to the distal cap 18093 of the CTO 18090. The distal tip 18020 can be oriented towards the vessel lumen 18095 by advancing or retracting the inner member 18005 such that the distal tip 18020 rotates such that the distal tip is oriented towards the vessel lumen 18095. FIG. 60D depicts the distal tip 18020 oriented towards the vessel lumen and the reentry wire 18080 being advanced through the tube lumen 18003, penetrating the intima and reenters the vessel lumen 18095. According to some embodiments, this can aid in restoring patency to a vessel.

According to some embodiments, a method for treating CTO includes a combined rotational and longitudinal motion of distal segment 18010. In such configurations, the combined rotational and longitudinal motion can result from longitudinal displacement of the cut portion of the tube 18001. In addition, a method for reentering the vessel lumen during subintimal crossing of a CTO includes rotational motion of the distal segment 18010 such that the distal tip 18020 is directed towards the vessel lumen wherein said rotational motion results from longitudinal displacement of the cut portion of the tube 18001.

As noted herein, any of the embodiments disclosed in the present application, or equivalents thereof, can be adapted such that the devices comprise a guidewire. Therefore, in some embodiments, the diameter or other cross-sectional shape can be configured to be within the range of guidewires, such as, for example, 0.008 inches to 0.038 inches (e.g., 0.008 to 0.038, 0.008 to 0.010, 0.010 to 0.012, 0.012 to 0.014, 0.014 to 0.016, 0.016 to 0.018, 0.018 to 0.020, 0.020 to 0.025, 0.025 to 0.030, 0.030 to 0.035, 0.035 to 0.038 inches, values between the foregoing ranges and values, etc.). According to some embodiments, at least a portion of the device, can be solid such that it does not include an inner lumen. For instance, in some arrangements, the distal portion of the guidewire is solid, while a proximal portion of the guidewire includes an inner opening or lumen. In some embodiments, the distal 1% to 20% (e.g., 1 to 20, 1 to 5, 5 to 10, 10 to 15, 15 to 20, 10 to 20%, percentages between the foregoing values and ranges, etc.) of the guidewire length includes a solid configuration (e.g., does not include an inner lumen). However, in other arrangements, the guidewire can include a solid configuration that is greater than 20%, as desired or required.

In some embodiments, the guidewire can be configured to both rotate and bend along its distal end, as discussed above with reference to certain arrangements. Thus, the guidewire can include one or more pull wires and/or other features that facilitate bending along the distal portion or aspect. In other embodiments, however, the guidewire is configured such that it can only rotate (but not bend).

It will now be evident to those skilled in the art that there has been described herein methods and apparatuses for improved rotation of the distal aspect of a device. Although the inventions hereof have been described by way of several embodiments, it will be evident that other adaptations and modifications can be employed without departing from the spirit and scope thereof. The terms and expressions employed herein have been used as terms of description and not of limitation; and thus, there is no intent of excluding equivalents, but on the contrary it is intended to cover any and all equivalents that may be employed without departing from the spirit and scope of the inventions.

While the disclosure has been described with reference to certain embodiments, it will be understood that various changes may be made and equivalents may be substituted for elements thereof without departing from the scope of the disclosure. In addition, many modifications will be appreciated to adapt a particular instrument, situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. Thus, it is intended that the scope of the present inventions herein disclosed should not be limited by the particular disclosed embodiments described above, but should be determined only by a fair reading of the claims that follow.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter or microcatheter" or "advancing one portion of the device (e.g., linearly) relative to another portion of the device to rotate the distal end of the device" include instructing advancing a catheter" or "instructing advancing one portion of the device," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A device comprising:

a tubular member with a longitudinal axis having a proximal end and a distal end;

at least one partial cut located at, along or near the distal end of the tubular member, the at least one partial cut comprising an orientation that is angled relative to both the longitudinal axis and an axis transverse to the longitudinal axis; and a second member positioned colinear to the tubular member and configured to selectively change a length of the at least one partial cut along the longitudinal axis and advance the distal end of the tubular member longitudinally, wherein the distal end of the tubular member is configured to at least partially rotate around the longitudinal axis when the second member is advanced relative to the tubular member so at to facilitate placement of the distal end in a particular branch of a subject's intraluminal network;

wherein the distal end of the tubular member is configured to longitudinally elongate along or near an area of the at least one partial cut; and wherein a degree of rotation of the tubular member depends on a change of the length of the area of the at least one partial cut.

2. The device of claim 1, wherein the at least one partial cut extends throughout an entire thickness of a wall of the tubular member.

3. The device of claim 1, wherein the at least one partial cut does not extend throughout an entire thickness of a wall of the tubular member.

4. The device of claim 1, wherein the at least one partial cut comprises a spiral or helical shape.

5. The device of claim 1, wherein an angle of the at least one partial cut relative to the longitudinal axis is between 10 and 80 degrees.

6. The device of claim 1, wherein the second member is secured to the tubular member along the distal end of the tubular member.

7. The device of claim 6, wherein the second member is secured to the tubular member using at least one of an adhesive and a mechanical connection.

8. The device of claim 1, wherein the second member is not secured to the tubular member.

9. The device of claim 1, wherein the tubular member comprises a lumen through which the second member is selectively moved.

10. The device of claim 1, further comprising a handle assembly, wherein a first portion of the handle assembly is secured to the tubular member and a second portion of the handle assembly is secured to the second member, wherein movement of the first portion relative to the second portion of the handle assembly facilitate movement of the tubular member relative to the second member.

11. The device of claim 1, wherein the device comprises a guidewire.

12. A device comprising:

a tubular member with a longitudinal axis having a proximal end and a distal end;

at least one partial cut located at, along or near the distal end of the tubular member, the at least one partial cut comprising an orientation that is angled relative to both the longitudinal axis and an axis transverse to the longitudinal axis; and an elongated member positioned colinear to the tubular member and configured to selectively modify a length of the tubular member along the at least one partial cut; and wherein movement of the elongated member relative to the tubular member converts longitudinal displacement into rotational movement, causing the distal end of the tubular member to at least partially rotate about the longitudinal axis when the elongated member is advanced relative to the tubular member so at to facilitate placement of the distal end in a particular branch of a subject's intraluminal network;

wherein the distal end of the tubular member is configured to longitudinally elongate along or near an area of the tubular member comprising the at least one partial cut; and wherein a degree of rotation of the tubular member depends on a change of the length of the area of the tubular member comprising the at least one partial cut.

13. The device of claim 12, wherein the at least one partial cut extends throughout an entire thickness of a wall of the tubular member.

14. The device of claim 12, wherein the at least one partial cut does not extend throughout an entire thickness of a wall of the tubular member.

15. The device of claim 12, wherein the at least one partial cut comprises a spiral or helical shape.

16. The device of claim 12, wherein the elongated member is secured to the tubular member along the distal end of the tubular member.

17. The device of claim 12, wherein the elongated member is not secured to the tubular member.

18. The device of claim 12, wherein the device comprises a guidewire.

19. A device comprising:

a first member with a longitudinal axis having a proximal end and a distal end, wherein a portion of the first member at, along or near the distal end comprises at least one feature having a spiral or helical shape; and a second member positioned colinear to the first member and configured to selectively modify a length of the portion of the first member comprising the at least one feature having a spiral or helical shape;

wherein movement of the second member relative to the first member converts longitudinal displacement into rotational movement, causing the distal end of the first member to at least partially rotate about the longitudinal axis when the second member is advanced relative to the first member; and wherein a degree of rotation of the first member depends on a change of the length of the portion of the first member comprising the at least one feature having a spiral or helical shape.

20. The device of claim 19, wherein the device comprises a guidewire.

* * * * *